(12) United States Patent
Sehgal et al.

(10) Patent No.: US 12,319,916 B2
(45) Date of Patent: Jun. 3, 2025

(54) MODULATION OF GENE TRANSCRIPTION USING ANTISENSE OLIGONUCLEOTIDES TARGETING REGULATORY RNAs

(71) Applicant: Camp4 Therapeutics Corporation, Cambridge, MA (US)

(72) Inventors: Alfica Sehgal, Belmont, MA (US); Bryan J. Matthews, Somerville, MA (US); David A. Bumcrot, Belmont, MA (US); Justin A. Caravella, Cambridge, MA (US); Mario Esteban Contreras Gamboa, Cambridge, MA (US); Rachana S. Kelkar, Malden, MA (US); Yun Joon Jung, Lexington, MA (US); Yuting Liu, Lexington, MA (US); Rutuja Sudhakar Pai, Charlestown, MA (US); Subhadeep Roy, Lafayette, CO (US); Yuchun Guo, Framingham, MA (US)

(73) Assignee: CAMP4 Therapeutics Corporation, Cambridge, MA (US)

( * ) Notice: Subject to any disclaimer, the term of this patent is extended or adjusted under 35 U.S.C. 154(b) by 0 days.

(21) Appl. No.: 18/752,290

(22) Filed: Jun. 24, 2024

(65) Prior Publication Data
US 2024/0336924 A1 Oct. 10, 2024

Related U.S. Application Data

(63) Continuation of application No. PCT/US2022/082295, filed on Dec. 22, 2022.

(60) Provisional application No. 63/308,373, filed on Feb. 9, 2022, provisional application No. 63/292,920, filed on Dec. 22, 2021.

(51) Int. Cl.
*C12N 15/11* (2006.01)
*A61P 13/00* (2006.01)
*C12N 15/113* (2010.01)

(52) U.S. Cl.
CPC .......... *C12N 15/1137* (2013.01); *A61P 13/00* (2018.01); *C12Y 603/04016* (2013.01); *C12N 2310/113* (2013.01); *C12N 2310/315* (2013.01); *C12N 2310/3231* (2013.01); *C12N 2310/3341* (2013.01); *C12N 2310/341* (2013.01); *C12N 2310/351* (2013.01); *C12N 2310/3525* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 4,837,028 A | 6/1989 | Allen |
| 4,897,355 A | 1/1990 | Eppstein et al. |
| 5,171,678 A | 12/1992 | Behr et al. |
| 5,283,185 A | 2/1994 | Epand et al. |
| 5,445,934 A | 8/1995 | Fodor et al. |
| 5,543,152 A | 8/1996 | Webb et al. |
| 5,677,195 A | 10/1997 | Winkler et al. |
| 5,744,305 A | 4/1998 | Fodor et al. |
| 5,770,722 A | 6/1998 | Lockhart et al. |
| 5,854,033 A | 12/1998 | Lizardi |
| 5,874,219 A | 2/1999 | Rava et al. |
| 5,976,567 A | 11/1999 | Wheeler et al. |
| 5,981,501 A | 11/1999 | Wheeler et al. |
| 6,268,490 B1 | 7/2001 | Imanishi et al. |
| 6,525,191 B1 | 2/2003 | Ramasamy |
| 6,534,484 B1 | 3/2003 | Wheeler et al. |
| 6,586,410 B1 | 7/2003 | Wheeler et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,815,432 B2 | 11/2004 | Wheeler et al. |
| 6,998,484 B2 | 2/2006 | Koch et al. |
| 7,034,133 B2 | 4/2006 | Wengel et al. |
| 7,053,207 B2 | 5/2006 | Wengel |
| 7,084,125 B2 | 8/2006 | Wengel |
| 7,250,496 B2 | 7/2007 | Bentwich |
| 7,399,845 B2 | 7/2008 | Seth et al. |
| 7,427,605 B2 | 9/2008 | Davis et al. |
| 7,427,672 B2 | 9/2008 | Imanishi et al. |
| 7,569,686 B1 | 8/2009 | Bhat et al. |
| 7,687,616 B1 | 3/2010 | Bentwich et al. |
| 7,741,457 B2 | 6/2010 | Seth et al. |
| 7,777,022 B2 | 8/2010 | Bentwich et al. |

(Continued)

FOREIGN PATENT DOCUMENTS

| | | |
|---|---|---|
| WO | WO-1988/004924 A1 | 7/1988 |
| WO | WO-1991/016024 A1 | 10/1991 |

(Continued)

OTHER PUBLICATIONS

Adam et al. (2019) "Overexpression of carbamoyl-phosphate synthase 1 significantly improves ureagenesis of human liver HepaRG cells only when cultured under shaking conditions," Mitochondrion 47:298-308.

Ah Mew et al. (2017) "Urea Cycle Disorders Overview," https://www.ncbi.nlm.nih.gov/books/ 20 pages.

Ai et al. (2012) "Regulation of hepatic LDL receptors by mTORC1 and PCSK9 in mice." *The Journal of clinical investigation* 122(4):1262-1270.

Aigner (2006) "Delivery Systems for the Direct Application of siRNAs to Induce RNA Interference (RNAi) In Vivo," Journal of Biomedicine and Biotechnology 2006:1-15.

(Continued)

*Primary Examiner* — Ekaterina Poliakova-Georgantas
(74) *Attorney, Agent, or Firm* — Goodwin Procter LLP

(57) ABSTRACT

Described herein are methods of modulating gene transcription using antisense oligonucleotides (ASOs) targeting regulatory RNAs, such as promoter-associated RNAs and enhancer RNAs. These methods are useful for modulating the levels of gene products, for example, increasing expression of Carbamoyl-Phosphatase Synthetase 1 (CPS1), thereby treating diseases associated with aberrant gene expression.

15 Claims, 27 Drawing Sheets
Specification includes a Sequence Listing.

(56) References Cited

U.S. PATENT DOCUMENTS

| | | |
|---|---|---|
| 7,834,170 B2 | 11/2010 | Khvorova et al. |
| 7,888,497 B2 | 2/2011 | Bentwich et al. |
| 7,943,754 B2 | 5/2011 | Bentwich et al. |
| 8,022,193 B2 | 9/2011 | Seth et al. |
| 8,030,467 B2 | 10/2011 | Seth et al. |
| 8,030,474 B2 | 10/2011 | Khvorova et al. |
| 8,039,608 B1 | 10/2011 | Bentwich |
| 8,084,598 B1 | 12/2011 | Bentwich |
| 8,178,503 B2 | 5/2012 | Rigoutsos et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,314,227 B2 | 11/2012 | Wengel |
| 8,362,230 B2 | 1/2013 | Plasterk et al. |
| 8,445,666 B2 | 5/2013 | Rigoutsos et al. |
| 8,494,784 B2 | 7/2013 | Huynh et al. |
| 8,691,829 B2 | 4/2014 | Ulrich |
| 9,518,261 B2 | 12/2016 | Freier et al. |
| 9,527,847 B2 | 12/2016 | Palombella et al. |
| 10,059,941 B2 | 8/2018 | Krieg et al. |
| 11,266,655 B2 | 3/2022 | Sehgal et al. |
| 2004/0171570 A1 | 9/2004 | Allerson et al. |
| 2004/0265865 A1 | 12/2004 | Mattick et al. |
| 2005/0019841 A1 | 1/2005 | Garman et al. |
| 2006/0058255 A1 | 3/2006 | Chen et al. |
| 2007/0280928 A1 | 12/2007 | Buck et al. |
| 2008/0039618 A1 | 2/2008 | Allerson et al. |
| 2008/0176786 A1 | 7/2008 | Ditullio et al. |
| 2009/0012281 A1 | 1/2009 | Swayze et al. |
| 2009/0111132 A1 | 4/2009 | Poynard |
| 2009/0258925 A1 | 10/2009 | Wahlestedt |
| 2010/0166784 A1 | 7/2010 | Murphy et al. |
| 2010/0324120 A1 | 12/2010 | Chen et al. |
| 2011/0313020 A1 | 12/2011 | Templin et al. |
| 2012/0028838 A1 | 2/2012 | Cantor et al. |
| 2012/0157511 A1 | 6/2012 | Manoharan et al. |
| 2013/0011922 A1 | 1/2013 | Quay et al. |
| 2013/0096289 A1 | 4/2013 | Wengel |
| 2013/0190383 A1 | 7/2013 | Vaish et al. |
| 2013/0237562 A1 | 9/2013 | Barda et al. |
| 2013/0245099 A1 | 9/2013 | Collard et al. |
| 2013/0317086 A1 | 11/2013 | Guire et al. |
| 2014/0038920 A1 | 2/2014 | Ballabio et al. |
| 2014/0135376 A1 | 5/2014 | Engbersen et al. |
| 2014/0342003 A1 | 11/2014 | Saltzman et al. |
| 2015/0133362 A1 | 5/2015 | Krieg et al. |
| 2015/0174549 A1 | 6/2015 | Lim et al. |
| 2015/0225717 A1 | 8/2015 | Lee et al. |
| 2015/0225719 A1 | 8/2015 | Chen et al. |
| 2015/0232858 A1 | 8/2015 | Ozsolak |
| 2015/0297598 A1 | 10/2015 | Friedman et al. |
| 2015/0307554 A1 | 10/2015 | Castillo Rodriguez |
| 2015/0335764 A1 | 11/2015 | Martinez Fong |
| 2016/0230189 A1 | 8/2016 | Kotha et al. |
| 2016/0251478 A1 | 9/2016 | Saltzman et al. |
| 2016/0264966 A1 | 9/2016 | Fitzgerald et al. |
| 2016/0271116 A1 | 9/2016 | Jia et al. |
| 2016/0279256 A1 | 9/2016 | Wang et al. |
| 2016/0312216 A1 | 10/2016 | Fitzgerald et al. |
| 2016/0348073 A1 | 12/2016 | Meissner et al. |
| 2016/0366813 A1 | 12/2016 | Haneda et al. |
| 2016/0369269 A1 | 12/2016 | Shen et al. |
| 2017/0121454 A1 | 5/2017 | Saltzman et al. |
| 2017/0130247 A1 | 5/2017 | Dowen et al. |
| 2017/0143682 A1 | 5/2017 | Melin |
| 2017/0175128 A1 | 6/2017 | Welstead et al. |
| 2017/0204407 A1 | 7/2017 | Gilbert et al. |
| 2017/0296653 A1 | 10/2017 | Mumm et al. |
| 2017/0349903 A1 | 12/2017 | Liu et al. |
| 2018/0201936 A1 | 7/2018 | Hinkle |
| 2018/0273609 A1 | 9/2018 | Porteus et al. |
| 2018/0320175 A1 | 11/2018 | Lee et al. |
| 2019/0040395 A1 | 2/2019 | Freier |
| 2019/0046471 A1 | 2/2019 | Koeberl et al. |
| 2019/0048337 A1 | 2/2019 | Hsu et al. |
| 2019/0136230 A1 | 5/2019 | Sather et al. |
| 2019/0153477 A1 | 5/2019 | Lundberg et al. |
| 2019/0270984 A1 | 9/2019 | Gourguechon |
| 2019/0309259 A1 | 10/2019 | Meissner et al. |
| 2019/0374655 A1 | 12/2019 | Kabadi et al. |
| 2020/0095579 A1 | 3/2020 | Lundberg et al. |
| 2020/0316038 A1 | 10/2020 | Sehgal et al. |
| 2021/0114996 A1 | 4/2021 | Sehgal et al. |
| 2021/0130804 A1 | 5/2021 | Baram et al. |
| 2021/0161997 A1 | 6/2021 | Bumcrot et al. |
| 2021/0180091 A1 | 6/2021 | Chakraborty et al. |
| 2021/0254056 A1 | 8/2021 | Liu et al. |
| 2022/0090036 A1 | 3/2022 | Oakes et al. |
| 2022/0107328 A1 | 4/2022 | Bumcrot et al. |
| 2022/0168316 A1 | 6/2022 | Sehgal et al. |
| 2022/0340898 A1 | 10/2022 | Chen et al. |
| 2023/0042624 A1 | 2/2023 | Gilbert et al. |

FOREIGN PATENT DOCUMENTS

| | | |
|---|---|---|
| WO | WO-1993/024640 A2 | 12/1993 |
| WO | WO-1994/000569 A1 | 1/1994 |
| WO | WO-1994/002595 A1 | 2/1994 |
| WO | WO-1996/037194 A1 | 11/1996 |
| WO | WO-1996/040964 A2 | 12/1996 |
| WO | WO-1997/013499 A1 | 4/1997 |
| WO | WO-1998/039352 A1 | 9/1998 |
| WO | WO-1998/039359 A1 | 9/1998 |
| WO | WO-1999/014226 A2 | 3/1999 |
| WO | WO-2000/003683 A2 | 1/2000 |
| WO | WO-2000/047599 A1 | 8/2000 |
| WO | WO-2000/066604 A2 | 11/2000 |
| WO | WO-2001/044465 A2 | 6/2001 |
| WO | WO-2004/046160 A2 | 6/2004 |
| WO | WO-2007/090071 A2 | 8/2007 |
| WO | WO-2007/134181 A2 | 11/2007 |
| WO | WO-2008/042973 A2 | 4/2008 |
| WO | WO-2008/046510 A1 | 4/2008 |
| WO | WO-2008/150729 A2 | 12/2008 |
| WO | WO-2008/154401 A2 | 12/2008 |
| WO | WO-2009/006478 A2 | 1/2009 |
| WO | WO-2009/067647 A1 | 5/2009 |
| WO | WO-2009/088891 A1 | 7/2009 |
| WO | WO-2009/132131 A1 | 10/2009 |
| WO | WO-2009/143371 A2 | 11/2009 |
| WO | WO-2010/036698 A1 | 4/2010 |
| WO | WO-2010/077578 A1 | 7/2010 |
| WO | WO-2011/005861 A1 | 1/2011 |
| WO | WO-2011/017521 A2 | 2/2011 |
| WO | WO-2011/081942 A1 | 7/2011 |
| WO | WO-2011/156202 A1 | 12/2011 |
| WO | WO-2012/170930 A1 | 12/2012 |
| WO | WO-2013/036868 A1 | 3/2013 |
| WO | WO-2013/149141 A1 | 10/2013 |
| WO | WO-2013/154798 A1 | 10/2013 |
| WO | WO-2013/173608 A1 | 11/2013 |
| WO | WO-2013/177248 A2 | 11/2013 |
| WO | WO-2014/066848 A1 | 5/2014 |
| WO | WO-2014/152211 A1 | 9/2014 |
| WO | WO-2014/161046 A1 | 10/2014 |
| WO | WO-2016/118697 A1 | 7/2016 |
| WO | WO-2016/130806 A2 | 8/2016 |
| WO | WO-2016/191427 A1 | 12/2016 |
| WO | WO-2016/207647 A1 | 12/2016 |
| WO | WO-2017/011710 A2 | 1/2017 |
| WO | WO-2017/031370 A1 | 2/2017 |
| WO | WO-2017/049157 A1 | 3/2017 |
| WO | WO-2017/049386 A1 | 3/2017 |
| WO | WO-2017/075406 A1 | 5/2017 |
| WO | WO-2017/106345 A1 | 6/2017 |
| WO | WO-2017/139212 A1 | 8/2017 |
| WO | WO-2017/158358 A1 | 9/2017 |
| WO | WO-2017/201342 A1 | 11/2017 |
| WO | WO-2018/204764 A1 | 11/2018 |
| WO | WO-2019/040471 A1 | 2/2019 |
| WO | WO-2019/071276 A1 | 4/2019 |
| WO | WO-2020/191153 A2 | 9/2020 |
| WO | WO-2020/191171 A1 | 9/2020 |
| WO | WO-2020/210642 A1 | 10/2020 |

(56) References Cited

FOREIGN PATENT DOCUMENTS

| WO | WO-2022/115539 A2 | 6/2022 |
|---|---|---|
| WO | WO-2022/236147 A1 | 11/2022 |
| WO | WO-2022/256448 A2 | 12/2022 |
| WO | WO-2023/034983 A2 | 3/2023 |
| WO | WO-2023/089153 A1 | 5/2023 |
| WO | WO-2023/102188 A1 | 6/2023 |
| WO | WO-2023/212584 A2 | 11/2023 |

OTHER PUBLICATIONS

Akhtar et al. (1992) "Cellular uptake and intracellular fate of antisense oligonucleotides," Trends in Cell Biology 2:139-144.
Akinc et al. (2008) "A combinatorial library of lipid-like materials for delivery of RNAi therapeutics," Nature Biotechnology 26(5):561-569.
Allegri et al. (2018) "Comprehensive characterization of ureagenesis in the spfash mouse, a modfel of human ornithine transcarbamylase deficiency, reveals age-dependency of ammonia detoxification," J. Inherit. Metab. Dis. 42(6):1064-76.
Allen et al. (1987) "Large unilamellar liposomes with low uptake into the reticuloendothelial system," FEBS Letters 223(1):42-46.
Arnold et al. (2007) "Specific β1-adrenergic receptor silencing with small interfering RNA lowers high blood pressure and improves cardiac function in myocardial ischemia," Journal of Hypertension 25(1):197-205.
Baclig et al. (2014) "Genetic variation I148M in patatin-like phospholipase 3 gene and risk of non-alcoholic fatty liver disease among Filipinos." International journal of clinical and experimental medicine 7(8):2129-2136.
Bangham et al. (1965) "Diffusion of Univalent Ions across the Lamellae of Swollen Phospholipids," J. Mol. Biol. 13:238-252.
Barany (1991) "Genetic disease detection and DNA amplification using cloned thermostable ligase," Pro. Natl. Acad. Sci. USA 88:189-193.
Barba et al. (2019) "Lipid Delivery Systems for Nucleic-Acid-Based-Drugs: From Production to Clinical Applications," Pharmaceutics 11, 360 26 pages.
Barbieri et al. (2016) "Proteogenomics: key driver for clinical discovery and personalized medicine." Proteogenomics, pp. 21-47.
BasuRay et al. (2017) "The PNPLA3 Variant Associated With Fatty Liver Disease (I148M) Accumulates on Lipid Droplets by Evading Ubiquitylation," Hepatology66(4):1111-1124.
Bhattacharjee et al. (2013) "Inhibition of Vascular Permeability by Antisense-Mediated Inhibition of Plasma Kallikrein and Coagulation Factor 12," Nucleic Acid Therapeutics 23(3):175-187.
Bonnet et al. (2008) "Systemic Delivery of DNA or siRNA Mediated by Linear Polyethylenimine (L-PEI) Does Not Induce an Inflammatory Response," Pharmaceutical Research 11 pages.
Briand et al. (1982) "Ornithine Transcarbamylase Deficiencies in Human Males. Kinetic and Immunochemical Classification," Biochim. Biophys. Acta 704(1):100-6.
Bruschi et al. (2017) "The PNPLA3 I148M Variant Modulates the Fibrogenic Phenotype of Human Hepatic Stellate Cells," Hepatology 65(6):1875-1890.
Bumcrot et al. (May 11, 2022) "Therapeutics Upregulation of Gene Expression by Antisense Oligonucleotide Targeting of Regulatory RNAs" [Conference presentation]. TIDES USA: Oligonucleotide & Peptide Therapeutics, Boston, MA, U.S.A., 27 pages.
Çeliktas et al. (2017) "Role of CPS1 in cell growth, metabolism, and prognosis in LKB1-inactivated lung adenocarcinoma," JNCI: Journal of the National Cancer Institute 109(3):9 pages.
Chen et al. (2015) "PNPLA3 I148M variant in nonalcoholic fatty liver disease: Demographic and ethnic characteristics and the role of the variant in nonalcoholic fatty liver fibrosis," World J Gastroenterol 21(3):794-802.
Chiang et al. (2007) "Dysregulation of C/EBPa by mutant Huntingtin causes the urea cycle deficiency in Huntington's disease." Human molecular genetics 16(5):483-498.

Chien et al. (2005) "Novel cationic cardiolipin analogue-based liposome for efficient DNA and small interfering RNA delivery in vitro and in vivo," Cancer Gene Therapy 12:321-328.
Conway et al. (2017) "A mouse model of hereditary coproporphyria identified in an ENU mutagenesis screen." *Disease models & mechanisms* 10(8):1005-1013.
Corces et al. (2017) "An improved ATAC-seq protocol reduces background and enables interrogation of frozen tissues," Nat Methods 14(10):959-962 (15 pages).
Cui et al. (2021) "Liver-Targeted Delivery of Oligonucleotides with N-Acetylgalactosamine Conjugation," ACS Omega 6:16259-16265.
Debacker et al. (2020) "Delivery of Oligonucleotides to the Liver Therapeutic Drug," Molecular Therapy 28(8):1759-1771.
Deleavey et al. (2012) "Designing Chemically Modified Oligonucleotides for Targeted Gene Silencing," Chemistry & Bilology 19:937-954.
Derwall et al. (2012) "Inhibition of bone morphogenetic protein signaling reduces vascular calcification and atherosclerosis," *Arteriosclerosis, thrombosis, and vascular biology* 32(3):613-622, 18 pages.
Dowen et al. (2014) "Control of cell identity genes occurs in insulated neighborhoods in mammalian chromosomes," Cell 159(2):374-387.
Du Plessis et al. (1992) "Topical delivery of liposomally encapsulated gamma-interferon," Antiviral Research 18:259-265.
Durymanov et al. (2018) "Non-viral Delivery of Nucleic Acids: Insight Into Mechanisms of Overcoming Intracellular Barriers," frontiers in Pharmacology 9, Article 971, 15 pages.
El Khoury et al. (2017) "PCSK9 mutations in familial hypercholesterolemia: from a groundbreaking discovery to anti-PCSK9 therapies," *Current atherosclerosis reports* 19(12):1-13.
Felgner et al. (1987) "Lipofection: A highly efficient, lipid-mediated DNA-transfection procedure," Pro. Natl. Acad. Sci. USA 84:7413-7417.
Felgner et al. (1994) "Enhanced Gene Delivery and Mechanism Studies with a Novel Series of Cationic Lipid Formulations," The Journal of Biological Chemistry 269(4):2550-2561.
Ferrin et al. (2020) "Activation of mTOR Signaling Pathway in Hepatocellular Carcinoma," Int. J. Mol. Sci. 21 (16 pages).
Fluiter et al. (2009) "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular BioSystems 5:838-843.
Frank-Kamenetsky et al. (2002) "Small-molecule modulators of Hedgehog signaling: identification and characterization of Smoothened agonists and antagonists," *Journal of Biology* 1(2):1-19.
Freier et al. (1997) "The ups and downs of nucleic acid duplex stability: structure-stability studies on chemically-modified DNA:RNA duplexes," Nucleic Acids Research 25(22):4429-4443.
Fukunaga et al. (1984) "Liposome Entrapment Enhances the Hypocalcemic Actions of Parenterally Administered Calcitonin," Endocrinology 115(2):757-761.
Gabizon et al. (1998) "Liposome formulations with prolonged circulation time in blood and enhanced uptake by tumors," Pro. Natl. Acad. Sci. USA 85:6949-6953.
Gao et al. (1991) "A Novel Cationic Liposome Reagent for Efficient Transfection of Mammalian Cells," Biochemical and Biophysical Research Communications 179(1):280-285.
Gershon et al. (1993) "Mode of Formulation and Structural Features of DNA-Cationic Liposome Complexes Used for Transfection," Biochemistry 32:7143-7151.
Grunweller et al. (2003) "Comparison of different antisense strategies in mammalian cells using locked nucleic acids, 2'-O-methyl RNA, phosphorothioates and small interfering RNA," 31(12):3185-3193.
Guatelli et al. (1990) "Isothermal, in vitro amplification of nucleic acids by a multienzyme reaction modeled after retroviral replication," Proc. Natl. Acad. Sci. USA 87:1874-1878.
Guo et al. (Mar. 11, 2022) "Accurate prediction of functional enhancer-promoter interactions using epigenomic data" [Poster presentation]. Systems Biology: Global Regulation of Gene Expression, Cold Spring Harbor, NY, U.S.A., 1 page.

(56) References Cited

OTHER PUBLICATIONS

Guo et al. (Mar. 2022) "Accurate prediction of functional enhancer-promoter interactions using epigenomic data." In Abstracts of papers presented at the 2022 meeting on Systems Biology: Global Regulation of Gene Expression, Mar. 9-Mar. 12, 2022; Cold Spring Harbor, NY, U.S.A. Cold Spring Harbor Laboratory, Cold Spring Harbor, NY, p. 68.

Han et al. (2002) "Increased vascular permeability in C1 inhibitor-deficient mice mediated by the bradykinin type 2 receptor," The Journal of Clinical Investigation 109(8):1057-1063.

Hangeland et al. (1995) "Cell-type specific and ligand specific enhancement of cellular uptake of oligodeoxynucleoside methylphosphonates covalently linked with a neoglycopeptide, YEE(ah-GalNAc)3," *Bioconjug Chem.* 6(6):695-701.

Hansen et al. (1965) "Entropy Titration. A Calorimetric Method for the Determination of ?G° (K), ?H° and ?S°1," Chemcial Communications 36-38.

Henninger et al. (2021) "RNA-mediated feedback control of transcriptional condensates," Cell 184(1):207-225.

Hnisz et al. (2016) "Activation of proto-oncogenes by disruption of chromosome neighborhoods." Science 351(6280):1454-1458.

Hnisz et al. (2016) "Insulated neighborhoods: structural and functional units of mammalian gene control." Cell 167(5):1188-1200.

Hodges et al. (1989) "The spfash mouse: A missense mutation in the ornithine transcarbamylase gene also causes aberrant mRNA splicing," Proc. Natl. Acad. Sci. USA 86(4142-4146).

Holdgate et al. (2005) "Measurements of binding thermodynamics in drug discover," DDT 10(22):1543-1550.

Hu et al. (1994) "Topical delivery of cyclosporin A from non-ionic liposomal systems: an in vivo/in vitro correlation using hairless mouse skin," S.T.P. Pharma. Sci., 4(6):466-9.

International Search Report and Written Opinion for PCT/US2022/082295 mailed May 15, 2023 15 pages.

Itani et al. (1987) "A simple and efficient liposome method for transfection of DNA into mammalian cells grown in suspension," Gene 56:267-376.

Jang et al. (2018) "Disease-causingmutations in the promoter and enhancer of the ornithine transcarbamylase gene," Human Mutation 39:527-536.

Jensen et al. (2008) "Unlocked nucleic acid (UNA) and (una derivatives: Thermal denaturation studies," Nucleic Acids Symposium Series No. 2:133-134.

Ji, et al. (2016) "3D chromosome regulatory landscape of human pluripotent cells," Cell stem cell 18(2):262-275.

Jiang et al. (2022) "Ornithine aminotransferase and carbamoyl phosphate synthetase 1 involved in ammonia metabolism serve as novel targets for early stages of gastric cancer," J Clin Lab Anal. 36:e24692 11 pages.

Johansson et al. (2008) "Polymorphisms in the adiponutrin gene are associated with increased insulin secretion and obesity." European journal of endocrinology 159(5):577-583.

Jung et al. (Nov. 18, 2021) "A Novel Treatment Approach for Treating OTC Deficiency By Targeting RegRNAs Using Oligonucleotides" [Conference presentation]. American Liver Foundation 20th Annual Irwin M. Arias Symposium, Bridging Basic Science and Liver Disease, Virtual Meeting.

Jung et al. (Oct. 2-5, 2022) "Targeting regRNAs with oligonucleotides to treat OTC deficiency" [Poster presentation]. The 18th Annual Meeting of the Oligonucleotide Therapeutics Society, Phoenix, AZ, U.S.A., 1 page.

Jung et al. (Sep. 23, 2022) "A Novel Treatment Approach for Treating OTC Deficiency By Targeting RegRNAs Using Oligonucleotides" [Conference presentation]. The 17th Annual Meeting of the Oligonucleotide Therapeutics Society, Virtual Meeting, 1 page.

Katayama et al. (2007) "Restenosis developing over one year after implantation with a sirolimus-eluting stent: two case reports," Journal of Cardiology 49(6):345-352.

Kim et al. (1983) "Preparation of Multivesicular Liposomes," Biochimica et Biophysica Acta 728:339-348.

Kim et al. (2010) "Widespread transcription at neuronal activity-regulated enhancers," Nature 465(7295):182-187.

Krawczyk et al. (2013) "PNPLA3-Associated Steatohepatitis: Toward a Gene-Based Classification of Fatty Liver Disease," Semin Liver Dis. 33(4):369-79.

Kubrusly et al. (2010) "A role for mammalian target of rapamycin-mTOR-pathway in non alcoholic steatohepatitis related-cirrhosis," Histology and histopathology 25m:1123-1131.

Kumar et al. (2021) "A deep intronic variant is a common cause of OTC deficiency in individuals with previously negative genetic testing," Mol. Genet. Metab. Rep. 26: 100706.

Kwoh et al. (1989) "Transcription-based amplification system and detection of amplified human immunodeficiency virus type 1 with a bead-based sandwich hybridization format," Pro. Natl. Acad. Sci. USA 86:1173-1177.

Lai et al. (2013) "Activating RNAs associate with Mediator to enhance chromatin architecture and transcription," Nature 494:497-501 7 pages.

Lake et al. (2005) "Expression, regulation, and triglyceride hydrolase activity of Adiponutrin family members," J Lipid Res. 46(11):2477-87.

Langer (1990) "New Methods of Drug Delivery," Articles 1527-1533.

Langmead et al. (2012) "Fast gapped-read alignment with Bowtie 2," Nature methods 9(4):357-359.

Langner et al. (2020) "Synthesis and Characterization of Thiophosphoramidate Morpholino Oligonucleotides and Chimeras," J. Am. Chem. Soc. 142:16240-16253.

Li et al. (2009) "The Sequence Alignment/Map Format and SAMtools," Bioinformatics 25(16):2078-2079.

Licciardello et al. (2017) "A combinatorial screen of the CLOUD uncovers a synergy targeting the androgen receptor," Nature chemical biology 13(7):771-778.

Lichter-Konecki (2016) "Defects of the urea cycle," Translational Science of Rare Disease 1:23-43.

Liu (2006) "Radiolabeled Multimeric Cyclic RGD Peptides as Integrin $\alpha v\beta 3$ Targeted Radiotracers for Tumor Imaging," Molecular Pharmaceutics 3(5):472-487.

Lizardi et al. (1988) "Exponential Amplification of Recombinant-RNA Hybridization Probes," Bio/technology 6:1197-1201.

Love et al. (2010) "Lipid-like materials for lwo-dose, in vivo gene silencing," PNAS 107(5):1864-1869.

Ma et al. (2015) "Co-expression of the carbamoyl-phosphate synthase 1 gene and its long non-coding RNA correlates with poor prognosis of patients with intrahepatic cholangiocarcinoma," Molecular Medicine Reports 12:7915-7926.

Maglio et al. (2014) "The PNPLA3 I148M variant and chronic liver disease: When a genetic mutation meets nutrients," *Food research international* 63:239-243.

Mahon et al. (2010) "Combinatorial Approach to Determine Functional Group Effects on Lipidoid-Mediated siRNA Delivery," Bioconjugate 21:1448-1454.

Malley et al. (2016) "The mTOR pathway in obesity driven gastrointestinal cancers: Potential targets and clinical trials." BBA clinical 5:29-40.

Mannino et al. (1998) "Liposome Mediated Gene Transfer," BioTechniques 6(7):682-690.

Mayer et al. (1986) "Vesicles of variable sizes produced by a rapid extrusion procedure," Biochimica et Biophysica Acta 858:161-168.

Mayhew et al. (1984) "Characterization of Liposomes Prepared Using a Microemulsifier," Biochimica et Biophysica Acta 775:169-174.

McTigue et al. (2004) "Sequence-Dependent Thermodynamic Parameters for Locked Nucleic Acid (LNA)-DNA Duplex Formation," Biochemistry 43:5388-5405.

Mergny et al. (2003) "Analysis of Thermal Melting Curves," Oligonucleotides 13:515-537.

Mitsuoka et al. (2009) "A bridged nucleic acid, 2',4'-BNACOC: synthesis of fully modified oligonucleotides bearing thymine, 5-methylcytosine, adenine and guanine 2',4'BNACOC monomers and RNA-selective nucleic-acid recognition," Nucleic Acids Res. 37(4): 1225-38.

(56) References Cited

OTHER PUBLICATIONS

Moore et al. (2020) "Expanded encyclopaedias of DNA elements in the human and mouse genomes," Nature 583(7818):699-710 (27 pages).
Mori et al. (1987) "Molecular Aspects of Urea Cycle Enzymes and Related Disorders," Enzyme 38(1-4): 220-6.
Morita et al. (2002) "2'-O,4'-C-ethylene-bridged nucleic acids (ENA): highly nuclease-resistant and thermodynamically stable oligonucleotides for antisense drug," Bioorganic & Med. Chem. Lett. 12(1): 73-6.
Morris (2002) "Regulation of Enzymes of the Urea Cycle and Arginine Metabolism," Annu. Rev. Nutr. 22:87-105.
Mousavi et al. (2013) "eRNAs Promote Transcription by Establishing Chomatin Accessibility at Defined Genomic Loci," Molecular Cell 51:606-617.
Muhammad et al. (2020) "Therapeutic Startegies for Cancer Sub-Types Overexpressing Cps1," Cancer Prevention: Current Research Journal 3(1):114 (4 pages).
Mullis et al. (1987) "Specific Synthesis of DNA in Vitro via a Polymerase-Catalyzed Chain Reaction," Methods in Enzymology 155:335-350.
Nabel et al. (1992) "Gene Transfer In Vivo with DNA-Liposome Complexes: Lack of Autoimmunity and Gonadal Localization," Human Gene Therapy 3:649-656.
Nabel et al. (1993) "Direct gene transfer with DNA-liposome complexes in melanoma: Expression, biologic activity, and lack of toxicity in humans," Proc. Natl. Acad. Sci USA 90:11307-11311.
Nakagawa et al. (2009) "SIRT5 Deacetylates carbamoyl phosphate synthetase 1 and regulates the urea cycle," Cell 137(3):560-570.
NC_000012.12: *Homo sapiens* chromosome 12, GRCh38.p13 Primary Assembly, NCBI GenBank, Dec. 21, 2017 {Dec. 21, 2017), Accession No. GCA_000001405.27, pp. 1 of 1. Retrieved from the Internet:<www.ncbl.nlm.nlh.gov/projectsfsviewer/?id=568815586&v=102822556:103550727> on Jun. 19, 2019 (Jun. 19, 2019). entire document.
Ni et al. (2019) "Synthetic Approaches for Nucleic Acid Delivery: Choosing the Right Carrier," Life 9(59) 28 pages.
Nicolau et al. (1987) "Liposomes as Carriers for in Vivo Gene Transfer and Expression," Methods in Enzymology 149:157-176.
Nischalke et al. (2011) "The PNPLA3 rs738409 148M/M Genotype Is a Risk Factor for Liver Cancer in Alcoholic Cirrhosis but Shows No or Weak Association in Hepatitis C Cirrhosis," PLoS One. 6(11):e27087 (6 pages).
Ohtake et al. (1986) "Molecular Basis of Ornithine Transcarbamylase Deficiency in spf and spf-ash Mutant Mice," J. Inherit. Metab. Dis. 9(3): 289-91.
Olson et al. (1979) "Preparation of Liposomes of Defined Size Distribution by Extrusion Through Polycarbonate Membranes," Biochimica et Biophysica Acta 557:9-23.
Pal et al. (2005) "Systemic delivery of RafsiRNA using cationic cardiolipin liposomes silences Raf-1 expression and inhibits tumor growth in xenograft model of human prostate cancer," International Journal of Oncology 26:1087-1091.
Papahadjopoulos et al. (1987) "Targeting of Liposomes to Tumor Cells in Vivoa" Annals New York Academy of Sciences 64-74.
PCT/US20/27693—International Preliminary Report on Patentability, Sep. 28, 2021, 7 pages.
PCT/US20/27693—International Search Report and Written Opinion, Jul. 21, 2020, 17 pages.
PCT/US2018/031056—International Search Report and Written Opinion, Oct. 16, 2018, 22 pages.
PCT/US2018/031056 International Search Report and Written Opinion, Oct. 16, 2018, 21 pages.
PCT/US2018/055087—International Preliminary Report on Patentability, Apr. 16, 2020, 14 pages.
PCT/US2018/055087—International Search Report and Written Opinion, Mar. 21, 2019, 21 pages.
PCT/US2022/075934—International Search Report and Written Opinion, Jun. 2, 2023, 11 pages.

Rahman et al. (2015) "TGF-β/BMP signaling and other molecular events: regulation of osteoblastogenesis and bone formation," Bone research 3(1):1-20.
Rajebhosale et al. (2010) "834 Designing Liver Cells Capable of Ammonia Detoxification Useful in Bio-Artificial Liver," Journal of Hepatology 52:S325-S326.
Renet al. (2017) "The combination of blueberry juice and probiotics ameliorate non-alcoholic steatohepatitis (NASH) by affecting SREBP-1c/PNPLA-3 pathway via PPAR-α," Nutrients 9(3):198, 25 pages.
Rivera-Barahona (2015) "Functional Characterization of the spf/ash Splicing Variation in OTC Deficiency of Mice and Man," PLoS One 10(4): e0122966.
Salameh et al. (2016) "PNPLA3 as a genetic determinant of risk for and severity of non-alcoholic fatty liver disease spectrum," Journal of clinical and translational hepatology 4(3):175.
SantaLucia (1998) "A unified view of polymer, dumbbell, and oligonucleotide DNA nearest-neighbor thermodynamics," Proc. Natl. Acad. Sci. USA 95:1460-1465.
Sartorelli et al. (2020) "Enhancer RNAs are an important regulatory layer of the epigenome," Nature Structural & Molecular Biology 27:521-528.
Scherer et al. (2006) "The finished DNA sequence of human chromosome 12," Nature 440(7082):346-351.
Schroeder et al. (2009) "Lipid-based nanotherapeutics for siRNA delivery," Journal of Internal Medicine 267:9-21.
Scorletti et al. (2015) "Treating liver fat and serum triglyceride levels in NAFLD, effects of PNPLA3 and TM6SF2 genotypes: results from the WELCOME trial," Journal of hepatology 63(6):1476-1483.
Seetin et al. (2012) "RNA Structure Prediction: An Overview of Methods," Methods in Molecular Biology 905:99-122.
Seth et al. (2010) "Synthesis and Biophysical Evaluation of 2',4'-Constrained 2'O-Methoxyethyl and 2',4'-Constrained 2'O-Ethyl Nucleic Acid Analogues," J. Org. Chem. 75:1569-1581.C.
Seth et al. (2011) "Pathogens of alcohol induced liver disease: Classical concepts and recent advances," Journal of Gastroenterology and hepatology 26(7):1089-1105.
Sharma et al. (2018) "Novel Cluster and Monomer-Based GalNAc Structures Induce Effective Uptake of siRNAs in Vitro and in Vivo," Bioconjugate Chem. 29:2478-2488.
Siegwart et al. (2011) "Combinatorial synthesis of chemically diverse core-shell nanoparticles for intracellular delivery," PNAS 108(32):12996-13001.
Sigova et al. (2015) "Transcription factor trapping by RNA in gene regulatory elements," Science 350(6263):978-981.
Smith et al. (Sep. 23, 2021) "Oligonucleotide Mediated Upregulation of Serping1 By Targeting Regulatory RNAs" [Conference presentation]. The 17th Annual Meeting of the Oligonucleotide Therapeutics Society, Virtual Meeting, 1 page.
Smith et al. (Oct. 2-5, 2022) "Upregulation of SerpinG1 for treatment of hereditary angioedema using RNA actuators" [Poster presentation]. The 18th Annual Meeting of the Oligonucleotide Therapeutics Society, Phoenix, AZ, U.S.A., 1 page.
Sorensen et al. (2003) "Gene Silencing by Systemic Delivery of Synthetic siRNAs in Adult Mice," J. Mol. Biol. 327:761-766.
Stewart et al. (1980) "Short Term Regulation of Ureagenesis," The Journal of Biological Chemistry 255(11):5270-5280.
Straubinger et al. (1983) "Liposomes as Carriers for Intrcellular Delivery of Nucleic Acids," Methods in Enzymology 101:512:527.
Strauss et al. (1992) "Molecular complementation of a collagen mutation in mammalian cells using yeast artificial chromosomes," The EMBO Journal 11(2):417-422.
Sugimoto et al. (1995) "Thermodynamic Parameters to Predict Stability of RNA/DNA Hybrid Duplexes," Biochemistry 34:11211-11216.
Suter et al. (2011) "Mammalian Genes Are Transcribed with Widely Different Bursting Kinetics," Science 332(6028):472-474.
Szoka et al. (1978) "Procedure for preparation of liposomes with large internal aqueous space and high capture by reverse-phase evaporation," Pro. Natl. Acad. Sci. USA 75(9):4194-4198.
Takiguchi et al. (1995) "Transcriptional regulation of genes for ornithine cycle enzymes," Biochem. J. 312:649-659.

(56) References Cited

OTHER PUBLICATIONS

Tian et al. (2010) "Variant in PNPLA3 is associated with alcoholic liver disease," Nature Genetics 42:21-23.
Tomalia et al. (2007) "Dendrimers as multi-purpose nanodevices for oncology drug delivery and diagnostic imaging," Biochemical Society Transactions 35:61-67.
Trépo et al. (2016) "PNPLA2 gene in liver diseases," J Hepatol. 65(2):399-412.
Uhlmann et al. (2000) "Recent advances in the medicinal chemistry of antisense oligonucleotides," Current Opinion in Drug Discovery & Development 3(2):203-213.
Unzu et al. (2010) "Porphobilinogen deaminase over-expression in hepatocytes, but not in erythrocytes, prevents accumulation of toxic porphyrin precursors in a mouse model of acute intermittent porphyria," *Journal of hepatology* 52(3):417-424.
Verma et al. (2003) "Small Interfering RNAs Directed against b-Catenin Inhibit the in Vitro and in Vivo Growth of Colon Cancer Cells," Clinical Cancer Research 9:1291-1300.
Wakiya et al. (2012) "Impact of enzyme activity assay on indication in liver transplantation for ornithine transcarbamylase deficiency," Mol. Gen. Med. 105: 404-7.
Wan et al. (2016) "The Medicinal Chemistry of Therapeutic Oligonucleotides," J. Med. Chem. 59:9645-9667.
Wang et al. (1987) "pH-sensitive immunoliposomes mediate target-cell-specific delivery and controlled expression of a foreign gene in mouse," Proc. Natl. Acad. Sci. USA 84:7851-7855.
Wang et al. (1987) "Plasmid DNA Adsorbed to pH-Sensitive Liposomes Efficiently Transforms the Target Cells," Biochemical and Biophysical Research Communications 147(3):980-985.
Wang et al. (2016) "Long noncoding RNA CPS1-IT1 suppresses the metastasis of hepatocellular carcinoma by regulating HIF-1a activity and inhibiting epithelial-mesenchymal transition," Oncotarget 7(28): 43588-43603.
Wang et al. (2018) "Fenofibrate exerts protective effects in diabetic retinopathy via inhibition of the ANGPTL3 pathway," *Investigative ophthalmology & visual science* 59(10):4210-4217.
Wei et al. (2000) "IL-4 and IL-13 upregulate arginase I expression by cAMP and JAK/STAT6 pathways in vascular smooth muscle cells," American Journal of Physiology-Cell Physiology 279(1):C248-C256.
Weiner et al. (1994) "Liposomes: A Novel Topical Delivery System for Pharmaceutical and Cosmetic Applications," Journal of Drug Targeting 2:405-410.
Willoughby et al. (2018) "Evaluation of GalNAc-siRNA Conjugate Activity in Pre-clinical Animal Models with Reduced Asialoglycoprotein Receptor Expression," Molecular Therapy 26(1):105-114 (12 pages).
Wong et al. (2012) "Hedgehog signaling is required for differentiation of endocardial progenitors in zebrafish," *Developmental biology* 361(2):377-391.
Wu et al. (1993) "Increased Microvascular Permeability Contributes to Preferential Accumulation of Stealth1 Liposomes in Tiimor Tissue2," Cancer Research 53:3765-3770.
Yilmaz et al. (2009) "Serum concentrations of human angiopoietin-like protein 3 in patients with nonalcoholic fatty liver disease: association with insulin resistance," Eur J Gastroenterol Hepatol 21:1247-1251.
Yiu et al., "Glucose-6-phosphate transporter gene therapy corrects metabolic and myeloid abnormalities in glycogen storage disease type Ib mice." *Gene therapy* 14, No. 3 (2007): 219-226.
Yoo et al. (1999) "PAMAM Dendrimers as Delivery Agents for Antisense Oligonucleotides," Pharmaceutical Research 16(12):1799-1804.
Yu et al. (2022) "Deliver the promise: RNAs as a new class of molecular entities for therapy and vaccination," Pharmacology & Therapeutics 230:107967, 19 pages.
Yun et al. (2011) "EC144, a synthetic inhibitor of heat shock protein 90, blocks innate and adaptive immune responses in models of inflammation and autoimmunity," *The Journal of Immunology* 186(1):563-575.
Zhang et al. (2008) "Model-based Analysis of ChIP-Seq (MACS)," Genome biology 9(9):1-9.
Zhang et al. (2010) "Synthesis of Glycerol Nucleic Acid (GNA) Phosphoramidite Monomers and Oligonucleotide Polymers," Current Protocols in Nucleic Acid Chemistry 4.40.1-4.40.18 (18 pages).
Zhao et al. (2021) "Review of machine learningmethods for RNA secondary structure prediction," PLOS Computational Biology 1-22.
Zhou et al. (1991) "Lipophilic polylysines mediate efficient DNA transfection in mammalian cells," Biochimica et Biophysica Acta 1065:8-14.
Zhou et al. (1992) "Targeted delivery of DNA by liposomes and polymers," Journal of Controlled Release 19:269-274.
Zhou et al. (2009) "Fine Tuning of Electrostatics around the Internucleotidic Phosphate through Incorporation of Modified 2',4'-Carbocyclic-LNAs and -ENAs Leads to Significant Modulation of Antisense Properties," J. Org. Chem. 74:118-134.
Zimmermann et al. (2006) "RNAi-mediated gene silencing in non-human primates," Nature 441:111-114.
PCT/US2022/082295—International Preliminary Report on Patentability, Jun. 20, 2024, 7 pages.

| Oligo | Sequence | | | | | | | | | | | | | | | | | | | SEQ ID NO |
|---|---|---|---|---|---|---|---|---|---|---|---|---|---|---|---|---|---|---|---|---|
| hCPS1-ASO-1a | | | | T | G | C* | A | G | G | C | A | C | A | C | A | T | C* | A | G | G | C* | | 16 |
| hCPS1-ASO-1g | | | | T | G | C* | A | G | G | C | A | C | A | C | A | T | C* | A | G | G | C* | | 22 |
| hCPS1-ASO-2 | | | A | A | T | G | C* | A | G | G | C | A | C | A | C | A | T | C* | A | G | G | C* | T | 23 |
| hCPS1-ASO-3 | | | A | A | T | G | C* | A | G | G | C | A | C | A | C | A | T | C* | A | G | G | C* | T | 24 |
| hCPS1-ASO-5a | | | A | A | T | G | C* | A | G | G | C | A | C | A | C | A | T | C* | A | G | | | | 26 |
| hCPS1-ASO-6a | T | G | A | A | T | G | | | | C | A | G | G | C | A | C | A | C* | A | T | C* | | | 27 |

Legend: ▒ MOE | PO ■ LNA *C: 5-Methyl C

| Oligo | Sequence | | | | | | | | | | | | | | | | | | | | | SEQ ID NO |
|---|---|---|---|---|---|---|---|---|---|---|---|---|---|---|---|---|---|---|---|---|---|---|
| hCPS1-ASO-1a | | | | T | G | C* | A | G | C | A | C | A | C | A | T | C* | A | G | G | C* | | 16 |
| hCPS1-ASO-1b | | | | T | G | C* | A | G | C | A | C | A | C | A | T | C* | A | G | G | C* | | 17 |
| hCPS1-ASO-1c | | | | T | G | C* | A | G | C | A | C | A | C* | A | T | C* | A | G | G | C* | | 18 |
| hCPS1-ASO-1d | | | | T | G | C* | A | G | C | A | C | A | C | A | T | C* | A | G | G | C* | | 19 |
| hCPS1-ASO-1e | | | | T | G | C* | A | G | C | A/C | A | C | A | A | T | C* | A | G | G | C* | | 20 |
| hCPS1-ASO-1f | | | | T | G | C* | A | G | C | A | C* | A | C | A | T | C* | A | G | G | C* | | 21 |
| hCPS1-ASO-1g | | | | T | G | C* | A | G | C | A | C | A | C* | A | T | C* | A | G | G | C* | | 22 |
| hCPS1-ASO-2 | | A | A | T | G | C* | A | G | C | A | C | A | C | A | T | C* | A | G | G | C* | T | 23 |
| hCPS1-ASO-3 | | A | A | T | G | C* | A | G | C | A | C | A | C | A | T | C* | A | G | G | C* | T | 24 |
| hCPS1-ASO-4a | | A | A | T | G | C* | A | G | C | A | C | A | C* | A | T | C | A | G | G | C | T | G | 25 |
| hCPS1-ASO-5a | | A | A | T | G | C* | A | G | C | A | C* | A | C | A | T | C* | A | G | G | | | 26 |
| hCPS1-ASO-6a | T | G | A | A | T | G | C* | A | G | C | A | C | A | T | C* | A | | | | | | 27 |
| hCPS1-ASO-4b | | A | A | T | G | C* | A | G | C | A | C | A | C* | A | T | C* | A | G | G | | G | | 28 |
| hCPS1-ASO-5b | | A | A | T | G | C* | A | G | C | A | C* | A | C | A | T | C* | A | G | | | | 29 |
| hCPS1-ASO-6b | T | G | A | A | T | G | C* | A | G | C | A | C | A | T | C* | A | | | | | | 30 |
| hCPS1-ASO-7a | | G | G | C | C | T | G | T | A | C | T | T | G | G | A | | | | | | | 31 |
| hCPS1-ASO-8a | | G | C* | A | G | A | C | A | G | G | C | A | T | G | A | | | | | | | 32 |
| hCPS1-ASO-9a | | T | G | A | T | T | G | C | T | T | G | A | A | T | G | | | | | | | 33 |
| hCPS1-ASO-10a | | G | T | C* | A | T | G | A | C | C | C | A | A | T | A | | | | | | | 34 |
| hCPS1-ASO-11a | | T | A | G | A | C | A | G | A | A | C | C | T | A | G | | | | | | | 35 |
| hCPS1-ASO-12a | | A | C | T | G | A | C | A | G | G | T | C* | A | C* | A | | | | | | | 36 |
| hCPS1-ASO-13a | | T | T | T | A | C | A | A | C | T | C | T | C* | T | T | | | | | | | 37 |
| hCPS1-ASO-14a | | C* | T | A | A | C | G | T | C* | C | G | G | T | G | A | | | | | | | 38 |
| hCPS1-ASO-15a | | T | C* | T | G | C* | A | C | T | A | G | C* | A | T | C* | | | | | | | 39 |
| hCPS1-ASO-9b | T | G | C* | A | T | G | A | A | G | T | C* | A | T | C* | A | G | | | | | | 40 |

FIG. 5A

| | | | | | | | | | | | | | | | | | | | | | |
|---|---|---|---|---|---|---|---|---|---|---|---|---|---|---|---|---|---|---|---|---|---|
| hCPS1-ASO-10b | G* | T | C* | A | A | T | G | C* | T | C* | A | A | A | T | A | G | T | | | | 41 |
| hCPS1-ASO-11b | T | A | G | C* | A | T | A | A | C* | A | C* | A | C* | A | C* | A | C* | | | | 42 |
| hCPS1-ASO-12b | G | T | C* | A | A | G | C* | T | A | G | T | T | G | T | A | T | T | | | | 43 |
| hCPS1-ASO-13b | T | T | A | G | C* | T | G | A | T | G | A | A | T | C* | C* | T | C* | A | | | 44 |
| hCPS1-ASO-14b | C* | C* | T | A | T | G | T | C* | T | G | A | C* | T | G | A | T | C* | A | | | 45 |
| hCPS1-ASO-15b | T | C* | T | T | G | T | C* | T | G | A | G | T | C* | A | T | G | A | T | C* | | 46 |
| hCPS1-ASO-7b | G | G | G | A | G | A | G | T | T | G | T | C* | T | T | G | G | A | A | | | 47 |
| hCPS1-ASO-8b | G | C* | A | G | T | A | G | G | A | C* | A | G | G | A | T | G | A | A | T | | 48 |

FIG. 5A (Cont.)

| Oligo | Sequence | | | | | | | | | | | | | | | | | | | SEQ ID NO |
|---|---|---|---|---|---|---|---|---|---|---|---|---|---|---|---|---|---|---|---|---|
| mCPS1-ASO-1 | T | G | G | A | C* | A | T | C | A | G | C | T | T | G | G | A | G | A | 51 |
| mCPS1-ASO-2 | C* | A | T | A | A | T | G | T | C | G | A | C | A | T | T | T | G | G | 52 |
| mCPS1-ASO-3 | G | T | A | T | G | A | C | A | C | T | G | C | T | T | G | A | T | A | 53 |
| mCPS1-ASO-4 | G | G | G | G | G | A | A | A | T | T | G | C | G | T | G | A | A | 54 |
| mCPS1-ASO-5 | G | C* | C* | C* | T | A | A | T | T | G | G | T | T | C* | T | T | A | C* | 55 |
| mCPS1-ASO-6 | T | A | T | A | T | A | T | T | G | T | A | T | A | C* | A | T | C* | 56 |
| mCPS1-ASO-7 | G | G | G | C* | A | A | A | G | T | A | G | C* | A | G | A | G | A | C* | 57 |
| mCPS1-ASO-8 | T | C* | T | T | T | A | A | C | T | G | T | A | C* | T | G | T | A | C* | 58 |
| mCPS1-ASO-9 | A | C* | C* | C* | C | G | G | T | C | G | G | G | C* | C* | A | C* | A | G | 59 |
| mCPS1-ASO-10 | G | G | G | A | A | A | G | A | A | G | C* | C* | G | C* | A | A | C* | 60 |
| mCPS1-ASO-11 | G | T | T | C* | T | T | A | T | T | G | A | T | G | T | T | A | G | C* | 61 |
| mCPS1-ASO-12 | C* | C* | C* | A | C | C | C | A | G | A | C* | C* | T | T | A | A | G | 62 |
| mCPS1-ASO-13 | T | T | T | C* | T | T | C | C | A | T | T | G | T | T | C* | A | A | C* | 63 |
| mCPS1-ASO-14 | A | A | C* | A | A | C | C | C | T | G | C | T | G | C* | G | G | T | 64 |
| mCPS1-ASO-15 | C* | G | A | T | C | A | C | A | T | C | A | T | T | T | T | T | G | T | 65 |
| mCPS1-ASO-16 | T | T | T | G | A | C | C | C | C | C | G | O | T | A | C* | C* | C* | 66 |
| mCPS1-ASO-17 | G | T | T | A | A | G | T | C | A | T | G | C | A | T | G | C* | T | C* | 67 |
| mCPS1-ASO-18 | G | G | T | G | T | C | T | T | C | A | G | C | T | A | C | A | T | 68 |

FIG. 5B

| First tier | C57BL6 | | | OTCD | | |
|---|---|---|---|---|---|---|
| | 1.25uM | 2.5uM | 5uM | 1.25uM | 2.5uM | 5uM |
| | FC | FC | FC | FC | FC | FC |
| mCPS1-ASO-2 | 2.12 | 3.33 | 4.30 | 1.58 | 1.77 | 2.03 |
| mCPS1-ASO-3 | 0.99 | 1.66 | 2.68 | 1.12 | 1.44 | 1.80 |
| mCPS1-ASO-4 | 1.49 | 2.60 | 4.47 | 1.32 | 1.91 | 2.54 |
| mCPS1-ASO-7 | 2.77 | 3.62 | 4.13 | 2.02 | 2.33 | 2.14 |
| mCPS1-ASO-12 | 0.91 | 1.45 | 2.26 | 1.37 | 1.26 | 1.76 |
| mCPS1-ASO-9 | 1.13 | 1.37 | 2.21 | 1.32 | 1.45 | 1.67 |
| mCPS1-ASO-10 | 1.45 | 1.83 | 3.14 | 1.17 | 1.32 | 1.84 |

FIG. 6B

| Second tier | C57BL6 | | | OTCD | | |
|---|---|---|---|---|---|---|
| | 1.25uM | 2.5uM | 5uM | 1.25uM | 2.5uM | 5uM |
| | FC | FC | FC | FC | FC | FC |
| mCPS1-ASO-1 | 2.16 | 2.46 | 2.29 | 1.16 | 1.70 | 1.37 |
| mCPS1-ASO-5 | 0.95 | 1.24 | 1.73 | 0.89 | 1.00 | 1.48 |
| mCPS1-ASO-6 | 0.82 | 1.26 | 1.94 | 0.97 | 1.08 | 1.62 |
| mCPS1-ASO-11 | 1.19 | 1.15 | 1.82 | 1.07 | 1.03 | 1.44 |
| mCPS1-ASO-8 | 1.18 | 1.31 | 1.98 | 1.32 | 1.40 | 1.94 |
| mCPS1-ASO-14 | 0.82 | 1.11 | 2.04 | 1.07 | 1.37 | 2.20 |
| mCPS1-ASO-18 | 0.69 | 1.22 | 1.81 | 1.20 | 1.30 | 1.65 |
| mCPS1-ASO-15 | 0.85 | 1.03 | 1.73 | 0.91 | 0.97 | 1.32 |

FIG. 6C

| First tier | CS7BL6 | | | OTCD | | |
|---|---|---|---|---|---|---|
| | 1.25uM | 2.5uM | 5uM | 1.25uM | 2.5uM | 5uM |
| | FC | FC | FC | FC | FC | FC |
| mCPS1-ASO-2 | 0.92 | 1.09 | 1.64 | 2.06 | 2.27 | 2.00 |
| mCPS1-ASO-3 | 0.83 | 0.83 | 1.29 | 1.42 | 1.33 | 2.17 |
| mCPS1-ASO-4 | 0.79 | 1.21 | 1.62 | 0.93 | 1.17 | 2.80 |
| mCPS1-ASO-7 | 1.04 | 1.07 | 1.67 | 1.27 | 2.23 | 1.62 |
| mCPS1-ASO-12 | 0.52 | 0.72 | 1.07 | 0.86 | 1.08 | 2.08 |
| mCPS1-ASO-9 | 0.73 | 0.69 | 0.90 | 1.20 | 1.43 | 1.63 |
| mCPS1-ASO-10 | 0.85 | 0.77 | 1.32 | 0.88 | 0.98 | 2.00 |

FIG. 7B

| Second tier | CS7BL6 | | | OTCD | | |
|---|---|---|---|---|---|---|
| | 1.25uM | 2.5uM | 5uM | 1.25uM | 2.5uM | 5uM |
| | FC | FC | FC | FC | FC | FC |
| mCPS1-ASO-1 | 0.92 | 1.27 | 1.79 | 1.09 | 2.04 | 1.44 |
| mCPS1-ASO-5 | 0.98 | 1.04 | 1.30 | 0.50 | 1.15 | 1.54 |
| mCPS1-ASO-6 | 0.62 | 0.78 | 0.93 | 0.87 | 1.31 | 2.73 |
| mCPS1-ASO-11 | 1.26 | 0.95 | 1.03 | 1.05 | 1.04 | 1.10 |
| mCPS1-ASO-8 | 0.72 | 0.76 | 1.05 | 1.18 | 2.31 | 2.81 |
| mCPS1-ASO-14 | 0.63 | 0.63 | 0.91 | 1.03 | 1.22 | 2.24 |
| mCPS1-ASO-18 | 0.60 | 0.69 | 0.99 | 1.39 | 1.69 | 2.14 |
| mCPS1-ASO-15 | 0.69 | 0.64 | 0.89 | 0.84 | 0.77 | 1.09 |

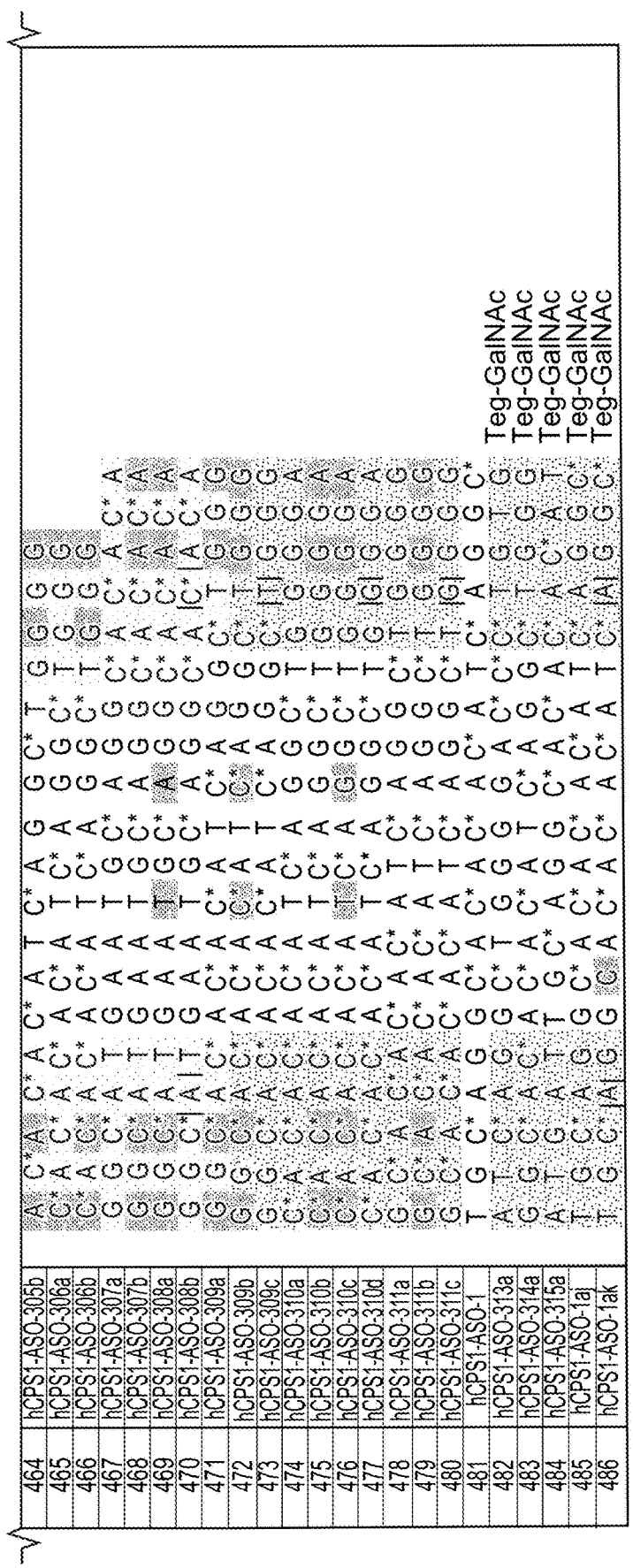
FIG. 14 (Cont. 2)

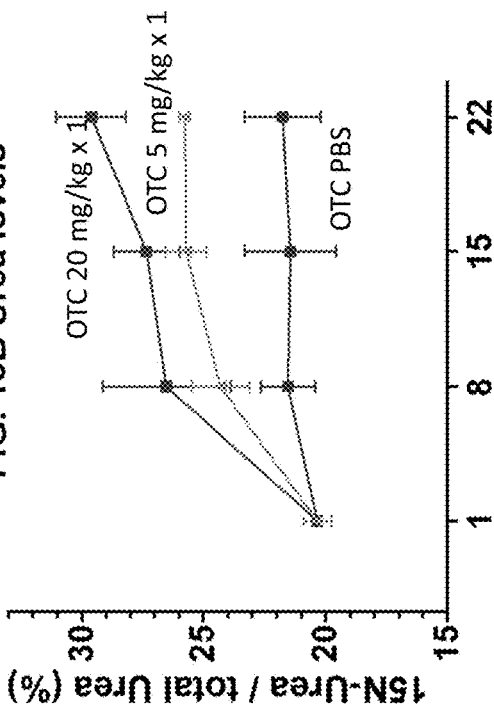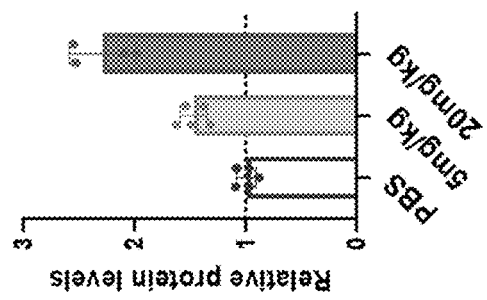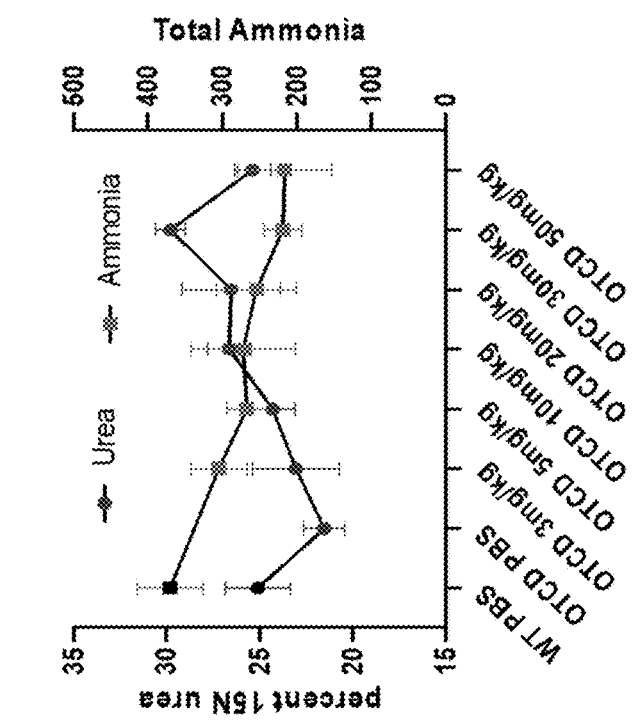

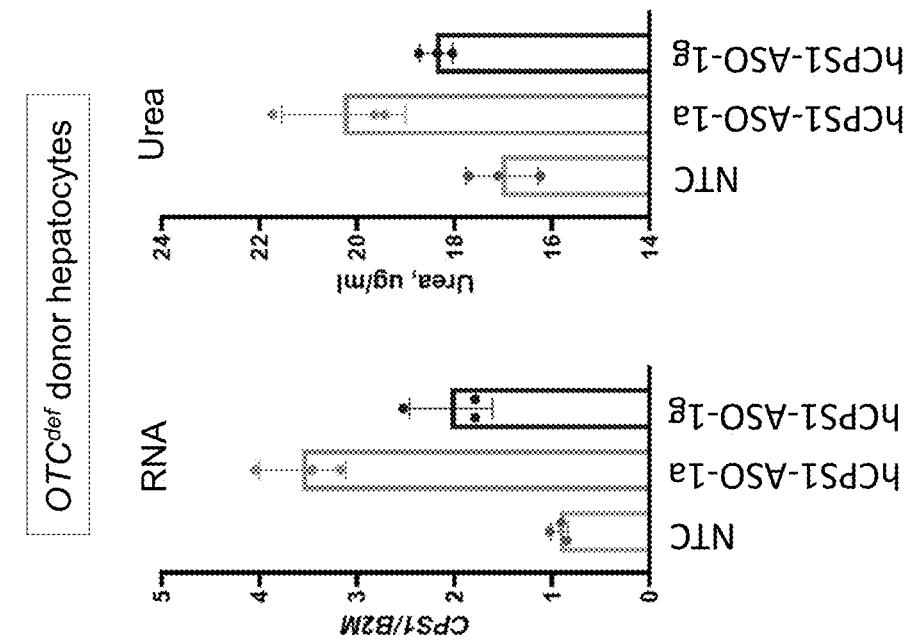
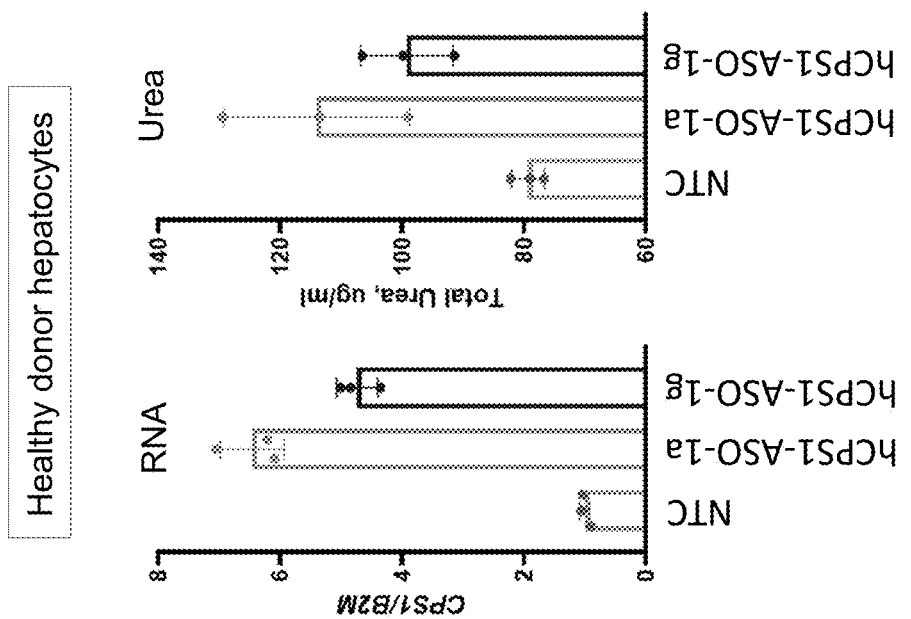
FIG. 16

SEQUENCE LISTING

```
Sequence total quantity: 662
SEQ ID NO: 1           moltype = RNA   length = 20
FEATURE                Location/Qualifiers
source                 1..20
                       mol_type = other RNA
                       organism = synthetic construct
SEQUENCE: 1
tgcaggcaca cacatcaggc                                              20

SEQ ID NO: 2           moltype = RNA   length = 22
FEATURE                Location/Qualifiers
source                 1..22
                       mol_type = other RNA
                       organism = synthetic construct
SEQUENCE: 2
atgcaggcac acacatcagg ct                                           22

SEQ ID NO: 3           moltype = RNA   length = 24
```

```
FEATURE                     Location/Qualifiers
source                      1..24
                            mol_type = other RNA
                            organism = synthetic construct
SEQUENCE: 3
aatgcaggca cacacatcag gctg                                              24

SEQ ID NO: 4                moltype = RNA   length = 20
FEATURE                     Location/Qualifiers
source                      1..20
                            mol_type = other RNA
                            organism = synthetic construct
SEQUENCE: 4
gcacacacat caggctgggg                                                   20

SEQ ID NO: 5                moltype = RNA   length = 20
FEATURE                     Location/Qualifiers
source                      1..20
                            mol_type = other RNA
                            organism = synthetic construct
SEQUENCE: 5
aatgcaggca cacacatcag                                                   20

SEQ ID NO: 6                moltype = RNA   length = 20
FEATURE                     Location/Qualifiers
source                      1..20
                            mol_type = other RNA
                            organism = synthetic construct
SEQUENCE: 6
tgaatgcagg cacacacatc                                                   20

SEQ ID NO: 7                moltype = RNA   length = 20
FEATURE                     Location/Qualifiers
source                      1..20
                            mol_type = other RNA
                            organism = synthetic construct
SEQUENCE: 7
gggaccctgt gtacttggaa                                                   20

SEQ ID NO: 8                moltype = RNA   length = 20
FEATURE                     Location/Qualifiers
source                      1..20
                            mol_type = other RNA
                            organism = synthetic construct
SEQUENCE: 8
gcagagtgac aggcatgaat                                                   20

SEQ ID NO: 9                moltype = RNA   length = 20
FEATURE                     Location/Qualifiers
source                      1..20
                            mol_type = other RNA
                            organism = synthetic construct
SEQUENCE: 9
tgccattgac ttgcataatg                                                   20

SEQ ID NO: 10               moltype = RNA   length = 20
FEATURE                     Location/Qualifiers
source                      1..20
                            mol_type = other RNA
                            organism = synthetic construct
SEQUENCE: 10
gtcaatgctc agaacatagt                                                   20

SEQ ID NO: 11               moltype = RNA   length = 20
FEATURE                     Location/Qualifiers
source                      1..20
                            mol_type = other RNA
                            organism = synthetic construct
SEQUENCE: 11
tagataataa cccaccacac                                                   20

SEQ ID NO: 12               moltype = RNA   length = 20
FEATURE                     Location/Qualifiers
source                      1..20
                            mol_type = other RNA
                            organism = synthetic construct
SEQUENCE: 12
gtcaagtact aggtttgtatt                                                  20
```

```
SEQ ID NO: 13              moltype = RNA  length = 20
FEATURE                    Location/Qualifiers
source                     1..20
                           mol_type = other RNA
                           organism = synthetic construct
SEQUENCE: 13
ttagcctgtg aaatccctca                                                    20

SEQ ID NO: 14              moltype = RNA  length = 20
FEATURE                    Location/Qualifiers
source                     1..20
                           mol_type = other RNA
                           organism = synthetic construct
SEQUENCE: 14
cttatgagtc actctctgat                                                    20

SEQ ID NO: 15              moltype = RNA  length = 20
FEATURE                    Location/Qualifiers
source                     1..20
                           mol_type = other RNA
                           organism = synthetic construct
SEQUENCE: 15
tctttgtgag ccaggtcatc                                                    20

SEQ ID NO: 16              moltype = DNA  length = 20
FEATURE                    Location/Qualifiers
source                     1..20
                           mol_type = other DNA
                           organism = synthetic construct
modified_base              order(1..5,16..20)
                           mod_base = OTHER
                           note = 2-prime-O-(2-Methoxyethyl) nucleotide
modified_base              order(3,16,20)
                           mod_base = OTHER
                           note = 5-methyl on the cytidine
misc_feature               6..15
                           note = DNA
misc_feature               order(1..5,16..20)
                           note = RNA
SEQUENCE: 16
tgcaggcaca cacatcaggc                                                    20

SEQ ID NO: 17              moltype = DNA  length = 20
FEATURE                    Location/Qualifiers
source                     1..20
                           mol_type = other DNA
                           organism = synthetic construct
modified_base              1..20
                           mod_base = OTHER
                           note = 2-prime-O-(2-Methoxyethyl) nucleotide
modified_base              order(3,7,9,11,13,16,20)
                           mod_base = OTHER
                           note = 5-methyl on the cytidine
SEQUENCE: 17
tgcaggcaca cacatcaggc                                                    20

SEQ ID NO: 18              moltype = DNA  length = 20
FEATURE                    Location/Qualifiers
source                     1..20
                           mol_type = other DNA
                           organism = synthetic construct
modified_base              order(1..5,9,12,16..20)
                           mod_base = OTHER
                           note = 2-prime-O-(2-Methoxyethyl) nucleotide
modified_base              order(3,9,16,20)
                           mod_base = OTHER
                           note = 5-methyl on the cytidine
misc_feature               order(6..8,10,11,13..15)
                           note = DNA
misc_feature               order(1..5,9,12,16..20)
                           note = RNA
SEQUENCE: 18
tgcaggcaca cacatcaggc                                                    20

SEQ ID NO: 19              moltype = DNA  length = 20
FEATURE                    Location/Qualifiers
source                     1..20
                           mol_type = other DNA
                           organism = synthetic construct
```

```
modified_base          order(1..5,16..20)
                       mod_base = OTHER
                       note = 2-prime-O-(2-Methoxyethyl) nucleotide
modified_base          order(3,9,16,20)
                       mod_base = OTHER
                       note = 5-methyl on the cytidine
modified_base          order(6,9,12,15)
                       mod_base = OTHER
                       note = Locked nucleic acid
misc_feature           order(1..5,9,12,1..20)
                       note = RNA
misc_feature           order(7,8,10,11,13,14)
                       note = DNA
SEQUENCE: 19
tgcaggcaca cacatcaggc                                          20

SEQ ID NO: 20          moltype = DNA   length = 20
FEATURE                Location/Qualifiers
source                 1..20
                       mol_type = other DNA
                       organism = synthetic construct
modified_base          order(1..5,17..20)
                       mod_base = OTHER
                       note = 2-prime-O-(2-Methoxyethyl) nucleotide
modified_base          order(3,16,20)
                       mod_base = OTHER
                       note = 5-methyl on the cytidine
modified_base          order(8,12,16)
                       mod_base = OTHER
                       note = Locked nucleic acid
misc_feature           order(6,7,9..11,13..15)
                       note = DNA
misc_feature           order(1..5,8,12,16..20)
                       note = RNA
SEQUENCE: 20
tgcaggcaca cacatcaggc                                          20

SEQ ID NO: 21          moltype = DNA   length = 20
FEATURE                Location/Qualifiers
source                 1..20
                       mol_type = other DNA
                       organism = synthetic construct
modified_base          order(1..5,16,18..20)
                       mod_base = OTHER
                       note = 2-prime-O-(2-Methoxyethyl) nucleotide
modified_base          order(3,9,13,16,20)
                       mod_base = OTHER
                       note = 5-methyl on the cytidine
modified_base          order(9,13,17)
                       mod_base = OTHER
                       note = Locked nucleic acid
misc_feature           order(1..5,16,18..20)
                       note = RNA
misc_feature           order(6..8,10..12,14,15)
                       note = DNA
SEQUENCE: 21
tgcaggcaca cacatcaggc                                          20

SEQ ID NO: 22          moltype = DNA   length = 20
FEATURE                Location/Qualifiers
source                 1..20
                       mol_type = other DNA
                       organism = synthetic construct
modified_base          order(1..5,16,18..20)
                       mod_base = OTHER
                       note = 2-prime-O-(2-Methoxyethyl) nucleotide
modified_base          order(3,16,20)
                       mod_base = OTHER
                       note = 5-methyl on the cytidine
modified_base          order(3^4,4^5)
                       mod_base = OTHER
                       note = Phosphodiester linkage
modified_base          order(16^17,17^18)
                       mod_base = OTHER
                       note = Phosphodiester linkage
misc_feature           order(1..5,16..20)
                       note = RNA
misc_feature           6..15
                       note = DNA
```

```
SEQUENCE: 22
tgcaggcaca cacatcaggc                                              20

SEQ ID NO: 23           moltype = DNA  length = 22
FEATURE                 Location/Qualifiers
source                  1..22
                        mol_type = other DNA
                        organism = synthetic construct
modified_base           order(1..6,17..22)
                        mod_base = OTHER
                        note = 2-prime-O-(2-Methoxyethyl) nucleotide
modified_base           order(4,17,21)
                        mod_base = OTHER
                        note = 5-methyl on the cytidine
misc_feature            order(1..6,17..22)
                        note = RNA
misc_feature            7..16
                        note = DNA
SEQUENCE: 23
atgcaggcac acacatcagg ct                                           22

SEQ ID NO: 24           moltype = DNA  length = 24
FEATURE                 Location/Qualifiers
source                  1..24
                        mol_type = other DNA
                        organism = synthetic construct
modified_base           order(1..7,18..24)
                        mod_base = OTHER
                        note = 2-prime-O-(2-Methoxyethyl) nucleotide
modified_base           order(5,18,22)
                        mod_base = OTHER
                        note = 5-methyl on the cytidine
misc_feature            order(1..7,18..24)
                        note = RNA
misc_feature            8..17
                        note = DNA
SEQUENCE: 24
aatgcaggca cacacatcag gctg                                         24

SEQ ID NO: 25           moltype = DNA  length = 20
FEATURE                 Location/Qualifiers
source                  1..20
                        mol_type = other DNA
                        organism = synthetic construct
modified_base           order(1..5,16,20)
                        mod_base = OTHER
                        note = 2-prime-O-(2-Methoxyethyl) nucleotide
modified_base           order(2,4)
                        mod_base = OTHER
                        note = 5-methyl on the cytidine
misc_feature            order(1..5,16..20)
                        note = RNA
misc_feature            6..15
                        note = DNA
SEQUENCE: 25
gcacacacat caggctgggg                                              20

SEQ ID NO: 26           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(5,18)
                        mod_base = OTHER
                        note = 5-methyl on the cytidine
misc_feature            order(1..5,16..20)
                        note = RNA
misc_feature            6..15
                        note = DNA
SEQUENCE: 26
aatgcaggca cacacatcag                                              20

SEQ ID NO: 27           moltype = DNA  length = 20
FEATURE                 Location/Qualifiers
```

```
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(17,20)
                        mod_base = OTHER
                        note = 5-methyl on the cytidine
misc_feature            order(1..5,16..20)
                        note = RNA
misc_feature            6..15
                        note = DNA
SEQUENCE: 27
tgaatgcagg cacacacatc                                                     20

SEQ ID NO: 28           moltype = DNA  length = 20
FEATURE                 Location/Qualifiers
source                  1..20
                        mol_type = other DNA
                        organism = synthetic construct
modified_base           1..20
                        mod_base = OTHER
                        note = 2-prime-O-(2-Methoxyethyl) nucleotide
modified_base           order(2,4,6,8,11,15)
                        mod_base = OTHER
                        note = 5-methyl on the cytidine
SEQUENCE: 28
gcacacacat caggctgggg                                                     20

SEQ ID NO: 29           moltype = DNA  length = 20
FEATURE                 Location/Qualifiers
source                  1..20
                        mol_type = other DNA
                        organism = synthetic construct
modified_base           1..20
                        mod_base = OTHER
                        note = 2-prime-O-(2-Methoxyethyl) nucleotide
modified_base           order(5,9,11,13,15,18)
                        mod_base = OTHER
                        note = 5-methyl on the cytidine
SEQUENCE: 29
aatgcaggca cacacatcag                                                     20

SEQ ID NO: 30           moltype = DNA  length = 20
FEATURE                 Location/Qualifiers
source                  1..20
                        mol_type = other DNA
                        organism = synthetic construct
modified_base           1..20
                        mod_base = OTHER
                        note = 2-prime-O-(2-Methoxyethyl) nucleotide
modified_base           order(7,11,13,15,17,20)
                        mod_base = OTHER
                        note = 5-methyl on the cytidine
SEQUENCE: 30
tgaatgcagg cacacacatc                                                     20

SEQ ID NO: 31           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           5
                        mod_base = OTHER
                        note = 5-methyl on the cytidine
misc_feature            order(1..5,16..20)
                        note = RNA
misc_feature            6..15
                        note = DNA
SEQUENCE: 31
gggaccctgt gtacttggaa                                                     20

SEQ ID NO: 32           moltype = DNA  length = 20
FEATURE                 Location/Qualifiers
```

```
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           2
                        mod_base = OTHER
                        note = 5-methyl on the cytidine
misc_feature            order(1..5,16..20)
                        note = RNA
misc_feature            6..15
                        note = DNA
SEQUENCE: 32
gcagagtgac aggcatgaat                                                    20

SEQ ID NO: 33           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           3..4
                        mod_base = OTHER
                        note = 5-methyl on the cytidine
misc_feature            order(1..5,16..20)
                        note = RNA
misc_feature            order(6,15)
                        note = DNA
SEQUENCE: 33
tgccattgac ttgcataatg                                                    20

SEQ ID NO: 34           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           3
                        mod_base = OTHER
                        note = 5-methyl on the cytidine
misc_feature            order(1..5,16..20)
                        note = RNA
misc_feature            6..15
                        note = DNA
SEQUENCE: 34
gtcaatgctc agaacatagt                                                    20

SEQ ID NO: 35           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(16,18,20)
                        mod_base = OTHER
                        note = 5-methyl on the cytidine
misc_feature            order(1..5,16..20)
                        note = RNA
misc_feature            6..15
                        note = DNA
SEQUENCE: 35
tagataataa cccaccacac                                                    20

SEQ ID NO: 36           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
```

```
modified_base           3
                        mod_base = OTHER
                        note = 5-methyl on the cytidine
misc_feature            order(1..5,16..20)
                        note = RNA
misc_feature            6..15
                        note = DNA
SEQUENCE: 36
gtcaagtact aggttgtatt                                                       20

SEQ ID NO: 37           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(5,16,17,19)
                        mod_base = OTHER
                        note = 5-methyl on the cytidine
misc_feature            order(1..5,16..20)
                        note = RNA
misc_feature            6..15
                        note = DNA
SEQUENCE: 37
ttagcctgtg aaatccctca                                                       20

SEQ ID NO: 38           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(1,16)
                        mod_base = OTHER
                        note = 5-methyl on the cytidine
misc_feature            order(1..5,16..20)
                        note = RNA
misc_feature            6..15
                        note = DNA
SEQUENCE: 38
cttatgagtc actctctgat                                                       20

SEQ ID NO: 39           moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(2,17,20)
                        mod_base = OTHER
                        note = 5-methyl on the cytidine
misc_feature            order(1..5,16..20)
                        note = RNA
misc_feature            6..15
                        note = DNA
SEQUENCE: 39
tctttgtgag ccaggtcatc                                                       20

SEQ ID NO: 40           moltype = DNA  length = 20
FEATURE                 Location/Qualifiers
source                  1..20
                        mol_type = other DNA
                        organism = synthetic construct
modified_base           1..20
                        mod_base = OTHER
                        note = 2-prime-O-(2-Methoxyethyl) nucleotide
modified_base           order(3,4,14)
                        mod_base = OTHER
                        note = 5-methyl on the cytidine
SEQUENCE: 40
tgccattgac ttgcataatg                                                       20

SEQ ID NO: 41           moltype = DNA  length = 20
```

```
FEATURE                     Location/Qualifiers
source                      1..20
                            mol_type = other DNA
                            organism = synthetic construct
modified_base               1..20
                            mod_base = OTHER
                            note = 2-prime-O-(2-Methoxyethyl) nucleotide
modified_base               order(3,8,10,15)
                            mod_base = OTHER
                            note = 5-methyl on the cytidine
SEQUENCE: 41
gtcaatgctc agaacatagt                                                      20

SEQ ID NO: 42               moltype = DNA   length = 20
FEATURE                     Location/Qualifiers
source                      1..20
                            mol_type = other DNA
                            organism = synthetic construct
modified_base               1..20
                            mod_base = OTHER
                            note = 2-prime-O-(2-Methoxyethyl) nucleotide
modified_base               order(11..13,15,16,18,20)
                            mod_base = OTHER
                            note = 5-methyl on the cytidine
SEQUENCE: 42
tagataataa cccaccacac                                                      20

SEQ ID NO: 43               moltype = DNA   length = 20
FEATURE                     Location/Qualifiers
source                      1..20
                            mol_type = other DNA
                            organism = synthetic construct
modified_base               1..20
                            mod_base = OTHER
                            note = 2-prime-O-(2-Methoxyethyl) nucleotide
modified_base               order(3,9)
                            mod_base = OTHER
                            note = 5-methyl on the cytidine
SEQUENCE: 43
gtcaagtact aggttgtatt                                                      20

SEQ ID NO: 44               moltype = DNA   length = 20
FEATURE                     Location/Qualifiers
source                      1..20
                            mol_type = other DNA
                            organism = synthetic construct
modified_base               order(5,6,15..17,19)
                            mod_base = OTHER
                            note = 5-methyl on the cytidine
modified_base               1..20
                            mod_base = OTHER
                            note = 2-prime-O-(2-Methoxyethyl) nucleotide
SEQUENCE: 44
ttagcctgtg aaatccctca                                                      20

SEQ ID NO: 45               moltype = DNA   length = 20
FEATURE                     Location/Qualifiers
source                      1..20
                            mol_type = other DNA
                            organism = synthetic construct
modified_base               1..20
                            mod_base = OTHER
                            note = 2-prime-O-(2-Methoxyethyl) nucleotide
modified_base               order(1,10,12,14,16)
                            mod_base = OTHER
                            note = 5-methyl on the cytidine
SEQUENCE: 45
cttatgagtc actctctgat                                                      20

SEQ ID NO: 46               moltype = DNA   length = 20
FEATURE                     Location/Qualifiers
source                      1..20
                            mol_type = other DNA
                            organism = synthetic construct
modified_base               1..20
                            mod_base = OTHER
                            note = 2-prime-O-(2-Methoxyethyl) nucleotide
```

```
modified_base         order(2,11,12,17,20)
                      mod_base = OTHER
                      note = 2-prime-O-(2-Methoxyethyl) nucleotide
SEQUENCE: 46
tctttgtgag ccaggtcatc                                              20

SEQ ID NO: 47         moltype = DNA   length = 20
FEATURE               Location/Qualifiers
source                1..20
                      mol_type = other DNA
                      organism = synthetic construct
modified_base         1..20
                      mod_base = OTHER
                      note = 2-prime-O-(2-Methoxyethyl) nucleotide
modified_base         order(5..7,14)
                      mod_base = OTHER
                      note = 5-methyl on the cytidine
SEQUENCE: 47
gggaccctgt gtacttggaa                                              20

SEQ ID NO: 48         moltype = DNA   length = 20
FEATURE               Location/Qualifiers
source                1..20
                      mol_type = other DNA
                      organism = synthetic construct
modified_base         1..20
                      mod_base = OTHER
                      note = 2-prime-O-(2-Methoxyethyl) nucleotide
modified_base         order(2,10,14)
                      mod_base = OTHER
                      note = 5-methyl on the cytidine
SEQUENCE: 48
gcagagtgac aggcatgaat                                              20

SEQ ID NO: 49         moltype = RNA   length = 2000
FEATURE               Location/Qualifiers
source                1..2000
                      mol_type = other RNA
                      organism = synthetic construct
SEQUENCE: 49
gcctgatgtg tgtgcctgca ttcatgcctg tcactctgct cagctgcgtg cagacagctt    60
atatgaagga ggactgtgta catgtggtca gagaagaaaa aaatgcttat tttttaaaat   120
gttttgaaaa ataatctgtc ctaaaagtgt aacatttcca ctaaattttt tcatgtctga   180
ctttaacatt ccctaccaac caactcttat agcctcaact cctttgatct atcctaatgt   240
aaactcccta ctaatgtgt aatatatttt tttccagttt ggttatagat ttcagtctag   300
cctgaacact caagtatgaa actagccact atttttatta ttggctgttc caacctccat   360
tgtggaatta taattgatgg attttccaag tctctaattc agaatattta atcaaatttt   420
ccaaaatttc tgccttctcc tccttcattc tgatgactaa agacatggac cataaaatat   480
atatacatat atacatacat atgtatatgt atgtatatac acatatatat atgtatgtat   540
atatacatac atatatatat gtatatatac acacacatat acatatgtat gtatatatac   600
acacacacat atatatatgt atgtatatat atacacatat atatat gtatgtatat   660
atatacacac acatatatat atgtatgtat atatatacac acacacaccg tagtttgcaa   720
gtctgcatct gggacccttt actgataaaa atgaaagccc attaaaactc tcatgccac   780
attcctctct agactttaga gtaggagaat tctatcctag aattgttgat tgttgacatt   840
tctatggaaa aacatgttta attcatcatg cttttgtagtc aactgctata aatggtgatg   900
aagtcttttc cttggtcaag ctctggactc tcagtactt ccactgctcat atttgattaa   960
aacataagtg atgaagggag gaaatatatt atagtattca ttgcatgggt accttagggt  1020
aatgggacta tgactgattt aaatttattt tgcatcctaa aaagttcca ttagtgggtg  1080
cagcacacca gcatggcaca tgtatacata tgtaactaac ctgcacaatg tgcacatgta  1140
ccctaaaact taaagtataa taataaaaga aaaaaaact taaaagaaa agtttccata  1200
atgaggattg agtttatatc gttttcttaa ttaaggaaag acaaccctca ctacacacac  1260
acacacacac acacacacac acataaaaag acaagaggtg agatcaaggc gtaaactagt  1320
attggactaa gccagtaagt actgcttctc agtcctcagt tctctaggtt gggagttttc  1380
cttttgctat tttcattctc ctccaattca ttttttcaatg atcttcaaca caaatttcgc  1440
ctttatttct tgttcaaaat acttccatga ctattatgaa tactatttat ggatgaaggc  1500
tgaacatttt aaggcatact aagtctccca tgatatggta cctttttcatt ttcccattct  1560
ataccctgca tctaggcttt taaaaaatat accacatgca ttcatgcctc taggcttattg  1620
ctcatgccac ggcatccctt ctgggttttt tcccctcttt atctacttgg tgaatttgca  1680
tccttcagta taacacagct caacataatt ctatgcttaa actttactga aaatgcacaa  1740
ggaacttgat ctttctttct tattttcccc attttatttta ttttcccatt gcatttgggc  1800
aactttcatg gcaccagtta ttttattaat tatttgtata aactagtatg agcctatttt  1860
gtttagcttt ctatccaccag gagcatgaaa gcacttgaa atcaaatact gtttgtactt  1920
gaatatatta agtaagcgtg aggacttaaa ttaaactttg ttcctcttta aaaaaatcct  1980
taccccaact ctagcactga                                             2000

SEQ ID NO: 50         moltype = RNA   length = 561
FEATURE               Location/Qualifiers
```

```
                         source           1..561
                                          mol_type = other RNA
                                          organism = synthetic construct
SEQUENCE: 50
atgaaaatgg aatatttgt aatcatttaa agtaatgttt taaaagaact ttgtaataac    60
atcaaaatac atttaacata atattgcctc caaaaagcat tatgcaagtc aatggcaatt  120
ttcaaaacta tgttctgagc attgacataa atgctagaag ataatacttt agtgttaaca  180
gagattatgt ttgtgtggtg ggttattatc tattattctg tatttccaca tttctttaaa  240
tatcaaatga aagtgaatac aacctagtac ttgacatttt aacattttca ataccagata  300
tgtcaataag gaattcataa aataaagtgc cctgagggat ttcacaggct aaatgcttct  360
attttttaaa atgtattaat agaaaagaag actaaatcta aaaaaaaaaa ttcattttat  420
cagagagtga ctcataagtt tagaaaacct ttgatgacct ggctcacaaa gaatgtactt  480
ccaagtacac agggtcccca gcctgatgtg tgtgcctgca ttcatgcctg tcactctgct  540
cagctgcgtg cagacagctt a                                            561

SEQ ID NO: 51           moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           5
                        mod_base = OTHER
                        note = 5-methyl on the cytidine
misc_feature            order(1..5,16..20)
                        note = RNA
misc_feature            6..15
                        note = DNA
SEQUENCE: 51
tggacatcag cttgggagga                                               20

SEQ ID NO: 52           moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           1
                        mod_base = OTHER
                        note = 5-methyl on the cytidine
misc_feature            order(1..5,16..20)
                        note = RNA
misc_feature            6..15
                        note = DNA
SEQUENCE: 52
cataatgttt gacagtttgg                                               20

SEQ ID NO: 53           moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
misc_feature            order(1..5,16..20)
                        note = RNA
misc_feature            6..15
                        note = DNA
SEQUENCE: 53
gtatgacatg tccattggaa                                               20

SEQ ID NO: 54           moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
misc_feature            order(1..5,16..20)
                        note = RNA
misc_feature            6..15
                        note = DNA
```

```
SEQUENCE: 54
gggttaccaa tagctttaaa                                                 20

SEQ ID NO: 55            moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(2..4,17,18,20)
                         mod_base = OTHER
                         note = 5-methyl on the cytidine
misc_feature             order(1..5,16..20)
                         note = RNA
misc_feature             6..15
                         note = DNA
SEQUENCE: 55
gcccaagtgt aagcttcctc                                                 20

SEQ ID NO: 56            moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            20
                         mod_base = OTHER
                         note = 5-methyl on the cytidine
misc_feature             order(1..5,16..20)
                         note = RNA
misc_feature             6..15
                         note = DNA
SEQUENCE: 56
tatgttgcaa tttgtatgac                                                 20

SEQ ID NO: 57            moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(5,7,20)
                         mod_base = OTHER
                         note = 5-methyl on the cytidine
misc_feature             6..15
                         note = DNA
misc_feature             order(1..5,16..20)
                         note = RNA
SEQUENCE: 57
gggtcatgtt attcagctac                                                 20

SEQ ID NO: 58            moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(2,17,19,20)
                         mod_base = OTHER
                         note = 5-methyl on the cytidine
misc_feature             order(1..5,16..20)
                         note = RNA
misc_feature             6..15
                         note = DNA
SEQUENCE: 58
tctgaagtga atgaggcacc                                                 20

SEQ ID NO: 59            moltype = DNA  length = 20
FEATURE                  Location/Qualifiers
```

```
                    -continued source              1..20
                    mol_type = other DNA
                    organism = synthetic construct
modified_base       order(1..5,16..20)
                    mod_base = OTHER
                    note = 2-prime-O-(2-Methoxyethyl) nucleotide
misc_feature        6..15
                    note = DNA
misc_feature        order(1..5,16..20)
                    note = RNA
modified_base       order(2..5,16,17,20)
                    mod_base = OTHER
                    note = 5-methyl on the cytidine
SEQUENCE: 59
acccctttga cttgcccaag                                              20

SEQ ID NO: 60       moltype = DNA  length = 20
FEATURE             Location/Qualifiers
source              1..20
                    mol_type = other DNA
                    organism = synthetic construct
modified_base       order(1..5,16..20)
                    mod_base = OTHER
                    note = 2-prime-O-(2-Methoxyethyl) nucleotide
misc_feature        order(1..5,16..20)
                    note = RNA
modified_base       order(5,20)
                    mod_base = OTHER
                    note = 5-methyl on the cytidine
misc_feature        6..15
                    note = DNA
SEQUENCE: 60
ggtgccactt gttatgttgc                                              20

SEQ ID NO: 61       moltype = DNA  length = 20
FEATURE             Location/Qualifiers
source              1..20
                    mol_type = other DNA
                    organism = synthetic construct
modified_base       order(1..5,16..20)
                    mod_base = OTHER
                    note = 2-prime-O-(2-Methoxyethyl) nucleotide
modified_base       order(4,12)
                    mod_base = OTHER
                    note = 5-methyl on the cytidine
misc_feature        6..15
                    note = RNA
misc_feature        order(1..5,16..20)
                    note = DNA
SEQUENCE: 61
gtacacctaa ggctgtttac                                              20

SEQ ID NO: 62       moltype = DNA  length = 20
FEATURE             Location/Qualifiers
source              1..20
                    mol_type = other DNA
                    organism = synthetic construct
modified_base       order(1..5,16..20)
                    mod_base = OTHER
                    note = 2-prime-O-(2-Methoxyethyl) nucleotide
misc_feature        order(1..5,16..20)
                    note = RNA
misc_feature        6..15
                    note = DNA
modified_base       order(1,2,5,16)
                    mod_base = OTHER
                    note = 5-methyl on the cytidine
SEQUENCE: 62
cctacccatc atgtcctaag                                              20

SEQ ID NO: 63       moltype = DNA  length = 20
FEATURE             Location/Qualifiers
source              1..20
                    mol_type = other DNA
                    organism = synthetic construct
modified_base       order(1..5,16..20)
                    mod_base = OTHER
                    note = 2-prime-O-(2-Methoxyethyl) nucleotide
```

```
modified_base         order(2,3,5,17,18,20)
                      mod_base = OTHER
                      note = 5-methyl on the cytidine
misc_feature          order(1..5,16..20)
                      note = RNA
misc_feature          6..15
                      note = DNA
SEQUENCE: 63
tccacaggag aaggtgccac                                              20

SEQ ID NO: 64         moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
misc_feature          6..15
                      note = DNA
misc_feature          order(1..5,16..20)
                      note = RNA
modified_base         2..3
                      mod_base = OTHER
                      note = 5-methyl on the cytidine
SEQUENCE: 64
accttttcca tatttgggtt                                              20

SEQ ID NO: 65         moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(1,18..20)
                      mod_base = OTHER
                      note = 5-methyl on the cytidine
misc_feature          order(1..5,16..20)
                      note = RNA
misc_feature          6..15
                      note = DNA
SEQUENCE: 65
cagtaaattc ctttgttccc                                              20

SEQ ID NO: 66         moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
misc_feature          order(1..5,16..20)
                      note = RNA
modified_base         19..20
                      mod_base = OTHER
                      note = 5-methyl on the cytidine
misc_feature          6..15
                      note = DNA
SEQUENCE: 66
tttgactgcc cactcttacc                                              20

SEQ ID NO: 67         moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
misc_feature          order(1..5,16..20)
                      note = RNA
misc_feature          6..15
                      note = DNA
SEQUENCE: 67
gtttgacccc agtgaatgtt                                              20
```

```
SEQ ID NO: 68               moltype = DNA  length = 20
FEATURE                     Location/Qualifiers
source                      1..20
                            mol_type = other DNA
                            organism = synthetic construct
modified_base               order(1..5,16..20)
                            mod_base = OTHER
                            note = 2-prime-O-(2-Methoxyethyl) nucleotide
modified_base               17
                            mod_base = OTHER
                            note = 5-methyl on the cytidine
misc_feature                order(1..5,16..20)
                            note = order(1..5,16..20)
misc_feature                6..15
                            note = DNA
SEQUENCE: 68
ggttgtaagt tctagtctat                                                 20

SEQ ID NO: 69               moltype = RNA  length = 2001
FEATURE                     Location/Qualifiers
source                      1..2001
                            mol_type = other RNA
                            organism = synthetic construct
SEQUENCE: 69
tagatagaaa ggagcagcca gagatgtgcc tcaggctgaa gccagtgctg caaatgggac     60
agcgctctca agctacatta tatgcatttc attatccaac aatttgttct gggaggacag    120
tttgattggc caggcaagaa attcaaaatg agagactttt aaatatcaca actcagctaa    180
aagagctctt ctgttttctg acctgagaaa ttcacttcta tcagtctcaa taagatgct     240
tgtaatatta ggtgatgcag actctgaaca tttgtccctc tggactgagt gcactcccga    300
tgatctgagt cttggggcta tgcctcaggc ttcacaattc ctagtgtgaa agctacttgc    360
atatccaccc ctccatccag ctgggttttg ttctgctttt cttgtgtaac taatgactgt    420
gagtcaaaaa gatgggaggt caactacttg cctttgacca ttaaataggt gtttaaacta    480
agctaactaa ggaataacat tgtttttcca tttcgtgata tcgttttcca ttttatccta    540
gattcttaac taggatgtga agaaaataat agtagtcaat attataaagt ttaaaataat    600
acaaagtagt cgatattata aacacagaca tatttctaga atggaacaat aagatagtag    660
gcttctatgt tttatttaa aaggttccga aattacccac ttaccatttg tgtgaccttg     720
aacaagttgc tttaactccg aacctcagtt tcttcatata caaatgggaa atacacctac    780
tatggaggtt tgctgataga atttaaacag aataagttac gcaaaatatc tggtgttagt    840
aaagaattct ctcagtgact catagcaaga gtataaattg gtctagtcac tttgtagcat    900
gatttgtcat tatacagtga aatgtaaaat gtgcatacct tacagcaatt acatttttc     960
aggatgaaac tcagaaaaat actaaaacat gtgcacaaaa tgatagatac atacatagat   1020
atatagatat tcattgcagc ataaatgaac cagtgggaat aatatttaaa tgcatgaatg   1080
ttcttttccc ttttgaaatt attttactga ccttctccac aaactcaccct atttctttg   1140
ggtggtttgg aattattaca acaggaaggc aaagagaaag aaaaagttaa tatttatctt   1200
ctggcaaggc aacgggattt gcagtaagaa cacagtgcta acaagtagat taatcaggg    1260
agaggggagt tcgttaaatt cttaaactgc tttaacttat cataactcaa actagaggat   1320
tcagattata tgaatttttc acatctggtg aagtggtagg aagaagaatg gaaacacaga   1380
cgtcacatca gcgtcctta tttccacttc cactttcaac ccctgatcca ggaccactct    1440
ttaaggcagt aaaggagcaa tgtagtagaa atgacagcag caggccagca gatacctatt   1500
cctgagacag agcccatggc attcagggcc tggaaactgg ggaccccaaaa taccccaagt   1560
ctggttgtga caacacagag gttctgagag tacaggaaga attaagaagc ctggggacaa   1620
ggtagaaaac cactgcaggt agatcataac agacaaggga caaatgacca gaccccctaa   1680
cgcccccaaag agcagatgtc aacagcacag agagcagacc agctcagctg ctctgcagat   1740
atcaaggagg actcagagga tacatcaatc tgattcccct ttccttctgc accactaaat   1800
catgtaaact aaacaaccag atgccctctt gaagaggaat aaggtaagca ggtcaaactt   1860
ggaaaagtgg aacaaattga ccaagcaagg acagggttac ctaaatggaa tattggactg   1920
cattactgga ctcaagacaa aacttaccag attagactcg tagatcagat cagttattta   1980
aaaaataaat aaaataaggt a                                             2001

SEQ ID NO: 70               moltype = RNA  length = 1001
FEATURE                     Location/Qualifiers
source                      1..1001
                            mol_type = other RNA
                            organism = synthetic construct
SEQUENCE: 70
gtccatcctg actcctggca gggaccaggg ccatccagtt atactacggt gttctttcac     60
cacctcagtg atggcagctg gctggagtcc aaagcgtttc agtactccca agctctgact    120
actttttct cttcttttct tcatcttgcc ctacacattt atccaaagaa aatatttagg     180
atgtgaaaga aggggtgtag ataagaaatg aatcaaagga gaaatgtgtg attataaac     240
aataaaatac gtaactgaac cttactgtgg cttaacacac agccaatagt gccaaagatc    300
atataacttc tgtctgctga agttttctct ttattaaatg gcattgacag agaaaaacta    360
taaagaataa ttaattgaaa tagactgcaa atcacttagc caacataaaa tgatgcaata    420
ttttatctga tgaagaaacc taagttaaa tattggttag atcaatttta tcaattttgtc    480
tatatcctca caatccttca agccatatg aaatcatact cttttaatga acttatgta     540
tgtatatctt gtttgtatca tacaattaat atactgtcca cgtactctta tttcacacat    600
taatatcttc ctggttgaaa tcattaaata gctccacact gcttaactac agtgcgaagt    660
taaaaatata atatattcat ttttctaaag ctttaggctt tgtttgctt cattcacgtt     720
gtgtgatcta aattagtatc ttcactgtct ctgtttaata tcgacaaatt agaaagagta    780
acaaccatga ccctctcatag tccataagta ataattaatt cttcaattcc ttctataaat   840
```

```
acttattaaa gcccttttac atgccaagca tggtgctaga tccgagaata aaaataagtc   900
tggaacacag acttgtccct caaaagctcc ctcttgagaa gcctttcagt tttattctta   960
gaagtggaca aaaatgtgta ttttctactc tcaagattga a                      1001

SEQ ID NO: 71           moltype = RNA  length = 1001
FEATURE                 Location/Qualifiers
source                  1..1001
                        mol_type = other RNA
                        organism = synthetic construct
SEQUENCE: 71
aaattaaaca tatttgagga tcacagagaa gcatgtggtg caacatgtct tgaagttacc    60
gacttcgtga agtgtaaggg gcagtagttt acactggaat gacgtagaga acaggtcacc   120
tacgcacatt cctactccac cccctttgt agaaaatttg ttatactgaa cctgatttct    180
tccatggcct cctattttca gcggaatgtg attcaggaag atacattcca ccctcctgga   240
aatcggaaat aggacccgtg ctttcacaaa cattaagttc catcttccct aaaactttat   300
tgcaattccc caggaatgga tcacagagct atttcttcct ccaggtttgt agatttgtaa   360
gttgagtcat agggcaggag tacctttttt tattttatat aggctaaaaa tttgttggag   420
aagattagtg atctggagag gggaaaaaaa agaagaacaa gaaggagatg aagaagggga   480
ggaagaagag aaagaaagac aaaggaagc caacccctaat ccttgaattc tacaaactac   540
taacaattag tcaaaagtgc ctacttggat ttcaataccct gacatgcctt tgagtgttga   600
agaattaaat gtttattct ggtattgttt tttgatgtca tttattttta acctatactt    660
gccccctatca agatcattct cagttgatag taagaaaaat atgtaatgtt gttgctaatt   720
tatcttgcat taggtaattg attatttcaa aagagcattc ttgaacatct tgtaaactaa    780
aaaagcaaag aactcggtat gaggaagtta aaaactctgt caagatttca aaaatttgtg   840
tataaaaatt aattgccatg ttagaagtcg aggtcaagca gtaatgatag aaattttgtg   900
aaatgatgat tagacataaa atgtaagaca aatgagagaa acaaaggtac acaatagaaa    960
aagtattatt agtactatat tagtgactct gaatggcata a                      1001

SEQ ID NO: 72           moltype = RNA  length = 3744
FEATURE                 Location/Qualifiers
source                  1..3744
                        mol_type = other RNA
                        organism = synthetic construct
SEQUENCE: 72
gtgcagaagg aaagggtaat cagattgatg tatcctctga gtcctccttg atatctgcag    60
agcagctgag ctggtctgct ctctgtgctg ttgacatctg ctctttgggg cgttaggggg   120
tctggtcatt tgtcccttgt ctgttatgat ctacctgcag tggttttcta ccttgtcccc   180
aggcttctta attcttcctg tactctcaga acctctgtgt tgtcacaacc agacttgggt   240
tattttgggt ccccagtttc caggccctga atgccatggg ctctgtctca ggaataggta   300
tctgctggcc tgctgctgtc atttctacta cattgctcct ttactgcctt aaagagtggt   360
cctggatcag gggttgaaag tggaagtgga ataaaggac gctgatgtga cgtctgtgtt   420
tccattcttc ttcctaccac ttcaccagat gtgaaaaatt catataatct gaatcctcta   480
gtttgagtta tgataagtta aagcagttta agaatttaag gaactccct ctccctgatt    540
aaatctactt gttagcactg tgttcttact gcaaatcccg ttgccttgcc agaagataaa   600
tattaacttt ttctttctct ttgccttcct gttgtaataa ttccaaacca cccaaaagaa   660
ataggtgagt ttgtggagaa ggtcagtaaa ataatttcaa aagggaaaag aacattcatg   720
catttaaata ttattcccac tggttcattt atgctgcaat gaatatctat atatctatgt   780
atgtatctat cattttgtgc acatgtttta gtatttttct gagtttcatc ctgaaaaaat   840
gtaattgctg taaggtatgc acattttaca tttcactgta taatgacaaa tcatgctaca   900
aagtgactag accaattat actcttgcta tgagtcactg agagaattct ttactaacac   960
cagatatttt gcgtaactta ttctgtttaa attctatcag caaacctcca tagtaggtag  1020
attcccattt tgtatatgaa gaaactgagg ttcggagtta agcaacttg ttcaaggtca   1080
cacaaatggt aagtgggtaa tttcggaacc ttttaaaata aaacatagaa gcctactatc   1140
ttattgttcc attctagaaa tatgtctgtg tttataatat cgactacttt gtattatttt   1200
aaactttata atattgacta ctattatttt cttcacatcc tagttaagaa tctaggataa   1260
aatggaaaac gatatcacga aatgggaaaaa caatgttatt ccttagttag cttagtttaa   1320
acacctattt aatggtcaaa ggcaagtagt tgacctccca tcttttttgac tcacagtcat   1380
tagttacaca agaaaagcag aacaaaaccc agctggatgg aggggtggat atgcaagtag   1440
cttcacact aggaattgtg aagcctgagg catagcccca agactcagat catcgggagt   1500
gcactcagtc cagagggaca aatgttcaga gtctgcatca cctaatatta caagcatctt   1560
tattgagact gatagaagtg aatttctcag gtcagaaaac agaagagctc ttttagctga   1620
gttgtgatat ttaaaagtct ctcatttga atttcttgcc tggccaatca aactgtcctc   1680
ccagaacaaa ttgttggata atgaaatgca tataatgtag cttgagagcg ctgtcccatt   1740
tgcagcactg gcttcagcct gaggcacatc tctggctgct cctttctatc tataagttaa   1800
agcaatggcc tcagcaagca gtacactctg tacagcagct gcaactcgtt atcggctttg   1860
tccagaataa caaacagaac aaacactttt gcaagggct tttaccccctc ttatgtagag   1920
aaggaggaat taagcaatca gtgaaatgct gattgatcag ttgtgctgac taagagaagt   1980
ccaaggccac attagtacta ttaagcccta aaaaacaaag caaaaagaaa atgttcttag   2040
aactttattt aaaccagtat ttctgtgatg tgaagtacat ttcccccaaa gggaaaaatg   2100
ggaaaatatt tgcatttcac ttagtacact ttactcatcc agactgcttt gtaatgtaat   2160
gatggttaag tattttaca aagataattc atgtttttg gcagattttg gttgatcatg   2220
gagtatcagg gttgtgtgaa ccaaaggtgt gatgcagagc agcttagta aaccatccca    2280
ttcctatgcc acccgtttga tttcagtacc aactgctgtg gccacatcta gaccactctt   2340
taccagaaac tgtgccacct tcaaaattcc agcaactcca cctttatttt              2400
tgatctcata tactcaagta ttcttagtgt aacaattctt tgagcattct ttcttatcta   2460
gcttaaaatc tagggctcac cattataatc attcctttca agataacctt aacttccaca   2520
ccccaatttc taactggcct ggcaaaactc agacctttgg tgcaaaatcc tccatctcta   2580
tgcctgagcc cttgtgtttg agaatggctg aagaaaacca tgtgcatgga cattctgatg   2640
tcactataaa ttcatggtca cggatctcaa atgggagccc aagactactg gctttcctgc   2700
```

```
tgtggttgtc taatgacagc atgatcttac tcttcacaga tattagttta aactctccaa  2760
ccttcaattg aaaagtctac atcttacttt attagaaagt agaaacaatc aagggttatg  2820
ctcccatttt cacactacca agtaaacaaa ccttcagtaa gagaagatat atttcctata  2880
tctcctccta ccctcctgtt aaagggtgca aacgtcccc cctcctaaca aaaccaatc    2940
cttcttcatg ctctttagat gccgtgttgt ctctcttttct caaagtcttc attttttggt 3000
tatactcttt ctctcatgca aattttctc tcttttttcaa gtagagcagg ctcagcagcc  3060
tacaaacgtg tcttgggcac cttttcatcaa aaaataaaaa acataaaaac aacaaacgaa 3120
acccttcttg gctccacatt ctcatccagt ttctattctt tcacttagct gcttttcttc  3180
tcatgttttg tctattttt aacatcctag tcactctctg atctacttca gtttgacttc   3240
tacctccatc acttgagtaa attcaataca tggtttcaag tatattctag ccctagcctg  3300
atccacaggg aaggttctgg accacaagca acatggcaga gttgttcact cttgaggtaa  3360
aggagtttgg cacctcatgc ccctataatg gattaaagaa acactcctta atcggggtta  3420
gtccctggga aaggttttag gtgtgagcaa ttagcaacca tcacccacag tggctgggag  3480
aggggggcac tagcccaata aagaggatct aagtagtgca cccaagcagg tctaccacag  3540
ttagcttcct atgtgggctc acgttgcatg cagtgcatct ctatacagca attaatctat  3600
ttcataatat taataaaata atttcacttt ccatgttaaa atccttcaat gacttcctat  3660
tgcactataa atggcaaatc aatatgttaa catgccctgc caacacctac agggtctggg  3720
gtctgattgc ctttcagatc tctc                                         3744

SEQ ID NO: 73          moltype = RNA  length = 1948
FEATURE                Location/Qualifiers
source                 1..1948
                       mol_type = other RNA
                       organism = synthetic construct
SEQUENCE: 73
gaaagaacac cgtagtataa ctggatggcc ctggtccctg ccaggagtca ggatggactt    60
tcagtgttga agagccatct tggcctgtta ctagcgctgc cccacaccat tgtgtttgcc   120
taagagctga gccaaagaat ttacatatgt atgagccaag gtctgaaaat agaagttaaa   180
aaaatggtgc taaattgaca tatttgctat tttatttttt tggtcagtta atatgataaa   240
cttttattta aatgtaaaca ttattttaaa aagcacttta tttaaataa ctgatttca    300
ttgaaattaa ttctggcctc taagcagagt tagctacaaa gacaatttgt aaaaatgcag   360
aaaattcaga gttaacttg gagttgttta aagtttattt tcatatttga gtctgatatt   420
tcagttcact gtaatatttc aatttatta aaatattatc aagacaaata ttgggttacc   480
ttcacaatat ttttttcatt tttcttaccc catatattaa aaatgaacaa aaatgaaaga   540
attatatagt ctagtggatg gcaattctct tggtacagta ctcacaggat gtcagaagtg   600
ctttgatttg catgcaaata gaaactgcat tcctaaaaga cccttaattg aagatattaa   660
taattttcat taggtttaa gtcttttaac cttatcatat ggatagaaaa gtaaagatg    720
tgtttaataa aatgtctttt acttatttt atttgtcatt tatttaaagg tttattagtg   780
aatctgttta cctggaaaat gtgcaattct atttgcaaat ttggagcact acatatattt   840
aagagaatcc ttagtttctg ttgggagtgg caatatttta taactgggcc ttcatattcc   900
tatgttacag ccctggtccc tgaaagtcct acagctatct ttgtttcaag tgtgtatgtg   960
ttataatag ataagtgtta attagttaat caagtactaa ttaacctttt taatttatag  1020
aaaaacagac atttatggac aagtaaattt ttggggtcaa agtctttaat aatttgaaga  1080
atgcagttat ttttagcaca aatattctaa tgtgaaaaga atttctttt ctgagttata  1140
tattttatg ccattcagag tcactaatat agtactaata atactttttc tattgtgtac  1200
cttgttct ctcatttgtc ttacatttta tgtctaatca tcatttcaca aaatttctat   1260
cattactgct tgacctcgac ttctaacatg gcaattaatt tttatacaca aattttttgaa  1320
atcttgacag agtttttaac ttcctcatac cgagttcttt gctttttag tttacaagat    1380
gttcaagaat gctctttga aataatcaat taccaatgc aagataaatt agcaacaaca    1440
ttacatattt ttcttactat caactgagaa tgatcttgat aggggcaagt ataggttaaa   1500
aataaatgac atcaaaaaac aataccagaa taaaacattt aattcttcaa cactcaaagg   1560
catgtcaggt attgaaatcc aagtaggcac ttttgactaa ttgttagtag tttgtagaat   1620
tcaaggatta gggttggctt ccttttgtct ttctttctct tcttcctccc cttcttcatc   1680
tccttcttgt tcttctttt tttccctct ccagatcact aatcttctcc aacaaatttt    1740
tagcctatat aaaataaaaa aaggtactcc tgccctatga ctcaacttac aaatctacaa   1800
acctggagga agaaatagct ctgtgatcca ttcctgggga attgcaataa agttttaggg   1860
aagatggaac ttaatgtttg tgaaagcacg ggtcctattt ccgatttcca ggagggtgga   1920
atgtatcttc ctgaatcaca ttccgctg                                     1948

SEQ ID NO: 74          moltype = RNA  length = 1858
FEATURE                Location/Qualifiers
source                 1..1858
                       mol_type = other RNA
                       organism = synthetic construct
SEQUENCE: 74
cattccgctg aaaataggag gccatggaag aaatcaggtt cagtataaca aatttttctac   60
aaaagggggt ggagtaggaa tgtgcgtagg tgacctgttc tctacgtcat ccagtgtaa    120
actactgccc cttacacttc acgaagtcgg taacttcaag acatgttgca ccacatgctt   180
ctctgtgatc ctcaaatatg tttaatttaa agagggtcca gtagtgtcct ggcacatgat   240
ctggattgcc atagataacc atctacctca cagctagggt tgctctttag aatcttgcaa   300
aatcatttgt ttactcttga caaaagttaa gaaaacaagc catcagagt tgtttgttct    360
gtcagcatgt tagaagatgg ttttgttgca atgataatcg ttgtgcaaag aagactgatg   420
atgattttt tttacatttt cttaacagta tttgctattt agaatgaatg ttgtctaatt    480
atttagccat tttatttgt aaaatttatg ttgtaggcat atttagacca agttataaga    540
aaatgcttca gccaaaatta agtgttgagt ttgatttgtg taattgttag tttctttact   600
agttgttcca tcatttacac aatttattct atttgaaatg cagtaattgt tcagaactta  660
tatttctata ctgatgtcta ctaacagctt tagatcaaat attaaataac tcaagaataa   720
tgagatgatc ttggcttact tagatatttg gtttttatat ctatagaaca aaggaattag   780
aaaataattt tgaagatttc atccagctat gtaaaactat ctagggaata catttactag   840
```

```
gttttcaatt ttctacaaaa catctttcag cagaaagcaa tcctgttttcc tgatatacaa   900
tgtctgatac atagaaacta ctcagtacat aattcctgaa ttgattattc ttttggaaat   960
cctagatttg atttctgaac aatcataaac atttaatggc atgaaattac ccagattcca  1020
tggttctgga atacataact tcaagcaata agatgcaaga tagaaacata taagacattc  1080
tttgctattt taggtaagtc cagctgaatc agttaatcag ctagaaacgt ggctcacaga  1140
tgaattagtt ttattattag gtggattact gaaaaattaa tagctttatt tccgtattac  1200
cttatcattt atttaatata aaacataata aaccagagaa gttgtggtta ctttcttctg  1260
tctcattgtt cagtttttac tgaagttatg ttttactgat tttcacgaaa tgcaaatatt  1320
tctgagcatc agaaatccag cttttgctac ctcccactca tgtattcttc ccatcaaatt  1380
gaatcttaac caggtcactc tttcctgttc attccatgct gttgcccctg ttttctccag  1440
atataattga catgctccaa gaggatgaac attgcctaag acttgatttc tggtcttggc  1500
tttgcaactt actagctgtg tgaccttgaa caagctactt aattctctga gactcatcat  1560
tattgtttat aaaataggga tagcattagc ttatttcaag aattgttttt aaaattagca  1620
aggaaggcat accaatgcct agctcagggg atcaacaagt ggcaagtacc tcaacttca   1680
ggcaagatca tacttatcat cagtggagcc aatagaacag attttattta ataccctatt  1740
ttcacttact ggcataacag caagtggtgt acatatttat atatctctct atatagatgc  1800
agataatata ctaatatatt gtggttatat cttccaatgt tttagtttct attgaggg    1858

SEQ ID NO: 75          moltype = RNA  length = 2000
FEATURE                Location/Qualifiers
source                 1..2000
                       mol_type = other RNA
                       organism = synthetic construct
SEQUENCE: 75
tcatataagc tgtctgcacg cagctgagca gagtgacagg catgaatgca ggcacacaca   60
tcaggctggg gaccctgtgt acttggaagt acattctttg tgagccaggt catcaaaggt  120
tttctaaact tatgagtcac tctctgataa aatgaatttt ttttttttaga tttagtcttc  180
ttttctatta atacattta aaaaatagaa gcatttagcc tgtgaaatcc ctcagggcac   240
tttatttttat gaattcctta ttgacatatc tggtattgaa aatgttaaaa tgtcaagtac  300
taggttgtat tcactttcat ttgatattta aagaaatgtg gaaatacaga ataatagata  360
ataacccacc acacaaacat aatctctgtt aacactaaag tattatcttc tagcatttat  420
gtcaatgctc agaacatagt tttgaaaatt gccattgact tgcataatgc ttttttggagg  480
caatattatg ttaaatgtat tttgatgtta ttacaaagtt cttttaaaac attactttaa  540
atgattacaa aatattccat tttcattgct gctacaatgc atgtcaatat tgccatattt  600
gattactatt tacaaatttc tctccaaaga gagtgtactc acctacatac cagtgcaata  660
tatgggtgtc ccttttaaaaa tgtcctcacc aacattatgt attatctttc atttttatttg  720
ctccgctgta gaaaatatta ttttgctttc atttctattt taaatcactg gtgaagttga  780
atacttcaca gtatgttttt aattgatact attcttttcat caactactgt ttacattttt  840
gtttccatta actcatttat attaatcatt aacgaaaatgt cttttaagga aacataaga   900
aacactgaca gcctgtgtct atactgattt aaacagtcca cttctcaaac agtccactct  960
tcatttaaac agtccactga cataagcaag ggaagacctg ctacagattg aaaaaaaaaa 1020
tgagaacagg atgtcttaga gaataaaggt cttaggtttt ggaatgaaga gaaaataagg 1080
gtgttagtaa ttccttttgaa ggtacagaga cttccaactg ccctcttgaa atgttcctaa 1140
gtaatgaatc agaaacaact ctaagaagtt ggtgcatcta tcaaaaagtc tctaacatag 1200
caagcatgca agagatgctt ctggaaaaat gactgaatga atggattgct gtgtgcttaa 1260
ttcctgcctg atcagtgatg attatttaag caggaacaaa taaaattaca tcagttaagc 1320
atgagaggaa ataaggatgc ttaggagtca tgaaaaaaaa aacctggcaa tcaataattc 1380
tataaagtct atttttgaag agatacatta aagcaaggag taaggtatga ctggagagca 1440
aacaaattca gagtaaaaagg aggtgcaata actcccgaa gaaagttcta ctgttttgtg 1500
tttgaccaga aatgtgtgaa aatagaatat aaaaggtaga agtaattggg ttcagttcta 1560
tgattttat tagccttagt atcataacaa ggaacacgtt cacaattaaa gatatggatg 1620
aagaaggcat ctctgaggga aagtggtgtg gattgtaccc atgtaaaagg cacacatttt 1680
ctcctatcac agaaactagg acaagctggt aggaggattc ctcaaagttt ggccaggaag 1740
aagacttaaa gttgtttgaa aaccttccca atatgtcaag gattgaaaat gacagacaga 1800
tatcatgttg ttagatgatg agggttcaaa ctaaccagat atccttggaa atccaatcaa 1860
gtaaaaccta ttcattaaga tccaattggc attttgagga atagaaagtg aggatcaaat 1920
tatgatgaat atgcttatca atctaacatt tgataacata agtttggag tgatacaaaa 1980
gaaggtgaaa aatgaagctg                                              2000

SEQ ID NO: 76          moltype = RNA  length = 2000
FEATURE                Location/Qualifiers
source                 1..2000
                       mol_type = other RNA
                       organism = synthetic construct
SEQUENCE: 76
gcctgatgtg tgtgcctgca ttcatgcctg tcactctgct cagctgcgtg cagacagctt   60
atatgaagga ggactgtgta catgtggtca gagaagaaaa aaatgcttat ttttttaaat  120
gttttgaaaa ataatctgtc ctaaaagtgt aacattttcca ctaaattttt tcatgtctga  180
ctttaacatt ccctaccaac caactcttat agcctcaact cctttgatct atcctaatgt  240
aaactccctc actaatgtgt aatatatttt tttccagttt ggttatagat ttcagtctag  300
cctgaacact caagtatgaa actagccact atttttattta ttggctgttc caacctccat  360
tgtggaatta taattgatgg atttttccaag tctctaattc agaatattta atcaaattttt  420
ccaaaatttc tgccttctcc tccttcattc tgatgactaa agacatggac cataaaaatat  480
atatacatat atacatacat atgtatatgt atgtatatac acatatgtat  atgtatgtat  540
atatacatac atatatatat gtatatatac acacacatat acatatgtat gtatatatac  600
acacacacat atatatatgt atgtatatat acacacacac atatatatat gtatgtatat  660
atatacacac acatatatat atgtatgtat atatatacac acacaccg tagttttgcaa   720
gtctgcatct gggaccctttt actgataaaa atgaaagccc attaaaactc tcatgcccac  780
atttctctct agacttagaa gtaggagaat tctatcctag aattgttgat tgttgacatt  840
```

```
tctatggaaa aacatgttta attcatcatg ctttgtagtc aactgctata aatggtgatg    900
aagtcttttc cttggtcaag ctctggactc ctcagtactt ccactgtcat atttgattaa    960
aacataagtg atgaagggag gaaatatatt atagtattca ttgcatgggt accttagggt   1020
aatgggacta tgactgattt aaatttattt tgcatcctaa aaagtttcca ttagtgggtg   1080
cagcacacca gcatggcaca tgtatacata tgtaactaac ctgcacaatg tgcacatgta   1140
ccctaaaact taaagtataa taataaaaga aaaaaaaact taaaaagaaa agtttccata   1200
atgaggattg agtttatatc gttttcttaa ttaaggaaag acaaccctca ctacacacac   1260
acacacacac acacacacac acataaaaag acaagaggtg agatcaaggc gtaaactagt   1320
attggactaa gccagtaagt actgcttctc agtcctcagt tctctaggtt gggagttttc   1380
cttttgctat tttcattctc ctccaattca tttttcaatg atcttcaaca caaatttcgc   1440
ctttatttct tgttcaaaat acttccatga ctattatgaa tactatttat ggatgaaggc   1500
tgaacatttt aaggcatact aagtctccca tgatatggta ccttttcatt ttcccattct   1560
ataccctgca tctaggcttt taaaaaatat accacatgac ttcatgcctc taggcttatg   1620
ctcatgccac ggcatccctt ctgggttttt tcccctgctt atctacttgg tgaatttgca   1680
tccttcagta taacacagct caacataatt ctatgcttaa actttactga aaatgcacaa   1740
ggaacttgat ctttctttct tattttcccc attttattta ttttcccatt gcatttgggc   1800
aactttcatg gcaccagtta ttttattaat tatttgtata aactagtatg agcctatttt   1860
gtttagcttt ctatcaccag gagccatgaa gcacttgaa atcaaatact gtttgtactt    1920
gaatatatta agtaagcgtg aggacttaaa ttaaactttg ttcctcttta aaaaaatcct   1980
taccccaact ctagcactga                                               2000

SEQ ID NO: 77        moltype = RNA   length = 3864
FEATURE              Location/Qualifiers
source               1..3864
                     mol_type = other RNA
                     organism = synthetic construct
SEQUENCE: 77
tcttcctatg ggaaaaaata atttcctcta tcagaggaaa aatttattac tattatgata     60
ataccccttc agacctttt ctagtcactt acaggtaaaa attgtagtac tggttggtac     120
atagtgtatt ttattaatgt tttactgcgt atattgttgt ataaattgct ttccgcactc    180
attggcatgc cttagaattc tttttattta ggcttcatga ctaatttgta gtggaacctc    240
aagaagatca cttatgtgct tcactttcca catatgtaaa atgggaataa caacagaatc    300
tgcctcatag tactgctgaa gggtgacatg ggaacacct gtgaggcatt cagaacagag    360
cctgtcatac aataaatgcc atgtcagtgt ttgctcttat tctcagtata cagagatctg    420
ctttgatctt ttcatcttct gcaaaatatt ccacaaattg gcatattgtg tttttgtaata    480
atctctattg attattttca agcaagattt ggaattatcc gcagtagttt caaatgtaca    540
aaaaagtacc ttattttatt tatttttta ataactgatc tgatctacga gtctaatctg    600
gtaagttttg tcttgagtcc agtaatgcag tccaatactc catttaggta accctgtcct    660
tgcttggtca atttgttcca cttttccaag tttgacctgc ttaccctatt cctcttcaag    720
agggcatctg gttgtttagt ttacatgatt tagtggtgca gaaggaaagg gtaatcagat    780
tgatgtatcc tctgagtcct ccttgatatc tgcagagcag ctgagctggt ctgctctctg    840
tgctgttgac atctgctctt tggggcgtta gggggtctgg tcatttgtcc cttgtctgtt    900
atgatctacc tgcagtggtt ttctaccttg tccccaggct tcttaattct tcctgtactc    960
tcagaacctc tgtgttgtca aaccagact tgggttattt tgggtcccca gtttccaggc   1020
cctgaatgcc atgggctctg tctcaggaat aggtatctgc tggcctgctg ctgtcatttc   1080
tactacattg ctccttact gccttaaaga gtggtcctgg atcaggggtt gaaagtgaaa   1140
gtggaaataa aggacgctga tgtgacgtct gtgtttccat tcttcttcct accacttcac   1200
cagatgtgaa aaattcatat aatctgaatc ctctcagttg agttatgaa agttaaagca   1260
gtttaagaat ttaacgaact cccctctccc tgattaaatc tacttgttag cactgtgttc   1320
ttactgcaaa tcccgttgcc ttgccagaag ataaatatta acttttctt tctctttgcc   1380
ttcctgttgt aataattcca aaccacccaa aagaaatagg tgagttttgtg gagaaggtca   1440
gtaaaataat ttcaaaaggg aaaagaacat tcatgcattt aaatattatt cccactggtt   1500
catttatgct gcaatgaata tctatatatc tatgtatgta tctatcattt tgtgcacatg   1560
ttttagtatt tttctgagtt tcatcctgaa aaaatgtaat tgctgtaagg tatgcacatt   1620
ttacatttca ctgtataatg acaaatcatg tacaaagtg actagaccaa tttatactct   1680
tgctatgagt cactgagaga attcttact aacaccagat attttgcgta acttattctg   1740
tttaaattct atcagcaaac ctccatagta ggtgtattcc catttgtat atgaagaaac   1800
tgaggttcgg agttaaagca acttgttcaa ggtcacacaa atggtaagtg ggtaatttcg   1860
gaacctttta aaataaaaca tagaagccta ctatcttatt gttccattct agaaatatgt   1920
ctgtgtttat aatatcgact actttgtatt attttaaact ttataatatt gactactatt   1980
attttcttca catcctagtt aagaatctag gataaaatgg aaaacgatat cacgaaatgg   2040
aaaaacaatg ttattcctta gttagcttag tttaaacacc tatttaatgg tcaaaggcaa   2100
gtagttgacc tccatctttt tgactcaca gtcattagtt acacaagaaa agcagaacaa   2160
aacccagctg gatggagggg tggatatgca agtagctttc acactaggaa ttgtgaagcc   2220
tgaggcatag ccccaagact cagatcatcg ggagtgcact cagtccagag ggacaaatgt   2280
tcagagtctg catcacctaa tattacaagc atctttattg agactgatag aagtgaattt   2340
ctcaggtcag aaaacagaag agctctttta gctgagttgt gatatttaaa agtctctcat   2400
tttgaatttc ttgcctggcc aatcaaactg tcctcccaga acaaattgtt ggataatgaa   2460
atgcatataa tgtagcttga gagcgctgtc ccatttgcag cactggcttc agcctgaggc   2520
acatctctgg ctgctccttt ctatctataa gttaaagcaa tggcctcagc aagcagtaca   2580
ctctgtacag cagctgcaac tcgttatcgg ctttgtccag aataacaaac agaacaaaca   2640
cattttgcaa gggcttttac ccctcttatg tagagaagga ggaattaagc aatcagtgaa   2700
atgctgattg atcagttgtg ctgactaaga gaagtccaag gccacattag tactattaag   2760
ccctaaaaaa caaagcaaaa agaaaatgtt cttagaactt tatttaaacc agtatttctg   2820
tgatgtgaag tacatttccc ccaaaggaa aatgggaaa atatttgcat ttcacttagt   2880
acactttact catccagact gctttgtaat gtaatgatgg ttaagtatt ttacaaagat   2940
aattcatgtt ttttgcaga ttttggttga tcatggagta tcaggttgt gtgaaccaaa   3000
ggtgtgatgc agagcagctt tagtaaacca tcccattcct atgccacccg tttgatttca   3060
gtaccaactg ctgtggccac atctagacca ctctttacca gaaactgtgc caccttcaaa   3120
```

```
attccagcat cctttcccc tcctcccta tttttgatc tcatatactc aagtattctt    3180
agtgtaacaa ttctttgagc attctttct atctagctta aaatctaggg tctaccatta    3240
taatcattcc tttcaagata accttaactt ccacacccca atttctaact ggcctggcaa    3300
aactcagacc tttggtgcaa aatcctccat ctctatgcct gagcccttgt gtttgagaat    3360
ggctgaagaa aaccatgtgc atggacattc tgatgtcact ataaattcat ggtcacggat    3420
ctcaaatggg agcccaagac tactggcttt cctgctgtgg ttgtctaatg acagcatgat    3480
cttactcttc acagatatta gtttaaactc tccaacttc aattgaaaag tctacatctt    3540
actttattag aaagtagaaa caatcaaggg ttatgctccc atttcacac taccaagtaa    3600
acaaaccttc agtaagagaa gatatatttc ctatatctcc tcctaccctc ctgttaaaag    3660
ggtgcaaacg tccccctcc taacaaaaac caatccttct tcatgctctt tagatgccgt    3720
gttgtctctc tttctcaaag tcttcatttt ttggttatac tctttctctc atgcaaattt    3780
ttctctcttt ttcaagtaga gcaggctcag cagcctacaa acgtgtcttg ggcacctttc    3840
atcaaaaaat aaaaaacata aaaa                                           3864

SEQ ID NO: 78         moltype = RNA   length = 2963
FEATURE               Location/Qualifiers
source                1..2963
                      mol_type = other RNA
                      organism = synthetic construct
SEQUENCE: 78
tgtttgttct gtttgttatt ctggacaaag ccgataacga gttgcagctg ctgtacagag    60
tgtactgctt gctgaggcca ttgctttaac ttatagatag aaaggagcag ccagagatgt    120
gcctcaggct gaagccagtg ctgcaaatgg gacagcgctc tcaagctaca ttatatgcat    180
ttcattatcc aacatttgt tctgggagga cagtttgatt ggccaggcaa gaaattcaaa    240
atgagagact tttaaatatc acaactcagc taaaagagct cttctgtttt ctgacctgag    300
aaattcactt ctatcagtct caataaagat gcttgtaaca ttaggtgatg cagactctga    360
acatttgtcc ctctggactg agtgcactcc cgatgatctg agtcttgggg ctatgcctca    420
ggcttcacaa ttcctagtgt gaaagctact tgcatatcca cccctccatc cagctgggtt    480
ttgttctgct tttcttgtgt aactaatgac tgtgagtcaa aaagatggga ggtcaactac    540
ttgcctttga ccattaaata ggtgtttaaa ctaagctaac taaggaataa cattgttttt    600
ccatttcgtg atatcgtttt ccatttatc ctagattctt aactaggatg tgaagaaaat    660
aatagtagtc aatattataa agtttaaaat aatacaaagt agtcgatatt ataaacacag    720
acatatttct agaatggaac aataagatag taggcttcta tgtttatttt taaaaggttc    780
cgaaattacc cacttaccat ttgtgtgacc ttgaacaagt tgcttaact cgcaacctca    840
gtttcttcat atacaaaatg ggaatacacc tactatggag gtttgctgat agaatttaaa    900
cagaataagt tacgcaaaat atctggtgtt agtaaagaat tctctcagtg actcatagca    960
agagtataaa ttggtctagt cactttgtag catgatttgt cattatacag tgaaatgtaa    1020
aatgtgcata ccttacagca attacatttt ttcaggatga aactcagaaa aatactaaaa    1080
catgtgcaca aaatgataga tacatacata gatatataga tattcattgc agcataaatg    1140
aaccagtggg aataatattt aaatgcatga atgttcttt ccctttgaa attattttac    1200
tgaccttctc cacaaactca cctatttctt tgggtggtt tggaattatt acaacaggaa    1260
ggcaaagaga aagaaaaagt taatatttat cttctggcaa ggcaacggga tttgcagtaa    1320
gaacacagtg ctaacaagta gatttaatca gggagagggg attcgttaa attcttaaac    1380
tgctttaact tatcataact caaactagag gattcagatt atatgaattt ttccacatctg    1440
gtgaagtggt aggaagaaga atggaaacac agacgtcaca tcagcgtcct ttatttccac    1500
ttccactttc aaccctgat ccaggaccac tcttaaggc agtaaaggag caatgtagta    1560
gaaatgacag cagcaggcca gcagatacct attcctgaca cagagcccat ggcattcagg    1620
gcctggaaac tgggaccca aaataaccca agtctggttg tgacaacaca gaggttctga    1680
gagtacagga agaattaaga agcctgggga caaggtagaa aaccactgca ggtagatcat    1740
aacagacaag ggacaaatga ccagaccccc taacgccca aagagcagat gtcaacagca    1800
cagagacgcag accagctcag ctgctctgca gatatcaag aggactcaga ggatacatca    1860
atctgattac cctttccttc tgcaccacta aatcatgtaa actaaacaac cagatgccct    1920
cttgaagagg aatagggtaa gcaggtcaaa cttggaaaag tggaacaaat tgaccaagca    1980
aggacagggt tacctaaatg gagtattgga ctgcattact ggactcaaga caaaacttac    2040
cagattagac tcgtagataa gatcagttat ttaaaaaata aataaaataa ggtacttttt    2100
tgtacatttg aaactactgc ggataattcc aaatcttgct tgaaaataat caatagagat    2160
tattacaaaa cacaatatgc caattgtggg aatattttgc agaagatgaa aagatcaaag    2220
cagatctctg tatactgaga ataagagcaa acactgacat ggcatttatt gtatgacagg    2280
ctctgttctg aatgcctcac aggtgttccc catgtcaccc ttcagcagta ctatgaggca    2340
gattctgttg ttattccat ttacatatg tggaaagtga agcacataag tgatcttctt    2400
gaggttccac tacaaattag tcatgaagcc taaataaaaa gaattctaag gcatgccaat    2460
gagtgcggaa agcaatttat acaacaatat acgcagtaaa acattaataa aatacactat    2520
gtaccaacca gtactacaat ttttacctgt aagtgactag aaaaaggtct gaaggggtat    2580
tatcataata gtaataaatt tttcctctga tagaggaaat tattttttcc cataggaaga    2640
tcttaaactt atttgtaatg tttcaatttt ttcacatgat gaacaaagca atacactgct    2700
catgttactg aaactcgata aaatatatga agctaaaatt ggtcatctaa aagtatgata    2760
atatataata tttatttct acttatctc caatatgctt atcatacaga aattataaca    2820
aaaatgcaagc aaatgttttg gataaattga aagttaataa gttgtacact gtagccctac    2880
catccccact gatgtcaaag ggctgatttt taattatgca atagtaatta aatagggatc    2940
aatgtcatta cctgagaaaa cac                                            2963

SEQ ID NO: 79         moltype = RNA   length = 5263
FEATURE               Location/Qualifiers
source                1..5263
                      mol_type = other RNA
                      organism = synthetic construct
SEQUENCE: 79
aattctaagt caggtggtcc aacaaggcct ctcatcctat tggtattaca gtatgaccctg   60
tctcctgaac tttgaagcca tttctttcct tcagaggaga taagaaaatg tgtcttatct    120
```

```
taagtctgga agaaacacgg agcccagtat caagggagtg gagtagttct tttcccagac    180
gtagcacagg gttttccaag cctgaagaaa aagattaatc tccttaaaac aaggctttgt    240
tgacttgggt ctggtcatgg caatcctgtt tccagccatc ctgtgtataa gctctaacgg    300
tcagaagttt gtttgctttg attttgatgt ggctcatctt ttcttagctg ctcatattca    360
agatttggaa aagaaggaac ggtggtgagc tgagcaatta attggattct gataaggagt    420
tctggagaaa ttttattatt cctgagtttt aaaccegtgt aactttaata taacttttgt    480
atgagccttt acattttttc tctgtgtttt tgtaattata ttgtggcatt cttattgggt    540
gtggtagtag caataaatta taaatgtatg aatttataca ttatggattt ataatttcat    600
aagttttttga gattttaaga cttactattt tttacacgat gccttatgta tttatagcat   660
ttaatattaa tctaaattca ttttgagata tattttatca tgctttatc ttttatatgt    720
tattagaaag cacttggtat tttaaaaata tatattaatg tgagatttca caatttatac    780
cttgtctttg tagtcacatg cgtagaggat atttacaatt ttactcaagt taatttgctc    840
agtgttgatc atcagacctt ttagccagta ttggctggga aaaaaagtgt aattcttttt    900
gttctcttga gaatttttg gatctaaagt gattcctagg gtgtgggtca acttcatga     960
tatgaaagat gacatggagg tttttttattt tgtgaagtgc attaataggt gatcacattt  1020
catcctggga gagctgctgg agaggaatat tgatttagcc tgttatggtt gagtctttgg   1080
ggtcttgagc ttcttagatt tttagttctt tttgttattc tttattgttc aatcttgaga   1140
gtagaaaata cacatttttg tccacttcta agaataaaac tgaaaggctt ctcaagaggg   1200
agcttttgag ggacaagtct gtgttccaga cttattttta ttctcggatc tagcaccatg   1260
cttggcatgt aaaagggctt taataagtat ttatagaagg aattgaagaa ttaattatta   1320
cttatggact atgagaggtc atggttgtta ctctttctaa tttgtcgata ttaaacagag   1380
acagtgaaga tactaattta gatcacacaa cgtgaatgaa gcaaacaaaa gcctaaagct   1440
ttagaaaaat gaatatatta tattttttaac ttcgcactgt agttaagcag tgtggagcta  1500
tttaatgatt tcaaccagga agatattaat gtgtgaaata agagtacgtg gacagtatat   1560
taattgtatg atacaaacaa gatatacata cataaagttc attaaaagag tatgatttca   1620
tatggctttg aaggattgat aggatataga caaattgata aaattgatct aaccaatatt   1680
taacttttagg tttcttcatc agataaaata ttgcatcatt ttatgttggc taagtgattt  1740
gcagtctatt tcaattaatt attctttata gtttttctct gtcaatgcca tttaataaag   1800
agaaaacttc agcagacaga agttatatga tctttggcac tattggctgt gtgttaagcc   1860
acagtaaggt tcagttacgt atttttattgt tttataatca cacattttctc ctttgattca  1920
tttcttatct acaccccttc tttcacatcc taaatatttt ctttggataa atgtgtaggg   1980
caagatgaag aaaagaagag aaaaaagtag tcagagcttg ggagtactga aacgctttgg   2040
actccagcca gctgccatca ctgaggtggt gaaagaacac cgtagtataa ctggatggcc   2100
ctggtccctg ccaggagtca ggatggactt tcagtgttga agagccatct tggcctgtta   2160
ctagcgctgc cccacaccat tgtgtttgcc taagagctga gccaaagaat ttacatatgt   2220
atgagccaag gtctgaaaat agaagttaaa aaaatggtgc taaattgaca tatttgctat   2280
tttatttttt tggtcagtta atatgataaa ctttttattta aatgtaaaca ttattttaaa  2340
aagcactttg ttttaaataa ctgattttca ttgaaattaa ttctggcctc taagcagagt   2400
tagctacaaa gacaatttgt aaaaatgcag aaaattcaga gtttaacttg gagttgttta   2460
aagtttattt tcatatttga gtctgatatt tcagttcact gtaatatttc aatttattta   2520
aaatattatc aagacaaata ttgggttacc ttcacaatat tttttcatt tttcttaccc    2580
catatattaa aaatgaacaa aaatgaaaga attatatagt ctagtggatg gcaattctct   2640
tggtacagta ctcacaggat gtcagaagtg ctttgattg catgcaaata gaaactgcat   2700
tcctaaaaga cccttaattg aagatattaa taatttcat taggttttaa gtcttttaac    2760
cttatcatat ggatagaaaa gtaaaagatg tgttaataa aatgtcttttt acttattttt   2820
atttgtcatt tatttaaagg tttattagtg aatctgttta cctggaaaat gtgcaattct   2880
atttgcaaat ttggagcact acatatattt aagagaatcc ttagttttctg ttgggagtgg   2940
caatatttta taactgggcc ttcatattcc tatgttacag ccctggtccc tgaaagtcct   3000
acagctatct ttgtttcaag tgtgtatgtg ttataataag ataagtgtta attagtaat    3060
caagtactaa ttaacctttt taatttatag aaaaacagac atttatggac aagtaaattt   3120
ttggggtcaa agtctttaat aatttgaaga atgcagttat ttttagcaca aatattctaa   3180
tgtgaaaaga atttctttttt ctgagttata tattttatg ccattcagag tcactaataat   3240
agtactaata atacttttttc tattgtgtac ctttgttttct ctcatttgtc ttacatttta  3300
tgtctaatca tcatttcaca aaatttctat cattactgct tgacctcgac ttctaacatg   3360
gcaattaatt tttatacaca aattttgaa atcttgacag agttttttaac ttcctcatac   3420
cgagttcttt gctttttttag tttacaagat gttcaagaat gctcttttga aataatcaat   3480
tacctaatgc aagataaatt agcaacaaca ttacatatt ttcttactat caactgagaa    3540
tgatcttgat aggggcaagt ataggttaaa aataaatgac atcaaaaaac aataccagaa   3600
taaacatttt aattcttcaa cactcaaagg catgtccaggt attgaaatcc aagtaggcac   3660
ttttgactaa ttgttagtag tttgtagaat tcaaggatta gggttggctt cctttttgtct  3720
ttctttctct tcttcctccc cttcttcatc tccttcttgt tcttctttttt tttcccctct   3780
ccagatcact aatcttctcc aacaattttt tagcctatat aaaataaaaa aaggtactcc   3840
tgccctatga ctcaacttac aaatctacaa acctggagga agaaatagct ctgtgatcca   3900
ttcctgggga attgcaataa agttttaggg aagatgaact ttaatgtttg tgaaagcacg   3960
ggtcctattt ccgatttcca ggagggtgga atgtatcttc ctgaatcaca ttccgctgaa   4020
aataggaggc catggaagaa atcaggttca gtataacaaa ttttctacaa aagggggtgg   4080
agtaggaatg tgcgtaggtg acctgttctc tacgtcattc cagtgtaaac tactgcccct   4140
tacacttcac gaagtcggta acttcaagac atgttgcacc acatgcttct ctgtgatcct   4200
caaatatgtt taatttaaag agggtccagt agtgtcctag cacatgatct ggattgccat   4260
agataaccat ctacctcaca gctagggttg ctcttttagaa tcttgcaaaa tcatttgttt  4320
actcttgaca aaagttaaga aaacaagccc atcagagttg tttgttctgt cagcatgtta   4380
gaagatggtt ttgttgcaat gataatcgtt gtgcaaagaa gactgatgat gatttttttt   4440
tacatttttct taacagtatt tgctatttag aatgaatgtt gtcaattat ttagccatttt  4500
tattttgtaa aatttatgtt gtaggcatat ttagaccaag tataagaaa atgcttcagc    4560
caaaattaag tgttgagttt gatttgtgta attgttagtt tctttactag ttgttccatc   4620
atttacacaa ttatttctat ttgaaatgca gtaattgttc agaacttata tttctatact   4680
gatgtctact aacagcttta gatcaaatat taaaaatcctc aagaataatg agatgatctt  4740
ggcttactta gatatttggt ttttatatct atagaacaaa ggaattagaa ataatttgtg   4800
aagatttcat ccagctatgt aaaactatct agggaataca tttactaggt tttcaatttt   4860
```

```
ctacaaaaca tctttcagca gaaagcaatc ctgtttcctg atatacaatg tctgatacat   4920
agaaactact cagtacataa ttcctgaatt gattattctt ttggaaatcc tagatttgat   4980
ttctgaacaa tcataaacat ttaatggcat gaaattaccc agattccatg gttctggaat   5040
acataacttc aagcaataag atgcaagata gaaacatata agacattctt tgctatttta   5100
ggtaagtcca gctgaatcag ttaatcagct agaaacgtgg ctcacagatg aattagtttt   5160
attattaggt ggattactga aaaattaata gctttatttc cgtattacct tatcatttat   5220
ttaatataaa acataataaa ccagagaagt tgtggttact ttc                     5263

SEQ ID NO: 80          moltype = RNA   length = 1413
FEATURE                Location/Qualifiers
source                 1..1413
                       mol_type = other RNA
                       organism = synthetic construct
SEQUENCE: 80
cactgctggt tccacctcct tctctcacca tggggagaaa aaggtgacct cttctggcat   60
tgcaagcaca acctgactca cagggcaatg cttttgtatc tgagtgtctt tcacaatcca   120
tttactatct gtaactagct gttctgttac taaccttttaa aaactgctcc catgcccttc   180
aatgcaatt atgtaaatat actctaatga cttttaacta tcttaaat actgtgccca      240
catcaaaaag aattaatttg gatgtgtatt tcttagaaaa ttgagtttta aaagagaagg   300
caaaaaaaaa atcatacata aaggactatt tcaaaataag tgactaagaa cacaggtccc   360
ccttggactc tgtgggactt taattcacta ccatgaagct taagaacttc catttttcat   420
gccttggcatt cctccaaagt tctggccagt aatgactgta tgtgagtaat ggcttttgca   480
ccttggaaatg atggcttatt cctcctgaaa atttgtcatt cttagctatg aactatggaa   540
gacccttgaa acagatctac caccatgagc tagaactgct ttcccagggg tcggtccaca   600
taattagctc atgttgttgt gtggtaattg ctgtgtagag tgcttgctga gtctagggat   660
ctgatttata attattgtgg cctccactat tcattgctct gttttttggta tttaacagag   720
acctgctcat ccttagctac ccacttctgt gagaataaag tggtccaggt gacacagttc   780
agaaatatga caaagcactt aaactgtaga tggtactgtt gtccttacag tttcttctct   840
tcaagatggc atgtgatgtc ttcaaggcat tgaaacactt aactaaagct aaaccaccat   900
tctctgtata tcaaggtact atgtccttat tgatgcttta gaatatccat tctcctttct   960
ggcttccatc ttattatcaa aatgaatcca acatggcttt cttaggcttt gtaataaatt   1020
ctcagggtag caggctcaag ttggtatcat gtcattgatg taagcataag tgtctctctc   1080
cctttccctc ccactcctcc tccccttccc catcctcctc ttcctctccc taccctccat   1140
gccaccatcc tttccttcca ccctcttttt ctctcccacc atcttctta tgtctctctc   1200
ctgtccctgg aatctataag aacctataga aattgcctgt tcccacacat gccagaatcc   1260
aaagcccctg aaatcctgac caaggcatta taagcaaaag aatctctttt ggtatagcat   1320
tggaaatgta aatgagctaa atacctaata aaaaatggaa aaaaaaaaag agtcaaatgt   1380
caaaaaaaaa aaaaaggaa tctaaggagc acc                                 1413

SEQ ID NO: 81          moltype = RNA   length = 1777
FEATURE                Location/Qualifiers
source                 1..1777
                       mol_type = other RNA
                       organism = synthetic construct
SEQUENCE: 81
acttcttttg cttcataatc atgttacaag aggcccttga cctgaggtac cctccactaa   60
atacacattt gatttgcaca gtggggtcat tggctctgac aaacagcagt gtcaacattg   120
ctaatctgaa acaacaatct ctcatgcccc tctctgcccc accttcaaac acacccacag   180
caagttctga caaacacttt atatgtgccg aactgagcat tctttatcac ttgagtagac   240
atgacaacca gctaacctug caggaacgtc cctctctcct ggcttctttc tagtgagaat   300
ggaatccagc tcaccttatc ctaaaatact tggtgtagaa catgaaattg ttttggagtt   360
ttcttcatat atatttagat ctagatagag cccatgctta tcttaagtta acgaaagaga   420
aattcaaatt aaaacaaaaa aaaaaacaaa caaacaaaca attgctcaat ccctcacact   480
tgttagctct gggcctggtc tttaaccccg gttttcatt tctactttag ttcttttctc    540
agtcagcagg gtttgctaag attcatgctt gcttacatt ttctacaaaa gcccagagac   600
tgaaaccatg tgttttaagt ggttttaact caaaatgttc tttttttgctt gttgagaact   660
cataacccaa cttgataaga tgttctttct aattataaag tattgtaatg aggtccctga   720
atccaagaag caccatttaa tgtccgctct gatctctgag ggttttattt ttacatcaat   780
ccagttctga ccaccagac atgaaagtgc cttggtcact gagccagcag caccctccag    840
ttggcaaaag caaggtcatg agaaatggtg acaaatttca gagcttctta ctcctcattt   900
ggattcaaag tccctaaaat ggaaatataa ttcttttacc acttcttgaa ctactctatc   960
aggcagggtt caaaaaataa aatccacttt gagagtttct ttaaatagta acaccccttaa   1020
taatatcaaa acatgatttg cataattgca ctctattaac taatatgagt gtatttcttg   1080
tgaatagtta tgttgaaaag acgttcttgg aagcatcaaa atattaact aaaatattta    1140
aagaatgatt taagctccat caaaatttta aaatgtttac tcaaaagata ctgttaagaa   1200
agtgaaaaat aaggcataga cttaaaagca aatattcaca aatgatatta ttggtaaaaa   1260
aaaaaaaaat tgtatccagg ccagatcaag agctttaga agtagatagc aagtagaatg   1320
agccaactta aaataagcag aataggagct ggaaaatgct cagtgggaaa atgcttgcta   1380
tgcaaacatg aggatcagat ctcagatacc caacacccct atagctcaca gccaacaatt   1440
ggactgagct ccaggggacc tggatggagg agatggagaa gggattgaag gagctagggg   1500
tttgcagccc catggaggga gcaagaagtg tcaacaggcc agatacccta gagcttccag   1560
ggactggatc aaccaccaaa gaatacacat ggagcagccc atggcgctgg ccacatatgt   1620
ggcagaagat ggctcggttg aacatcagtg agaggaggcc ccttgggcc tgaaggtgtt    1680
caatgtccca gtgtaggaga atgccaggga gggagaatgg gagtgaggga gtcggggagc   1740
accctcatag aggcatggga gggggaatgg gataggg                             1777

SEQ ID NO: 82          moltype = RNA   length = 2348
FEATURE                Location/Qualifiers
```

```
source                  1..2348
                        mol_type = other RNA
                        organism = synthetic construct
SEQUENCE: 82
agttttggca caccatttta atgagacagc agatgcaaaa gtgcttacaa cagctgccct    60
aagtagacat tttatcatcc tccctcacag cagccattct gtgccttctt ctgcatggct   120
atttagcaat tgtaagtctc tagaaccatt caatggtatt ctgtacagtt aatgttttta   180
attatattct gcttcagact ttgattcttt tgtaagcttt ttctttacat aaaatttacc   240
aactgcttct tttccttctt ggacttacac atgtctatca taaccacact gactttattt   300
ggagacaaag taataaggta actaaacttt acttactcat tatagtgtta aggaatcaac   360
ctcatgtctc acacagacta ggtaactgtt ctgtcactga gctgattcct agcctttcta   420
atgttctatg agtgattatt ataatctacg aaagactaag ggcacagtaa ggaacaaacc   480
aaaattttct gcctccactg aacttgtatt gtaaatgtta taatgaaatg tagggaccat   540
gaatgaataa tggatatggt atctccaaat cttatgcatc gtcatttcct aattcctgta   600
tcctgatatt ttgtgggaaa cttgctaccc tgtttgactg atgtcttggt gggacagtct   660
ttgatcttac tccaatctcg ttctctttgc caacttgtag acacctgatc atgcttgtcc   720
aatcagactc tcaggaaaac tgaatataat tggactatgt tcaactcaaa gatggctctt   780
tgacaaaggc cattgactcc tgccacctag tcctcaggga ctcatttgtc cttatttgtt   840
ccaaaggcct ctttccttgg ctactccttg tatgcaaaat cttcactgtt tcttgcaagt   900
tatttttaagt gtaattttgt gttggctgga atccagttat tctaatacat taaatttggc   960
aaaggaaaga gcatagcatt tctttatttc tccaagtcaa ctgtcttatc cttttatcca  1020
ctgggcttgt aagaaattaa attgaaactt tagtggggat tcccctctat attccgtgg   1080
ctgagaacca gtagccagtt tctgaggtgt ccactgtggc cgcctttgtt ctatgccagg  1140
gataagaaga tcgttagaga gactggttat cagggagcta aggttcgctt ctacaggtgc  1200
aacgtgcaaa gcctactgta tgtaagtctg tattatgcct gggagacttt gtaccatcgg  1260
gctgattact ctgatgcaaa gcctccctca gacagttaac ttatcttaaa gcctctgtta  1320
tcgttcatga acagagggca aactcatgtc cattctgtct tgttctccca cctgtctctt  1380
aagttgctct ggattgctac attaaactct gaggaacaat gaacccattc ttccatttag  1440
tatgaattta gtaagtgtct gatccattcc aaattctcta tgagactctg aaaagacaaa  1500
gggaaactcc atttagttat tgttctacag gagtacattt tggggttggag aaagggaaga  1560
ttaagtaagc tagtggctaa gcaacagggc agtgatgaac tcgacaagaa ccatgacaac  1620
ataacaatag aaaagatctg agtctatttg gagaatgtca tgtcagacat ggactacaaa  1680
aggagagaac ggctggggttg gacctttggg aggatgtggg aatttgctta ctatacaggt  1740
gaccagtaat ggcacatacc aaatcataga gggaggagga aagaaggaa ggaaaagagc   1800
aggttataaa gaaggaggaa gaaacaacat gggaaaaaaa caggtcaga gaagaggcaa   1860
gaataagaac aagagagaag gaaggaggga gaggaaaagg aaaaggaaga aagaaaagaa  1920
aaaaaaaaca gaagaaggct ggggtggggg gggttatgtt gtcctgtaac aagtagcaca  1980
ctatagctga caggattagg gtgaagtcca ctaaggaggct tgggtgagac agacatagga  2040
aacaggtaga cagaaaaacc cagaaggaac attgtcatct tgctctcctg tgtgaaaacg  2100
gaagctttgc ctctgtgaat ccaagaaaga gacgtacctc tgttcttatc tacacaaaag  2160
agaaggtggc agaaacctca tcttactgtc actgagagga ctaaatggac ttttgaatca  2220
aaagcactta gcacagtacc taccacacag cagaaatcaa gggcttttac ctgtcctcct  2280
tcttccaaac ctcacaccct gaaaatccat cacaaaccct gtggaaccat aaaaagatat  2340
ccaccct                                                           2348
SEQ ID NO: 83           moltype = RNA  length = 5638
FEATURE                 Location/Qualifiers
source                  1..5638
                        mol_type = other RNA
                        organism = synthetic construct
SEQUENCE: 83
cctctatctc cactctcatt aatatgggtg tcctattgct cttatttctc tattaaaaga     60
aaaggggggac acagacacac acataaatat atacaaacac atgcacacac acatacatat   120
atacacacat gtacatacac tccaagatgt tttgatgaaa aaggcagtta taaattagaa    180
tctggatgag aatcaagcca ggcaggtttt atttcttgct atctgttggt ttggttttac    240
ttgggttttgg agactagggc tgtgttttga gatgggagac aatgaacaaa tatctggata   300
tttacctgga aagtggagtt gtaaatttt atgatagaaa gggtataacc aaggagtaaa    360
gactcaaaga gtggccaaag gggggatatg aagaagatgg aaagtaagtc atttctgatc   420
tgccagacat acttccacta gtataactgg aaggcagaag gactagacaa cctttccttc   480
ctgcaagttg ataaattcag tagtgtaaag agtagagcac agccatctca tgacttccat   540
tttttcagtga tgtggggtgc agttttttcac tgaaggttgc aaggatgcaa acccttttaaa  600
ggatttgacc tgtgatagcc tgcccatgac ccagtagatg ccctgtacct atgctcatac    660
tggcagcact aagtaaactc agtgagttta aaaaacaaaa cgaatataaa gctttggga    720
gggagggggat ggtggtgggc aggaaggagg agttggaagg gggagaatgg aaggagacta   780
gatcaaaaca tgttatgtgc ctgaatgaat tctcaaacag taacaaaaga aaactcctta    840
ggagtaaaact agatcaaaac atgttatgtg cattcatgaa ttcccaaaca gtaacaaaag   900
aaaagtctca ggaaactagg gccatgttct ccttacagta agatcctcag tagtatcaga   960
ttttcacccg cgatagcaat ggtgaattca tatgcacata gaattgtaca gaatatgct   1020
ttctccagct attttcaaaa acaagtgtgc agcctagcag gtggcatatt actcaccgag  1080
agttcaagca ttacctagca atataggaag aaatggggtg tgaaatatga gactctagaa  1140
agaaataact acaatagtag accctaaatt ctaagacaaa tgaaaagatt gctcaaaagt  1200
gaggagatgt ctcagtcagt ggtggcacat accttttaatc ccagcaccct agaggcaggg  1260
gaatctctga gttcgaggac agacaagtaa gtctccagag caagtctgg gacagccaag  1320
gctacacaga gaatccctga cacatgcatg tgcacatatg tacctacgtg tacacaccac  1380
acacacacac acacacacac acacacacac acaaaaatca cagctctaaa aactactgag  1440
gcagattctg aaagatccat acagtaaata tatgaattca aaaaatagga aaaaagatga  1500
gaaaactaag acatttggat tttaaaggtg gctctgttttc tgataaagat catctcgggag  1560
ttggggggggg cataattaag ctgttacgct gacaatcttt tttcatttca cacaattcta  1620
cctctctgtg gtcaaccaac acagtccaaa tactatgaat cctgttttata aggcataacc  1680
```

```
accatcaata tgagaaaatc ataataaaca aagcaaattt ctttcctttc tttaggcaaa  1740
attgaacatc acagaaatat tagtataaat aaagttctaa gagtaatctt tgttgagatt  1800
ttctttttc attttacagg gttaatagca ctcatgtggc cttgaacctc tctatgccag   1860
tacaattgat caatcagcat ttcaccgatt gcttcactcc tccttctccc cataagagga  1920
gagaaaccct tgcaaaacgt gtttgttctg tttgttattc tggataaagc cgataacgag  1980
ttgcagctgc tgaacagggt gtactgcttg ccgaggccac ggctgtaact tatagataga  2040
acagagcagc caaagatgtg cctcgggctg gagccagctc tgcaaatagg ccacactctg  2100
ggctatgata catgcatttc attagctgac aatttactcc tggagaagct tgattggcga  2160
cagactcaaa aagagagaat ttgaaatatc actcctcagc tcaaagtgtt tttctctgtt  2220
tctgacctga aggattggct tatgtcagtc tcaatcaaga tgcctttagt agtacttgag  2280
gctgacttgg aacaatatgg gtccctctgg acagagtgta cacctgatga ttcgtgtctt  2340
ggggcaatgc ctgaggccgc acagtcccta gtgctgaaac tgagctcacg cccaactcaa  2400
ctgagttttg tgcctcttcc ctgtgtactt aagggctgtg ggccaaaaag acatgcagcc  2460
aacaatctgc cctgaaccat taaacagctc tctaaaccga gctgatgggg aacagagtat  2520
cattgtccat tatttataat gtgatcttct acttttatcc tcaattatta agacacaagg  2580
aaaacaagaa cagtcaacat tataaggatt gggtcaaaat gaatacatgc tttgagcata  2640
aaccagaatc aagataactc ttgtgcttgc ttgaaaaaag ttttcaagcc ttcatccttt  2700
agcaagttgc tctgactcct cagacctctg tttgttcaca ggtagaatgg gaatgatcct  2760
cacagctgtg gagggttatc cagagacttc tgataaagta agttatatga aatgtctacc  2820
attagcaagg aatactctaa agttgtctag cagaaatgac gagcaggttc agccagtcaa  2880
ggttcctgtc accaagcctg aagactaact tcatccccgg gatccacata atggaaggag  2940
agtgagaacc ccacagttgt cctctacata cacacacgca catacaccac aaaataagat  3000
gtaataaaat atgttctaat gcaattttc attatatagt ggaatatcaa ttgtgtatat   3060
cctatagtaa ttgtactttt caatatgaa cttaaagaga tacaaaaatg tgtgcaaaaa   3120
ttatatatgt ttttacaata agaatatata tatatacaca ctgtgccatt aatgaatcaa  3180
gccaaataac attttaatgt attagtgttc ttttctgttt tgaaagtcat cttactggcc  3240
ttgcccgctt atatgtttga actccttttg gattattgta actggaaaac aatgtgaggt  3300
ctgggatcca gataaaaaga ctccctgagg cagattactc cacacaccta agtatcacat  3360
ggctgaacca gtatccagta ccacactcag tgaacagact gagcagcaaa caaggcgctg  3420
agggccaata cagggccccc aacaattcat ccctctgcag aaatcatgga tggtccagag  3480
cacaccactg gtccctacca cctttcccct ctctaccacc caatcaatca catgagctaa  3540
acaactgtct tgaattggaa tggcgagcca gttccctaaa tggagggctt ggaccgcaga  3600
gctgcaccta agaagagaat ttagctcgtt aaatgaaaga tgtgtttcca gtcaatgaaa  3660
tagatcaggt taattattta aaaatctcca gcttcattgc acatgtgagt cgactgcagg  3720
gaattcgaaa ccttgctgca aagtaatcaa tagagatatt tctaggcaaa aaaaaaaaaa  3780
gtatgttggt gagcatggtg gcacacgcct taatcccag cagtcaggag gcaagtggag   3840
ccatgagtgc gaggccagcc tgatctacag agtgagttct gggacagcca ggactacaca  3900
gagacaccat ctcaaaaaat aataataata acaacaataa taataaaagt atttggacca  3960
caggctgcac gtctctctca caagatcaga gtgacctgac acagtgtcac tgcataacag  4020
ctctggtctg agggtttcaa agacattaac tggtatcatg cataatgcaa gatagatgct  4080
gttgttcttt ccattacaca tataaggaa ctgaagcaga gactcccta agttgtcttc    4140
tcaaggtttc cctatttatt tatgatgggg cttaaattga aaaagtccta aggcacacag  4200
atgtgtcttt tttttaagca attatacaga gcaatgcatc tcttcaaacg ttagtaatgc  4260
agacacatgc cggcatttca tagtttcatt agcaaatgac taggacaaaa tctaaagaaa  4320
tattgtaaag ttcatcatga tgcttccctc tgcacttaaa aatattatca cttcataggg  4380
aggtttgttt ttaagtttat ctctgataat ttaattatct cactttggaa atatggcaat  4440
gtactgctca tttgactaaa attggataaa ataaatgaag ctaagaagga tggtatggta  4500
atattagcaa tagtttgtac tttatttgaa atacgtttgt attatagaaa taaaagtaaa  4560
catggggaag tatgttagat gctgttgaaa aacagtgcca cattgtttcc ctaacattcc  4620
cagtgattgt caaagagctg ctttctaatt atagaatagt atttaaatag ggaccaatga  4680
cattctaaag aacactaata gaaagtagtt attattctcc tgtatttctt taataataat  4740
agctactttc tattagtgtt ctttagaata gaaccttggt tgagtggtta ctctggtcag  4800
tctacccttg attttctgtc ttggatgagt ttgcgttgtg tgtctacaaa aaaatctcac  4860
aaacagcagc atatgaggaa tcacattaaa acttctttga aaaagaaag tatttattat   4920
aagcaacata atttccattg aaaagtaaaa gaatggaaag tcaatttcta aaattaaata  4980
cataaggata actcacttca ataaattgag taagttttgc aattataaa ttatattttc   5040
ctaaattctc atgaagaagt aaacatctgt aattccagaa cttgggaagc taaaccaaga  5100
aaatcatgag tttggagcta acctgaactt catagtcacc ctgactcaaa acaaaagttc  5160
tgattcctga taaagagcaa tttgatactc atttctatatg ggttctatta tgcaatcttt  5220
aatatacaaa acagaatact ttaaaatgac attattattg ttgaattgatg gaaaaaatag  5280
acaaagcttt attataaaat taaatataag tttgtatgaa attcataatg tcctttaaaa  5340
tgtgaatgac atattagaaa aaagtcacc ttatcaactg tgaatctaat tttatatata   5400
gttacattat ctttataact gttttaagtc ctgtcagaaa aaaatgtata attaatgaaa  5460
gatgatgact gacagcacca tctctcagat caggaaaacc agctcagatg aaatgagaaa  5520
agaatacaat gttcactacc aaaaaaatcta tatcaggtag tttatttatt tagatttta   5580
acattgttcc tggtctatat atcaaggtga tgcagataga tagatagata gatagata    5638

SEQ ID NO: 84         moltype = RNA  length = 2042
FEATURE               Location/Qualifiers
source                1..2042
                      mol_type = other RNA
                      organism = synthetic construct
SEQUENCE: 84
tttaaataat taacctgatc tatttcattg actggaaaca catctttcat ttaacgagct  60
aaattctctt cttaggtgca gctctgcggt ccaagccctc catttaggga actggctcgc  120
cattccaatt caagacagtt gtttagctca tgtgattgat tgggtggtag agaggggaaa  180
ggtggtaggg accagtggtg tgctctggac catccgatgt ttctgcagag ggatgaattg  240
ttgggggccc tgtattggcc ctcagcgcct tgtttgctgc tcagtctgtt cactgagtgt  300
ggtactggat actggttcag ccatgtgata cttaggtgtg tggagtaatc tgcctcaggg  360
```

```
agtcttttta tctggatccc agacctcaca ttgttttcca gttacaataa tccaaaagga    420
gttcaaacat ataagcgggc aaggccagta agatgacttt caaaacagaa aagaacacta    480
atacattaaa atgttatttg gcttgattca ttaatggcac agtgtgtata tatatatatt    540
cttattgtaa aaacatatat aattttttgca cacattttg tatctcttta agttacatat   600
tgaaaagtac aattactata ggatatacac aattgatatt ccactatata atgaaaaatt   660
gcattagaac atattttatt acatcttatt ttgtggtgta tgtgcgtgtg tgtatgtaga    720
ggacaactgt ggggttctca ctctccttcc attatgtgga tcccggggat gaagttagtc    780
ttcaggcttg gtgacaggaa ccttgactgg ctgaacctgc tcgtcatttc tgctagacaa    840
ctttagagta ttccttgcta atggtagaca tttcatataa cttactttat cagaagtctc    900
tggataaccc tccacagctg tggaggtcat tcccattcta cctgtgaaca aacagaggtc    960
tgaggagtca gagcaacttg ctaaaggatg aaggcttgaa aacttttttc aagcaagcac   1020
aagagttatc ttgattctgg tttatgctca aagcatgtat tcattttgac ccaatcctta   1080
taatgttgac tgttcttgtt ttccttgtgt cttaataatt gaggataaaa gtagaagatc   1140
acattataaa taatggacaa tgatactctg ttccccatca gctcggttta gagagctgtt   1200
taatggttca gggcagattg ttggctgcat gtctttttgg cccacagccc ttaagtacac   1260
agggaagagg cacaaaactc agttgagttg ggcgtgagct cagtttcagc actagggact   1320
gtgcggcctc aggcattgcc ccaagacacg aatcatcagg tgtacactct gtccagaggg   1380
acccatattg ttccaagtca gcctcaagta ctactaaagg caccaggatt gagactgaca   1440
taagccaatc cttcaggtca gaaacagaga aaaacactt gagctgagga gtgatatttc   1500
aaattctctc ttttttgagtc tgtcgccaat caagcttctc caggagtaaa ttgtcagcta   1560
atgaaatgca tgtatcatag cccagagtgt ggcctatttg cagagctggc tccagcccga   1620
ggcacatctt tggctgctct gttctatcta taagttacag ccgtggcctc ggcaagcagt   1680
acaccctgtt cagcagctgc aactcgttat cggctttatc cagaataaca aacagaacaa   1740
acacgttttg caagggtttc tctcctctta tggggagaag gaggagtgaa gcaatcggtg   1800
aaatgctgat tgatcaattg tactggcata gagaggttca aggccacatg agtgctatta   1860
accctgtaaa atgaaaaaag aaaatctcaa caaagattac tcttagaact ttatttatac   1920
taatatttct gtgatgttca attttgccta aagaaaggaa agaaatttgc tttgtttatt   1980
atgattttct catattgatg gtggttatgc cttataaaca ggattcatag tatttggact   2040
gt                                                                  2042

SEQ ID NO: 85         moltype = RNA   length = 983
FEATURE               Location/Qualifiers
source                1..983
                      mol_type = other RNA
                      organism = synthetic construct
SEQUENCE: 85
agaaagttca gtgttattca gcggcagatt tcctcacagg gcaaagcatt gcattaattt     60
atgttggctg agtgagtcac agtctgctct atttattttt ccctgtcaa cttcattttg    120
tacagagaaa actttagtaa acacaaggcg gatggtttta gacacaggga gtgtcaagcc    180
actgtaaaga atcagttatg tatttagct gtattatttt acaatcatgt ggtcccctc     240
ccccccggg atttttttt ttcttcttct ttgccccca ctctatcatg tccttagtaa       300
tttttctgt tgaaatttgt attgctagag gagaaagta tcatgtggga ttgtgagtac     360
tagaacaggc tggagtccag ccagccgtcc tagtgaagaa ttcacagaac tggatcttcc    420
tctccctagt ctctgccaga aatctctgtt cacagtaatg ctcaaaagcc attttggcct    480
atcaccgtcc ctgtcacacc tagaatatga tctcaaaatt ctactttcaa acttaagggg   540
cggaaaaagg accatgtaaa tgaagcaatg atgctaaatt aatatattt ctactttgt     600
cttatagaag catttacttc aatgtaaatc ttatttaaga aagtgcttcc tcgttaaaac    660
atagactttc atggtacttc tcctgatgtc gacgtgaagt gaagtagcta caaaggcagt    720
ttgtatgtgc agacaactca gaactagtt ttgagatatt aaaacttctt attaccatag     780
ttgcattcct actcctcagg tcactataac attttaatt tctataatca agacaagttg     840
gactatatct tcacaataag tacatttatt tctcttacct tgtctaccaa aaagaaaatt    900
aaaatggaag tttttttctt tttcgccatc ctaatggaca acaaatcttt tgtgctgtgt    960
tcaaagaaca accaaggtgt ttt                                            983

SEQ ID NO: 86         moltype = RNA   length = 1986
FEATURE               Location/Qualifiers
source                1..1986
                      mol_type = other RNA
                      organism = synthetic construct
SEQUENCE: 86
gagcagtttg ttctgttcag cacattataa gaggggagg gttttggcaa taataatcac      60
tgtgcaaaga agggctgctg atgaatttgc tgttttcaaa aaacattttc gtagaaataa    120
tttactagtt agaatgagca catatctaat gatttagtca tcacactcta tgaaatttac    180
actgtaagca tgttttggtc aagttttaag aaacttcttt gaccaggatt agctaaactg    240
acacagttag catctttcta attgttttaa tattcatcaa gttattttt taaaggtatc    300
aattatgtgg aactcaggtc tagattgacc cttttttcct tttaaagaa aagctaaact     360
aaaaactttt actaaaggct atttagtact gaataactca taaataacga gatgactcta    420
tatttatcca gatgccagat tttatatat acaaaacagaa agaaccagaa aactatttta   480
aaggtttatt ttttaatcta tctaaaacta tctatataat ttatactatt tgccttctaa   540
aaatgtaggt aaggcactta gatgttgtga attttcttga aatcatttt agttaaagcc    600
aatactgttt cctgatatat attgattgat atcctagcat ttcttagtaa gcatttcctg    660
aattcttttta gttactctac atcttatttc caaacaaata taagaattca gtgagactaa   720
agtactcaga tcctgtggct ttggaatgaa aaattataaa caataaggta taagatagaa    780
aacagtgaga acatgatttg ctattgtagt caagtctcaa tccaatttac                840
ctgatctgaa ttacaaaaac aagatagcca gtataattcc ctgctatttg aatattgttg    900
ttattttttaa atttaaatgt aataccaaaa gtaaagtcag aattactttc atccctcatt   960
ttttgacatt tacttaagtt gtatcatctt aactttacgt gatggcataa acccttctga   1020
gctctgaaat ctgttctttg cacctccact ctcgggtgtg ctttctgtct tgctggatct   1080
tgcccagccc actctctcca cctcattcta caccgtcaca cccgcttttc caagtatgac   1140
```

-continued

```
caatacacag gaagaggatg gacattggct aagagctgaa ttctgattct ggcctcgact   1200
ctttcagtgt ggtgctagac aagctagtta caaagctaag acacactatc agctatacaa   1260
caggaacagc aatcgataac caggagttgt ttctaaactt aatggagaag caagcaggt    1320
gcctaacgat gagaataaat ggcaaattac ttaacattat tcatgactag aacaattaaa   1380
acaagtttat ttaaatatgt attatgcac acatagacat accttttatt ataaatatgc    1440
aatgtgctaa aattgtaatc atacactagt gtcttagctt cttatgtaag atttttaaat   1500
ttattattga ataatttcca tttttcatca ttaaagatta agtttgatta attaactcta    1560
catgacatgt ttttaaattt taattgtcac caaagtagta cttttacat ctttattcaa     1620
tatttaactt tacaagtaat tttcagttta ttttcttaat ttctattcta gattctgtta   1680
tctaaatata ctttatgcaa gcatagtcag ctatgactaa cttaggacct cttgctattc   1740
aatattagca ctacatatgc ctgtcttcca aaaaacaatc tatccaccac agttttcttt   1800
tttggcagac atttttcctc catctttggg actgacttac atctgacctt cccacttgga   1860
ttttgctctg ctctgtttct gtttaactgt gccttcaatt tttccaaggt cacttgaatt   1920
ctgaatcaac tttcgaagga gttgtctatt ttcttttcat ttcacttgcc ctcaacatac   1980
ttggct                                                              1986

SEQ ID NO: 87          moltype = RNA  length = 5030
FEATURE                Location/Qualifiers
source                 1..5030
                       mol_type = other RNA
                       organism = synthetic construct
SEQUENCE: 87
tccctttagc aggatatttg atataataaa tctgacacct tctgggccct cctgtttcca    60
agggaatttg atctaggaag atgtgtttca gattctcgga aactggaata atgctttcac   120
aaactttaag tttcattatc ctaaaatgtt atcgcagctc gccaggaaag gaacgcacaa    180
ttatttctcc ctccaatgtc gaaggttgag aatggcatta ttataaggca tgagtattgt   240
tgttgttgtt gctgctgctg ctgctgctgc tgctgctgct gttcttgttc ttgttgacgt   300
ggttatggta gtgagatgga gttggtggtg gtgttgttta taaagacttt ttattttaga   360
aaatcaatgc tatgaaagga aaatgagaat aagctagaaa ggaaggacaa taaaaggaga   420
aagaaagaga aggcggcaga ctgatctctg aactctacta actgctaaca attagtcaaa   480
gaacctcctt ggatatcaaa tttctgtatat agctttgagt attggagaat tggttggttt    540
cttttttctg gtattgttca cttgatgtca ttcatcctta acctgctctt gcttcacta    600
agatcattca cagctcagaa gaattaaata tatattccca tcaattgatt ctgggttgga   660
aaataaaaag tgttcttaaa aacttcagga aattcaaaag caaagcaagg atcatttttt   720
aaaaagttaa agactgtgaa aagatttcaa aatgttgtat ttaaagtta cctgactaac    780
tgggcatttg gcgggtgggc ctgtaaaatc tcaacacttg agagatggga aggcctgaag   840
ttcaaggcca gtctttagct gctacatagt aagtttaaga ctaaactgtg ctatgttaga   900
ccttgtctca aaaatgaaaa gcaaatgtta ttgtggtgag aagctgaggc tgaagtagtg   960
ttctaggagt ctgacaaaaa gaatgattac acatgtttaa agagcagggg aaatgacata   1020
atcaaagtac tgtgttagta taaatcgtac attaacgtgt tgcttggaaa agggctttc    1080
aaatgtgaat aataattatg ttacaatgg taaatgcatt ctttaaatta ttaaatattc     1140
tgactcagtc acttgcccat gtctggtttc tacaattgtc ttctctctct ctctctctct   1200
ctctctctct ctctctctct ctctctctct ctctctcaga gctgaggact              1260
aaacccaaga tcttgcactt actaggcaag cgctctacca ctgagctaaa tcccaaccc    1320
cttctactgt tgtctaatca atttatttgt gtttgattga ctcagcaaca cttatcttat   1380
tacaatccat ctatctttta aatcaaagat aaatgaaggg ctcttaggga acaggcttat   1440
aacataaaag tgcaaaggcc ccagtataaa atgttactac tctcatagga actgaggact   1500
ctctaagaag tggaaccaac tcatctctaa atctcaaaca catacaactg aagatcatat   1560
agatagattg gttcacagac aaaccttaa ataaaggaca aaaatacttt aaataaagac    1620
ttttattgcc tgtggttgaa ttagggaaag actggaagaa gctgaggagg agggcgaccc   1680
tgtaggagga ccagcagtct caattaacct ggtcctccga gatctctcaa acactggacc   1740
atcatgcacc aactgatatg aggccccaa cacatacaca gcagaggact tcaggatttg    1800
gtttcagcca gagaagatgt acctaaccct caagagactg gaggcccaa agagtttaga    1860
gttctggttg ggtgtggggt gggtgatagg gacatactcg tggagacagg ggggcgggga   1920
ggaggtatgg gatgtggaaa attaggaggg tggaccaggt agggaataaa tctgcagtgt   1980
aaattaatta attaatttaa aaaaactttt gttggcactt tattttttt tcttttcctc    2040
tccagaggct gaggctggac cacctgacca taacaaaagc tccatgcctt cgtccagaca   2100
cttttcagga cggtaatttt tattcacacg tgaatcaaaa caccttggtt gttcttgaa     2160
cacagcacaa aagatttgtt gtccattagg atggcgaaaa aagaaaaaac ttccatttta   2220
atttttcttt tggtagacaa ggtaagagaa ataaatgtac ttattgtgaa gatatagtcc   2280
aacttgtctt gattatagaa aattaaaatg ttatagtgac ctgaggagta ggaatgcaac   2340
tatggtaata agaagttta atatctcaaa actaagttct gagttgtctg cacatacaaa    2400
ctgccttttgt agctacttca cttcacgtcg acatcaggag aagtaccatg aaagtctatg   2460
ttttaacgag gaagcacttt cttaaataag aagtaaatgc ttctataaga ttctataaga   2520
caaaagtaga aaatatatta atttagcatc attgcttcat ttacatggtc cttttccgc    2580
ccttaaagtt tgaaagtaga attttgagat catattctag gtgtgacagg gacggtgata   2640
ggccaaaatg gcttttgagc attactgtga acagagattt ctggcagaga ctagggagag   2700
gaagatccag ttctgtgaat tcttcactag gacggctggc tggactccag cctgttctag   2760
tactcacaat cccacatgat caaatttcac tctagcactt caagaaaaat                2820
tactaaggac atgatagagt ggggggcaaa gaagaagaaa aaaaaaaatc ccggggggggg  2880
agggggacca catgattgta aaataataca gctaaaatac ataactgatt ctttacagtg   2940
gcttgacact ccctgtgtca aaaccatcc gccttgtgtt tactaaagtt ttctctgtac    3000
aaaatgaagt tgacagggga aaaataaata gagcagactg tgactcactc agccaacata   3060
aatgca aattaatgca ttttgcc ctgtgaggaa atctgccgct gaataactat                 3120
tgtttgcctg tattcgatga aatctttgaa ttcctacaga atgctgttct ttttttttttt  3180
ttttctgaca tgagacaaat tctttataaa catcttgttt ggatcagcca ccacattgta   3240
acattgtttc ttacactaag gctactattc tataaaactg ttacatatct ccactctaac   3300
tacagtgcaa agctaaaaaa aaattaaaaa aaataaaaaa ataaaaaaaa gcaacaccttt    3360
cagttttcta agactttact ctcattgctt ccacatttgt gatgtataat cctaaattaa   3420
```

```
tctcttcctt gcctctttt agcatcaaca aataggatat ttcctaatgt agcaagcatt    3480
agttctatga gccatgaggg gtagttttta acccctcctt cattcaatgt taactaaaag    3540
tcttttacat gccaagaggg ctacagtcaa gccactgtaa agaatcagtt atgtatttta    3600
gctgtattat tttatttatt ttattacttt atttattatt tattttcaaa agttctgaaa    3660
ataaaaatga gctcagaaac tctctctgca aactcactct caaagagcct ttacagttta    3720
ttcttagaaa gagccatgtc gtatctagtc tcaagactaa acaataaaga aagacaaagg    3780
gaactgtaaa cctacaaatc tcaagacccc aagacccaag aacaacagac caaatcaata    3840
ttcctctcca gcagccacac gacgatgaag tgtgagcatg tgtctgtaca cttcacaaaa    3900
tacaaagccc cctgcatcag cttttcatatc ccaaaggagt tgacccacac ttctaggaag    3960
cccttcacat cctacaactt ctcgaaaac aagaagaatc agattttttt gagcagacaa    4020
ttgtggctgg aagttgagtt attattactg agcaaattga ctaaactttt aacatatgca    4080
ggactaaaag ataagtata aaatgaaaac tcatatatat gagtaacttt ttaaaacaaa    4140
tgttttctaa aaatatatga aagataagtc caagatcaaa tgtgtttcat ggacttagat    4200
taatagtcaa tggtagaaac atgagtcaaa acattttttc ataaaataac aaatcttaaa    4260
ttaaaacccc aaatactcat gaaacaacaa atctttagct cttatcccac ctaacaaata    4320
taccacaata taattactac ttgacagaga gaaaagtaaa ggttcatacc agattatgtt    4380
aaagttatag ggatttgtaa tcaattttct caagatctcc tcatcagaat ccaatgagtc    4440
actcagctca ccactgtttc ttctttttcca aatcttgact gtgagcagct aagaaaagat    4500
gagccacatc agaatcaagg caagcaaagt tttgactgtt caagcttaga ctcaggatgg    4560
ctggaaacaa gacttccatg tccaagccca agtcaggaca gtccttttt aaagcagatt    4620
aatctttttc ttcagacttg aaaactctgt gctatgtcta ggaaagtaac tactccgcta    4680
ccttgatact gaactctgtg tttctcccag acctaagata agacacctt ctttatctcc    4740
tctggggaaa gaaaatggct tcaaagtcca gtccaggaga caagccatac ggcaatgcca    4800
atagtatcag aggccttgtt ggatcacctg acttagaatt actataggag gcaatgtaac    4860
aaacacttca attttaaaa atccaaaatt agcatatttc cttagtaaaa atggtcacga    4920
atgtcttaca gaatgtcact attaagtgac aactattggt ttgcacatta actaatgctt    4980
ctggatgatt taaccaacag aaatgtgcta caacttacaa ctttaatctc                5030

SEQ ID NO: 88              moltype = RNA   length = 843
FEATURE                    Location/Qualifiers
source                     1..843
                           mol_type = other RNA
                           organism = synthetic construct
SEQUENCE: 88
ttggtcatac ttggaaaagc gggtgtgacg gtgtagaatg aggtggagag agtgggctgg     60
gcaagatcca gcaagacaga aagcacaccc gagagtggag gtgcaaagaa cagatttcag    120
agctcagaag ggtttatgcc atcacgtaaa gttaagatga tacaacttaa gtaaatgtca    180
aaaaatgagg atgaaagta attctgactt tactttggt attacattta aatttaaaaa    240
taacaacaat attcaaatag cagggaatta tactggctat cttgttttg taattcagat    300
caggtaaatt ggattgagac ttgaccagac ttaactacaa tagcaaatca tgttctcact    360
gttttctatc ttataccta ttgtttaaa ttttcattc caaagccaca ggatctgagt    420
actttagtct cactgaattc ttatatttgt ttggaaataa gatgtagagt aactaaaaga    480
attcaggaaa tgcttactaa gaaatgctaa gatatcaatt aatatatatc aggaaacagt    540
attggcttta actaaaaatg atttcaagaa aattcacaac atctaagtgc cttacctaca    600
ttttttagaag gcaaatagta taaattatat agatagtttt agatagatta aaaaataaac    660
cttttaaaata gttttctggt tcttttgttt tgtatatata aaaatctggc atctggataa    720
atatagagtc atctcgttat ttatgagtta ttcagtacta aatagccttt agtaaaagtt    780
tttagtttag cttttcttta aaaggaaaa aagggtcaat ctagacctga gttccacata    840
att                                                                  843

SEQ ID NO: 89              moltype = RNA   length = 1797
FEATURE                    Location/Qualifiers
source                     1..1797
                           mol_type = other RNA
                           organism = synthetic construct
SEQUENCE: 89
ttcttatcaa ataccttgtc attgcaacaa cttgtagtcc ataaaaaaca taaggactct     60
ttgatctaac cctctactaa gtccttctac taaaatgtat agaatggaat ttttttttaa    120
atatccagtt tttgctttaa aatgttcagt ttaatggttt aaatttaaaa ctttaaagat    180
ttttgagaat tgttcatgtg tgacaatcac ataatttgtc aagtaaatca gtcatcatttt    240
gcactataca gatgacaaaa cttaggttca gagaatatgt gacttgtcca agaacagggc    300
attaggaaat gcataacagg ggttagattc cagatctttt tgtgcccaat ccagagtata    360
tcccactatt acactgttac agcctgctga atgtaataat gagtgctgaa cattttcagt    420
actaatggaa aaagattatg gtatctaaaa cttttttagta tttagtattt tatggttgtt    480
gatcatttat acccttgata tcaacttttct ttaaaatata gagcaccttg aaattctttc    540
ctctttcctg taagtaaaat acaactgtgc cgattggcaa agcactctat aaatattagc    600
cgctgacaaa tacccaggga agggccacat aaaattataa gtgcgtcatt gctgtcgtca    660
aacccaccgt ctctgtcatc aaagagagag gaaaacaaa cctcaaaata tgtcgaaaaa    720
gcaacccaat ttacagggca atgattatag atgtgactac agggtgtctt tcccaatcca    780
tttaccatct ataactggac ataatgctac taacctttaa agtgactgtt ctcagtgccc    840
ttcactgacc attatgtaac tacatcctaa tgattttaac tatctttaaa atatgatgtc    900
catctaaaaa tagtaaattt ggatatattt ttctaagaca gttgagtttt taagtgaag    960
gcaggaagaa aagtagatag aggactttt cacaataact gaataataac acaagtcccc   1020
ttgggctgtt ctatggaatt ttaattcact attgtgaagt tcaagaactt ctattttttg   1080
tgcttggcat tcctccaaaa ctctggccag taatgattga gtgtgagtaa tggctttac    1140
accatgaaat gatggcttag tgctcctaca aatttgtcat tcttagctgt gcactgtgac   1200
agaccccttga aacagatctg tcaccatgag ctagaactgc tttcacagta atccatccac   1260
ataattagac cattttgtcg tggttgtgat tgtggtggtg gttgtatgga gcacttattg   1320
tgatcttgga gaattggatt ctaatttcaa tcatatctgt gccatttaa gtaagtactc   1380
```

```
aatttcgcgg tttctggggt ctgatgaaga tgcacctatc cttacctaca tacctacctt   1440
ctcacagagt gagaagaaga tattccaagt cacccaactt tgaagtatta gatggcacat   1500
ataatcatag gggataactt tcattactat tgattttctc tgaactgata catgagtacc   1560
ttgaggtatt actaacaata aattctcata gtttacatct agttacaatg tctttgatgt   1620
tagtttagaa tattctcctt tcccattctt ttgctataat taagctaaat tcaagaaaat   1680
atatataact agacataatg ccactaacct ttagtgactg ctcccagtgc cctttatggc   1740
cattatgtaa ctcatcccta atgattttaa ctatctttaa aacatgatgt ccattta      1797

SEQ ID NO: 90          moltype = RNA   length = 2393
FEATURE                Location/Qualifiers
source                 1..2393
                       mol_type = other RNA
                       organism = synthetic construct
SEQUENCE: 90
ttatggtatt gctgttgaat catttatcta cgtaaactat ttgcacttca gaaaaagtag     60
aggccccaca tgttttttt  ccattttcac caaggcctaa ggctatataa catacgtgct    120
ttctggctta cctgatgttt ctaagctatt agttcgcctc agtactcatc ctcttaaaaa    180
ataaatctga actaagcact gaaaagtaga aagcctaaag ccagaattta tttcaggtaa    240
ttattgtgta gataatatgg taaaaagtta aaatcaagta aatgaaatct tattctttta    300
ttcttggaat tacactatta agatatggat ttttgaaatt tagaatttca gcacaatttg    360
tctttgaaat atttcatgag acttctctgc agttacaagg cctaacactt caaaattctg    420
aagcactgta acagcagtaa tcaattaggc cttaccacat tctcagttaa taatcttaca    480
acattccaag ttaatattaa gtcatccgtc tttggttaaa cataagccaa tgttaagggg    540
acaaaatcaa aaggttaatt tacttaagta ctttttatgt tgaacattta taaacaaaag    600
attaagattt atgaatcatt tttattctaa taaggtttct cattgtaaat aaaatacagc    660
atttataaaa atttcattac aaagtatgtt cataaagtgt aggtttatta atatgccttta   720
ctgagcatct gctatgtggc aagttgttca gaatcctgga ggaacctaca tatcataagc    780
taattttttac tgtatggtgg tgataaatta aaatggtctt atatttcagt ctgcattata   840
gaagaaactt agtaaaattc tttcataatg tagcaaccct attgattcat ttatgagaac    900
ttcaaattag tcagttacct ccctatgaaa tttaaaagat caatgtatag catttaacaa    960
gttgaaaaaa ataaaaagca aacagagtag ccttgaaaat atttttataa gttcaactca   1020
tttagatcac atgaagaaaa tcaaatgaaa gctaaagatc cctagggcta aggagcctaa   1080
cacaaacttt gaccttggcc cgcgcagctt ttttcgggcc tccgtcattg caaatgcccc   1140
aggaaataca aatcccatca agggcagtca gcgtagcata ccaaactcct cctgaaggct   1200
tgaagtgaat tctagcatgc ccattgccta acagcaccca tcaattttg gaacaggttg    1260
tcaattttg gaacaggttg gaaatatgaa gaaagtctaa tacagatgta aaggcagagg    1320
aatagtctcc atttccatag caataagacc taatgtcacc tctagatcgt cagaaagtct   1380
ggctagacat gagcaaattg gaatgaggga gaggaaagca caggtcaaga ttagtactag   1440
tcccttgggc agttctacag ccagatgct tagcttctga cccaaagctg ggactagggt    1500
actgagtgat gtgcttaggg cctaactctc aaagagatac accatgacac taacagtgac   1560
agcctcctta aattttgcat ctcaggtacc tcactcactt aacctagtct aggacattta   1620
aactatagtt ttttcaagag ttttatgtca agaagctcat aatgtcaagg cgttgttggt   1680
gactaataaa tgaatctata tttttagaaaa ttggggatat aaaaaatgga aaaaattaaa   1740
atgttcaaaa gaaaggccat ctcccaatta gagaagtatt gcatgccaaa agtatgtaaa   1800
gttgtccatc aggcaaacta attctgcaac agctcatttg ggactgaaca caattaatat   1860
ttcaaaaatg tagtttgcca tagatgaaat ccgtcctaaa atgtgtctat atgtagtaaa   1920
agtccaataa aatagttatt cttaaaagtg tgtgataacc catcccccac tcttacatct   1980
aacgtgtaca gaggctccaa tatgataatg agttatattt cctgtgacta tctttaaagc   2040
tactacaatg taagtaaatt attctaattg taggagtttt tatagttgcc aatttctaat   2100
caaatgacaa tagctcctca agacggaact aaatagatac ttctatgtga aaatcagaat   2160
ataaatcttt aaaaatgaat gcctttcaaa agaaataatg actaccagtg ctcattcgta   2220
gctgaagtat cagagaggac acttggattg ttaggttcct agcttaatta taacacaggt   2280
caccattgtt aaaaaatgag tggattaatg ttagaaggag tacttattga acactttct    2340
attcataggg aacttaagct ttacaattta atactttga tttccaaatt cat           2393

SEQ ID NO: 91          moltype = RNA   length = 20
FEATURE                Location/Qualifiers
source                 1..20
                       mol_type = other RNA
                       organism = synthetic construct
SEQUENCE: 91
cgcagctgag cagagtgaca                                                 20

SEQ ID NO: 92          moltype = RNA   length = 20
FEATURE                Location/Qualifiers
source                 1..20
                       mol_type = other RNA
                       organism = synthetic construct
SEQUENCE: 92
cagtcctcct tcatataagc                                                 20

SEQ ID NO: 93          moltype = RNA   length = 20
FEATURE                Location/Qualifiers
source                 1..20
                       mol_type = other RNA
                       organism = synthetic construct
SEQUENCE: 93
tgaccacatg tacacagtcc                                                 20
```

-continued

```
SEQ ID NO: 94           moltype = RNA  length = 20
FEATURE                 Location/Qualifiers
source                  1..20
                        mol_type = other RNA
                        organism = synthetic construct
SEQUENCE: 94
gttacactttt aggacagat                                                    20

SEQ ID NO: 95           moltype = RNA  length = 20
FEATURE                 Location/Qualifiers
source                  1..20
                        mol_type = other RNA
                        organism = synthetic construct
SEQUENCE: 95
ggtagggaat gttaaagtca                                                    20

SEQ ID NO: 96           moltype = RNA  length = 20
FEATURE                 Location/Qualifiers
source                  1..20
                        mol_type = other RNA
                        organism = synthetic construct
SEQUENCE: 96
tataagagtt ggttggtagg                                                    20

SEQ ID NO: 97           moltype = RNA  length = 20
FEATURE                 Location/Qualifiers
source                  1..20
                        mol_type = other RNA
                        organism = synthetic construct
SEQUENCE: 97
caaaggagtt gaggctataa                                                    20

SEQ ID NO: 98           moltype = RNA  length = 20
FEATURE                 Location/Qualifiers
source                  1..20
                        mol_type = other RNA
                        organism = synthetic construct
SEQUENCE: 98
gggagtttac attaggatag                                                    20

SEQ ID NO: 99           moltype = RNA  length = 20
FEATURE                 Location/Qualifiers
source                  1..20
                        mol_type = other RNA
                        organism = synthetic construct
SEQUENCE: 99
ggctagactg aaatctataa                                                    20

SEQ ID NO: 100          moltype = RNA  length = 20
FEATURE                 Location/Qualifiers
source                  1..20
                        mol_type = other RNA
                        organism = synthetic construct
SEQUENCE: 100
gctagtttca tacttgagtg                                                    20

SEQ ID NO: 101          moltype = RNA  length = 20
FEATURE                 Location/Qualifiers
source                  1..20
                        mol_type = other RNA
                        organism = synthetic construct
SEQUENCE: 101
cacaatggag gttggaacag                                                    20

SEQ ID NO: 102          moltype = RNA  length = 20
FEATURE                 Location/Qualifiers
source                  1..20
                        mol_type = other RNA
                        organism = synthetic construct
SEQUENCE: 102
tccatcaatt ataattccac                                                    20

SEQ ID NO: 103          moltype = RNA  length = 20
FEATURE                 Location/Qualifiers
source                  1..20
                        mol_type = other RNA
                        organism = synthetic construct
SEQUENCE: 103
attagagact tggaaaatcc                                                    20
```

| | | |
|---|---|---|
| SEQ ID NO: 104<br>FEATURE<br>source | moltype = RNA length = 20<br>Location/Qualifiers<br>1..20<br>mol_type = other RNA<br>organism = synthetic construct | |
| SEQUENCE: 104<br>ggtccatgtc tttagtcatc | | 20 |
| SEQ ID NO: 105<br>FEATURE<br>source | moltype = RNA length = 20<br>Location/Qualifiers<br>1..20<br>mol_type = other RNA<br>organism = synthetic construct | |
| SEQUENCE: 105<br>agacttgcaa actacggtgt | | 20 |
| SEQ ID NO: 106<br>FEATURE<br>source | moltype = RNA length = 20<br>Location/Qualifiers<br>1..20<br>mol_type = other RNA<br>organism = synthetic construct | |
| SEQUENCE: 106<br>ttttatcagt aaagggtccc | | 20 |
| SEQ ID NO: 107<br>FEATURE<br>source | moltype = RNA length = 20<br>Location/Qualifiers<br>1..20<br>mol_type = other RNA<br>organism = synthetic construct | |
| SEQUENCE: 107<br>agtctagaga gaaatgtggg | | 20 |
| SEQ ID NO: 108<br>FEATURE<br>source | moltype = RNA length = 20<br>Location/Qualifiers<br>1..20<br>mol_type = other RNA<br>organism = synthetic construct | |
| SEQUENCE: 108<br>ggatagaatt ctcctactct | | 20 |
| SEQ ID NO: 109<br>FEATURE<br>source | moltype = RNA length = 20<br>Location/Qualifiers<br>1..20<br>mol_type = other RNA<br>organism = synthetic construct | |
| SEQUENCE: 109<br>caacaatcaa caattctagg | | 20 |
| SEQ ID NO: 110<br>FEATURE<br>source | moltype = RNA length = 20<br>Location/Qualifiers<br>1..20<br>mol_type = other RNA<br>organism = synthetic construct | |
| SEQUENCE: 110<br>ttccatagaa atgtcaacaa | | 20 |
| SEQ ID NO: 111<br>FEATURE<br>source | moltype = RNA length = 20<br>Location/Qualifiers<br>1..20<br>mol_type = other RNA<br>organism = synthetic construct | |
| SEQUENCE: 111<br>gactacaaag catgatgaat | | 20 |
| SEQ ID NO: 112<br>FEATURE<br>source | moltype = RNA length = 20<br>Location/Qualifiers<br>1..20<br>mol_type = other RNA<br>organism = synthetic construct | |
| SEQUENCE: 112<br>catttatagc agttgactac | | 20 |
| SEQ ID NO: 113<br>FEATURE<br>source | moltype = RNA length = 20<br>Location/Qualifiers<br>1..20<br>mol_type = other RNA<br>organism = synthetic construct | |

```
SEQUENCE: 113
gcttgaccaa ggaaaagact                                                    20

SEQ ID NO: 114          moltype = RNA   length = 20
FEATURE                 Location/Qualifiers
source                  1..20
                        mol_type = other RNA
                        organism = synthetic construct
SEQUENCE: 114
gtggaagtac tgaggagtcc                                                    20

SEQ ID NO: 115          moltype = RNA   length = 20
FEATURE                 Location/Qualifiers
source                  1..20
                        mol_type = other RNA
                        organism = synthetic construct
SEQUENCE: 115
taatcaaata tgacagtgga                                                    20

SEQ ID NO: 116          moltype = RNA   length = 20
FEATURE                 Location/Qualifiers
source                  1..20
                        mol_type = other RNA
                        organism = synthetic construct
SEQUENCE: 116
cctcccttca tcacttatgt                                                    20

SEQ ID NO: 117          moltype = RNA   length = 20
FEATURE                 Location/Qualifiers
source                  1..20
                        mol_type = other RNA
                        organism = synthetic construct
SEQUENCE: 117
actataatat atttcctccc                                                    20

SEQ ID NO: 118          moltype = RNA   length = 20
FEATURE                 Location/Qualifiers
source                  1..20
                        mol_type = other RNA
                        organism = synthetic construct
SEQUENCE: 118
ccctaaggta cccatgcaat                                                    20

SEQ ID NO: 119          moltype = RNA   length = 20
FEATURE                 Location/Qualifiers
source                  1..20
                        mol_type = other RNA
                        organism = synthetic construct
SEQUENCE: 119
gtcatagtcc cattacccta                                                    20

SEQ ID NO: 120          moltype = RNA   length = 20
FEATURE                 Location/Qualifiers
source                  1..20
                        mol_type = other RNA
                        organism = synthetic construct
SEQUENCE: 120
ggaaactttt taggatgcaa                                                    20

SEQ ID NO: 121          moltype = RNA   length = 20
FEATURE                 Location/Qualifiers
source                  1..20
                        mol_type = other RNA
                        organism = synthetic construct
SEQUENCE: 121
cctcattatg gaaactttc                                                     20

SEQ ID NO: 122          moltype = RNA   length = 20
FEATURE                 Location/Qualifiers
source                  1..20
                        mol_type = other RNA
                        organism = synthetic construct
SEQUENCE: 122
cgatataaac tcaatcctca                                                    20

SEQ ID NO: 123          moltype = RNA   length = 20
FEATURE                 Location/Qualifiers
```

```
source                  1..20
                        mol_type = other RNA
                        organism = synthetic construct
SEQUENCE: 123
gtagtgaggg ttgtctttcc                                                    20

SEQ ID NO: 124          moltype = RNA   length = 20
FEATURE                 Location/Qualifiers
source                  1..20
                        mol_type = other RNA
                        organism = synthetic construct
SEQUENCE: 124
ctcttgtctt tttatgtgtg                                                    20

SEQ ID NO: 125          moltype = RNA   length = 20
FEATURE                 Location/Qualifiers
source                  1..20
                        mol_type = other RNA
                        organism = synthetic construct
SEQUENCE: 125
cgccttgatc tcacctcttg                                                    20

SEQ ID NO: 126          moltype = RNA   length = 20
FEATURE                 Location/Qualifiers
source                  1..20
                        mol_type = other RNA
                        organism = synthetic construct
SEQUENCE: 126
gtccaatact agtttacgcc                                                    20

SEQ ID NO: 127          moltype = RNA   length = 20
FEATURE                 Location/Qualifiers
source                  1..20
                        mol_type = other RNA
                        organism = synthetic construct
SEQUENCE: 127
agtacttact ggcttagtcc                                                    20

SEQ ID NO: 128          moltype = RNA   length = 20
FEATURE                 Location/Qualifiers
source                  1..20
                        mol_type = other RNA
                        organism = synthetic construct
SEQUENCE: 128
ctagagaact gaggactgag                                                    20

SEQ ID NO: 129          moltype = RNA   length = 20
FEATURE                 Location/Qualifiers
source                  1..20
                        mol_type = other RNA
                        organism = synthetic construct
SEQUENCE: 129
ggaaaactcc caacctagag                                                    20

SEQ ID NO: 130          moltype = RNA   length = 20
FEATURE                 Location/Qualifiers
source                  1..20
                        mol_type = other RNA
                        organism = synthetic construct
SEQUENCE: 130
aaatgaattg gaggagaatg                                                    20

SEQ ID NO: 131          moltype = RNA   length = 20
FEATURE                 Location/Qualifiers
source                  1..20
                        mol_type = other RNA
                        organism = synthetic construct
SEQUENCE: 131
ggcgaaattt gtgttgaaga                                                    20

SEQ ID NO: 132          moltype = RNA   length = 20
FEATURE                 Location/Qualifiers
source                  1..20
                        mol_type = other RNA
                        organism = synthetic construct
SEQUENCE: 132
ttgaacaaga aataaaggcg                                                    20

SEQ ID NO: 133          moltype = RNA   length = 20
```

```
FEATURE                 Location/Qualifiers
source                  1..20
                        mol_type = other RNA
                        organism = synthetic construct
SEQUENCE: 133
gtattcataa tagtcatgga                                                    20

SEQ ID NO: 134          moltype = RNA   length = 20
FEATURE                 Location/Qualifiers
source                  1..20
                        mol_type = other RNA
                        organism = synthetic construct
SEQUENCE: 134
tcagccttca tccataaata                                                    20

SEQ ID NO: 135          moltype = RNA   length = 20
FEATURE                 Location/Qualifiers
source                  1..20
                        mol_type = other RNA
                        organism = synthetic construct
SEQUENCE: 135
tatgccttaa aatgttcagc                                                    20

SEQ ID NO: 136          moltype = RNA   length = 20
FEATURE                 Location/Qualifiers
source                  1..20
                        mol_type = other RNA
                        organism = synthetic construct
SEQUENCE: 136
catgggagac ttagtatgcc                                                    20

SEQ ID NO: 137          moltype = RNA   length = 20
FEATURE                 Location/Qualifiers
source                  1..20
                        mol_type = other RNA
                        organism = synthetic construct
SEQUENCE: 137
tgaaaaggta ccatatcatg                                                    20

SEQ ID NO: 138          moltype = RNA   length = 20
FEATURE                 Location/Qualifiers
source                  1..20
                        mol_type = other RNA
                        organism = synthetic construct
SEQUENCE: 138
gtatagaatg ggaaaatgaa                                                    20

SEQ ID NO: 139          moltype = RNA   length = 20
FEATURE                 Location/Qualifiers
source                  1..20
                        mol_type = other RNA
                        organism = synthetic construct
SEQUENCE: 139
agcctagatg cagggtatag                                                    20

SEQ ID NO: 140          moltype = RNA   length = 20
FEATURE                 Location/Qualifiers
source                  1..20
                        mol_type = other RNA
                        organism = synthetic construct
SEQUENCE: 140
atgaagtcat gtggtatatt                                                    20

SEQ ID NO: 141          moltype = RNA   length = 20
FEATURE                 Location/Qualifiers
source                  1..20
                        mol_type = other RNA
                        organism = synthetic construct
SEQUENCE: 141
gccgtggcat gagcaatagc                                                    20

SEQ ID NO: 142          moltype = RNA   length = 20
FEATURE                 Location/Qualifiers
source                  1..20
                        mol_type = other RNA
                        organism = synthetic construct
SEQUENCE: 142
tgcaaattca ccaagtagat                                                    20
```

```
SEQ ID NO: 143              moltype = RNA  length = 20
FEATURE                     Location/Qualifiers
source                      1..20
                            mol_type = other RNA
                            organism = synthetic construct
SEQUENCE: 143
tgtgttatac tgaaggatgc                                                    20

SEQ ID NO: 144              moltype = RNA  length = 20
FEATURE                     Location/Qualifiers
source                      1..20
                            mol_type = other RNA
                            organism = synthetic construct
SEQUENCE: 144
gcatagaatt atgttgagct                                                    20

SEQ ID NO: 145              moltype = RNA  length = 20
FEATURE                     Location/Qualifiers
source                      1..20
                            mol_type = other RNA
                            organism = synthetic construct
SEQUENCE: 145
agatcaagtt ccttgtgcat                                                    20

SEQ ID NO: 146              moltype = RNA  length = 20
FEATURE                     Location/Qualifiers
source                      1..20
                            mol_type = other RNA
                            organism = synthetic construct
SEQUENCE: 146
ctggtgccat gaaagttgcc                                                    20

SEQ ID NO: 147              moltype = RNA  length = 20
FEATURE                     Location/Qualifiers
source                      1..20
                            mol_type = other RNA
                            organism = synthetic construct
SEQUENCE: 147
ggctcatact agtttataca                                                    20

SEQ ID NO: 148              moltype = RNA  length = 20
FEATURE                     Location/Qualifiers
source                      1..20
                            mol_type = other RNA
                            organism = synthetic construct
SEQUENCE: 148
aagctaaaca aaataggctc                                                    20

SEQ ID NO: 149              moltype = RNA  length = 20
FEATURE                     Location/Qualifiers
source                      1..20
                            mol_type = other RNA
                            organism = synthetic construct
SEQUENCE: 149
catggctcct ggtgatagaa                                                    20

SEQ ID NO: 150              moltype = RNA  length = 20
FEATURE                     Location/Qualifiers
source                      1..20
                            mol_type = other RNA
                            organism = synthetic construct
SEQUENCE: 150
gatttcaaag tgcttcatgg                                                    20

SEQ ID NO: 151              moltype = RNA  length = 20
FEATURE                     Location/Qualifiers
source                      1..20
                            mol_type = other RNA
                            organism = synthetic construct
SEQUENCE: 151
agtcctcacg cttacttaat                                                    20

SEQ ID NO: 152              moltype = RNA  length = 20
FEATURE                     Location/Qualifiers
source                      1..20
                            mol_type = other RNA
                            organism = synthetic construct
SEQUENCE: 152
caggcacaca catcaggctg                                                    20
```

| | | |
|---|---|---|
| SEQ ID NO: 153<br>FEATURE<br>source | moltype = RNA length = 20<br>Location/Qualifiers<br>1..20<br>mol_type = other RNA<br>organism = synthetic construct | |
| SEQUENCE: 153<br>gcaggcacac acatcaggct | | 20 |
| SEQ ID NO: 154<br>FEATURE<br>source | moltype = RNA length = 20<br>Location/Qualifiers<br>1..20<br>mol_type = other RNA<br>organism = synthetic construct | |
| SEQUENCE: 154<br>atgcaggcac acacatcagg | | 20 |
| SEQ ID NO: 155<br>FEATURE<br>source | moltype = RNA length = 20<br>Location/Qualifiers<br>1..20<br>mol_type = other RNA<br>organism = synthetic construct | |
| SEQUENCE: 155<br>gaatgcaggc acacacatca | | 20 |
| SEQ ID NO: 156<br>FEATURE<br>source | moltype = RNA length = 20<br>Location/Qualifiers<br>1..20<br>mol_type = other RNA<br>organism = synthetic construct | |
| SEQUENCE: 156<br>tgcaggcaca cacatcaggc | | 20 |
| SEQ ID NO: 157<br>FEATURE<br>source | moltype = RNA length = 22<br>Location/Qualifiers<br>1..22<br>mol_type = other RNA<br>organism = synthetic construct | |
| SEQUENCE: 157<br>tgcaggcaca cacatcaggc tg | | 22 |
| SEQ ID NO: 158<br>FEATURE<br>source | moltype = RNA length = 20<br>Location/Qualifiers<br>1..20<br>mol_type = other RNA<br>organism = synthetic construct | |
| SEQUENCE: 158<br>caggcacaca catcaggctg | | 20 |
| SEQ ID NO: 159<br>FEATURE<br>source | moltype = RNA length = 20<br>Location/Qualifiers<br>1..20<br>mol_type = other RNA<br>organism = synthetic construct | |
| SEQUENCE: 159<br>gcaggcacac acatcaggct | | 20 |
| SEQ ID NO: 160<br>FEATURE<br>source | moltype = RNA length = 20<br>Location/Qualifiers<br>1..20<br>mol_type = other RNA<br>organism = synthetic construct | |
| SEQUENCE: 160<br>atgcaggcac acacatcagg | | 20 |
| SEQ ID NO: 161<br>FEATURE<br>source | moltype = RNA length = 20<br>Location/Qualifiers<br>1..20<br>mol_type = other RNA<br>organism = synthetic construct | |
| SEQUENCE: 161<br>tgcaggcaca cacatcaggc | | 20 |
| SEQ ID NO: 162<br>FEATURE<br>source | moltype = RNA length = 19<br>Location/Qualifiers<br>1..19<br>mol_type = other RNA<br>organism = synthetic construct | |

| | | |
|---|---|---|
| SEQUENCE: 162 tgcaggcaca cacatcagg | | 19 |
| SEQ ID NO: 163 FEATURE source | moltype = RNA  length = 18 Location/Qualifiers 1..18 mol_type = other RNA organism = synthetic construct | |
| SEQUENCE: 163 tgcaggcaca cacatcag | | 18 |
| SEQ ID NO: 164 FEATURE source | moltype = RNA  length = 15 Location/Qualifiers 1..15 mol_type = other RNA organism = synthetic construct | |
| SEQUENCE: 164 tgcaggcaca cacat | | 15 |
| SEQ ID NO: 165 SEQUENCE: 165 000 | moltype =   length = | |
| SEQ ID NO: 166 FEATURE source | moltype = RNA  length = 20 Location/Qualifiers 1..20 mol_type = other RNA organism = synthetic construct | |
| SEQUENCE: 166 tgcaggcaca cacatcaggc | | 20 |
| SEQ ID NO: 167 FEATURE source | moltype = RNA  length = 20 Location/Qualifiers 1..20 mol_type = other RNA organism = synthetic construct | |
| SEQUENCE: 167 caggcatgaa tgcaggcaca | | 20 |
| SEQ ID NO: 168 FEATURE source | moltype = RNA  length = 20 Location/Qualifiers 1..20 mol_type = other RNA organism = synthetic construct | |
| SEQUENCE: 168 acaggcatga atgcaggcac | | 20 |
| SEQ ID NO: 169 FEATURE source | moltype = RNA  length = 20 Location/Qualifiers 1..20 mol_type = other RNA organism = synthetic construct | |
| SEQUENCE: 169 gtgacaggca tgaatgcagg | | 20 |
| SEQ ID NO: 170 FEATURE source | moltype = RNA  length = 20 Location/Qualifiers 1..20 mol_type = other RNA organism = synthetic construct | |
| SEQUENCE: 170 agtgacaggc atgaatgcag | | 20 |
| SEQ ID NO: 171 FEATURE source | moltype = RNA  length = 20 Location/Qualifiers 1..20 mol_type = other RNA organism = synthetic construct | |
| SEQUENCE: 171 gagtgacagg catgaatgca | | 20 |
| SEQ ID NO: 172 FEATURE source | moltype = RNA  length = 16 Location/Qualifiers 1..16 mol_type = other RNA organism = synthetic construct | |
| SEQUENCE: 172 aatgcaggca cacaca | | 16 |

```
SEQ ID NO: 173            moltype = RNA   length = 16
FEATURE                   Location/Qualifiers
source                    1..16
                          mol_type = other RNA
                          organism = synthetic construct
SEQUENCE: 173
tgaatgcagg cacaca                                                         16

SEQ ID NO: 174            moltype = RNA   length = 16
FEATURE                   Location/Qualifiers
source                    1..16
                          mol_type = other RNA
                          organism = synthetic construct
SEQUENCE: 174
catgaatgca ggcaca                                                         16

SEQ ID NO: 175            moltype = RNA   length = 16
FEATURE                   Location/Qualifiers
source                    1..16
                          mol_type = other RNA
                          organism = synthetic construct
SEQUENCE: 175
tgcaggcaca cacatc                                                         16

SEQ ID NO: 176            moltype = RNA   length = 16
FEATURE                   Location/Qualifiers
source                    1..16
                          mol_type = other RNA
                          organism = synthetic construct
SEQUENCE: 176
caggcacaca catcag                                                         16

SEQ ID NO: 177            moltype = RNA   length = 16
FEATURE                   Location/Qualifiers
source                    1..16
                          mol_type = other RNA
                          organism = synthetic construct
SEQUENCE: 177
ggcacacaca tcaggc                                                         16

SEQ ID NO: 178            moltype = RNA   length = 16
FEATURE                   Location/Qualifiers
source                    1..16
                          mol_type = other RNA
                          organism = synthetic construct
SEQUENCE: 178
cacacacatc aggctg                                                         16

SEQ ID NO: 179            moltype = RNA   length = 16
FEATURE                   Location/Qualifiers
source                    1..16
                          mol_type = other RNA
                          organism = synthetic construct
SEQUENCE: 179
cacacatcag gctggg                                                         16

SEQ ID NO: 180            moltype = RNA   length = 30
FEATURE                   Location/Qualifiers
source                    1..30
                          mol_type = other RNA
                          organism = synthetic construct
SEQUENCE: 180
tgcaggcaca cacatcaggc tttttttttt                                          30

SEQ ID NO: 181            moltype = RNA   length = 30
FEATURE                   Location/Qualifiers
source                    1..30
                          mol_type = other RNA
                          organism = synthetic construct
SEQUENCE: 181
tttttttttt tgcaggcaca cacatcaggc                                          30

SEQ ID NO: 182            moltype = RNA   length = 20
FEATURE                   Location/Qualifiers
source                    1..20
                          mol_type = other RNA
                          organism = synthetic construct
SEQUENCE: 182
acattacttt aaatgattac                                                     20
```

| | | |
|---|---|---|
| SEQ ID NO: 183<br>FEATURE<br>source | moltype = RNA   length = 20<br>Location/Qualifiers<br>1..20<br>mol_type = other RNA<br>organism = synthetic construct | |
| SEQUENCE: 183<br>gatgttatta caaagttctt | | 20 |
| SEQ ID NO: 184<br>FEATURE<br>source | moltype = RNA   length = 20<br>Location/Qualifiers<br>1..20<br>mol_type = other RNA<br>organism = synthetic construct | |
| SEQUENCE: 184<br>ggaggcaata ttatgttaaa | | 20 |
| SEQ ID NO: 185<br>FEATURE<br>source | moltype = RNA   length = 20<br>Location/Qualifiers<br>1..20<br>mol_type = other RNA<br>organism = synthetic construct | |
| SEQUENCE: 185<br>gcataatgct ttttggaggc | | 20 |
| SEQ ID NO: 186<br>FEATURE<br>source | moltype = RNA   length = 20<br>Location/Qualifiers<br>1..20<br>mol_type = other RNA<br>organism = synthetic construct | |
| SEQUENCE: 186<br>cttgcataat gctttttgga | | 20 |
| SEQ ID NO: 187<br>FEATURE<br>source | moltype = RNA   length = 20<br>Location/Qualifiers<br>1..20<br>mol_type = other RNA<br>organism = synthetic construct | |
| SEQUENCE: 187<br>acttgcataa tgctttttgg | | 20 |
| SEQ ID NO: 188<br>FEATURE<br>source | moltype = RNA   length = 20<br>Location/Qualifiers<br>1..20<br>mol_type = other RNA<br>organism = synthetic construct | |
| SEQUENCE: 188<br>gacttgcata atgctttttg | | 20 |
| SEQ ID NO: 189<br>FEATURE<br>source | moltype = RNA   length = 20<br>Location/Qualifiers<br>1..20<br>mol_type = other RNA<br>organism = synthetic construct | |
| SEQUENCE: 189<br>ccattgactt gcataatgct | | 20 |
| SEQ ID NO: 190<br>FEATURE<br>source | moltype = RNA   length = 20<br>Location/Qualifiers<br>1..20<br>mol_type = other RNA<br>organism = synthetic construct | |
| SEQUENCE: 190<br>gccattgact tgcataatgc | | 20 |
| SEQ ID NO: 191<br>FEATURE<br>source | moltype = RNA   length = 20<br>Location/Qualifiers<br>1..20<br>mol_type = other RNA<br>organism = synthetic construct | |
| SEQUENCE: 191<br>tctagcattt atgtcaatgc | | 20 |
| SEQ ID NO: 192<br>FEATURE<br>source | moltype = RNA   length = 20<br>Location/Qualifiers<br>1..20<br>mol_type = other RNA<br>organism = synthetic construct | |

-continued

| | | |
|---|---|---|
| SEQUENCE: 192<br>ctctgttaac actaaagtat | | 20 |
| SEQ ID NO: 193<br>FEATURE<br>source | moltype = RNA   length = 20<br>Location/Qualifiers<br>1..20<br>mol_type = other RNA<br>organism = synthetic construct | |
| SEQUENCE: 193<br>tctctgttaa cactaaagta | | 20 |
| SEQ ID NO: 194<br>FEATURE<br>source | moltype = RNA   length = 20<br>Location/Qualifiers<br>1..20<br>mol_type = other RNA<br>organism = synthetic construct | |
| SEQUENCE: 194<br>atctctgtta acactaaagt | | 20 |
| SEQ ID NO: 195<br>FEATURE<br>source | moltype = RNA   length = 20<br>Location/Qualifiers<br>1..20<br>mol_type = other RNA<br>organism = synthetic construct | |
| SEQUENCE: 195<br>gataataacc caccacacaa | | 20 |
| SEQ ID NO: 196<br>FEATURE<br>source | moltype = RNA   length = 20<br>Location/Qualifiers<br>1..20<br>mol_type = other RNA<br>organism = synthetic construct | |
| SEQUENCE: 196<br>gaaatgtgga aatacagaat | | 20 |
| SEQ ID NO: 197<br>FEATURE<br>source | moltype = RNA   length = 20<br>Location/Qualifiers<br>1..20<br>mol_type = other RNA<br>organism = synthetic construct | |
| SEQUENCE: 197<br>atgtcaagta ctaggttgta | | 20 |
| SEQ ID NO: 198<br>FEATURE<br>source | moltype = RNA   length = 20<br>Location/Qualifiers<br>1..20<br>mol_type = other RNA<br>organism = synthetic construct | |
| SEQUENCE: 198<br>ccttattgac atatctggta | | 20 |
| SEQ ID NO: 199<br>FEATURE<br>source | moltype = RNA   length = 20<br>Location/Qualifiers<br>1..20<br>mol_type = other RNA<br>organism = synthetic construct | |
| SEQUENCE: 199<br>tcagggcact ttattttatg | | 20 |
| SEQ ID NO: 200<br>FEATURE<br>source | moltype = RNA   length = 20<br>Location/Qualifiers<br>1..20<br>mol_type = other RNA<br>organism = synthetic construct | |
| SEQUENCE: 200<br>gaaatccctc agggcacttt | | 20 |
| SEQ ID NO: 201<br>FEATURE<br>source | moltype = RNA   length = 20<br>Location/Qualifiers<br>1..20<br>mol_type = other RNA<br>organism = synthetic construct | |
| SEQUENCE: 201<br>tgaaatccct cagggcactt | | 20 |
| SEQ ID NO: 202<br>FEATURE | moltype = RNA   length = 20<br>Location/Qualifiers | |

```
source                      1..20
                            mol_type = other RNA
                            organism = synthetic construct
SEQUENCE: 202
gtgaaatccc tcagggcact                                                   20

SEQ ID NO: 203              moltype = RNA   length = 20
FEATURE                     Location/Qualifiers
source                      1..20
                            mol_type = other RNA
                            organism = synthetic construct
SEQUENCE: 203
tgtgaaatcc ctcagggcac                                                   20

SEQ ID NO: 204              moltype = RNA   length = 20
FEATURE                     Location/Qualifiers
source                      1..20
                            mol_type = other RNA
                            organism = synthetic construct
SEQUENCE: 204
ctgtgaaatc cctcagggca                                                   20

SEQ ID NO: 205              moltype = RNA   length = 20
FEATURE                     Location/Qualifiers
source                      1..20
                            mol_type = other RNA
                            organism = synthetic construct
SEQUENCE: 205
gcatttagcc tgtgaaatcc                                                   20

SEQ ID NO: 206              moltype = RNA   length = 20
FEATURE                     Location/Qualifiers
source                      1..20
                            mol_type = other RNA
                            organism = synthetic construct
SEQUENCE: 206
tagaagcatt tagcctgtga                                                   20

SEQ ID NO: 207              moltype = RNA   length = 20
FEATURE                     Location/Qualifiers
source                      1..20
                            mol_type = other RNA
                            organism = synthetic construct
SEQUENCE: 207
gtcttctttt ctattaatac                                                   20

SEQ ID NO: 208              moltype = RNA   length = 20
FEATURE                     Location/Qualifiers
source                      1..20
                            mol_type = other RNA
                            organism = synthetic construct
SEQUENCE: 208
agtcactctc tgataaaatg                                                   20

SEQ ID NO: 209              moltype = RNA   length = 20
FEATURE                     Location/Qualifiers
source                      1..20
                            mol_type = other RNA
                            organism = synthetic construct
SEQUENCE: 209
gtgagccagg tcatcaaagg                                                   20

SEQ ID NO: 210              moltype = RNA   length = 20
FEATURE                     Location/Qualifiers
source                      1..20
                            mol_type = other RNA
                            organism = synthetic construct
SEQUENCE: 210
tttgtgagcc aggtcatcaa                                                   20

SEQ ID NO: 211              moltype = RNA   length = 20
FEATURE                     Location/Qualifiers
source                      1..20
                            mol_type = other RNA
                            organism = synthetic construct
SEQUENCE: 211
cattctttgt gagccaggtc                                                   20

SEQ ID NO: 212              moltype = RNA   length = 20
```

```
FEATURE                 Location/Qualifiers
source                  1..20
                        mol_type = other RNA
                        organism = synthetic construct
SEQUENCE: 212
ggaagtacat tctttgtgag                                                       20

SEQ ID NO: 213          moltype = RNA   length = 20
FEATURE                 Location/Qualifiers
source                  1..20
                        mol_type = other RNA
                        organism = synthetic construct
SEQUENCE: 213
acttggaagt acattctttg                                                       20

SEQ ID NO: 214          moltype = RNA   length = 20
FEATURE                 Location/Qualifiers
source                  1..20
                        mol_type = other RNA
                        organism = synthetic construct
SEQUENCE: 214
gtgtacttgg aagtacattc                                                       20

SEQ ID NO: 215          moltype = RNA   length = 20
FEATURE                 Location/Qualifiers
source                  1..20
                        mol_type = other RNA
                        organism = synthetic construct
SEQUENCE: 215
gaccctgtgt acttggaagt                                                       20

SEQ ID NO: 216          moltype = RNA   length = 20
FEATURE                 Location/Qualifiers
source                  1..20
                        mol_type = other RNA
                        organism = synthetic construct
SEQUENCE: 216
tggggaccct gtgtacttgg                                                       20

SEQ ID NO: 217          moltype = RNA   length = 20
FEATURE                 Location/Qualifiers
source                  1..20
                        mol_type = other RNA
                        organism = synthetic construct
SEQUENCE: 217
atcaggctgg ggaccctgtg                                                       20

SEQ ID NO: 218          moltype = RNA   length = 20
FEATURE                 Location/Qualifiers
source                  1..20
                        mol_type = other RNA
                        organism = synthetic construct
SEQUENCE: 218
acacatcagg ctggggaccc                                                       20

SEQ ID NO: 219          moltype = RNA   length = 20
FEATURE                 Location/Qualifiers
source                  1..20
                        mol_type = other RNA
                        organism = synthetic construct
SEQUENCE: 219
ggcacacaca tcaggctggg                                                       20

SEQ ID NO: 220          moltype = RNA   length = 20
FEATURE                 Location/Qualifiers
source                  1..20
                        mol_type = other RNA
                        organism = synthetic construct
SEQUENCE: 220
atgaatgcag gcacacacat                                                       20

SEQ ID NO: 221          moltype = RNA   length = 20
FEATURE                 Location/Qualifiers
source                  1..20
                        mol_type = other RNA
                        organism = synthetic construct
SEQUENCE: 221
aggcatgaat gcaggcacac                                                       20
```

| | | |
|---|---|---|
| SEQ ID NO: 222<br>FEATURE<br>source | moltype = RNA   length = 20<br>Location/Qualifiers<br>1..20<br>mol_type = other RNA<br>organism = synthetic construct | |
| SEQUENCE: 222<br>tgacaggcat gaatgcaggc | | 20 |
| SEQ ID NO: 223<br>FEATURE<br>source | moltype = RNA   length = 20<br>Location/Qualifiers<br>1..20<br>mol_type = other RNA<br>organism = synthetic construct | |
| SEQUENCE: 223<br>agagtgacag gcatgaatgc | | 20 |
| SEQ ID NO: 224<br>FEATURE<br>source | moltype = RNA   length = 20<br>Location/Qualifiers<br>1..20<br>mol_type = other RNA<br>organism = synthetic construct | |
| SEQUENCE: 224<br>gagcagagtg acaggcatga | | 20 |
| SEQ ID NO: 225<br>FEATURE<br>source | moltype = RNA   length = 20<br>Location/Qualifiers<br>1..20<br>mol_type = other RNA<br>organism = synthetic construct | |
| SEQUENCE: 225<br>cagctgagca gagtgacagg | | 20 |
| SEQ ID NO: 226<br>FEATURE<br>source | moltype = RNA   length = 20<br>Location/Qualifiers<br>1..20<br>mol_type = other RNA<br>organism = synthetic construct | |
| SEQUENCE: 226<br>tgcacgcagc tgagcagagt | | 20 |
| SEQ ID NO: 227<br>FEATURE<br>source | moltype = RNA   length = 20<br>Location/Qualifiers<br>1..20<br>mol_type = other RNA<br>organism = synthetic construct | |
| SEQUENCE: 227<br>tgtctgcacg cagctgagca | | 20 |
| SEQ ID NO: 228<br>FEATURE<br>source | moltype = RNA   length = 20<br>Location/Qualifiers<br>1..20<br>mol_type = other RNA<br>organism = synthetic construct | |
| SEQUENCE: 228<br>aagctgtctg cacgcagctg | | 20 |
| SEQ ID NO: 229<br>FEATURE<br>source | moltype = RNA   length = 20<br>Location/Qualifiers<br>1..20<br>mol_type = other RNA<br>organism = synthetic construct | |
| SEQUENCE: 229<br>atataagctg tctgcacgca | | 20 |
| SEQ ID NO: 230<br>FEATURE<br>source | moltype = RNA   length = 20<br>Location/Qualifiers<br>1..20<br>mol_type = other RNA<br>organism = synthetic construct | |
| SEQUENCE: 230<br>ccttcatata agctgtctgc | | 20 |
| SEQ ID NO: 231<br>FEATURE<br>source | moltype = RNA   length = 20<br>Location/Qualifiers<br>1..20<br>mol_type = other RNA<br>organism = synthetic construct | |
| SEQUENCE: 231<br>gtcctccttc atataagctg | | 20 |

| | | |
|---|---|---|
| SEQ ID NO: 232<br>FEATURE<br>source | moltype = RNA   length = 20<br>Location/Qualifiers<br>1..20<br>mol_type = other RNA<br>organism = synthetic construct | |
| SEQUENCE: 232<br>ttcttctctg accacatgta | | 20 |
| SEQ ID NO: 233<br>FEATURE<br>source | moltype = RNA   length = 20<br>Location/Qualifiers<br>1..20<br>mol_type = other RNA<br>organism = synthetic construct | |
| SEQUENCE: 233<br>acattttaaa aaataagcat | | 20 |
| SEQ ID NO: 234<br>FEATURE<br>source | moltype = RNA   length = 20<br>Location/Qualifiers<br>1..20<br>mol_type = other RNA<br>organism = synthetic construct | |
| SEQUENCE: 234<br>acactttag gacagattat | | 20 |
| SEQ ID NO: 235<br>FEATURE<br>source | moltype = RNA   length = 20<br>Location/Qualifiers<br>1..20<br>mol_type = other RNA<br>organism = synthetic construct | |
| SEQUENCE: 235<br>tgttacactt ttaggacaga | | 20 |
| SEQ ID NO: 236<br>FEATURE<br>source | moltype = RNA   length = 20<br>Location/Qualifiers<br>1..20<br>mol_type = other RNA<br>organism = synthetic construct | |
| SEQUENCE: 236<br>ggaaatgtta cacttttagg | | 20 |
| SEQ ID NO: 237<br>FEATURE<br>source | moltype = RNA   length = 20<br>Location/Qualifiers<br>1..20<br>mol_type = other RNA<br>organism = synthetic construct | |
| SEQUENCE: 237<br>gacatgaaaa aatttagtgg | | 20 |
| SEQ ID NO: 238<br>FEATURE<br>source | moltype = RNA   length = 20<br>Location/Qualifiers<br>1..20<br>mol_type = other RNA<br>organism = synthetic construct | |
| SEQUENCE: 238<br>ggttggtagg gaatgttaaa | | 20 |
| SEQ ID NO: 239<br>FEATURE<br>source | moltype = RNA   length = 20<br>Location/Qualifiers<br>1..20<br>mol_type = other RNA<br>organism = synthetic construct | |
| SEQUENCE: 239<br>tggttggtag ggaatgttaa | | 20 |
| SEQ ID NO: 240<br>FEATURE<br>source | moltype = RNA   length = 20<br>Location/Qualifiers<br>1..20<br>mol_type = other RNA<br>organism = synthetic construct | |
| SEQUENCE: 240<br>ttggttggta gggaatgtta | | 20 |
| SEQ ID NO: 241<br>FEATURE<br>source | moltype = RNA   length = 20<br>Location/Qualifiers<br>1..20<br>mol_type = other RNA<br>organism = synthetic construct | |

-continued

```
SEQUENCE: 241
gttggttggt agggaatgtt                                                   20

SEQ ID NO: 242         moltype = RNA   length = 20
FEATURE                Location/Qualifiers
source                 1..20
                       mol_type = other RNA
                       organism = synthetic construct
SEQUENCE: 242
agttggttgg tagggaatgt                                                   20

SEQ ID NO: 243         moltype = RNA   length = 20
FEATURE                Location/Qualifiers
source                 1..20
                       mol_type = other RNA
                       organism = synthetic construct
SEQUENCE: 243
gagttggttg gtagggaatg                                                   20

SEQ ID NO: 244         moltype = RNA   length = 20
FEATURE                Location/Qualifiers
source                 1..20
                       mol_type = other RNA
                       organism = synthetic construct
SEQUENCE: 244
agagttggtt ggtagggaat                                                   20

SEQ ID NO: 245         moltype = RNA   length = 20
FEATURE                Location/Qualifiers
source                 1..20
                       mol_type = other RNA
                       organism = synthetic construct
SEQUENCE: 245
aagagttggt tggtagggaa                                                   20

SEQ ID NO: 246         moltype = RNA   length = 20
FEATURE                Location/Qualifiers
source                 1..20
                       mol_type = other RNA
                       organism = synthetic construct
SEQUENCE: 246
taagagttgg ttggtaggga                                                   20

SEQ ID NO: 247         moltype = RNA   length = 20
FEATURE                Location/Qualifiers
source                 1..20
                       mol_type = other RNA
                       organism = synthetic construct
SEQUENCE: 247
ataagagttg gttggtaggg                                                   20

SEQ ID NO: 248         moltype = RNA   length = 20
FEATURE                Location/Qualifiers
source                 1..20
                       mol_type = other RNA
                       organism = synthetic construct
SEQUENCE: 248
ctataagagt tggttggtag                                                   20

SEQ ID NO: 249         moltype = RNA   length = 20
FEATURE                Location/Qualifiers
source                 1..20
                       mol_type = other RNA
                       organism = synthetic construct
SEQUENCE: 249
gagggagttt acattaggat                                                   20

SEQ ID NO: 250         moltype = RNA   length = 20
FEATURE                Location/Qualifiers
source                 1..20
                       mol_type = other RNA
                       organism = synthetic construct
SEQUENCE: 250
tggaaaaaaa tatattacac                                                   20

SEQ ID NO: 251         moltype = RNA   length = 20
FEATURE                Location/Qualifiers
```

```
source                        1..20
                              mol_type = other RNA
                              organism = synthetic construct
SEQUENCE: 251
gctagactga aatctataac                                                    20

SEQ ID NO: 252                moltype = RNA   length = 20
FEATURE                       Location/Qualifiers
source                        1..20
                              mol_type = other RNA
                              organism = synthetic construct
SEQUENCE: 252
gtgttcaggc tagactgaaa                                                    20

SEQ ID NO: 253                moltype = RNA   length = 20
FEATURE                       Location/Qualifiers
source                        1..20
                              mol_type = other RNA
                              organism = synthetic construct
SEQUENCE: 253
agtgttcagg ctagactgaa                                                    20

SEQ ID NO: 254                moltype = RNA   length = 20
FEATURE                       Location/Qualifiers
source                        1..20
                              mol_type = other RNA
                              organism = synthetic construct
SEQUENCE: 254
gagtgttcag gctagactga                                                    20

SEQ ID NO: 255                moltype = RNA   length = 20
FEATURE                       Location/Qualifiers
source                        1..20
                              mol_type = other RNA
                              organism = synthetic construct
SEQUENCE: 255
tgagtgttca ggctagactg                                                    20

SEQ ID NO: 256                moltype = RNA   length = 20
FEATURE                       Location/Qualifiers
source                        1..20
                              mol_type = other RNA
                              organism = synthetic construct
SEQUENCE: 256
ttgagtgttc aggctagact                                                    20

SEQ ID NO: 257                moltype = RNA   length = 20
FEATURE                       Location/Qualifiers
source                        1..20
                              mol_type = other RNA
                              organism = synthetic construct
SEQUENCE: 257
cttgagtgtt caggctagac                                                    20

SEQ ID NO: 258                moltype = RNA   length = 20
FEATURE                       Location/Qualifiers
source                        1..20
                              mol_type = other RNA
                              organism = synthetic construct
SEQUENCE: 258
acttgagtgt tcaggctaga                                                    20

SEQ ID NO: 259                moltype = RNA   length = 20
FEATURE                       Location/Qualifiers
source                        1..20
                              mol_type = other RNA
                              organism = synthetic construct
SEQUENCE: 259
tacttgagtg ttcaggctag                                                    20

SEQ ID NO: 260                moltype = RNA   length = 20
FEATURE                       Location/Qualifiers
source                        1..20
                              mol_type = other RNA
                              organism = synthetic construct
SEQUENCE: 260
atacttgagt gttcaggcta                                                    20

SEQ ID NO: 261                moltype = RNA   length = 20
```

```
                              -continued

FEATURE             Location/Qualifiers
source              1..20
                    mol_type = other RNA
                    organism = synthetic construct
SEQUENCE: 261
catacttgag tgttcaggct                                               20

SEQ ID NO: 262      moltype = RNA   length = 20
FEATURE             Location/Qualifiers
source              1..20
                    mol_type = other RNA
                    organism = synthetic construct
SEQUENCE: 262
tcatacttga gtgttcaggc                                               20

SEQ ID NO: 263      moltype = RNA   length = 20
FEATURE             Location/Qualifiers
source              1..20
                    mol_type = other RNA
                    organism = synthetic construct
SEQUENCE: 263
ttcatacttg agtgttcagg                                               20

SEQ ID NO: 264      moltype = RNA   length = 20
FEATURE             Location/Qualifiers
source              1..20
                    mol_type = other RNA
                    organism = synthetic construct
SEQUENCE: 264
gtttcatact tgagtgttca                                               20

SEQ ID NO: 265      moltype = RNA   length = 20
FEATURE             Location/Qualifiers
source              1..20
                    mol_type = other RNA
                    organism = synthetic construct
SEQUENCE: 265
ggctagtttc atacttgagt                                               20

SEQ ID NO: 266      moltype = RNA   length = 20
FEATURE             Location/Qualifiers
source              1..20
                    mol_type = other RNA
                    organism = synthetic construct
SEQUENCE: 266
gtggctagtt tcatacttga                                               20

SEQ ID NO: 267      moltype = RNA   length = 20
FEATURE             Location/Qualifiers
source              1..20
                    mol_type = other RNA
                    organism = synthetic construct
SEQUENCE: 267
agtggctagt ttcatacttg                                               20

SEQ ID NO: 268      moltype = RNA   length = 20
FEATURE             Location/Qualifiers
source              1..20
                    mol_type = other RNA
                    organism = synthetic construct
SEQUENCE: 268
ggaggttgga acagccaata                                               20

SEQ ID NO: 269      moltype = RNA   length = 20
FEATURE             Location/Qualifiers
source              1..20
                    mol_type = other RNA
                    organism = synthetic construct
SEQUENCE: 269
caatggaggt tggaacagcc                                               20

SEQ ID NO: 270      moltype = RNA   length = 20
FEATURE             Location/Qualifiers
source              1..20
                    mol_type = other RNA
                    organism = synthetic construct
SEQUENCE: 270
acaatggagg ttggaacagc                                               20
```

-continued

| | | |
|---|---|---|
| SEQ ID NO: 271<br>FEATURE<br>source | moltype = RNA   length = 20<br>Location/Qualifiers<br>1..20<br>mol_type = other RNA<br>organism = synthetic construct | |
| SEQUENCE: 271<br>ccacaatgga ggttggaaca | | 20 |
| SEQ ID NO: 272<br>FEATURE<br>source | moltype = RNA   length = 20<br>Location/Qualifiers<br>1..20<br>mol_type = other RNA<br>organism = synthetic construct | |
| SEQUENCE: 272<br>tccacaatgg aggttggaac | | 20 |
| SEQ ID NO: 273<br>FEATURE<br>source | moltype = RNA   length = 20<br>Location/Qualifiers<br>1..20<br>mol_type = other RNA<br>organism = synthetic construct | |
| SEQUENCE: 273<br>ttccacaatg gaggttggaa | | 20 |
| SEQ ID NO: 274<br>FEATURE<br>source | moltype = RNA   length = 20<br>Location/Qualifiers<br>1..20<br>mol_type = other RNA<br>organism = synthetic construct | |
| SEQUENCE: 274<br>attccacaat ggaggttgga | | 20 |
| SEQ ID NO: 275<br>FEATURE<br>source | moltype = RNA   length = 20<br>Location/Qualifiers<br>1..20<br>mol_type = other RNA<br>organism = synthetic construct | |
| SEQUENCE: 275<br>aattccacaa tggaggttgg | | 20 |
| SEQ ID NO: 276<br>FEATURE<br>source | moltype = RNA   length = 20<br>Location/Qualifiers<br>1..20<br>mol_type = other RNA<br>organism = synthetic construct | |
| SEQUENCE: 276<br>taattccaca atggaggttg | | 20 |
| SEQ ID NO: 277<br>FEATURE<br>source | moltype = RNA   length = 20<br>Location/Qualifiers<br>1..20<br>mol_type = other RNA<br>organism = synthetic construct | |
| SEQUENCE: 277<br>atccatcaat tataattcca | | 20 |
| SEQ ID NO: 278<br>FEATURE<br>source | moltype = RNA   length = 20<br>Location/Qualifiers<br>1..20<br>mol_type = other RNA<br>organism = synthetic construct | |
| SEQUENCE: 278<br>aatccatcaa ttataattcc | | 20 |
| SEQ ID NO: 279<br>FEATURE<br>source | moltype = RNA   length = 20<br>Location/Qualifiers<br>1..20<br>mol_type = other RNA<br>organism = synthetic construct | |
| SEQUENCE: 279<br>aaatccatca attataattc | | 20 |
| SEQ ID NO: 280<br>FEATURE<br>source | moltype = RNA   length = 20<br>Location/Qualifiers<br>1..20<br>mol_type = other RNA<br>organism = synthetic construct | |
| SEQUENCE: 280<br>aaaatccatc aattataatt | | 20 |

| | | |
|---|---|---|
| SEQ ID NO: 281<br>FEATURE<br>source | moltype = RNA   length = 20<br>Location/Qualifiers<br>1..20<br>mol_type = other RNA<br>organism = synthetic construct | |
| SEQUENCE: 281<br>gaaaatccat caattataat | | 20 |
| SEQ ID NO: 282<br>FEATURE<br>source | moltype = RNA   length = 20<br>Location/Qualifiers<br>1..20<br>mol_type = other RNA<br>organism = synthetic construct | |
| SEQUENCE: 282<br>ggaaaatcca tcaattataa | | 20 |
| SEQ ID NO: 283<br>FEATURE<br>source | moltype = RNA   length = 20<br>Location/Qualifiers<br>1..20<br>mol_type = other RNA<br>organism = synthetic construct | |
| SEQUENCE: 283<br>tggaaaatcc atcaattata | | 20 |
| SEQ ID NO: 284<br>FEATURE<br>source | moltype = RNA   length = 20<br>Location/Qualifiers<br>1..20<br>mol_type = other RNA<br>organism = synthetic construct | |
| SEQUENCE: 284<br>ttggaaaatc catcaattat | | 20 |
| SEQ ID NO: 285<br>FEATURE<br>source | moltype = RNA   length = 20<br>Location/Qualifiers<br>1..20<br>mol_type = other RNA<br>organism = synthetic construct | |
| SEQUENCE: 285<br>cttggaaaat ccatcaatta | | 20 |
| SEQ ID NO: 286<br>FEATURE<br>source | moltype = RNA   length = 20<br>Location/Qualifiers<br>1..20<br>mol_type = other RNA<br>organism = synthetic construct | |
| SEQUENCE: 286<br>acttggaaaa tccatcaatt | | 20 |
| SEQ ID NO: 287<br>FEATURE<br>source | moltype = RNA   length = 20<br>Location/Qualifiers<br>1..20<br>mol_type = other RNA<br>organism = synthetic construct | |
| SEQUENCE: 287<br>gacttggaaa atccatcaat | | 20 |
| SEQ ID NO: 288<br>FEATURE<br>source | moltype = RNA   length = 20<br>Location/Qualifiers<br>1..20<br>mol_type = other RNA<br>organism = synthetic construct | |
| SEQUENCE: 288<br>agacttggaa aatccatcaa | | 20 |
| SEQ ID NO: 289<br>FEATURE<br>source | moltype = RNA   length = 20<br>Location/Qualifiers<br>1..20<br>mol_type = other RNA<br>organism = synthetic construct | |
| SEQUENCE: 289<br>gagacttgga aaatccatca | | 20 |
| SEQ ID NO: 290<br>FEATURE<br>source | moltype = RNA   length = 20<br>Location/Qualifiers<br>1..20<br>mol_type = other RNA<br>organism = synthetic construct | |

```
SEQUENCE: 290
agagacttgg aaaatccatc                                           20

SEQ ID NO: 291         moltype = RNA   length = 20
FEATURE                Location/Qualifiers
source                 1..20
                       mol_type = other RNA
                       organism = synthetic construct
SEQUENCE: 291
gaattagaga cttggaaaat                                           20

SEQ ID NO: 292         moltype = RNA   length = 20
FEATURE                Location/Qualifiers
source                 1..20
                       mol_type = other RNA
                       organism = synthetic construct
SEQUENCE: 292
tgaattagag acttggaaaa                                           20

SEQ ID NO: 293         moltype = RNA   length = 20
FEATURE                Location/Qualifiers
source                 1..20
                       mol_type = other RNA
                       organism = synthetic construct
SEQUENCE: 293
ctgaattaga gacttggaaa                                           20

SEQ ID NO: 294         moltype = RNA   length = 20
FEATURE                Location/Qualifiers
source                 1..20
                       mol_type = other RNA
                       organism = synthetic construct
SEQUENCE: 294
tctgaattag agacttggaa                                           20

SEQ ID NO: 295         moltype = RNA   length = 20
FEATURE                Location/Qualifiers
source                 1..20
                       mol_type = other RNA
                       organism = synthetic construct
SEQUENCE: 295
ttctgaatta gagacttgga                                           20

SEQ ID NO: 296         moltype = RNA   length = 20
FEATURE                Location/Qualifiers
source                 1..20
                       mol_type = other RNA
                       organism = synthetic construct
SEQUENCE: 296
attctgaatt agagacttgg                                           20

SEQ ID NO: 297         moltype = RNA   length = 20
FEATURE                Location/Qualifiers
source                 1..20
                       mol_type = other RNA
                       organism = synthetic construct
SEQUENCE: 297
tattctgaat tagagacttg                                           20

SEQ ID NO: 298         moltype = RNA   length = 20
FEATURE                Location/Qualifiers
source                 1..20
                       mol_type = other RNA
                       organism = synthetic construct
SEQUENCE: 298
ggagaaggca gaaattttgg                                           20

SEQ ID NO: 299         moltype = RNA   length = 20
FEATURE                Location/Qualifiers
source                 1..20
                       mol_type = other RNA
                       organism = synthetic construct
SEQUENCE: 299
gtccatgtct ttagtcatca                                           20

SEQ ID NO: 300         moltype = RNA   length = 20
FEATURE                Location/Qualifiers
```

```
                         source               1..20
                                              mol_type = other RNA
                                              organism = synthetic construct
                         SEQUENCE: 300
                         acggtgtgtg tgtgtatata                                           20

SEQ ID NO: 301       moltype = RNA   length = 20
                         FEATURE              Location/Qualifiers
                         source               1..20
                                              mol_type = other RNA
                                              organism = synthetic construct
                         SEQUENCE: 301
                         aactacggtg tgtgtgtgta                                           20

SEQ ID NO: 302       moltype = RNA   length = 20
                         FEATURE              Location/Qualifiers
                         source               1..20
                                              mol_type = other RNA
                                              organism = synthetic construct
                         SEQUENCE: 302
                         tgcaaactac ggtgtgtgtg                                           20

SEQ ID NO: 303       moltype = RNA   length = 20
                         FEATURE              Location/Qualifiers
                         source               1..20
                                              mol_type = other RNA
                                              organism = synthetic construct
                         SEQUENCE: 303
                         gacttgcaaa ctacggtgtg                                           20

SEQ ID NO: 304       moltype = RNA   length = 20
                         FEATURE              Location/Qualifiers
                         source               1..20
                                              mol_type = other RNA
                                              organism = synthetic construct
                         SEQUENCE: 304
                         atgcagactt gcaaactacg                                           20

SEQ ID NO: 305       moltype = RNA   length = 20
                         FEATURE              Location/Qualifiers
                         source               1..20
                                              mol_type = other RNA
                                              organism = synthetic construct
                         SEQUENCE: 305
                         ccagatgcag acttgcaaac                                           20

SEQ ID NO: 306       moltype = RNA   length = 20
                         FEATURE              Location/Qualifiers
                         source               1..20
                                              mol_type = other RNA
                                              organism = synthetic construct
                         SEQUENCE: 306
                         ggtcccagat gcagacttgc                                           20

SEQ ID NO: 307       moltype = RNA   length = 20
                         FEATURE              Location/Qualifiers
                         source               1..20
                                              mol_type = other RNA
                                              organism = synthetic construct
                         SEQUENCE: 307
                         aaagggtccc agatgcagac                                           20

SEQ ID NO: 308       moltype = RNA   length = 20
                         FEATURE              Location/Qualifiers
                         source               1..20
                                              mol_type = other RNA
                                              organism = synthetic construct
                         SEQUENCE: 308
                         cagtaaaggg tcccagatgc                                           20

SEQ ID NO: 309       moltype = RNA   length = 20
                         FEATURE              Location/Qualifiers
                         source               1..20
                                              mol_type = other RNA
                                              organism = synthetic construct
                         SEQUENCE: 309
                         tatcagtaaa gggtcccaga                                           20

SEQ ID NO: 310       moltype = RNA   length = 20
```

```
FEATURE              Location/Qualifiers
source               1..20
                     mol_type = other RNA
                     organism = synthetic construct
SEQUENCE: 310
ggcatgagag ttttaatggg                                               20

SEQ ID NO: 311       moltype = RNA   length = 20
FEATURE              Location/Qualifiers
source               1..20
                     mol_type = other RNA
                     organism = synthetic construct
SEQUENCE: 311
gatagaattc tcctactcta                                               20

SEQ ID NO: 312       moltype = RNA   length = 20
FEATURE              Location/Qualifiers
source               1..20
                     mol_type = other RNA
                     organism = synthetic construct
SEQUENCE: 312
ccatagaaat gtcaacaatc                                               20

SEQ ID NO: 313       moltype = RNA   length = 20
FEATURE              Location/Qualifiers
source               1..20
                     mol_type = other RNA
                     organism = synthetic construct
SEQUENCE: 313
gcatgatgaa ttaaacatgt                                               20

SEQ ID NO: 314       moltype = RNA   length = 20
FEATURE              Location/Qualifiers
source               1..20
                     mol_type = other RNA
                     organism = synthetic construct
SEQUENCE: 314
ccatttatag cagttgacta                                               20

SEQ ID NO: 315       moltype = RNA   length = 20
FEATURE              Location/Qualifiers
source               1..20
                     mol_type = other RNA
                     organism = synthetic construct
SEQUENCE: 315
ttgaccaagg aaaagacttc                                               20

SEQ ID NO: 316       moltype = RNA   length = 20
FEATURE              Location/Qualifiers
source               1..20
                     mol_type = other RNA
                     organism = synthetic construct
SEQUENCE: 316
agcttgacca aggaaaagac                                               20

SEQ ID NO: 317       moltype = RNA   length = 20
FEATURE              Location/Qualifiers
source               1..20
                     mol_type = other RNA
                     organism = synthetic construct
SEQUENCE: 317
agtccagagc ttgaccaagg                                               20

SEQ ID NO: 318       moltype = RNA   length = 20
FEATURE              Location/Qualifiers
source               1..20
                     mol_type = other RNA
                     organism = synthetic construct
SEQUENCE: 318
gaggagtcca gagcttgacc                                               20

SEQ ID NO: 319       moltype = RNA   length = 20
FEATURE              Location/Qualifiers
source               1..20
                     mol_type = other RNA
                     organism = synthetic construct
SEQUENCE: 319
agtactgagg agtccagagc                                               20
```

| | | |
|---|---|---|
| SEQ ID NO: 320<br>FEATURE<br>source | moltype = RNA   length = 20<br>Location/Qualifiers<br>1..20<br>mol_type = other RNA<br>organism = synthetic construct | |
| SEQUENCE: 320<br>agtggaagta ctgaggagtc | | 20 |
| SEQ ID NO: 321<br>FEATURE<br>source | moltype = RNA   length = 20<br>Location/Qualifiers<br>1..20<br>mol_type = other RNA<br>organism = synthetic construct | |
| SEQUENCE: 321<br>tgacagtgga agtactgagg | | 20 |
| SEQ ID NO: 322<br>FEATURE<br>source | moltype = RNA   length = 20<br>Location/Qualifiers<br>1..20<br>mol_type = other RNA<br>organism = synthetic construct | |
| SEQUENCE: 322<br>tatgacagtg gaagtactga | | 20 |
| SEQ ID NO: 323<br>FEATURE<br>source | moltype = RNA   length = 20<br>Location/Qualifiers<br>1..20<br>mol_type = other RNA<br>organism = synthetic construct | |
| SEQUENCE: 323<br>tcctcccttc atcacttatg | | 20 |
| SEQ ID NO: 324<br>FEATURE<br>source | moltype = RNA   length = 20<br>Location/Qualifiers<br>1..20<br>mol_type = other RNA<br>organism = synthetic construct | |
| SEQUENCE: 324<br>acccatgcaa tgaatactat | | 20 |
| SEQ ID NO: 325<br>FEATURE<br>source | moltype = RNA   length = 20<br>Location/Qualifiers<br>1..20<br>mol_type = other RNA<br>organism = synthetic construct | |
| SEQUENCE: 325<br>tacccatgca atgaatacta | | 20 |
| SEQ ID NO: 326<br>FEATURE<br>source | moltype = RNA   length = 20<br>Location/Qualifiers<br>1..20<br>mol_type = other RNA<br>organism = synthetic construct | |
| SEQUENCE: 326<br>gtacccatgc aatgaatact | | 20 |
| SEQ ID NO: 327<br>FEATURE<br>source | moltype = RNA   length = 20<br>Location/Qualifiers<br>1..20<br>mol_type = other RNA<br>organism = synthetic construct | |
| SEQUENCE: 327<br>ggtacccatg caatgaatac | | 20 |
| SEQ ID NO: 328<br>FEATURE<br>source | moltype = RNA   length = 20<br>Location/Qualifiers<br>1..20<br>mol_type = other RNA<br>organism = synthetic construct | |
| SEQUENCE: 328<br>aggtacccat gcaatgaata | | 20 |
| SEQ ID NO: 329<br>FEATURE<br>source | moltype = RNA   length = 20<br>Location/Qualifiers<br>1..20<br>mol_type = other RNA<br>organism = synthetic construct | |
| SEQUENCE: 329<br>aaggtaccca tgcaatgaat | | 20 |

| | | |
|---|---|---|
| SEQ ID NO: 330<br>FEATURE<br>source | moltype = RNA length = 20<br>Location/Qualifiers<br>1..20<br>mol_type = other RNA<br>organism = synthetic construct | |
| SEQUENCE: 330<br>taaggtaccc atgcaatgaa | | 20 |
| SEQ ID NO: 331<br>FEATURE<br>source | moltype = RNA length = 20<br>Location/Qualifiers<br>1..20<br>mol_type = other RNA<br>organism = synthetic construct | |
| SEQUENCE: 331<br>cctaaggtac ccatgcaatg | | 20 |
| SEQ ID NO: 332<br>FEATURE<br>source | moltype = RNA length = 20<br>Location/Qualifiers<br>1..20<br>mol_type = other RNA<br>organism = synthetic construct | |
| SEQUENCE: 332<br>tttaaatcag tcatagtccc | | 20 |
| SEQ ID NO: 333<br>FEATURE<br>source | moltype = RNA length = 20<br>Location/Qualifiers<br>1..20<br>mol_type = other RNA<br>organism = synthetic construct | |
| SEQUENCE: 333<br>gctgcaccca ctaatggaaa | | 20 |
| SEQ ID NO: 334<br>FEATURE<br>source | moltype = RNA length = 20<br>Location/Qualifiers<br>1..20<br>mol_type = other RNA<br>organism = synthetic construct | |
| SEQUENCE: 334<br>gtgctgcacc cactaatgga | | 20 |
| SEQ ID NO: 335<br>FEATURE<br>source | moltype = RNA length = 20<br>Location/Qualifiers<br>1..20<br>mol_type = other RNA<br>organism = synthetic construct | |
| SEQUENCE: 335<br>ggaaactttt cttttaagt | | 20 |
| SEQ ID NO: 336<br>FEATURE<br>source | moltype = RNA length = 20<br>Location/Qualifiers<br>1..20<br>mol_type = other RNA<br>organism = synthetic construct | |
| SEQUENCE: 336<br>acgatataaa ctcaatcctc | | 20 |
| SEQ ID NO: 337<br>FEATURE<br>source | moltype = RNA length = 20<br>Location/Qualifiers<br>1..20<br>mol_type = other RNA<br>organism = synthetic construct | |
| SEQUENCE: 337<br>tagtgagggt tgtctttcct | | 20 |
| SEQ ID NO: 338<br>FEATURE<br>source | moltype = RNA length = 20<br>Location/Qualifiers<br>1..20<br>mol_type = other RNA<br>organism = synthetic construct | |
| SEQUENCE: 338<br>tgtagtgagg gttgtctttc | | 20 |
| SEQ ID NO: 339<br>FEATURE<br>source | moltype = RNA length = 20<br>Location/Qualifiers<br>1..20<br>mol_type = other RNA<br>organism = synthetic construct | |

```
SEQUENCE: 339
gtgtagtgag ggttgtcttt                                            20

SEQ ID NO: 340         moltype = RNA   length = 20
FEATURE                Location/Qualifiers
source                 1..20
                       mol_type = other RNA
                       organism = synthetic construct
SEQUENCE: 340
gtgtgtagtg agggttgtct                                            20

SEQ ID NO: 341         moltype = RNA   length = 20
FEATURE                Location/Qualifiers
source                 1..20
                       mol_type = other RNA
                       organism = synthetic construct
SEQUENCE: 341
tcttgtcttt ttatgtgtgt                                            20

SEQ ID NO: 342         moltype = RNA   length = 20
FEATURE                Location/Qualifiers
source                 1..20
                       mol_type = other RNA
                       organism = synthetic construct
SEQUENCE: 342
tactagttta cgccttgatc                                            20

SEQ ID NO: 343         moltype = RNA   length = 20
FEATURE                Location/Qualifiers
source                 1..20
                       mol_type = other RNA
                       organism = synthetic construct
SEQUENCE: 343
gcagtactta ctggcttagt                                            20

SEQ ID NO: 344         moltype = RNA   length = 20
FEATURE                Location/Qualifiers
source                 1..20
                       mol_type = other RNA
                       organism = synthetic construct
SEQUENCE: 344
gaaaactccc aacctagaga                                            20

SEQ ID NO: 345         moltype = RNA   length = 20
FEATURE                Location/Qualifiers
source                 1..20
                       mol_type = other RNA
                       organism = synthetic construct
SEQUENCE: 345
ttggaggaga atgaaaatag                                            20

SEQ ID NO: 346         moltype = RNA   length = 20
FEATURE                Location/Qualifiers
source                 1..20
                       mol_type = other RNA
                       organism = synthetic construct
SEQUENCE: 346
cgaaatttgt gttgaagatc                                            20

SEQ ID NO: 347         moltype = RNA   length = 20
FEATURE                Location/Qualifiers
source                 1..20
                       mol_type = other RNA
                       organism = synthetic construct
SEQUENCE: 347
cataatagtc atggaagtat                                            20

SEQ ID NO: 348         moltype = RNA   length = 20
FEATURE                Location/Qualifiers
source                 1..20
                       mol_type = other RNA
                       organism = synthetic construct
SEQUENCE: 348
aatgttcagc cttcatccat                                            20

SEQ ID NO: 349         moltype = RNA   length = 20
FEATURE                Location/Qualifiers
```

```
source                        1..20
                              mol_type = other RNA
                              organism = synthetic construct
SEQUENCE: 349
tcatgggaga cttagtatgc                                                    20

SEQ ID NO: 350                moltype = RNA   length = 20
FEATURE                       Location/Qualifiers
source                        1..20
                              mol_type = other RNA
                              organism = synthetic construct
SEQUENCE: 350
ctagatgcag ggtatagaat                                                    20

SEQ ID NO: 351                moltype = RNA   length = 20
FEATURE                       Location/Qualifiers
source                        1..20
                              mol_type = other RNA
                              organism = synthetic construct
SEQUENCE: 351
catgaagtca tgtggtatat                                                    20

SEQ ID NO: 352                moltype = RNA   length = 20
FEATURE                       Location/Qualifiers
source                        1..20
                              mol_type = other RNA
                              organism = synthetic construct
SEQUENCE: 352
ccgtggcatg agcaatagcc                                                    20

SEQ ID NO: 353                moltype = RNA   length = 20
FEATURE                       Location/Qualifiers
source                        1..20
                              mol_type = other RNA
                              organism = synthetic construct
SEQUENCE: 353
aagtagataa agagggaaa                                                     20

SEQ ID NO: 354                moltype = RNA   length = 16
FEATURE                       Location/Qualifiers
source                        1..16
                              mol_type = other RNA
                              organism = synthetic construct
SEQUENCE: 354
ggcatgaatg caggca                                                        16

SEQ ID NO: 355                moltype = RNA   length = 16
FEATURE                       Location/Qualifiers
source                        1..16
                              mol_type = other RNA
                              organism = synthetic construct
SEQUENCE: 355
caggcatgaa tgcagg                                                        16

SEQ ID NO: 356                moltype = RNA   length = 16
FEATURE                       Location/Qualifiers
source                        1..16
                              mol_type = other RNA
                              organism = synthetic construct
SEQUENCE: 356
gacaggcatg aatgca                                                        16

SEQ ID NO: 357                moltype = RNA   length = 16
FEATURE                       Location/Qualifiers
source                        1..16
                              mol_type = other RNA
                              organism = synthetic construct
SEQUENCE: 357
gtgacaggca tgaatg                                                        16

SEQ ID NO: 358                moltype = RNA   length = 16
FEATURE                       Location/Qualifiers
source                        1..16
                              mol_type = other RNA
                              organism = synthetic construct
SEQUENCE: 358
cacatcaggc tgggga                                                        16

SEQ ID NO: 359                moltype = RNA   length = 16
```

```
FEATURE             Location/Qualifiers
source              1..16
                    mol_type = other RNA
                    organism = synthetic construct
SEQUENCE: 359
catcaggctg gggacc                                                               16

SEQ ID NO: 360      moltype = RNA   length = 16
FEATURE             Location/Qualifiers
source              1..16
                    mol_type = other RNA
                    organism = synthetic construct
SEQUENCE: 360
tcaggctggg gaccct                                                               16

SEQ ID NO: 361      moltype = RNA   length = 16
FEATURE             Location/Qualifiers
source              1..16
                    mol_type = other RNA
                    organism = synthetic construct
SEQUENCE: 361
aggctgggga ccctgt                                                               16

SEQ ID NO: 362      moltype = RNA   length = 16
FEATURE             Location/Qualifiers
source              1..16
                    mol_type = other RNA
                    organism = synthetic construct
SEQUENCE: 362
catgaatgca ggcaca                                                               16

SEQ ID NO: 363      moltype = RNA   length = 16
FEATURE             Location/Qualifiers
source              1..16
                    mol_type = other RNA
                    organism = synthetic construct
SEQUENCE: 363
tgaatgcagg cacaca                                                               16

SEQ ID NO: 364      moltype = RNA   length = 16
FEATURE             Location/Qualifiers
source              1..16
                    mol_type = other RNA
                    organism = synthetic construct
SEQUENCE: 364
aatgcaggca cacaca                                                               16

SEQ ID NO: 365      moltype = RNA   length = 16
FEATURE             Location/Qualifiers
source              1..16
                    mol_type = other RNA
                    organism = synthetic construct
SEQUENCE: 365
tgcaggcaca cacatc                                                               16

SEQ ID NO: 366      moltype = RNA   length = 16
FEATURE             Location/Qualifiers
source              1..16
                    mol_type = other RNA
                    organism = synthetic construct
SEQUENCE: 366
caggcacaca catcag                                                               16

SEQ ID NO: 367      moltype = RNA   length = 16
FEATURE             Location/Qualifiers
source              1..16
                    mol_type = other RNA
                    organism = synthetic construct
SEQUENCE: 367
ggcacacaca tcaggc                                                               16

SEQ ID NO: 368      moltype = RNA   length = 16
FEATURE             Location/Qualifiers
source              1..16
                    mol_type = other RNA
                    organism = synthetic construct
SEQUENCE: 368
cacacacatc aggctg                                                               16
```

-continued

```
SEQ ID NO: 369           moltype = RNA   length = 16
FEATURE                  Location/Qualifiers
source                   1..16
                         mol_type = other RNA
                         organism = synthetic construct
SEQUENCE: 369
cacacatcag gctggg                                                       16

SEQ ID NO: 370           moltype = RNA   length = 16
FEATURE                  Location/Qualifiers
source                   1..16
                         mol_type = other RNA
                         organism = synthetic construct
SEQUENCE: 370
ggcatgaatg caggca                                                       16

SEQ ID NO: 371           moltype = RNA   length = 16
FEATURE                  Location/Qualifiers
source                   1..16
                         mol_type = other RNA
                         organism = synthetic construct
SEQUENCE: 371
caggcatgaa tgcagg                                                       16

SEQ ID NO: 372           moltype = RNA   length = 16
FEATURE                  Location/Qualifiers
source                   1..16
                         mol_type = other RNA
                         organism = synthetic construct
SEQUENCE: 372
gacaggcatg aatgca                                                       16

SEQ ID NO: 373           moltype = RNA   length = 16
FEATURE                  Location/Qualifiers
source                   1..16
                         mol_type = other RNA
                         organism = synthetic construct
SEQUENCE: 373
gtgacaggca tgaatg                                                       16

SEQ ID NO: 374           moltype = RNA   length = 16
FEATURE                  Location/Qualifiers
source                   1..16
                         mol_type = other RNA
                         organism = synthetic construct
SEQUENCE: 374
cacatcaggc tggga                                                        16

SEQ ID NO: 375           moltype = RNA   length = 16
FEATURE                  Location/Qualifiers
source                   1..16
                         mol_type = other RNA
                         organism = synthetic construct
SEQUENCE: 375
catcaggctg gggacc                                                       16

SEQ ID NO: 376           moltype = RNA   length = 16
FEATURE                  Location/Qualifiers
source                   1..16
                         mol_type = other RNA
                         organism = synthetic construct
SEQUENCE: 376
tcaggctggg gaccct                                                       16

SEQ ID NO: 377           moltype = RNA   length = 16
FEATURE                  Location/Qualifiers
source                   1..16
                         mol_type = other RNA
                         organism = synthetic construct
SEQUENCE: 377
aggctgggga ccctgt                                                       16

SEQ ID NO: 378           moltype = RNA   length = 18
FEATURE                  Location/Qualifiers
source                   1..18
                         mol_type = other RNA
                         organism = synthetic construct
SEQUENCE: 378
gcatgaatgc aggcacac                                                     18
```

```
SEQ ID NO: 379           moltype = RNA   length = 18
FEATURE                  Location/Qualifiers
source                   1..18
                         mol_type = other RNA
                         organism = synthetic construct
SEQUENCE: 379
gcacacacat caggctgg                                                      18

SEQ ID NO: 380           moltype = RNA   length = 18
FEATURE                  Location/Qualifiers
source                   1..18
                         mol_type = other RNA
                         organism = synthetic construct
SEQUENCE: 380
acacacatca ggctgggg                                                      18

SEQ ID NO: 381           moltype = RNA   length = 18
FEATURE                  Location/Qualifiers
source                   1..18
                         mol_type = other RNA
                         organism = synthetic construct
SEQUENCE: 381
cacacacatc aggctggg                                                      18

SEQ ID NO: 382           moltype = RNA   length = 20
FEATURE                  Location/Qualifiers
source                   1..20
                         mol_type = other RNA
                         organism = synthetic construct
SEQUENCE: 382
ggcatgaatg caggcacaca                                                    20

SEQ ID NO: 383           moltype = RNA   length = 20
FEATURE                  Location/Qualifiers
source                   1..20
                         mol_type = other RNA
                         organism = synthetic construct
SEQUENCE: 383
ggcatgaatg caggcacaca                                                    20

SEQ ID NO: 384           moltype = RNA   length = 20
FEATURE                  Location/Qualifiers
source                   1..20
                         mol_type = other RNA
                         organism = synthetic construct
SEQUENCE: 384
ggcacacaca tcaggctggg                                                    20

SEQ ID NO: 385           moltype = RNA   length = 20
FEATURE                  Location/Qualifiers
source                   1..20
                         mol_type = other RNA
                         organism = synthetic construct
SEQUENCE: 385
cacacacatc aggctgggga                                                    20

SEQ ID NO: 386           moltype = RNA   length = 20
FEATURE                  Location/Qualifiers
source                   1..20
                         mol_type = other RNA
                         organism = synthetic construct
SEQUENCE: 386
gcacacacat caggctgggg                                                    20

SEQ ID NO: 387           moltype = RNA   length = 20
FEATURE                  Location/Qualifiers
source                   1..20
                         mol_type = other RNA
                         organism = synthetic construct
SEQUENCE: 387
tgcaggcaca cacatcaggc                                                    20

SEQ ID NO: 388           moltype = RNA   length = 20
FEATURE                  Location/Qualifiers
source                   1..20
                         mol_type = other RNA
                         organism = synthetic construct
```

-continued

```
SEQUENCE: 388
atcaggctgg ggaccctgtg                                                20

SEQ ID NO: 389          moltype = RNA   length = 20
FEATURE                 Location/Qualifiers
source                  1..20
                        mol_type = other RNA
                        organism = synthetic construct
SEQUENCE: 389
ggcacacaca tcaggctggg                                                20

SEQ ID NO: 390          moltype = RNA   length = 20
FEATURE                 Location/Qualifiers
source                  1..20
                        mol_type = other RNA
                        organism = synthetic construct
SEQUENCE: 390
atgaatgcag gcacacacat                                                20

SEQ ID NO: 391          moltype = RNA   length = 20
FEATURE                 Location/Qualifiers
source                  1..20
                        mol_type = other RNA
                        organism = synthetic construct
SEQUENCE: 391
tgcaggcaca cacatcaggc                                                20

SEQ ID NO: 392          moltype = DNA   length = 20
FEATURE                 Location/Qualifiers
source                  1..20
                        mol_type = other DNA
                        organism = synthetic construct
modified_base           order(1..5,7,8,10,11,13,14,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(6,9,12,15)
                        mod_base = OTHER
                        note = Locked nucleic acid
SEQUENCE: 392
tgcaggcaca cacatcaggc                                                20

SEQ ID NO: 393          moltype = DNA   length = 20
FEATURE                 Location/Qualifiers
source                  1..20
                        mol_type = other DNA
                        organism = synthetic construct
modified_base           order(1..3,5,7,9,11,13,15,17,19,20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(4,6,8,10,12,14,16,18)
                        mod_base = OTHER
                        note = Locked nucleic acid
SEQUENCE: 393
tgcaggcaca cacatcaggc                                                20

SEQ ID NO: 394          moltype = DNA   length = 20
FEATURE                 Location/Qualifiers
source                  1..20
                        mol_type = other DNA
                        organism = synthetic construct
modified_base           order(1,2,4,6,8,10,12,14,16,18..20)
                        mod_base = OTHER
                        note = 2-prime-O-(2-Methoxyethyl) nucleotide
modified_base           order(3,5,7,9,11,13,15,17)
                        mod_base = OTHER
                        note = Locked nucleic acid
modified_base           order(3,7,9,11,13,16,20)
                        mod_base = OTHER
                        note = 5-methyl on the cytidine
SEQUENCE: 394
tgcaggcaca cacatcaggc                                                20

SEQ ID NO: 395          moltype = DNA   length = 20
```

```
FEATURE                 Location/Qualifiers
source                  1..20
                        mol_type = other DNA
                        organism = synthetic construct
modified_base           order(1,2,4,5,7,8,10,11,13,14,16,17,19,20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(3,6,9,12,15,18)
                        mod_base = OTHER
                        note = Locked nucleic acid
SEQUENCE: 395
tgcaggcaca cacatcaggc                                                     20

SEQ ID NO: 396          moltype = DNA   length = 20
FEATURE                 Location/Qualifiers
source                  1..20
                        mol_type = other DNA
                        organism = synthetic construct
modified_base           order(1..4,6..8,10..12,14..16,18..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(5,9,13,17)
                        mod_base = OTHER
                        note = Locked nucleic acid
SEQUENCE: 396
tgcaggcaca cacatcaggc                                                     20

SEQ ID NO: 397          moltype = DNA   length = 20
FEATURE                 Location/Qualifiers
source                  1..20
                        mol_type = other DNA
                        organism = synthetic construct
modified_base           order(1..3,5..7,9..11,13..15,17..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(4,8,12,16)
                        mod_base = OTHER
                        note = Locked nucleic acid
SEQUENCE: 397
tgcaggcaca cacatcaggc                                                     20

SEQ ID NO: 398          moltype = DNA   length = 20
FEATURE                 Location/Qualifiers
source                  1..20
                        mol_type = other DNA
                        organism = synthetic construct
modified_base           order(1..5,7..10,12..15,17..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(6,11,16)
                        mod_base = OTHER
                        note = Locked nucleic acid
SEQUENCE: 398
tgcaggcaca cacatcaggc                                                     20

SEQ ID NO: 399          moltype = DNA   length = 20
FEATURE                 Location/Qualifiers
source                  1..20
                        mol_type = other DNA
                        organism = synthetic construct
modified_base           order(1..4,6..9,11..14,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
```

```
modified_base           order(5,10,15)
                        mod_base = OTHER
                        note = Locked nucleic acid
SEQUENCE: 399
tgcaggcaca cacatcaggc                                                    20

SEQ ID NO: 400          moltype = DNA   length = 20
FEATURE                 Location/Qualifiers
source                  1..20
                        mol_type = other DNA
                        organism = synthetic construct
modified_base           order(2,4,17,19)
                        mod_base = OTHER
                        note = 2-prime-O-(2-Methoxyethyl) nucleotide
modified_base           order(3,16,20)
                        mod_base = OTHER
                        note = 5-methyl on the cytidine
modified_base           order(1,3,5,16,18,20)
                        mod_base = OTHER
                        note = Locked nucleic acid
misc_feature            6..15
                        note = DNA
misc_feature            order(1..5,16..20)
                        note = RNA
SEQUENCE: 400
tgcaggcaca cacatcaggc                                                    20

SEQ ID NO: 401          moltype = DNA   length = 20
FEATURE                 Location/Qualifiers
source                  1..20
                        mol_type = other DNA
                        organism = synthetic construct
modified_base           order(2,4,6..15,17,19)
                        mod_base = OTHER
                        note = 2-prime-O-(2-Methoxyethyl) nucleotide
modified_base           order(3,7,9,13,16,20)
                        mod_base = OTHER
                        note = 5-methyl on the cytidine
modified_base           order(1,3,5,16,18,20)
                        mod_base = OTHER
                        note = Locked nucleic acid
SEQUENCE: 401
tgcaggcaca cacatcaggc                                                    20

SEQ ID NO: 402          moltype = DNA   length = 20
FEATURE                 Location/Qualifiers
source                  1..20
                        mol_type = other DNA
                        organism = synthetic construct
modified_base           order(1..6,9,12,15..20)
                        mod_base = OTHER
                        note = 2-prime-O-(2-Methoxyethyl) nucleotide
modified_base           order(3,9,16,20)
                        mod_base = OTHER
                        note = 5-methyl on the cytidine
misc_feature            order(7,8,10,11,13,14)
                        note = DNA
misc_feature            order(1..6,9,12,15..20)
                        note = RNA
SEQUENCE: 402
tgcaggcaca cacatcaggc                                                    20

SEQ ID NO: 403          moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
misc_feature            6..15
                        note = DNA
misc_feature            order(1..5,16..20)
                        note = RNA
```

```
                        -continued modified_base           order(4^5,16^17)
                        mod_base = OTHER
                        note = Phosphodiester linkage
SEQUENCE: 403
tgcaggcaca cacatcaggc                                               20

SEQ ID NO: 404          moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
misc_feature            6..15
                        note = DNA
misc_feature            order(1..5,16..20)
                        note = RNA
modified_base           order(3^4,4^5,16^17,17^18)
                        mod_base = OTHER
                        note = Phosphodiester linkage
SEQUENCE: 404
tgcaggcaca cacatcaggc                                               20

SEQ ID NO: 405          moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
misc_feature            6..15
                        note = DNA
misc_feature            order(1..5,16..20)
                        note = RNA
modified_base           order(2^3,3^4,4^5,16^17,17^18,18^19)
                        mod_base = OTHER
                        note = Phosphodiester linkage
SEQUENCE: 405
tgcaggcaca cacatcaggc                                               20

SEQ ID NO: 406          moltype = DNA   length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
misc_feature            6..15
                        note = DNA
misc_feature            order(1..5,16..20)
                        note = RNA
modified_base           order(1^2,2^3,3^4,4^5)
                        mod_base = OTHER
                        note = Phosphodiester linkage
modified_base           order(16^17,17^18,18^19,19^20)
                        mod_base = OTHER
                        note = Phosphodiester linkage
SEQUENCE: 406
tgcaggcaca cacatcaggc                                               20

SEQ ID NO: 407          moltype = DNA   length = 22
FEATURE                 Location/Qualifiers
source                  1..22
                        mol_type = other DNA
                        organism = synthetic construct
```

```
modified_base         order(1..6,17..22)
                      mod_base = OTHER
                      note = 2-prime-O-(2-Methoxyethyl) nucleotide
modified_base         order(3,20)
                      mod_base = OTHER
                      note = 5-methyl on the cytidine
misc_feature          7..16
                      note = DNA
misc_feature          order(1..16,17..22)
                      note = RNA
SEQUENCE: 407
tgcaggcaca cacatcaggc tg                                                   22

SEQ ID NO: 408        moltype = DNA  length = 20
FEATURE               Location/Qualifiers
source                1..20
                      mol_type = other DNA
                      organism = synthetic construct
modified_base         order(1,2,4,17,19,20)
                      mod_base = OTHER
                      note = 2-prime-O-(2-Methoxyethyl) nucleotide
modified_base         order(3,16,20)
                      mod_base = OTHER
                      note = 5-methyl on the cytidine
modified_base         order(3,5,16,18)
                      mod_base = OTHER
                      note = Locked nucleic acid
misc_feature          order(1..5,16..20)
                      note = RNA
misc_feature          6..15
                      note = DNA
SEQUENCE: 408
tgcaggcaca cacatcaggc                                                      20

SEQ ID NO: 409        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(3,7,9,11,13,16,20)
                      mod_base = OTHER
                      note = 5-methyl on the cytidine
modified_base         order(3^4,4^5,16^17,17^18)
                      mod_base = OTHER
                      note = Phosphodiester linkage
misc_feature          order(1..5,16..20)
                      note = RNA
misc_feature          6..15
                      note = DNA
SEQUENCE: 409
tgcaggcaca cacatcaggc                                                      20

SEQ ID NO: 410        moltype = DNA  length = 19
FEATURE               Location/Qualifiers
source                1..19
                      mol_type = other DNA
                      organism = synthetic construct
modified_base         order(1..5,16..19)
                      mod_base = OTHER
                      note = 2-prime-O-(2-Methoxyethyl) nucleotide
modified_base         order(3,16)
                      mod_base = OTHER
                      note = 5-methyl on the cytidine
misc_feature          order(1..5,16..19)
                      note = RNA
misc_feature          6..15
                      note = DNA
modified_base         order(3^4,4^5,16^17,17^18)
                      mod_base = OTHER
                      note = Phosphodiester linkage
SEQUENCE: 410
tgcaggcaca cacatcagg                                                       19

SEQ ID NO: 411        moltype = DNA  length = 18
FEATURE               Location/Qualifiers
```

```
source                  1..18
                        mol_type = other DNA
                        organism = synthetic construct
modified_base           order(1..5,16..18)
                        mod_base = OTHER
                        note = 2-prime-O-(2-Methoxyethyl) nucleotide
modified_base           order(2,16)
                        mod_base = OTHER
                        note = 5-methyl on the cytidine
modified_base           order(3^4,4^5,16^17,17^18)
                        mod_base = OTHER
                        note = Phosphodiester linkage
misc_feature            order(1..5,16..18)
                        note = RNA
misc_feature            6..15
                        note = DNA
SEQUENCE: 411
tgcaggcaca cacatcag                                                                 18

SEQ ID NO: 412          moltype = DNA  length = 15
FEATURE                 Location/Qualifiers
source                  1..15
                        mol_type = other DNA
                        organism = synthetic construct
modified_base           1..5
                        mod_base = OTHER
                        note = 2-prime-O-(2-Methoxyethyl) nucleotide
modified_base           3
                        mod_base = OTHER
                        note = 5-methyl on the cytidine
modified_base           order(3^4,4^5)
                        mod_base = OTHER
                        note = Phosphodiester linkage
misc_feature            1..5
                        note = RNA
misc_feature            6..15
                        note = DNA
SEQUENCE: 412
tgcaggcaca cacat                                                                    15

SEQ ID NO: 413          moltype =   length =
SEQUENCE: 413
000

SEQ ID NO: 414          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(3^4,4^5,16^17,17^18)
                        mod_base = OTHER
                        note = Phosphodiester linkage
misc_feature            order(1..5,16..20)
                        note = RNA
misc_feature            6..15
                        note = DNA
SEQUENCE: 414
tgcaggcaca cacatcaggc                                                               20

SEQ ID NO: 415          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(3^4,4^5,5^6,6^7,7^8,8^9,9^10,10^11,11^12,12^13,13^14,14^15,15^16,
16^17,17^18)
                        mod_base = OTHER
                        note = Phosphodiester linkage
```

```
misc_feature              order(1..5,16..20)
                          note = RNA
misc_feature              6..15
                          note = DNA
SEQUENCE: 415
tgcaggcaca cacatcaggc                                                       20

SEQ ID NO: 416            moltype = DNA  length = 20
FEATURE                   Location/Qualifiers
source                    1..20
                          mol_type = other DNA
                          organism = synthetic construct
modified_base             order(3,7,9,11,13,16,20)
                          mod_base = OTHER
                          note = 5-methyl on the cytidine
SEQUENCE: 416
tgcaggcaca cacatcaggc                                                       20

SEQ ID NO: 417            moltype = DNA  length = 20
FEATURE                   Location/Qualifiers
source                    1..20
                          mol_type = other DNA
                          organism = synthetic construct
modified_base             order(1..5,16..20)
                          mod_base = OTHER
                          note = 2-prime-O-(2-Methoxyethyl) nucleotide
modified_base             order(3,7,9,11,13,16,20)
                          mod_base = OTHER
                          note = 5-methyl on the cytidine
misc_feature              order(1..5,16..20)
                          note = RNA
misc_feature              6..15
                          note = DNA
SEQUENCE: 417
tgcaggcaca cacatcaggc                                                       20

SEQ ID NO: 418            moltype = DNA  length = 20
FEATURE                   Location/Qualifiers
source                    1..20
                          mol_type = other DNA
                          organism = synthetic construct
modified_base             order(1..5,16..20)
                          mod_base = OTHER
                          note = 2-prime-O-(2-Methoxyethyl) nucleotide
modified_base             order(3,7,9,11,13,16,20)
                          mod_base = OTHER
                          note = 5-methyl on the cytidine
modified_base             order(4^5,16^17)
                          mod_base = OTHER
                          note = Phosphodiester linkage
misc_feature              order(1..5,16..20)
                          note = RNA
misc_feature              6..15
                          note = DNA
SEQUENCE: 418
tgcaggcaca cacatcaggc                                                       20

SEQ ID NO: 419            moltype = DNA  length = 20
FEATURE                   Location/Qualifiers
source                    1..20
                          mol_type = other DNA
                          organism = synthetic construct
modified_base             order(1..5,16,20)
                          mod_base = OTHER
                          note = 2-prime-O-(2-Methoxyethyl) nucleotide
modified_base             order(3,7,9,11,13,16,20)
                          mod_base = OTHER
                          note = 5-methyl on the cytidine
modified_base             order(3^4,4^5,16^17,17^18)
                          mod_base = OTHER
                          note = Phosphodiester linkage
misc_feature              order(1..5,16..20)
                          note = RNA
modified_base             6..15
                          mod_base = OTHER
                          note = DNA
SEQUENCE: 419
tgcaggcaca cacatcaggc                                                       20
```

```
SEQ ID NO: 420           moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(3,7,9,11,13,16,20)
                         mod_base = OTHER
                         note = 5-methyl on the cytidine
modified_base            order(1^2,2^3,3^4,4^5,16^17,17^18,18^19,19^20)
                         mod_base = OTHER
                         note = Phosphodiester linkage
misc_feature             order(1..5,16..20)
                         note = RNA
misc_feature             6..15
                         note = DNA
SEQUENCE: 420
tgcaggcaca cacatcaggc                                                   20

SEQ ID NO: 421           moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(3,7,9,11,13,16,20)
                         mod_base = OTHER
                         note = 5-methyl on the cytidine
misc_feature             order(1..5,16..20)
                         note = RNA
misc_feature             6..15
                         note = DNA
SEQUENCE: 421
tgcaggcaca cacatcaggc                                                   20

SEQ ID NO: 422           moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(3,7,9,11,13,16,20)
                         mod_base = OTHER
                         note = 5-methyl on the cytidine
misc_feature             order(1..5,16..20)
                         note = RNA
modified_base            6..15
                         mod_base = OTHER
                         note = DNA
modified_base            order(4^5,16^17)
                         mod_base = OTHER
                         note = Phosphodiester linkage
SEQUENCE: 422
tgcaggcaca cacatcaggc                                                   20

SEQ ID NO: 423           moltype = DNA  length = 20
FEATURE                  Location/Qualifiers
source                   1..20
                         mol_type = other DNA
                         organism = synthetic construct
modified_base            order(1..5,16..20)
                         mod_base = OTHER
                         note = 2-prime-O-(2-Methoxyethyl) nucleotide
modified_base            order(3,7,9,11,13,16,20)
                         mod_base = OTHER
                         note = 5-methyl on the cytidine
modified_base            order(3^4,4^5,16^17,17^18)
                         mod_base = OTHER
                         note = Phosphodiester linkage
misc_feature             order(1..5,16..20)
                         note = RNA
misc_feature             6..15
                         note = DNA
```

```
SEQUENCE: 423
tgcaggcaca cacatcaggc                                              20

SEQ ID NO: 424          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(1^2,2^3,3^4,4^5,16^17,17^18,18^19,19^20)
                        mod_base = OTHER
                        note = Phosphodiester linkage
misc_feature            order(1..5,16..20)
                        note = RNA
misc_feature            6..15
                        note = DNA
SEQUENCE: 424
tgcaggcaca cacatcaggc                                              20

SEQ ID NO: 425          moltype = DNA  length = 16
FEATURE                 Location/Qualifiers
source                  1..16
                        mol_type = other DNA
                        organism = synthetic construct
modified_base           order(1..3,14..16)
                        mod_base = OTHER
                        note = Constrained ethyl 2-prime-4-prime-bridged nucleic
                         acid
modified_base           order(5,9,11,13,15)
                        mod_base = OTHER
                        note = 5-methyl on the cytidine
misc_feature            order(1..3,14..16)
                        note = RNA
misc_feature            4..13
                        note = DNA
SEQUENCE: 425
aatgcaggca cacaca                                                  16

SEQ ID NO: 426          moltype = DNA  length = 16
FEATURE                 Location/Qualifiers
source                  1..16
                        mol_type = other DNA
                        organism = synthetic construct
modified_base           order(1..3,14..16)
                        mod_base = OTHER
                        note = Constrained ethyl 2-prime-4-prime-bridged nucleic
                         acid
modified_base           order(7,11,13,15)
                        mod_base = OTHER
                        note = 5-methyl on the cytidine
misc_feature            4..13
                        note = DNA
misc_feature            order(1..3,14..16)
                        note = RNA
SEQUENCE: 426
tgaatgcagg cacaca                                                  16

SEQ ID NO: 427          moltype = DNA  length = 16
FEATURE                 Location/Qualifiers
source                  1..16
                        mol_type = other DNA
                        organism = synthetic construct
modified_base           order(1..3,14..16)
                        mod_base = OTHER
                        note = Constrained ethyl 2-prime-4-prime-bridged nucleic
                         acid
modified_base           order(1,9,13,15)
                        mod_base = OTHER
                        note = 5-methyl on the cytidine
misc_feature            4..13
                        note = DNA
misc_feature            order(1..3,14..16)
                        note = RNA
```

```
SEQUENCE: 427
catgaatgca ggcaca                                                 16

SEQ ID NO: 428           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Constrained ethyl 2-prime-4-prime-bridged nucleic
                          acid
modified_base            order(3,7,9,11,13,16)
                         mod_base = OTHER
                         note = 5-methyl on the cytidine
misc_feature             4..13
                         note = DNA
misc_feature             order(1..3,14..16)
                         note = RNA
SEQUENCE: 428
tgcaggcaca cacatc                                                 16

SEQ ID NO: 429           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Constrained ethyl 2-prime-4-prime-bridged nucleic
                          acid
modified_base            order(1,5,7,9,11,14)
                         mod_base = OTHER
                         note = 5-methyl on the cytidine
misc_feature             4..13
                         note = DNA
misc_feature             order(1..3,14..16)
                         note = RNA
SEQUENCE: 429
caggcacaca catcag                                                 16

SEQ ID NO: 430           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Constrained ethyl 2-prime-4-prime-bridged nucleic
                          acid
modified_base            order(3,5,7,9,12,16)
                         mod_base = OTHER
                         note = 5-methyl on the cytidine
misc_feature             4..13
                         note = DNA
misc_feature             order(1..3,14..16)
                         note = RNA
SEQUENCE: 430
ggcacacaca tcaggc                                                 16

SEQ ID NO: 431           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Constrained ethyl 2-prime-4-prime-bridged nucleic
                          acid
modified_base            order(1,3,5,7,10,14)
                         mod_base = OTHER
                         note = 5-methyl on the cytidine
misc_feature             4..13
                         note = DNA
misc_feature             order(1..3,14..16)
                         note = RNA
SEQUENCE: 431
cacacacatc aggctg                                                 16
```

```
SEQ ID NO: 432          moltype = DNA   length = 16
FEATURE                 Location/Qualifiers
source                  1..16
                        mol_type = other DNA
                        organism = synthetic construct
modified_base           order(1..3,14..16)
                        mod_base = OTHER
                        note = Constrained ethyl 2-prime-4-prime-bridged nucleic
                         acid
modified_base           order(1,3,5,8,12)
                        mod_base = OTHER
                        note = 5-methyl on the cytidine
misc_feature            4..13
                        note = DNA
misc_feature            order(1..3,14..16)
                        note = RNA
SEQUENCE: 432
cacacatcag gctggg                                                            16

SEQ ID NO: 433          moltype = DNA   length = 30
FEATURE                 Location/Qualifiers
source                  1..30
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,7,9,11,13,16,20)
                        mod_base = OTHER
                        note = 5-methyl on the cytidine
modified_base           order(1^2,2^3,3^4,4^5,5^6,6^7,7^8,8^9,9^10,10^11,11^12,12^13,13^14,14^15)
                        mod_base = OTHER
                        note = 5-methyl on the cytidine
modified_base           order(15^16,16^17,17^18,18^19,19^20,20^21)
                        mod_base = OTHER
                        note = 5-methyl on the cytidine
modified_base           order(21^22,22^23,23^24,24^25,25^26,26^27,27^28,28^29,29^30)
                        mod_base = OTHER
                        note = 5-methyl on the cytidine
misc_feature            order(1..5,14..18)
                        note = RNA
misc_feature            order(6..15,21..30)
                        note = DNA
SEQUENCE: 433
tgcaggcaca cacatcaggc tttttttttt                                             30

SEQ ID NO: 434          moltype = DNA   length = 30
FEATURE                 Location/Qualifiers
source                  1..30
                        mol_type = other DNA
                        organism = synthetic construct
modified_base           order(11..15,26..30)
                        mod_base = OTHER
                        note = 2-prime-O-(2-Methoxyethyl) nucleotide
modified_base           order(13,17,19,21,23,26,30)
                        mod_base = OTHER
                        note = 5-methyl on the cytidine
modified_base           order(1^2,2^3,3^4,4^5,5^6,6^7,7^8,8^9,9^10,10^11,11^12,12^13,13^14,14^15,
15^16,16^17,17^18,18^19,19^20,20^21,21^22,22^23,23^24,24^25,25^26,26^27,27^28,28^29,29^30)
                        mod_base = OTHER
                        note = Phosphodiester linkage
misc_feature            order(1..10,16..25)
                        note = DNA
misc_feature            order(11..15,26..30)
                        note = RNA
SEQUENCE: 434
tttttttttt tgcaggcaca cacatcaggc                                             30

SEQ ID NO: 435          moltype = DNA   length = 16
FEATURE                 Location/Qualifiers
source                  1..16
                        mol_type = other DNA
                        organism = synthetic construct
modified_base           order(1..3,14..16)
                        mod_base = OTHER
                        note = Constrained ethyl 2-prime-4-prime-bridged nucleic
                         acid
modified_base           order(3,11,15)
                        mod_base = OTHER
                        note = 5-methyl on the cytidine
```

```
misc_feature              4..13
                          note = DNA
misc_feature              order(1..3,14..16)
                          note = RNA
SEQUENCE: 435
ggcatgaatg caggca                                                              16

SEQ ID NO: 436            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Constrained ethyl 2-prime-4-prime-bridged nucleic
                           acid
modified_base             order(1,5,13)
                          mod_base = OTHER
                          note = 5-methyl on the cytidine
misc_feature              4..13
                          note = DNA
misc_feature              order(1..3,14..16)
                          note = RNA
SEQUENCE: 436
caggcatgaa tgcagg                                                              16

SEQ ID NO: 437            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Constrained ethyl 2-prime-4-prime-bridged nucleic
                           acid
modified_base             order(3,7,15)
                          mod_base = OTHER
                          note = 5-methyl on the cytidine
misc_feature              4..13
                          note = DNA
misc_feature              order(1..3,14..16)
                          note = RNA
SEQUENCE: 437
gacaggcatg aatgca                                                              16

SEQ ID NO: 438            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Constrained ethyl 2-prime-4-prime-bridged nucleic
                           acid
modified_base             order(5,9)
                          mod_base = OTHER
                          note = 5-methyl on the cytidine
misc_feature              order(1..3,14..16)
                          note = RNA
misc_feature              4..13
                          note = DNA
SEQUENCE: 438
gtgacaggca tgaatg                                                              16

SEQ ID NO: 439            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Constrained ethyl 2-prime-4-prime-bridged nucleic
                           acid
modified_base             order(1,3,6)
                          mod_base = OTHER
                          note = 5-methyl on the cytidine
misc_feature              order(1..3,14..16)
                          note = RNA
```

| | | |
|---|---|---|
| misc_feature | 4..13 | |
| | note = DNA | |
| SEQUENCE: 439 | | |
| cacatcaggc tgggga | | 16 |
| | | |
| SEQ ID NO: 440 | moltype = DNA   length = 16 | |
| FEATURE | Location/Qualifiers | |
| source | 1..16 | |
| | mol_type = other DNA | |
| | organism = synthetic construct | |
| modified_base | order(1..3,14..16) | |
| | mod_base = OTHER | |
| | note = Constrained ethyl 2-prime-4-prime-bridged nucleic acid | |
| modified_base | order(4,15,16) | |
| | mod_base = OTHER | |
| | note = 5-methyl on the cytidine | |
| misc_feature | 4..13 | |
| | note = DNA | |
| misc_feature | order(1..3,14..16) | |
| | note = RNA | |
| SEQUENCE: 440 | | |
| catcaggctg gggacc | | 16 |
| | | |
| SEQ ID NO: 441 | moltype = DNA   length = 16 | |
| FEATURE | Location/Qualifiers | |
| source | 1..16 | |
| | mol_type = other DNA | |
| | organism = synthetic construct | |
| modified_base | order(1..3,14..16) | |
| | mod_base = OTHER | |
| | note = Constrained ethyl 2-prime-4-prime-bridged nucleic acid | |
| misc_feature | order(1..3,14..16) | |
| | note = RNA | |
| modified_base | order(2,6,13..15) | |
| | mod_base = OTHER | |
| | note = 5-methyl on the cytidine | |
| misc_feature | 4..14 | |
| | note = DNA | |
| SEQUENCE: 441 | | |
| tcaggctggg gaccct | | 16 |
| | | |
| SEQ ID NO: 442 | moltype = DNA   length = 16 | |
| FEATURE | Location/Qualifiers | |
| source | 1..16 | |
| | mol_type = other DNA | |
| | organism = synthetic construct | |
| modified_base | order(1..3,14..16) | |
| | mod_base = OTHER | |
| | note = Constrained ethyl 2-prime-4-prime-bridged nucleic acid | |
| modified_base | order(4,11..13) | |
| | mod_base = OTHER | |
| | note = 5-methyl on the cytidine | |
| misc_feature | order(1..3,14..16) | |
| | note = RNA | |
| misc_feature | 4..13 | |
| | note = DNA | |
| SEQUENCE: 442 | | |
| aggctgggga ccctgt | | 16 |
| | | |
| SEQ ID NO: 443 | moltype = DNA   length = 16 | |
| FEATURE | Location/Qualifiers | |
| source | 1..16 | |
| | mol_type = other DNA | |
| | organism = synthetic construct | |
| modified_base | order(1..3,14..16) | |
| | mod_base = OTHER | |
| | note = Locked nucleic acid | |
| modified_base | order(1,9,13,15) | |
| | mod_base = OTHER | |
| | note = 5-methyl on the cytidine | |
| misc_feature | 4..13 | |
| | note = DNA | |
| misc_feature | order(1..3,14..16) | |
| | note = RNA | |
| SEQUENCE: 443 | | |
| catgaatgca ggcaca | | 16 |

```
SEQ ID NO: 444           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Locked nucleic acid
modified_base            order(7,11,13,15)
                         mod_base = OTHER
                         note = 5-methyl on the cytidine
misc_feature             order(1..3,14..16)
                         note = RNA
misc_feature             4..13
                         note = DNA
SEQUENCE: 444
tgaatgcagg cacaca                                                        16

SEQ ID NO: 445           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Locked nucleic acid
modified_base            order(5,9,11,13,15)
                         mod_base = OTHER
                         note = 5-methyl on the cytidine
misc_feature             order(1..3,14..16)
                         note = RNA
misc_feature             4..13
                         note = DNA
SEQUENCE: 445
aatgcaggca cacaca                                                        16

SEQ ID NO: 446           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Locked nucleic acid
modified_base            order(3,7,9,11,13,16)
                         mod_base = OTHER
                         note = 5-methyl on the cytidine
misc_feature             order(1..3,14..16)
                         note = RNA
misc_feature             4..13
                         note = DNA
SEQUENCE: 446
tgcaggcaca cacatc                                                        16

SEQ ID NO: 447           moltype = DNA  length = 16
FEATURE                  Location/Qualifiers
source                   1..16
                         mol_type = other DNA
                         organism = synthetic construct
modified_base            order(1..3,14..16)
                         mod_base = OTHER
                         note = Locked nucleic acid
modified_base            order(1,5,7,9,11,14)
                         mod_base = OTHER
                         note = 5-methyl on the cytidine
misc_feature             order(1..3,14..16)
                         note = RNA
misc_feature             4..13
                         note = DNA
SEQUENCE: 447
caggcacaca catcag                                                        16

SEQ ID NO: 448           moltype = DNA  length = 16
FEATURE                  Location/Qualifiers
source                   1..16
                         mol_type = other DNA
                         organism = synthetic construct
```

```
modified_base              order(1..3,14..16)
                           mod_base = OTHER
                           note = Locked nucleic acid
modified_base              order(3,5,7,9,12,16)
                           mod_base = OTHER
                           note = 5-methyl on the cytidine
misc_feature               order(1..3,14..16)
                           note = RNA
misc_feature               4..13
                           note = DNA
SEQUENCE: 448
ggcacacaca tcaggc                                                        16

SEQ ID NO: 449             moltype = DNA  length = 16
FEATURE                    Location/Qualifiers
source                     1..16
                           mol_type = other DNA
                           organism = synthetic construct
modified_base              order(1..3,14..16)
                           mod_base = OTHER
                           note = Locked nucleic acid
modified_base              order(1,3,5,7,10,14)
                           mod_base = OTHER
                           note = 5-methyl on the cytidine
misc_feature               order(1..3,14..16)
                           note = RNA
misc_feature               4..13
                           note = DNA
SEQUENCE: 449
cacacacatc aggctg                                                        16

SEQ ID NO: 450             moltype = DNA  length = 16
FEATURE                    Location/Qualifiers
source                     1..16
                           mol_type = other DNA
                           organism = synthetic construct
modified_base              order(1..3,14..16)
                           mod_base = OTHER
                           note = Locked nucleic acid
modified_base              order(1,3,5,8,12)
                           mod_base = OTHER
                           note = 5-methyl on the cytidine
misc_feature               order(1..3,14..16)
                           note = RNA
misc_feature               4..13
                           note = DNA
SEQUENCE: 450
cacacatcag gctggg                                                        16

SEQ ID NO: 451             moltype = DNA  length = 16
FEATURE                    Location/Qualifiers
source                     1..16
                           mol_type = other DNA
                           organism = synthetic construct
modified_base              order(1..3,14..16)
                           mod_base = OTHER
                           note = Locked nucleic acid
modified_base              order(3,11,15)
                           mod_base = OTHER
                           note = 5-methyl on the cytidine
misc_feature               order(1..3,14..16)
                           note = RNA
misc_feature               4..13
                           note = DNA
SEQUENCE: 451
ggcatgaatg caggca                                                        16

SEQ ID NO: 452             moltype = DNA  length = 16
FEATURE                    Location/Qualifiers
source                     1..16
                           mol_type = other DNA
                           organism = synthetic construct
modified_base              order(1..3,14..16)
                           mod_base = OTHER
                           note = Locked nucleic acid
modified_base              order(1,5,13)
                           mod_base = OTHER
                           note = 5-methyl on the cytidine
```

```
misc_feature              order(1..3,14..16)
                          note = RNA
misc_feature              4..13
                          note = DNA
SEQUENCE: 452
caggcatgaa tgcagg                                                        16

SEQ ID NO: 453            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Locked nucleic acid
modified_base             order(3,7,15)
                          mod_base = OTHER
                          note = Locked nucleic acid
misc_feature              order(1..3,14..16)
                          note = RNA
misc_feature              4..13
                          note = DNA
SEQUENCE: 453
gacaggcatg aatgca                                                        16

SEQ ID NO: 454            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Locked nucleic acid
modified_base             order(5,9)
                          mod_base = OTHER
                          note = 5-methyl on the cytidine
misc_feature              order(1..3,14..16)
                          note = RNA
misc_feature              4..13
                          note = DNA
SEQUENCE: 454
gtgacaggca tgaatg                                                        16

SEQ ID NO: 455            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Locked nucleic acid
modified_base             order(1,3,6,10)
                          mod_base = OTHER
                          note = 5-methyl on the cytidine
misc_feature              order(1..3,14..16)
                          note = RNA
misc_feature              4..13
                          note = DNA
SEQUENCE: 455
cacatcaggc tgggga                                                        16

SEQ ID NO: 456            moltype = DNA  length = 16
FEATURE                   Location/Qualifiers
source                    1..16
                          mol_type = other DNA
                          organism = synthetic construct
modified_base             order(1..3,14..16)
                          mod_base = OTHER
                          note = Locked nucleic acid
modified_base             order(1,4,8,15,16)
                          mod_base = OTHER
                          note = 5-methyl on the cytidine
misc_feature              order(1..3,14..16)
                          note = RNA
misc_feature              4..13
                          note = DNA
SEQUENCE: 456
catcaggctg gggacc                                                        16
```

| | | |
|---|---|---|
| SEQ ID NO: 457 | moltype = DNA   length = 16 | |
| FEATURE | Location/Qualifiers | |
| source | 1..16 | |
| | mol_type = other DNA | |
| | organism = synthetic construct | |
| modified_base | order(1..3,14..16) | |
| | mod_base = OTHER | |
| | note = Locked nucleic acid | |
| modified_base | order(2,6,13,15) | |
| | mod_base = OTHER | |
| | note = 5-methyl on the cytidine | |
| misc_feature | order(1..3,14..16) | |
| | note = RNA | |
| misc_feature | 4..13 | |
| | note = DNA | |
| SEQUENCE: 457 | | |
| tcaggctggg gaccct | | 16 |
| | | |
| SEQ ID NO: 458 | moltype = DNA   length = 16 | |
| FEATURE | Location/Qualifiers | |
| source | 1..16 | |
| | mol_type = other DNA | |
| | organism = synthetic construct | |
| modified_base | order(1..3,14..16) | |
| | mod_base = OTHER | |
| | note = Locked nucleic acid | |
| modified_base | order(4,11..13) | |
| | mod_base = OTHER | |
| | note = 5-methyl on the cytidine | |
| misc_feature | order(1..3,14..16) | |
| | note = RNA | |
| misc_feature | 4..13 | |
| | note = DNA | |
| SEQUENCE: 458 | | |
| aggctgggga ccctgt | | 16 |
| | | |
| SEQ ID NO: 459 | moltype = DNA   length = 18 | |
| FEATURE | Location/Qualifiers | |
| source | 1..18 | |
| | mol_type = other DNA | |
| | organism = synthetic construct | |
| modified_base | order(1..4,15..18) | |
| | mod_base = OTHER | |
| | note = 2-prime-O-(2-Methoxyethyl) nucleotide | |
| modified_base | order(2,10,14,16,18) | |
| | mod_base = OTHER | |
| | note = 5-methyl on the cytidine | |
| misc_feature | 5..14 | |
| | note = DNA | |
| misc_feature | order(1..4,15..18) | |
| | note = RNA | |
| SEQUENCE: 459 | | |
| gcatgaatgc aggcacac | | 18 |
| | | |
| SEQ ID NO: 460 | moltype = DNA   length = 18 | |
| FEATURE | Location/Qualifiers | |
| source | 1..18 | |
| | mol_type = other DNA | |
| | organism = synthetic construct | |
| modified_base | order(1,3,16,18) | |
| | mod_base = OTHER | |
| | note = Locked nucleic acid | |
| modified_base | order(2,4,15,17) | |
| | mod_base = OTHER | |
| | note = 2-prime-O-(2-Methoxyethyl) nucleotide | |
| modified_base | order(2,10,14,16,18) | |
| | mod_base = OTHER | |
| | note = 5-methyl on the cytidine | |
| misc_feature | order(1..4,15..18) | |
| | note = RNA | |
| misc_feature | 5..14 | |
| | note = DNA | |
| SEQUENCE: 460 | | |
| gcatgaatgc aggcacac | | 18 |
| | | |
| SEQ ID NO: 461 | moltype = DNA   length = 18 | |
| FEATURE | Location/Qualifiers | |

```
source            1..18
                  mol_type = other DNA
                  organism = synthetic construct
modified_base     order(1..4,15..18)
                  mod_base = OTHER
                  note = 2-prime-O-(2-Methoxyethyl) nucleotide
modified_base     order(2,4,6,8,11,15)
                  mod_base = OTHER
                  note = 5-methyl on the cytidine
misc_feature      5..14
                  note = DNA
misc_feature      order(1..4,15..18)
                  note = RNA
SEQUENCE: 461
gcacacacat caggctgg                                               18

SEQ ID NO: 462    moltype = DNA  length = 18
FEATURE           Location/Qualifiers
source            1..18
                  mol_type = other DNA
                  organism = synthetic construct
modified_base     order(2,4,15,17)
                  mod_base = OTHER
                  note = 2-prime-O-(2-Methoxyethyl) nucleotide
modified_base     order(1,3,16,18)
                  mod_base = OTHER
                  note = Locked nucleic acid
modified_base     order(2,4,6,8,11,15)
                  mod_base = OTHER
                  note = 5-methyl on the cytidine
misc_feature      order(1..4,15..18)
                  note = RNA
modified_base     5..14
                  mod_base = OTHER
                  note = 5-methyl on the cytidine
SEQUENCE: 462
gcacacacat caggctgg                                               18

SEQ ID NO: 463    moltype = DNA  length = 18
FEATURE           Location/Qualifiers
source            1..18
                  mol_type = other DNA
                  organism = synthetic construct
modified_base     order(1..4,15..18)
                  mod_base = OTHER
                  note = 2-prime-O-(2-Methoxyethyl) nucleotide
modified_base     order(2,4,6,8,11,15)
                  mod_base = OTHER
                  note = 5-methyl on the cytidine
misc_feature      order(1..4,15..18)
                  note = RNA
misc_feature      5..14
                  note = DNA
SEQUENCE: 463
acacacatca ggctgggg                                               18

SEQ ID NO: 464    moltype = DNA  length = 18
FEATURE           Location/Qualifiers
source            1..18
                  mol_type = other DNA
                  organism = synthetic construct
modified_base     order(2,4,15,17)
                  mod_base = OTHER
                  note = 2-prime-O-(2-Methoxyethyl) nucleotide
modified_base     order(1,3,16,18)
                  mod_base = OTHER
                  note = Locked nucleic acid
modified_base     order(2,4,6,9,13)
                  mod_base = OTHER
                  note = 5-methyl on the cytidine
misc_feature      order(1..4,15..18)
                  note = RNA
misc_feature      5..14
                  note = DNA
SEQUENCE: 464
acacacatca ggctgggg                                               18

SEQ ID NO: 465    moltype = DNA  length = 18
FEATURE           Location/Qualifiers
```

```
source                  1..18
                        mol_type = other DNA
                        organism = synthetic construct
modified_base           order(2..4,15..17)
                        mod_base = OTHER
                        note = 2-prime-O-(2-Methoxyethyl) nucleotide
modified_base           order(1,18)
                        mod_base = OTHER
                        note = Locked nucleic acid
modified_base           order(1,3,5,7,10,14)
                        mod_base = OTHER
                        note = 5-methyl on the cytidine
misc_feature            5..14
                        note = DNA
misc_feature            order(1..4,15..18)
                        note = RNA
SEQUENCE: 465
cacacacatc aggctggg                                                        18

SEQ ID NO: 466          moltype = DNA  length = 18
FEATURE                 Location/Qualifiers
source                  1..18
                        mol_type = other DNA
                        organism = synthetic construct
modified_base           order(2,4,15,17)
                        mod_base = OTHER
                        note = 2-prime-O-(2-Methoxyethyl) nucleotide
modified_base           order(1,3,16,18)
                        mod_base = OTHER
                        note = Locked nucleic acid
modified_base           order(1,3,5,7,10,14)
                        mod_base = OTHER
                        note = 5-methyl on the cytidine
misc_feature            5..14
                        note = DNA
misc_feature            order(1..4,15..18)
                        note = RNA
SEQUENCE: 466
cacacacatc aggctggg                                                        18

SEQ ID NO: 467          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,11,15,17,19)
                        mod_base = OTHER
                        note = 5-methyl on the cytidine
misc_feature            order(1..5,16..20)
                        note = RNA
misc_feature            6..15
                        note = DNA
SEQUENCE: 467
ggcatgaatg caggcacaca                                                      20

SEQ ID NO: 468          moltype = DNA  length = 20
FEATURE                 Location/Qualifiers
source                  1..20
                        mol_type = other DNA
                        organism = synthetic construct
modified_base           order(2,4,5,16,17,19)
                        mod_base = OTHER
                        note = 2-prime-O-(2-Methoxyethyl) nucleotide
modified_base           order(1,3,18,20)
                        mod_base = OTHER
                        note = Locked nucleic acid
modified_base           order(3,11,15,17,19)
                        mod_base = OTHER
                        note = 5-methyl on the cytidine
misc_feature            order(1..5,16..20)
                        note = RNA
misc_feature            6..15
                        note = DNA
SEQUENCE: 468
ggcatgaatg caggcacaca                                                      20
```

```
SEQ ID NO: 469          moltype = DNA  length = 20
FEATURE                 Location/Qualifiers
source                  1..20
                        mol_type = other DNA
                        organism = synthetic construct
modified_base           order(2,4,5,16,17,19)
                        mod_base = OTHER
                        note = 2-prime-O-(2-Methoxyethyl) nucleotide
modified_base           order(1,3,9,12,18,20)
                        mod_base = OTHER
                        note = Locked nucleic acid
modified_base           order(3,11,15,17,19)
                        mod_base = OTHER
                        note = 5-methyl on the cytidine
misc_feature            order(1..5,16..20)
                        note = RNA
misc_feature            6..15
                        note = DNA
SEQUENCE: 469
ggcatgaatg caggcacaca                                                   20

SEQ ID NO: 470          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,11,15,17,19)
                        mod_base = OTHER
                        note = 5-methyl on the cytidine
misc_feature            order(1..5,16..20)
                        note = RNA
misc_feature            6..15
                        note = DNA
SEQUENCE: 470
ggcatgaatg caggcacaca                                                   20

SEQ ID NO: 471          moltype = DNA  length = 20
FEATURE                 Location/Qualifiers
source                  1..20
                        mol_type = other DNA
                        organism = synthetic construct
modified_base           order(1,3,18,20)
                        mod_base = OTHER
                        note = Locked nucleic acid
modified_base           order(2,4,5,16,17,19)
                        mod_base = OTHER
                        note = 2-prime-O-(2-Methoxyethyl) nucleotide
modified_base           order(3,5,7,9,12,16)
                        mod_base = OTHER
                        note = 5-methyl on the cytidine
misc_feature            order(1..5,16..20)
                        note = RNA
misc_feature            6..15
                        note = DNA
SEQUENCE: 471
ggcacacaca tcaggctggg                                                   20

SEQ ID NO: 472          moltype = DNA  length = 20
FEATURE                 Location/Qualifiers
source                  1..20
                        mol_type = other DNA
                        organism = synthetic construct
modified_base           order(2,4,5,16,17,19)
                        mod_base = OTHER
                        note = 2-prime-O-(2-Methoxyethyl) nucleotide
modified_base           order(1,3,9,12,18,20)
                        mod_base = OTHER
                        note = Locked nucleic acid
modified_base           order(3,5,7,9,12,16)
                        mod_base = OTHER
                        note = 5-methyl on the cytidine
misc_feature            order(1..5,9,12,16..20)
                        note = RNA
misc_feature            6..15
                        note = DNA
```

```
SEQUENCE: 472
ggcacacaca tcaggctggg                                                   20

SEQ ID NO: 473          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(3,5,7,9,12,16)
                        mod_base = OTHER
                        note = 5-methyl on the cytidine
modified_base           order(3^4,4^5,16^17,17^18)
                        mod_base = OTHER
                        note = Phosphodiester linkage
misc_feature            order(1..5,16..20)
                        note = RNA
misc_feature            6..15
                        note = DNA
SEQUENCE: 473
ggcacacaca tcaggctggg                                                   20

SEQ ID NO: 474          moltype = DNA  length = 20
FEATURE                 Location/Qualifiers
source                  1..20
                        mol_type = other DNA
                        organism = synthetic construct
modified_base           order(1..5,16..20)
                        mod_base = OTHER
                        note = 2-prime-O-(2-Methoxyethyl) nucleotide
modified_base           order(1,3,5,7,10,14)
                        mod_base = OTHER
                        note = 5-methyl on the cytidine
misc_feature            order(1..5,16..20)
                        note = RNA
misc_feature            6..15
                        note = DNA
SEQUENCE: 474
cacacacatc aggctgggga                                                   20

SEQ ID NO: 475          moltype = DNA  length = 20
FEATURE                 Location/Qualifiers
source                  1..20
                        mol_type = other DNA
                        organism = synthetic construct
modified_base           order(2,4,5,16,17,19)
                        mod_base = OTHER
                        note = 2-prime-O-(2-Methoxyethyl) nucleotide
modified_base           order(1,3,18,20)
                        mod_base = OTHER
                        note = Locked nucleic acid
modified_base           order(1,3,5,7,10,14)
                        mod_base = OTHER
                        note = 5-methyl on the cytidine
misc_feature            order(1..5,16..20)
                        note = RNA
misc_feature            6..15
                        note = DNA
SEQUENCE: 475
cacacacatc aggctgggga                                                   20

SEQ ID NO: 476          moltype = DNA  length = 20
FEATURE                 Location/Qualifiers
source                  1..20
                        mol_type = other DNA
                        organism = synthetic construct
modified_base           order(2,4,5,16,17,19)
                        mod_base = OTHER
                        note = 2-prime-O-(2-Methoxyethyl) nucleotide
modified_base           order(1,3,9,12,18,20)
                        mod_base = OTHER
                        note = Locked nucleic acid
modified_base           order(1,3,5,7,10,14)
                        mod_base = OTHER
                        note = 5-methyl on the cytidine
misc_feature            order(1..5,9,12,16..20)
                        note = RNA
```

```
misc_feature          order(6..8,10,11,13..15)
                      note = DNA
SEQUENCE: 476
cacacacatc aggctgggga                                                    20

SEQ ID NO: 477        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(1,3,5,7,10,14)
                      mod_base = OTHER
                      note = 5-methyl on the cytidine
modified_base         order(3^4,4^5,16^17,17^18)
                      mod_base = OTHER
                      note = Phosphodiester linkage
misc_feature          order(1..5,16..20)
                      note = RNA
misc_feature          6..15
                      note = DNA
SEQUENCE: 477
cacacacatc aggctgggga                                                    20

SEQ ID NO: 478        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(2,4,6,8,11,15)
                      mod_base = OTHER
                      note = 5-methyl on the cytidine
misc_feature          order(1..5,16..20)
                      note = RNA
misc_feature          6..15
                      note = DNA
SEQUENCE: 478
gcacacacat caggctgggg                                                    20

SEQ ID NO: 479        moltype = DNA  length = 20
FEATURE               Location/Qualifiers
source                1..20
                      mol_type = other DNA
                      organism = synthetic construct
modified_base         order(2,4,5,16,17,19)
                      mod_base = OTHER
                      note = 2-prime-O-(2-Methoxyethyl) nucleotide
modified_base         order(1,3,18,20)
                      mod_base = OTHER
                      note = Locked nucleic acid
modified_base         order(2,4,6,8,11,15)
                      mod_base = OTHER
                      note = 5-methyl on the cytidine
misc_feature          6..15
                      note = DNA
misc_feature          order(1..5,16..20)
                      note = RNA
SEQUENCE: 479
gcacacacat caggctgggg                                                    20

SEQ ID NO: 480        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(2,4,6,8,11,15)
                      mod_base = OTHER
                      note = 5-methyl on the cytidine
modified_base         order(3^4,4^5,16^17,17^18)
                      mod_base = OTHER
                      note = Phosphodiester linkage
```

```
misc_feature          order(1..5,16..18)
                      note = RNA
modified_base         6..15
                      mod_base = OTHER
                      note = DNA
SEQUENCE: 480
gcacacacat caggctgggg                                               20

SEQ ID NO: 481        moltype = DNA  length = 20
FEATURE               Location/Qualifiers
source                1..20
                      mol_type = other DNA
                      organism = synthetic construct
modified_base         order(3,7,9,11,13,16,20)
                      mod_base = OTHER
                      note = 5-methyl on the cytidine
SEQUENCE: 481
tgcaggcaca cacatcaggc                                               20

SEQ ID NO: 482        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(3,7,14,15,16)
                      mod_base = OTHER
                      note = 5-methyl on the cytidine
misc_feature          6..15
                      note = DNA
misc_feature          order(1..5,16..20)
                      note = RNA
SEQUENCE: 482
atcaggctgg ggaccctgtg                                               20

SEQ ID NO: 483        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(3,5,7,9,12,16)
                      mod_base = OTHER
                      note = 5-methyl on the cytidine
misc_feature          6..15
                      note = DNA
misc_feature          order(1..5,16..20)
                      note = RNA
SEQUENCE: 483
ggcacacaca tcaggctggg                                               20

SEQ ID NO: 484        moltype = DNA  length = 20
FEATURE               Location/Qualifiers
source                1..20
                      mol_type = other DNA
                      organism = synthetic construct
modified_base         order(1..5,16..20)
                      mod_base = OTHER
                      note = 2-prime-O-(2-Methoxyethyl) nucleotide
modified_base         order(8,12,14,16,18)
                      mod_base = OTHER
                      note = 5-methyl on the cytidine
misc_feature          order(1..5,16..20)
                      note = RNA
misc_feature          6..15
                      note = DNA
SEQUENCE: 484
atgaatgcag gcacacacat                                               20

SEQ ID NO: 485        moltype = DNA  length = 20
FEATURE               Location/Qualifiers
source                1..20
                      mol_type = other DNA
                      organism = synthetic construct
```

```
                        -continued modified_base          order(1..5,16..20)
                       mod_base = OTHER
                       note = 2-prime-O-(2-Methoxyethyl) nucleotide
misc_feature           order(1..5,16..20)
                       note = RNA
modified_base          order(3,7,9,11,13,16,20)
                       mod_base = OTHER
                       note = 5-methyl on the cytidine
misc_feature           6..15
                       note = DNA
SEQUENCE: 485
tgcaggcaca cacatcaggc                                                   20

SEQ ID NO: 486         moltype = DNA  length = 20
FEATURE                Location/Qualifiers
source                 1..20
                       mol_type = other DNA
                       organism = synthetic construct
modified_base          order(1..5,16..20)
                       mod_base = OTHER
                       note = 2-prime-O-(2-Methoxyethyl) nucleotide
modified_base          order(3,9,11,13,16,20)
                       mod_base = OTHER
                       note = 5-methyl on the cytidine
misc_feature           order(1..5,7,16..20)
                       note = RNA
misc_feature           order(6,8..15)
                       note = DNA
modified_base          7
                       mod_base = OTHER
                       note = Constrained ethyl 2-prime-4-prime-bridged nucleic
                        acid
modified_base          order(3^4,4^5,16^17,17^18)
                       mod_base = OTHER
                       note = Phosphodiester linkage
SEQUENCE: 486
tgcaggcaca cacatcaggc                                                   20

SEQ ID NO: 487         moltype = RNA  length = 20
FEATURE                Location/Qualifiers
source                 1..20
                       mol_type = other RNA
                       organism = synthetic construct
SEQUENCE: 487
gcaatgacaa ggtatttgat                                                   20

SEQ ID NO: 488         moltype = RNA  length = 20
FEATURE                Location/Qualifiers
source                 1..20
                       mol_type = other RNA
                       organism = synthetic construct
SEQUENCE: 488
ggactacaag ttgttgcaat                                                   20

SEQ ID NO: 489         moltype = RNA  length = 20
FEATURE                Location/Qualifiers
source                 1..20
                       mol_type = other RNA
                       organism = synthetic construct
SEQUENCE: 489
gttagatcaa agagtcctta                                                   20

SEQ ID NO: 490         moltype = RNA  length = 20
FEATURE                Location/Qualifiers
source                 1..20
                       mol_type = other RNA
                       organism = synthetic construct
SEQUENCE: 490
ttagtagagg gttagatcaa                                                   20

SEQ ID NO: 491         moltype = RNA  length = 20
FEATURE                Location/Qualifiers
source                 1..20
                       mol_type = other RNA
                       organism = synthetic construct
SEQUENCE: 491
gtagaaggac ttagtagagg                                                   20

SEQ ID NO: 492         moltype = RNA  length = 20
```

```
FEATURE                     Location/Qualifiers
source                      1..20
                            mol_type = other RNA
                            organism = synthetic construct
SEQUENCE: 492
gtcacacatg aacaattctc                                                       20

SEQ ID NO: 493              moltype = RNA   length = 20
FEATURE                     Location/Qualifiers
source                      1..20
                            mol_type = other RNA
                            organism = synthetic construct
SEQUENCE: 493
gatgactgat ttacttgaca                                                       20

SEQ ID NO: 494              moltype = RNA   length = 20
FEATURE                     Location/Qualifiers
source                      1..20
                            mol_type = other RNA
                            organism = synthetic construct
SEQUENCE: 494
tgtatagtgc aaatgatgac                                                       20

SEQ ID NO: 495              moltype = RNA   length = 20
FEATURE                     Location/Qualifiers
source                      1..20
                            mol_type = other RNA
                            organism = synthetic construct
SEQUENCE: 495
ttttgtcatc tgtatagtgc                                                       20

SEQ ID NO: 496              moltype = RNA   length = 20
FEATURE                     Location/Qualifiers
source                      1..20
                            mol_type = other RNA
                            organism = synthetic construct
SEQUENCE: 496
tcacatattc tctgaaccta                                                       20

SEQ ID NO: 497              moltype = RNA   length = 20
FEATURE                     Location/Qualifiers
source                      1..20
                            mol_type = other RNA
                            organism = synthetic construct
SEQUENCE: 497
ttcttggaca agtcacatat                                                       20

SEQ ID NO: 498              moltype = RNA   length = 20
FEATURE                     Location/Qualifiers
source                      1..20
                            mol_type = other RNA
                            organism = synthetic construct
SEQUENCE: 498
taatgccctg ttcttggaca                                                       20

SEQ ID NO: 499              moltype = RNA   length = 20
FEATURE                     Location/Qualifiers
source                      1..20
                            mol_type = other RNA
                            organism = synthetic construct
SEQUENCE: 499
ctgttatgca tttcctaatg                                                       20

SEQ ID NO: 500              moltype = RNA   length = 20
FEATURE                     Location/Qualifiers
source                      1..20
                            mol_type = other RNA
                            organism = synthetic construct
SEQUENCE: 500
gaatctaacc cctgttatgc                                                       20

SEQ ID NO: 501              moltype = RNA   length = 20
FEATURE                     Location/Qualifiers
source                      1..20
                            mol_type = other RNA
                            organism = synthetic construct
SEQUENCE: 501
ggcacaaaaa gatctggaat                                                       20
```

| | | |
|---|---|---|
| SEQ ID NO: 502<br>FEATURE<br>source | moltype = RNA   length = 20<br>Location/Qualifiers<br>1..20<br>mol_type = other RNA<br>organism = synthetic construct | |
| SEQUENCE: 502<br>gtaatagtgg gatatactct | | 20 |
| SEQ ID NO: 503<br>FEATURE<br>source | moltype = RNA   length = 20<br>Location/Qualifiers<br>1..20<br>mol_type = other RNA<br>organism = synthetic construct | |
| SEQUENCE: 503<br>aggctgtaac agtgtaatag | | 20 |
| SEQ ID NO: 504<br>FEATURE<br>source | moltype = RNA   length = 20<br>Location/Qualifiers<br>1..20<br>mol_type = other RNA<br>organism = synthetic construct | |
| SEQUENCE: 504<br>ttattacatt cagcaggctg | | 20 |
| SEQ ID NO: 505<br>FEATURE<br>source | moltype = RNA   length = 20<br>Location/Qualifiers<br>1..20<br>mol_type = other RNA<br>organism = synthetic construct | |
| SEQUENCE: 505<br>gaaaatgttc agcactcatt | | 20 |
| SEQ ID NO: 506<br>FEATURE<br>source | moltype = RNA   length = 20<br>Location/Qualifiers<br>1..20<br>mol_type = other RNA<br>organism = synthetic construct | |
| SEQUENCE: 506<br>ggtataaatg atcaacaacc | | 20 |
| SEQ ID NO: 507<br>FEATURE<br>source | moltype = RNA   length = 20<br>Location/Qualifiers<br>1..20<br>mol_type = other RNA<br>organism = synthetic construct | |
| SEQUENCE: 507<br>gaaagttgat atcaagggta | | 20 |
| SEQ ID NO: 508<br>FEATURE<br>source | moltype = RNA   length = 20<br>Location/Qualifiers<br>1..20<br>mol_type = other RNA<br>organism = synthetic construct | |
| SEQUENCE: 508<br>agaatttcaa ggtgctctat | | 20 |
| SEQ ID NO: 509<br>FEATURE<br>source | moltype = RNA   length = 20<br>Location/Qualifiers<br>1..20<br>mol_type = other RNA<br>organism = synthetic construct | |
| SEQUENCE: 509<br>ttttacttac aggaaagagg | | 20 |
| SEQ ID NO: 510<br>FEATURE<br>source | moltype = RNA   length = 20<br>Location/Qualifiers<br>1..20<br>mol_type = other RNA<br>organism = synthetic construct | |
| SEQUENCE: 510<br>ccaatcggca cagttgtatt | | 20 |
| SEQ ID NO: 511<br>FEATURE<br>source | moltype = RNA   length = 20<br>Location/Qualifiers<br>1..20<br>mol_type = other RNA<br>organism = synthetic construct | |
| SEQUENCE: 511<br>tagagtgctt tgccaatcgg | | 20 |

```
SEQ ID NO: 512          moltype = RNA   length = 20
FEATURE                 Location/Qualifiers
source                  1..20
                        mol_type = other RNA
                        organism = synthetic construct
SEQUENCE: 512
gcggctaata tttatagagt                                                   20

SEQ ID NO: 513          moltype = RNA   length = 20
FEATURE                 Location/Qualifiers
source                  1..20
                        mol_type = other RNA
                        organism = synthetic construct
SEQUENCE: 513
ggtatttgtc agcggctaat                                                   20

SEQ ID NO: 514          moltype = RNA   length = 20
FEATURE                 Location/Qualifiers
source                  1..20
                        mol_type = other RNA
                        organism = synthetic construct
SEQUENCE: 514
taattttatg tggcccttcc                                                   20

SEQ ID NO: 515          moltype = RNA   length = 20
FEATURE                 Location/Qualifiers
source                  1..20
                        mol_type = other RNA
                        organism = synthetic construct
SEQUENCE: 515
gcaatgacgc acttataatt                                                   20

SEQ ID NO: 516          moltype = RNA   length = 20
FEATURE                 Location/Qualifiers
source                  1..20
                        mol_type = other RNA
                        organism = synthetic construct
SEQUENCE: 516
gtttgacgac agcaatgacg                                                   20

SEQ ID NO: 517          moltype = RNA   length = 20
FEATURE                 Location/Qualifiers
source                  1..20
                        mol_type = other RNA
                        organism = synthetic construct
SEQUENCE: 517
gagacggtgg gtttgacgac                                                   20

SEQ ID NO: 518          moltype = RNA   length = 20
FEATURE                 Location/Qualifiers
source                  1..20
                        mol_type = other RNA
                        organism = synthetic construct
SEQUENCE: 518
tttgatgaca gagacggtgg                                                   20

SEQ ID NO: 519          moltype = RNA   length = 20
FEATURE                 Location/Qualifiers
source                  1..20
                        mol_type = other RNA
                        organism = synthetic construct
SEQUENCE: 519
ttcctctctc tttgatgaca                                                   20

SEQ ID NO: 520          moltype = RNA   length = 20
FEATURE                 Location/Qualifiers
source                  1..20
                        mol_type = other RNA
                        organism = synthetic construct
SEQUENCE: 520
aggtttgctt ttcctctctc                                                   20

SEQ ID NO: 521          moltype = RNA   length = 20
FEATURE                 Location/Qualifiers
source                  1..20
                        mol_type = other RNA
                        organism = synthetic construct
```

-continued

```
SEQUENCE: 521
cgacatattt agaggtttgc                                              20

SEQ ID NO: 522         moltype = RNA   length = 20
FEATURE                Location/Qualifiers
source                 1..20
                       mol_type = other RNA
                       organism = synthetic construct
SEQUENCE: 522
gggttgcttt ttcgacatat                                              20

SEQ ID NO: 523         moltype = RNA   length = 20
FEATURE                Location/Qualifiers
source                 1..20
                       mol_type = other RNA
                       organism = synthetic construct
SEQUENCE: 523
cctgtaaatt gggttgcttt                                              20

SEQ ID NO: 524         moltype = RNA   length = 20
FEATURE                Location/Qualifiers
source                 1..20
                       mol_type = other RNA
                       organism = synthetic construct
SEQUENCE: 524
catctataat cattgccctg                                              20

SEQ ID NO: 525         moltype = RNA   length = 20
FEATURE                Location/Qualifiers
source                 1..20
                       mol_type = other RNA
                       organism = synthetic construct
SEQUENCE: 525
agacaccctg tagtcacatc                                              20

SEQ ID NO: 526         moltype = RNA   length = 20
FEATURE                Location/Qualifiers
source                 1..20
                       mol_type = other RNA
                       organism = synthetic construct
SEQUENCE: 526
tagatggtaa atggattggg                                              20

SEQ ID NO: 527         moltype = RNA   length = 20
FEATURE                Location/Qualifiers
source                 1..20
                       mol_type = other RNA
                       organism = synthetic construct
SEQUENCE: 527
tatgtccagt tatagatggt                                              20

SEQ ID NO: 528         moltype = RNA   length = 20
FEATURE                Location/Qualifiers
source                 1..20
                       mol_type = other RNA
                       organism = synthetic construct
SEQUENCE: 528
aaggttagta gcattatgtc                                              20

SEQ ID NO: 529         moltype = RNA   length = 20
FEATURE                Location/Qualifiers
source                 1..20
                       mol_type = other RNA
                       organism = synthetic construct
SEQUENCE: 529
cagtcacttt aaaggttagt                                              20

SEQ ID NO: 530         moltype = RNA   length = 20
FEATURE                Location/Qualifiers
source                 1..20
                       mol_type = other RNA
                       organism = synthetic construct
SEQUENCE: 530
gtagttacat aatggtcagt                                              20

SEQ ID NO: 531         moltype = RNA   length = 20
FEATURE                Location/Qualifiers
```

-continued

```
source                     1..20
                           mol_type = other RNA
                           organism = synthetic construct
SEQUENCE: 531
atcattagga tgtagttaca                                                    20

SEQ ID NO: 532             moltype = RNA   length = 20
FEATURE                    Location/Qualifiers
source                     1..20
                           mol_type = other RNA
                           organism = synthetic construct
SEQUENCE: 532
gccttcactt taaaaactca                                                    20

SEQ ID NO: 533             moltype = RNA   length = 20
FEATURE                    Location/Qualifiers
source                     1..20
                           mol_type = other RNA
                           organism = synthetic construct
SEQUENCE: 533
actttcttc ctgccttcac                                                     20

SEQ ID NO: 534             moltype = RNA   length = 20
FEATURE                    Location/Qualifiers
source                     1..20
                           mol_type = other RNA
                           organism = synthetic construct
SEQUENCE: 534
tagtcctcta tctactttc                                                     20

SEQ ID NO: 535             moltype = RNA   length = 20
FEATURE                    Location/Qualifiers
source                     1..20
                           mol_type = other RNA
                           organism = synthetic construct
SEQUENCE: 535
gttattgtga aatagtcctc                                                    20

SEQ ID NO: 536             moltype = RNA   length = 20
FEATURE                    Location/Qualifiers
source                     1..20
                           mol_type = other RNA
                           organism = synthetic construct
SEQUENCE: 536
ggacttgtgt tattattcag                                                    20

SEQ ID NO: 537             moltype = RNA   length = 20
FEATURE                    Location/Qualifiers
source                     1..20
                           mol_type = other RNA
                           organism = synthetic construct
SEQUENCE: 537
attccataga acagcccaag                                                    20

SEQ ID NO: 538             moltype = RNA   length = 20
FEATURE                    Location/Qualifiers
source                     1..20
                           mol_type = other RNA
                           organism = synthetic construct
SEQUENCE: 538
ggaggaatgc caagcacaaa                                                    20

SEQ ID NO: 539             moltype = RNA   length = 20
FEATURE                    Location/Qualifiers
source                     1..20
                           mol_type = other RNA
                           organism = synthetic construct
SEQUENCE: 539
ccagagtttt ggaggaatgc                                                    20

SEQ ID NO: 540             moltype = RNA   length = 20
FEATURE                    Location/Qualifiers
source                     1..20
                           mol_type = other RNA
                           organism = synthetic construct
SEQUENCE: 540
caatcattac tggccagagt                                                    20

SEQ ID NO: 541             moltype = RNA   length = 20
```

```
FEATURE                 Location/Qualifiers
source                  1..20
                        mol_type = other RNA
                        organism = synthetic construct
SEQUENCE: 541
gccattactc acactcaatc                                                    20

SEQ ID NO: 542          moltype = RNA   length = 20
FEATURE                 Location/Qualifiers
source                  1..20
                        mol_type = other RNA
                        organism = synthetic construct
SEQUENCE: 542
tcatttcatg gtgtaaaagc                                                    20

SEQ ID NO: 543          moltype = RNA   length = 20
FEATURE                 Location/Qualifiers
source                  1..20
                        mol_type = other RNA
                        organism = synthetic construct
SEQUENCE: 543
cactaagcca tcatttcatg                                                    20

SEQ ID NO: 544          moltype = RNA   length = 20
FEATURE                 Location/Qualifiers
source                  1..20
                        mol_type = other RNA
                        organism = synthetic construct
SEQUENCE: 544
gacaaatttg taggagcact                                                    20

SEQ ID NO: 545          moltype = RNA   length = 20
FEATURE                 Location/Qualifiers
source                  1..20
                        mol_type = other RNA
                        organism = synthetic construct
SEQUENCE: 545
acagtgcaca gctaagaatg                                                    20

SEQ ID NO: 546          moltype = RNA   length = 20
FEATURE                 Location/Qualifiers
source                  1..20
                        mol_type = other RNA
                        organism = synthetic construct
SEQUENCE: 546
aagggtctgt cacagtgcac                                                    20

SEQ ID NO: 547          moltype = RNA   length = 20
FEATURE                 Location/Qualifiers
source                  1..20
                        mol_type = other RNA
                        organism = synthetic construct
SEQUENCE: 547
acagatctgt ttcaagggtc                                                    20

SEQ ID NO: 548          moltype = RNA   length = 20
FEATURE                 Location/Qualifiers
source                  1..20
                        mol_type = other RNA
                        organism = synthetic construct
SEQUENCE: 548
cagttctagc tcatggtgac                                                    20

SEQ ID NO: 549          moltype = RNA   length = 20
FEATURE                 Location/Qualifiers
source                  1..20
                        mol_type = other RNA
                        organism = synthetic construct
SEQUENCE: 549
ggatggatta ctgtgaaagc                                                    20

SEQ ID NO: 550          moltype = RNA   length = 20
FEATURE                 Location/Qualifiers
source                  1..20
                        mol_type = other RNA
                        organism = synthetic construct
SEQUENCE: 550
tggtctaatt atgtggatgg                                                    20
```

| | | |
|---|---|---|
| SEQ ID NO: 551<br>FEATURE<br>source | moltype = RNA length = 20<br>Location/Qualifiers<br>1..20<br>mol_type = other RNA<br>organism = synthetic construct | |
| SEQUENCE: 551<br>ccacgacaaa atggtctaat | | 20 |
| SEQ ID NO: 552<br>FEATURE<br>source | moltype = RNA length = 20<br>Location/Qualifiers<br>1..20<br>mol_type = other RNA<br>organism = synthetic construct | |
| SEQUENCE: 552<br>tccatacaac caccaccaca | | 20 |
| SEQ ID NO: 553<br>FEATURE<br>source | moltype = RNA length = 20<br>Location/Qualifiers<br>1..20<br>mol_type = other RNA<br>organism = synthetic construct | |
| SEQUENCE: 553<br>caataagtgc tccatacaac | | 20 |
| SEQ ID NO: 554<br>FEATURE<br>source | moltype = RNA length = 20<br>Location/Qualifiers<br>1..20<br>mol_type = other RNA<br>organism = synthetic construct | |
| SEQUENCE: 554<br>gaatccaatt ctccaagatc | | 20 |
| SEQ ID NO: 555<br>FEATURE<br>source | moltype = RNA length = 20<br>Location/Qualifiers<br>1..20<br>mol_type = other RNA<br>organism = synthetic construct | |
| SEQUENCE: 555<br>ggcacagata tgattgaaat | | 20 |
| SEQ ID NO: 556<br>FEATURE<br>source | moltype = RNA length = 20<br>Location/Qualifiers<br>1..20<br>mol_type = other RNA<br>organism = synthetic construct | |
| SEQUENCE: 556<br>gagtacttac ttaaaatggc | | 20 |
| SEQ ID NO: 557<br>FEATURE<br>source | moltype = RNA length = 20<br>Location/Qualifiers<br>1..20<br>mol_type = other RNA<br>organism = synthetic construct | |
| SEQUENCE: 557<br>accgcgaaat tgagtactta | | 20 |
| SEQ ID NO: 558<br>FEATURE<br>source | moltype = RNA length = 20<br>Location/Qualifiers<br>1..20<br>mol_type = other RNA<br>organism = synthetic construct | |
| SEQUENCE: 558<br>agacccaga aaccgcgaaa | | 20 |
| SEQ ID NO: 559<br>FEATURE<br>source | moltype = RNA length = 20<br>Location/Qualifiers<br>1..20<br>mol_type = other RNA<br>organism = synthetic construct | |
| SEQUENCE: 559<br>ggtgcatctt catcagaccc | | 20 |
| SEQ ID NO: 560<br>FEATURE<br>source | moltype = RNA length = 20<br>Location/Qualifiers<br>1..20<br>mol_type = other RNA<br>organism = synthetic construct | |
| SEQUENCE: 560<br>gtaggtaagg ataggtgcat | | 20 |

```
SEQ ID NO: 561         moltype = RNA   length = 20
FEATURE                Location/Qualifiers
source                 1..20
                       mol_type = other RNA
                       organism = synthetic construct
SEQUENCE: 561
cactctgtga aaggtaggt                                              20

SEQ ID NO: 562         moltype = RNA   length = 20
FEATURE                Location/Qualifiers
source                 1..20
                       mol_type = other RNA
                       organism = synthetic construct
SEQUENCE: 562
gaatatcttc ttctcactct                                             20

SEQ ID NO: 563         moltype = RNA   length = 20
FEATURE                Location/Qualifiers
source                 1..20
                       mol_type = other RNA
                       organism = synthetic construct
SEQUENCE: 563
gggtgacttg gaatatcttc                                             20

SEQ ID NO: 564         moltype = RNA   length = 20
FEATURE                Location/Qualifiers
source                 1..20
                       mol_type = other RNA
                       organism = synthetic construct
SEQUENCE: 564
taatacttca aagttgggtg                                             20

SEQ ID NO: 565         moltype = RNA   length = 20
FEATURE                Location/Qualifiers
source                 1..20
                       mol_type = other RNA
                       organism = synthetic construct
SEQUENCE: 565
tatgtgccat ctaatacttc                                             20

SEQ ID NO: 566         moltype = RNA   length = 20
FEATURE                Location/Qualifiers
source                 1..20
                       mol_type = other RNA
                       organism = synthetic construct
SEQUENCE: 566
ccctatgatt atatgtgcca                                             20

SEQ ID NO: 567         moltype = RNA   length = 20
FEATURE                Location/Qualifiers
source                 1..20
                       mol_type = other RNA
                       organism = synthetic construct
SEQUENCE: 567
gtaatgaaag ttatcccta                                              20

SEQ ID NO: 568         moltype = RNA   length = 20
FEATURE                Location/Qualifiers
source                 1..20
                       mol_type = other RNA
                       organism = synthetic construct
SEQUENCE: 568
gtactcatgt atcagttcag                                             20

SEQ ID NO: 569         moltype = RNA   length = 20
FEATURE                Location/Qualifiers
source                 1..20
                       mol_type = other RNA
                       organism = synthetic construct
SEQUENCE: 569
ttgttagtaa tacctcaagg                                             20

SEQ ID NO: 570         moltype = RNA   length = 20
FEATURE                Location/Qualifiers
source                 1..20
                       mol_type = other RNA
                       organism = synthetic construct
```

```
SEQUENCE: 570
actagatgta aactatgaga                                                      20

SEQ ID NO: 571          moltype = RNA   length = 20
FEATURE                 Location/Qualifiers
source                  1..20
                        mol_type = other RNA
                        organism = synthetic construct
SEQUENCE: 571
agacattgta actagatgta                                                      20

SEQ ID NO: 572          moltype = RNA   length = 20
FEATURE                 Location/Qualifiers
source                  1..20
                        mol_type = other RNA
                        organism = synthetic construct
SEQUENCE: 572
tagcaaaaga atgggaaagg                                                      20

SEQ ID NO: 573          moltype = RNA   length = 20
FEATURE                 Location/Qualifiers
source                  1..20
                        mol_type = other RNA
                        organism = synthetic construct
SEQUENCE: 573
aaggttagtg gcattatgtc                                                      20

SEQ ID NO: 574          moltype = RNA   length = 20
FEATURE                 Location/Qualifiers
source                  1..20
                        mol_type = other RNA
                        organism = synthetic construct
SEQUENCE: 574
ggagcagtca ctaaaggtta                                                      20

SEQ ID NO: 575          moltype = RNA   length = 20
FEATURE                 Location/Qualifiers
source                  1..20
                        mol_type = other RNA
                        organism = synthetic construct
SEQUENCE: 575
gcacgtatgt tatatagcct                                                      20

SEQ ID NO: 576          moltype = RNA   length = 20
FEATURE                 Location/Qualifiers
source                  1..20
                        mol_type = other RNA
                        organism = synthetic construct
SEQUENCE: 576
gtaagccaga aagcacgtat                                                      20

SEQ ID NO: 577          moltype = RNA   length = 20
FEATURE                 Location/Qualifiers
source                  1..20
                        mol_type = other RNA
                        organism = synthetic construct
SEQUENCE: 577
cttagaaaca tcaggtaagc                                                      20

SEQ ID NO: 578          moltype = RNA   length = 20
FEATURE                 Location/Qualifiers
source                  1..20
                        mol_type = other RNA
                        organism = synthetic construct
SEQUENCE: 578
aggcgaacta atagcttaga                                                      20

SEQ ID NO: 579          moltype = RNA   length = 20
FEATURE                 Location/Qualifiers
source                  1..20
                        mol_type = other RNA
                        organism = synthetic construct
SEQUENCE: 579
ggatgagtac tgaggcgaac                                                      20

SEQ ID NO: 580          moltype = RNA   length = 20
FEATURE                 Location/Qualifiers
```

```
source                    1..20
                          mol_type = other RNA
                          organism = synthetic construct
SEQUENCE: 580
ttcagtgctt agttcagatt                                                       20

SEQ ID NO: 581            moltype = RNA   length = 20
FEATURE                   Location/Qualifiers
source                    1..20
                          mol_type = other RNA
                          organism = synthetic construct
SEQUENCE: 581
ggctttctac ttttcagtgc                                                       20

SEQ ID NO: 582            moltype = RNA   length = 20
FEATURE                   Location/Qualifiers
source                    1..20
                          mol_type = other RNA
                          organism = synthetic construct
SEQUENCE: 582
tctggcttta ggctttctac                                                       20

SEQ ID NO: 583            moltype = RNA   length = 20
FEATURE                   Location/Qualifiers
source                    1..20
                          mol_type = other RNA
                          organism = synthetic construct
SEQUENCE: 583
gacaaattgt gctgaaattc                                                       20

SEQ ID NO: 584            moltype = RNA   length = 20
FEATURE                   Location/Qualifiers
source                    1..20
                          mol_type = other RNA
                          organism = synthetic construct
SEQUENCE: 584
ccttgtaact gcagagaagt                                                       20

SEQ ID NO: 585            moltype = RNA   length = 20
FEATURE                   Location/Qualifiers
source                    1..20
                          mol_type = other RNA
                          organism = synthetic construct
SEQUENCE: 585
gaagtgttag gccttgtaac                                                       20

SEQ ID NO: 586            moltype = RNA   length = 20
FEATURE                   Location/Qualifiers
source                    1..20
                          mol_type = other RNA
                          organism = synthetic construct
SEQUENCE: 586
gctgttacag tgcttcagaa                                                       20

SEQ ID NO: 587            moltype = RNA   length = 20
FEATURE                   Location/Qualifiers
source                    1..20
                          mol_type = other RNA
                          organism = synthetic construct
SEQUENCE: 587
attgattact gctgttacag                                                       20

SEQ ID NO: 588            moltype = RNA   length = 20
FEATURE                   Location/Qualifiers
source                    1..20
                          mol_type = other RNA
                          organism = synthetic construct
SEQUENCE: 588
gtggtaaggc ctaattgatt                                                       20

SEQ ID NO: 589            moltype = RNA   length = 20
FEATURE                   Location/Qualifiers
source                    1..20
                          mol_type = other RNA
                          organism = synthetic construct
SEQUENCE: 589
aactgagaat gtggtaaggc                                                       20

SEQ ID NO: 590            moltype = RNA   length = 20
```

```
FEATURE                 Location/Qualifiers
source                  1..20
                        mol_type = other RNA
                        organism = synthetic construct
SEQUENCE: 590
taaccaaaga ccgatgactt                                                    20

SEQ ID NO: 591          moltype = RNA   length = 20
FEATURE                 Location/Qualifiers
source                  1..20
                        mol_type = other RNA
                        organism = synthetic construct
SEQUENCE: 591
ggcttatgtt taaccaaaga                                                    20

SEQ ID NO: 592          moltype = RNA   length = 20
FEATURE                 Location/Qualifiers
source                  1..20
                        mol_type = other RNA
                        organism = synthetic construct
SEQUENCE: 592
ccccttaaca ttggcttatg                                                    20

SEQ ID NO: 593          moltype = RNA   length = 20
FEATURE                 Location/Qualifiers
source                  1..20
                        mol_type = other RNA
                        organism = synthetic construct
SEQUENCE: 593
taacctttg attttgtccc                                                     20

SEQ ID NO: 594          moltype = RNA   length = 20
FEATURE                 Location/Qualifiers
source                  1..20
                        mol_type = other RNA
                        organism = synthetic construct
SEQUENCE: 594
cctcacttt atgaacatac                                                     20

SEQ ID NO: 595          moltype = RNA   length = 20
FEATURE                 Location/Qualifiers
source                  1..20
                        mol_type = other RNA
                        organism = synthetic construct
SEQUENCE: 595
gctcagtaag gcatattaat                                                    20

SEQ ID NO: 596          moltype = RNA   length = 20
FEATURE                 Location/Qualifiers
source                  1..20
                        mol_type = other RNA
                        organism = synthetic construct
SEQUENCE: 596
ctgaacaact tgccacatag                                                    20

SEQ ID NO: 597          moltype = RNA   length = 20
FEATURE                 Location/Qualifiers
source                  1..20
                        mol_type = other RNA
                        organism = synthetic construct
SEQUENCE: 597
ctccaggatt ctgaacaact                                                    20

SEQ ID NO: 598          moltype = RNA   length = 20
FEATURE                 Location/Qualifiers
source                  1..20
                        mol_type = other RNA
                        organism = synthetic construct
SEQUENCE: 598
ttatgatatg taggttcctc                                                    20

SEQ ID NO: 599          moltype = RNA   length = 20
FEATURE                 Location/Qualifiers
source                  1..20
                        mol_type = other RNA
                        organism = synthetic construct
SEQUENCE: 599
atttatcacc accatacagt                                                    20
```

-continued

| | | |
|---|---|---|
| SEQ ID NO: 600<br>FEATURE<br>source | moltype = RNA   length = 20<br>Location/Qualifiers<br>1..20<br>mol_type = other RNA<br>organism = synthetic construct | |
| SEQUENCE: 600<br>gcagactgaa atataagacc | | 20 |
| SEQ ID NO: 601<br>FEATURE<br>source | moltype = RNA   length = 20<br>Location/Qualifiers<br>1..20<br>mol_type = other RNA<br>organism = synthetic construct | |
| SEQUENCE: 601<br>cttctataat gcagactgaa | | 20 |
| SEQ ID NO: 602<br>FEATURE<br>source | moltype = RNA   length = 20<br>Location/Qualifiers<br>1..20<br>mol_type = other RNA<br>organism = synthetic construct | |
| SEQUENCE: 602<br>ggttgctaca ttatgaaaga | | 20 |
| SEQ ID NO: 603<br>FEATURE<br>source | moltype = RNA   length = 20<br>Location/Qualifiers<br>1..20<br>mol_type = other RNA<br>organism = synthetic construct | |
| SEQUENCE: 603<br>tgaatcaata gggttgctac | | 20 |
| SEQ ID NO: 604<br>FEATURE<br>source | moltype = RNA   length = 20<br>Location/Qualifiers<br>1..20<br>mol_type = other RNA<br>organism = synthetic construct | |
| SEQUENCE: 604<br>ggtaactgac taatttgaag | | 20 |
| SEQ ID NO: 605<br>FEATURE<br>source | moltype = RNA   length = 20<br>Location/Qualifiers<br>1..20<br>mol_type = other RNA<br>organism = synthetic construct | |
| SEQUENCE: 605<br>aaatttcata gggaggtaac | | 20 |
| SEQ ID NO: 606<br>FEATURE<br>source | moltype = RNA   length = 20<br>Location/Qualifiers<br>1..20<br>mol_type = other RNA<br>organism = synthetic construct | |
| SEQUENCE: 606<br>ttcaaggcta ctctgtttgc | | 20 |
| SEQ ID NO: 607<br>FEATURE<br>source | moltype = RNA   length = 20<br>Location/Qualifiers<br>1..20<br>mol_type = other RNA<br>organism = synthetic construct | |
| SEQUENCE: 607<br>gtgatctaaa tgagttgaac | | 20 |
| SEQ ID NO: 608<br>FEATURE<br>source | moltype = RNA   length = 20<br>Location/Qualifiers<br>1..20<br>mol_type = other RNA<br>organism = synthetic construct | |
| SEQUENCE: 608<br>gcttccattt gattttcttc | | 20 |
| SEQ ID NO: 609<br>FEATURE<br>source | moltype = RNA   length = 20<br>Location/Qualifiers<br>1..20<br>mol_type = other RNA<br>organism = synthetic construct | |
| SEQUENCE: 609<br>ccctagggat ctttagcttc | | 20 |

| | | |
|---|---|---|
| SEQ ID NO: 610 | moltype = RNA length = 20 | |
| FEATURE | Location/Qualifiers | |
| source | 1..20 | |
| | mol_type = other RNA | |
| | organism = synthetic construct | |
| SEQUENCE: 610 | | |
| ggtcaaagtt tgtgttaggc | | 20 |
| SEQ ID NO: 611 | moltype = RNA length = 20 | |
| FEATURE | Location/Qualifiers | |
| source | 1..20 | |
| | mol_type = other RNA | |
| | organism = synthetic construct | |
| SEQUENCE: 611 | | |
| gaggcccgaa aaaagctgcg | | 20 |
| SEQ ID NO: 612 | moltype = RNA length = 20 | |
| FEATURE | Location/Qualifiers | |
| source | 1..20 | |
| | mol_type = other RNA | |
| | organism = synthetic construct | |
| SEQUENCE: 612 | | |
| atttgcaatg acggaggccc | | 20 |
| SEQ ID NO: 613 | moltype = RNA length = 20 | |
| FEATURE | Location/Qualifiers | |
| source | 1..20 | |
| | mol_type = other RNA | |
| | organism = synthetic construct | |
| SEQUENCE: 613 | | |
| cttgatggga tttgtatttc | | 20 |
| SEQ ID NO: 614 | moltype = RNA length = 20 | |
| FEATURE | Location/Qualifiers | |
| source | 1..20 | |
| | mol_type = other RNA | |
| | organism = synthetic construct | |
| SEQUENCE: 614 | | |
| tacgctgact gcccttgatg | | 20 |
| SEQ ID NO: 615 | moltype = RNA length = 20 | |
| FEATURE | Location/Qualifiers | |
| source | 1..20 | |
| | mol_type = other RNA | |
| | organism = synthetic construct | |
| SEQUENCE: 615 | | |
| gaggagtttg gtatgctacg | | 20 |
| SEQ ID NO: 616 | moltype = RNA length = 20 | |
| FEATURE | Location/Qualifiers | |
| source | 1..20 | |
| | mol_type = other RNA | |
| | organism = synthetic construct | |
| SEQUENCE: 616 | | |
| tcacttcaag ccttcaggag | | 20 |
| SEQ ID NO: 617 | moltype = RNA length = 20 | |
| FEATURE | Location/Qualifiers | |
| source | 1..20 | |
| | mol_type = other RNA | |
| | organism = synthetic construct | |
| SEQUENCE: 617 | | |
| ggcatgctag aattcacttc | | 20 |
| SEQ ID NO: 618 | moltype = RNA length = 20 | |
| FEATURE | Location/Qualifiers | |
| source | 1..20 | |
| | mol_type = other RNA | |
| | organism = synthetic construct | |
| SEQUENCE: 618 | | |
| tcagtatctc ttaggcaatg | | 20 |
| SEQ ID NO: 619 | moltype = RNA length = 20 | |
| FEATURE | Location/Qualifiers | |
| source | 1..20 | |
| | mol_type = other RNA | |
| | organism = synthetic construct | |

-continued

| | | |
|---|---|---|
| SEQUENCE: 619 gggtgctgta gaaagttttc | | 20 |
| SEQ ID NO: 620 FEATURE source | moltype = RNA length = 20 Location/Qualifiers 1..20 mol_type = other RNA organism = synthetic construct | |
| SEQUENCE: 620 catatttcca acctgttcca | | 20 |
| SEQ ID NO: 621 FEATURE source | moltype = RNA length = 20 Location/Qualifiers 1..20 mol_type = other RNA organism = synthetic construct | |
| SEQUENCE: 621 gcctttacat ctgtattaga | | 20 |
| SEQ ID NO: 622 FEATURE source | moltype = RNA length = 20 Location/Qualifiers 1..20 mol_type = other RNA organism = synthetic construct | |
| SEQUENCE: 622 gactattcct ctgcctttac | | 20 |
| SEQ ID NO: 623 FEATURE source | moltype = RNA length = 20 Location/Qualifiers 1..20 mol_type = other RNA organism = synthetic construct | |
| SEQUENCE: 623 tgctatggaa atggagacta | | 20 |
| SEQ ID NO: 624 FEATURE source | moltype = RNA length = 20 Location/Qualifiers 1..20 mol_type = other RNA organism = synthetic construct | |
| SEQUENCE: 624 taggtcttat tgctatggaa | | 20 |
| SEQ ID NO: 625 FEATURE source | moltype = RNA length = 20 Location/Qualifiers 1..20 mol_type = other RNA organism = synthetic construct | |
| SEQUENCE: 625 cgatctagag gtgacattag | | 20 |
| SEQ ID NO: 626 FEATURE source | moltype = RNA length = 20 Location/Qualifiers 1..20 mol_type = other RNA organism = synthetic construct | |
| SEQUENCE: 626 gactttctga cgatctagag | | 20 |
| SEQ ID NO: 627 FEATURE source | moltype = RNA length = 20 Location/Qualifiers 1..20 mol_type = other RNA organism = synthetic construct | |
| SEQUENCE: 627 atttgctcat gtctagccag | | 20 |
| SEQ ID NO: 628 FEATURE source | moltype = RNA length = 20 Location/Qualifiers 1..20 mol_type = other RNA organism = synthetic construct | |
| SEQUENCE: 628 ccctcattcc aatttgctca | | 20 |
| SEQ ID NO: 629 FEATURE | moltype = RNA length = 20 Location/Qualifiers | |

```
source                      1..20
                            mol_type = other RNA
                            organism = synthetic construct
SEQUENCE: 629
gtgctttcct ctccctcatt                                                       20

SEQ ID NO: 630              moltype = RNA   length = 20
FEATURE                     Location/Qualifiers
source                      1..20
                            mol_type = other RNA
                            organism = synthetic construct
SEQUENCE: 630
taatcttgac ctgtgctttc                                                       20

SEQ ID NO: 631              moltype = RNA   length = 20
FEATURE                     Location/Qualifiers
source                      1..20
                            mol_type = other RNA
                            organism = synthetic construct
SEQUENCE: 631
ggactagtac taatcttgac                                                       20

SEQ ID NO: 632              moltype = RNA   length = 20
FEATURE                     Location/Qualifiers
source                      1..20
                            mol_type = other RNA
                            organism = synthetic construct
SEQUENCE: 632
actgcccaag ggactagtac                                                       20

SEQ ID NO: 633              moltype = RNA   length = 20
FEATURE                     Location/Qualifiers
source                      1..20
                            mol_type = other RNA
                            organism = synthetic construct
SEQUENCE: 633
agcattctgg ctgtagaact                                                       20

SEQ ID NO: 634              moltype = RNA   length = 20
FEATURE                     Location/Qualifiers
source                      1..20
                            mol_type = other RNA
                            organism = synthetic construct
SEQUENCE: 634
ttgggtcaga agctaagcat                                                       20

SEQ ID NO: 635              moltype = RNA   length = 20
FEATURE                     Location/Qualifiers
source                      1..20
                            mol_type = other RNA
                            organism = synthetic construct
SEQUENCE: 635
cagtacccta gtcccagctt                                                       20

SEQ ID NO: 636              moltype = RNA   length = 20
FEATURE                     Location/Qualifiers
source                      1..20
                            mol_type = other RNA
                            organism = synthetic construct
SEQUENCE: 636
gcacatcact cagtacccta                                                       20

SEQ ID NO: 637              moltype = RNA   length = 20
FEATURE                     Location/Qualifiers
source                      1..20
                            mol_type = other RNA
                            organism = synthetic construct
SEQUENCE: 637
ctttgagagt taggccctaa                                                       20

SEQ ID NO: 638              moltype = RNA   length = 20
FEATURE                     Location/Qualifiers
source                      1..20
                            mol_type = other RNA
                            organism = synthetic construct
SEQUENCE: 638
tagtgtcatg gtgtatctct                                                       20

SEQ ID NO: 639              moltype = RNA   length = 20
```

```
FEATURE                 Location/Qualifiers
source                  1..20
                        mol_type = other RNA
                        organism = synthetic construct
SEQUENCE: 639
aggaggctgt cactgttagt                                                   20

SEQ ID NO: 640          moltype = RNA   length = 20
FEATURE                 Location/Qualifiers
source                  1..20
                        mol_type = other RNA
                        organism = synthetic construct
SEQUENCE: 640
gagtgaggta cctgagatgc                                                   20

SEQ ID NO: 641          moltype = RNA   length = 20
FEATURE                 Location/Qualifiers
source                  1..20
                        mol_type = other RNA
                        organism = synthetic construct
SEQUENCE: 641
ctaggttaag tgagtgaggt                                                   20

SEQ ID NO: 642          moltype = RNA   length = 20
FEATURE                 Location/Qualifiers
source                  1..20
                        mol_type = other RNA
                        organism = synthetic construct
SEQUENCE: 642
gtttaaatgt cctagactag                                                   20

SEQ ID NO: 643          moltype = RNA   length = 20
FEATURE                 Location/Qualifiers
source                  1..20
                        mol_type = other RNA
                        organism = synthetic construct
SEQUENCE: 643
gagcttcttg acataaaact                                                   20

SEQ ID NO: 644          moltype = RNA   length = 20
FEATURE                 Location/Qualifiers
source                  1..20
                        mol_type = other RNA
                        organism = synthetic construct
SEQUENCE: 644
caacgccttg acattatgag                                                   20

SEQ ID NO: 645          moltype = RNA   length = 20
FEATURE                 Location/Qualifiers
source                  1..20
                        mol_type = other RNA
                        organism = synthetic construct
SEQUENCE: 645
tagtcaccaa caacgccttg                                                   20

SEQ ID NO: 646          moltype = RNA   length = 20
FEATURE                 Location/Qualifiers
source                  1..20
                        mol_type = other RNA
                        organism = synthetic construct
SEQUENCE: 646
agatggcctt tcttttgaac                                                   20

SEQ ID NO: 647          moltype = RNA   length = 20
FEATURE                 Location/Qualifiers
source                  1..20
                        mol_type = other RNA
                        organism = synthetic construct
SEQUENCE: 647
tctaattggg agatggcctt                                                   20

SEQ ID NO: 648          moltype = RNA   length = 20
FEATURE                 Location/Qualifiers
source                  1..20
                        mol_type = other RNA
                        organism = synthetic construct
SEQUENCE: 648
gcaatacttc tctaattggg                                                   20
```

```
SEQ ID NO: 649           moltype = RNA  length = 20
FEATURE                  Location/Qualifiers
source                   1..20
                         mol_type = other RNA
                         organism = synthetic construct
SEQUENCE: 649
tacttttggc atgcaatact                                                    20

SEQ ID NO: 650           moltype = RNA  length = 20
FEATURE                  Location/Qualifiers
source                   1..20
                         mol_type = other RNA
                         organism = synthetic construct
SEQUENCE: 650
gatggacaac tttacatact                                                    20

SEQ ID NO: 651           moltype = RNA  length = 20
FEATURE                  Location/Qualifiers
source                   1..20
                         mol_type = other RNA
                         organism = synthetic construct
SEQUENCE: 651
aattagtttg cctgatggac                                                    20

SEQ ID NO: 652           moltype = RNA  length = 20
FEATURE                  Location/Qualifiers
source                   1..20
                         mol_type = other RNA
                         organism = synthetic construct
SEQUENCE: 652
gagctgttgc agaattagtt                                                    20

SEQ ID NO: 653           moltype = RNA  length = 20
FEATURE                  Location/Qualifiers
source                   1..20
                         mol_type = other RNA
                         organism = synthetic construct
SEQUENCE: 653
agtcccaaat gagctgttgc                                                    20

SEQ ID NO: 654           moltype = RNA  length = 20
FEATURE                  Location/Qualifiers
source                   1..20
                         mol_type = other RNA
                         organism = synthetic construct
SEQUENCE: 654
ttaattgtgt tcagtcccaa                                                    20

SEQ ID NO: 655           moltype = RNA  length = 20
FEATURE                  Location/Qualifiers
source                   1..20
                         mol_type = other RNA
                         organism = synthetic construct
SEQUENCE: 655
catctatggc aaactacatt                                                    20

SEQ ID NO: 656           moltype = RNA  length = 20
FEATURE                  Location/Qualifiers
source                   1..20
                         mol_type = other RNA
                         organism = synthetic construct
SEQUENCE: 656
ggacggattt catctatggc                                                    20

SEQ ID NO: 657           moltype = RNA  length = 20
FEATURE                  Location/Qualifiers
source                   1..20
                         mol_type = other RNA
                         organism = synthetic construct
SEQUENCE: 657
tatagacaca ttttaggacg                                                    20

SEQ ID NO: 658           moltype = RNA  length = 20
FEATURE                  Location/Qualifiers
source                   1..20
                         mol_type = other RNA
                         organism = synthetic construct
SEQUENCE: 658
ggttatcaca cacttttaag                                                    20
```

```
SEQ ID NO: 659         moltype = RNA  length = 20
FEATURE                Location/Qualifiers
source                 1..20
                       mol_type = other RNA
                       organism = synthetic construct
SEQUENCE: 659
gtacacgtta gatgtaagag                                                   20

SEQ ID NO: 660         moltype = RNA  length = 20
FEATURE                Location/Qualifiers
source                 1..20
                       mol_type = other RNA
                       organism = synthetic construct
SEQUENCE: 660
tattggagcc tctgtacacg                                                   20

SEQ ID NO: 661         moltype = RNA  length = 20
FEATURE                Location/Qualifiers
source                 1..20
                       mol_type = other RNA
                       organism = synthetic construct
SEQUENCE: 661
ctcattatca tattggagcc                                                   20

SEQ ID NO: 662         moltype = RNA  length = 20
FEATURE                Location/Qualifiers
source                 1..20
                       mol_type = other RNA
                       organism = synthetic construct
SEQUENCE: 662
gtcacaggaa atataactca                                                   20
```

US 12,319,916 B2

MODULATION OF GENE TRANSCRIPTION USING ANTISENSE OLIGONUCLEOTIDES TARGETING REGULATORY RNAs

CROSS REFERENCE TO RELATED APPLICATIONS

This application is a continuation of International Application No. PCT/US2022/082295, filed Dec. 22, 2022, which claims the benefit of U.S. Provisional Application No. 63/292,920, filed Dec. 22, 2021, and U.S. Provisional Application No. 63/308,373, filed Feb. 9, 2022, each of which are hereby incorporated in their entirety by reference.

SEQUENCE LISTING

The instant application contains a Sequence Listing which has been submitted via EFS-Web and is hereby incorporated by reference in its entirety. Said XML copy, created on Dec. 21, 2022, is named CTC-028WO_140628340009.xml, and is 925,586 bytes in size.

FIELD OF THE INVENTION

The disclosure relates to methods of upregulating or downregulating gene transcription using antisense oligonucleotides (ASOs) targeting regulatory RNAs (e.g. CPS1 regulatory RNAs), such as promoter-associated RNAs and enhancer RNAs.

BACKGROUND

Transcription factors bind specific sequences in promoter and enhancer DNA elements to regulate gene transcription. It was recently reported that active promoters and enhancer elements are themselves transcribed, generating noncoding regulatory RNAs (regRNAs) such as promoter-associated RNAs (paRNAs) and enhancer RNAs (eRNAs) (see Sartorelli and Lauberth, Nat. Struct. Mol. Biol. (2020) 27, 521-28). Unlike coding RNAs, regRNAs are transcribed bi-directionally. Various models have been proposed for the functions of regRNAs, including nucleosome remodeling (see Mousavi et al., Mol. Cell (2013) 51(5):606-17), modulation of enhancer-promoter looping (see Lai et al., Nature (2013) 494(7438):497-501), and direct interaction with transcription regulators (see Sigova et al., Science (2015) 350, 978-81).

Gene expression has been generally known as an undruggable biological process. Despite on-going efforts into understanding the biology of gene transcription and regRNAs, clinically suitable methods of modulating gene expression are limited. There remains a need for new and useful methods for treating diseases associated with aberrant gene expression.

SUMMARY

In one aspect, provided herein are antisense oligonucleotides (ASO) complementary to at least 8 contiguous nucleotides of a regulatory RNA (regRNA) of Carbamoyl-Phosphate Synthetase 1 (CPS1), wherein the regRNA has a nucleotide sequence selected from the group consisting of SEQ ID NO: 49, 50, 69-79 and 89-90.

In some embodiments, the ASO is complementary to a sequence in the regRNA that is no more than 200 nucleotides from the 3' end of the regRNA.

In some embodiments, the ASO is complementary to a sequence in the regRNA that is no more than 200 nucleotides from the 5' end of the regRNA.

In some embodiments, the regulatory RNA has a nucleotide sequence of SEQ ID NO: 49, and the ASO comprises a nucleotide sequence of SEQ ID NO: 1.

In some embodiments, the regulatory RNA has a nucleotide sequence of SEQ ID NO: 49, and the ASO comprises a nucleotide sequence of SEQ ID NO: 2.

In some embodiments, the regulatory RNA has a nucleotide sequence of SEQ ID NO: 49, and the ASO comprises a nucleotide sequence selected from the group consisting of SEQ ID NOs: 1-3.

In some embodiments, the regulatory RNA has a nucleotide sequence of SEQ ID NO: 50, and the ASO comprises a nucleotide sequence selected from the group consisting of SEQ ID NOs: 4-15.

In some embodiments, the regulatory RNA has a nucleotide sequence of SEQ ID NO: 89, and the ASO comprises a nucleotide sequence selected from the group consisting of SEQ ID NOs: 487-574.

In some embodiments, the regulatory RNA has a nucleotide sequence of SEQ ID NO: 90, and the ASO comprises a nucleotide sequence selected from the group consisting of SEQ ID NOs: 575-662.

In some embodiments, the ASO is no more than 50, 40, 30, or 25 nucleotides in length.

In some embodiments, the ASO comprises an polynucleotide comprising one or more chemical modifications. In some embodiments, the ASO comprises an RNA polynucleotide comprising one or more chemical modifications. In some embodiments, the ASO comprises an RNA and DNA polynucleotide comprising one or more chemical modifications.

In some embodiments, at least 3, 4, or 5 nucleotides at the 5' end and at least 3, 4, or 5 nucleotides at the 3' end of the ASO comprise ribonucleotides with one or more chemical modifications.

In some embodiments, the one or more chemical modifications comprise a nucleotide sugar modification comprising one or more of 2'-O—C1-4alkyl such as 2'-O-methyl (2'-OMe), 2'-deoxy (2'-H), 2'-O—C1-3alkyl-O—C1-3alkyl such as 2'-methoxyethyl ("2'-MOE"), 2'-fluoro ("2'-F"), 2'-amino ("2'-NH2"), 2'-arabinosyl ("2'-arabino") nucleotide, 2'-F-arabinosyl ("2'-F-arabino") nucleotide, 2'-locked nucleic acid ("LNA") nucleotide, 2'-amido bridge nucleic acid (AmNA), 2'-unlocked nucleic acid ("ULNA") nucleotide, a sugar in L form ("L-sugar"), 4'-thioribosyl nucleotide, constrained ethyl (cET), 2'-fluoro-arabino (FANA), or thiomorpholino.

In some embodiments, the one or more chemical modifications comprise an internucleotide linkage modification comprising one or more of phosphorothioate ("PS" or (P(S))), phosphoramidate (P(NR1R2) such as dimethylaminophosphoramidate (P(N(CH3)2)), phosphonocarboxylate (P(CH2)nCOOR) such as phosphonoacetate "PACE" (P(CH2COO—)), thiophosphonocarboxylate ((S)P(CH2)nCOOR) such as thiophosphonoacetate "thioPACE" ((S)P(CH2COO—)), alkylphosphonate (P(C1-3alkyl) such as methylphosphonate —P(CH3), boranophosphonate (P(BH3)), or phosphorodithioate (P(S)2).

In some embodiments, the one or more chemical modifications comprise a nucleobase modification comprising one or more of 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil ("5-allylU"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), isocytosine ("isoC") a glycerol nucleic acid (GNA), glycerol nucleic acid (GNA), or thiophosphoramidate morpholinos (TMOs).

In some embodiments, the one or more chemical modifications comprise 2'-O-methoxyethyl, 5-methyl cytidine, locked nucleic acid (LNA), and phosphorothioate internucleotide bond.

In some embodiments, the ASO comprises 8 or more contiguous nucleotides of unmodified DNA flanked by at least 3 nucleotides of modified ribonucleotides at each of the 5' end and the 3' end.

In some embodiments, the ASO comprises the nucleotide sequence and/or chemical modification of any one of SEQ ID NO: 16, 22-27, 31-39, 403-412, 414-415, 417-432, 435-480, or 482-486.

In some embodiments, the ASO comprises the nucleotide sequence and/or chemical modification of SEQ ID NO: 409.

In some embodiments, the ASO further comprises at least one phosphorothioate internucleotide bond.

In some embodiments, the ASO comprises the nucleotide sequence of SEQ ID NOs: 403-406, 409-415, 417-424, 470, 473, 477, 480, or 486.

In some embodiments, the chemical modification is cET.

In some embodiments, the ASO comprises the nucleotide sequence of SEQ ID NOs: 425-432 or 435-442.

In some embodiments, the chemical modification is LNA.

In some embodiments, the ASO comprises the nucleotide sequence of SEQ ID NOs: 443-458.

In some embodiments, the chemical modification is LNA and 2'-O-methoxyethyl.

In some embodiments, the ASO comprises the nucleotide sequence of SEQ ID NOs: 400, 408, 460, 462, 464-466, 468, 469, 471, 472, 475, 476, or 479.

In some embodiments, the ASO does not comprise 8 or more contiguous nucleotides of unmodified DNA.

In some embodiments, the ASO does not comprise an unmodified ribonucleotide.

In some embodiments, the ASO does not comprise a deoxyribonucleotide.

In some embodiments, the length of the ASO is 2×n+4 nucleotides (n is an integer of 8 or greater), wherein the nucleotides at positions 2×m are ribonucleotides modified by LNA (m is an integer from 1 to n) and the remaining nucleotides are ribonucleotides modified by 2'-O-methoxyethyl.

In some embodiments, the ASO comprises the nucleotide sequence of SEQ ID NOs: 393 or 394.

In some embodiments, the length of the ASO is 3×n+2 nucleotides (n is an integer of 4 or greater), wherein the nucleotides at positions 3×m are ribonucleotides modified by LNA (m is an integer from 1 to n) and the remaining nucleotides are ribonucleotides modified by 2'-O-methoxyethyl.

In some embodiments, the ASO comprises the nucleotide sequence of SEQ ID NOs: 392 or 395.

In some embodiments, the length of the ASO is 3×n+2 nucleotides (n is an integer of 6 or greater), wherein the nucleotides at positions 3×m are ribonucleotides modified by LNA (m is an integer from 1 to n) and the five nucleotides at the 3' and 5' positions are ribonucleotides modified by 2'-O-methoxyethyl.

In some embodiments, the ASO comprises the nucleotide sequence of SEQ ID NO: 19 or 20.

In some embodiments, the length of the ASO is 4×n nucleotides (n is an integer of 3 or greater), wherein the nucleotides at positions 4×m are ribonucleotides modified by LNA (m is an integer from 1 to n) and the five nucleotides at the 3' and 5' positions are ribonucleotides modified by 2'-O-methoxyethyl.

In some embodiments, the ASO comprises the nucleotide sequence of SEQ ID NO: 21.

In some embodiments, the length of the ASO is 4×n+4 nucleotides (n is an integer of 3 or greater), wherein the nucleotides at positions 4×m are ribonucleotides modified by LNA (m is an integer from 1 to n) and the remaining nucleotides are ribonucleotides modified by 2'-O-methoxyethyl.

In some embodiments, the ASO comprises the nucleotide sequence of SEQ ID NOs: 396 or 397

In some embodiments, each ribonucleotide of the ASO is modified by 2'-O-methoxyethyl.

In some embodiments, the ASO comprises the nucleotide sequence of any one of SEQ ID NOs: 17, 28-30, and 40-48.

In some embodiments, each nucleotide of the ASO is a ribonucleotide modified by 2'-O-methoxyethyl.

In some embodiments, the ASO comprises the nucleotide sequence of any one of SEQ ID NOs: 17, 28-30, and 40-48.

In some embodiments, each cytidine in the ASO is modified by 5-methyl.

In some embodiments, the length of the ASO is 5×n+5 nucleotides (n is an integer of 3 or greater), wherein the nucleotides at positions 5×m are ribonucleotides modified by LNA (m is an integer from 1 to n) and the nucleotides at the remaining positions are ribonucleotides modified by 2'-O-methoxyethyl.

In some embodiments, the ASO comprises the nucleotide sequence of SEQ ID NOs: 398 or 399.

In some embodiments, the ASO further comprises a GalNAc moiety, optionally a GalNAc3 moiety.

In some embodiments, the ASO further comprises a biotin or cholesterol moiety.

In some embodiments, each cytidine in the ASO is modified by 5-methyl.

In some embodiments, the regRNA is an enhancer RNA (eRNA).

In another aspect, provided herein are pharmaceutical compositions comprising the ASO disclosed herein and a pharmaceutically acceptable carrier or excipient carrier.

In another aspect, provided herein are methods of increasing transcription of CPS1 in a human cell, the method comprising contacting the cell with the ASO disclosed herein or the pharmaceutical composition disclosed herein.

In some embodiments, the cell is a hepatocyte.

In some embodiments, the ASO increases the amount of the regulatory RNA in the cell as compared to a cell that has not been contacted with the ASO or the pharmaceutical composition.

In some embodiments, the ASO increases the stability of the regulatory RNA in the cell as compared to a cell that has not been contacted with the ASO or the pharmaceutical composition.

In another aspect, provided herein are methods of treating a urea cycle disorder, the method comprising administering to a subject in need thereof an effective amount of the ASO disclosed herein or the pharmaceutical composition disclosed herein.

In some embodiments, the urea cycle disorder is CPS1-deficiency.

In some embodiments, the urea cycle disorder is hyperammonemia.

In some embodiments, the ASO increases the amount of the regulatory RNA in a cell of the subject (e.g., as compared to a cell (e.g., a similar cell from the subject) that has not been contacted with the ASO or the pharmaceutical composition).

In some embodiments, the ASO increases the stability of the regulatory RNA in a cell of the subject (e.g., as compared to a cell (e.g., a similar cell from the subject) that has not been contacted with the ASO or the pharmaceutical composition).

In some embodiments, the cell is a hepatocyte.

BRIEF DESCRIPTION OF THE DRAWINGS

FIG. 5A shows a schematic of various human CPS1 ASOs with chemical modifications. Light gray indicates a 2'-O-(2-methoxyethyl) (2'-MOE) modification. Dark gray indicates a locked nucleic acid (LNA) modification. Line brackets indicate a phosphodiester (PO) linkage. *C indicates a 5-methyl on the cytidine. Unique sequence identifiers are assigned to nucleotide sequences having the specific chemical modifications shown in this figure. FIG. 5B shows a schematic of various mouse CPS1 ASOs with chemical modifications.

FIG. 14 provides shows a schematic of various human CPS1 ASOs with chemical modifications. Unique sequence identifiers are assigned to nucleotide sequences having the specific chemical modifications shown in this figure.

FIG. 15A shows that hCPS1-ASO-1x decreased in vivo plasma ammonia in the $OTC^{def}$ mice with humanized liver. FIG. 15B shows that hCPS1-ASO-1x increased in vivo urea in the $OTC^{def}$ mice with humanized liver. FIG. 15C shows that hCPS1-ASO-1g also increased OTC protein levels after treatment with 5 mg/kg and 20 mg/kg ASO.

FIG. 16 shows that the indicated ASOs increased CPS1 mRNA and ureagenesis in both healthy and $OTC^{def}$ primary human hepatocytes FIG. 17 also provides the ammonia AUC both over time and per dose in the NHP experiment.

DETAILED DESCRIPTION

Figure 1:
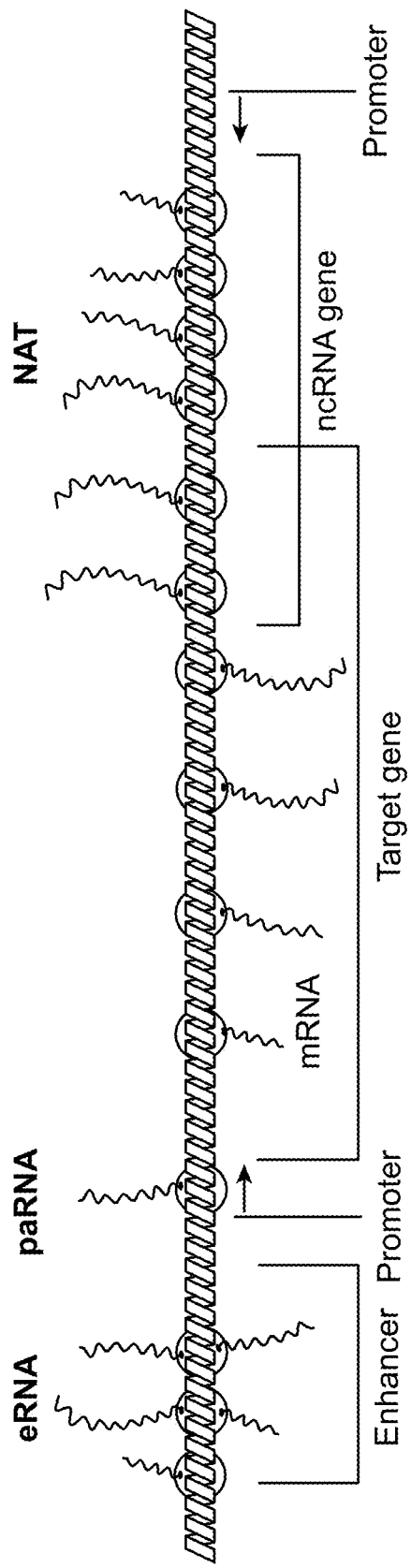
FIG. 1 shows an illustrative schematic of eRNA, paRNA, mRNA, and natural antisense transcript (NAT) of a gene on the chromosome. The eRNA, paRNA, and NAT are all non-coding RNAs. The eRNA is transcribed bidirectionally from an enhancer of the gene. The paRNA is transcribed from the promoter of the gene, same as the mRNA, but in the antisense direction. The NAT is transcribed from a downstream promoter of its own in the antisense direction, such that the transcript overlaps at least partially with the mRNA. Generally, eRNAs and paRNAs upregulate gene expression whereas NATs downregulate gene expression.

The present disclosure provides antisense oligonucleotides (ASOs) targeting regulatory RNAs, such as promoter-associated RNAs and enhancer RNAs, and methods using these ASOs to regulate gene expression. These methods are useful for modulating the levels of gene products, for example, modulating expression levels of disease-causing genes such as Carbamoyl-Phosphate Synthetase 1 (CPS1), thereby to treat diseases associated with aberrant gene expression such as a urea cycle disorder. Urea cycle disorders are reviewed in Haberle et al., 2012, Orphanet J. Rare Dis. 7:32, hereby incorporated by reference in its entirety. Urea cycle disorders result in the accumulation of ammonia and other precursor metabolites, causing development of hyperammonia and related symptoms, such as cerebral edema and the related signs of lethargy, anorexia, hyper- or hypoventilation, hypothermia, seizures, neurologic posturing, and coma. Milder or partial urea cycle enzyme deficiencies cause ammonia accumulation and elevations of plasma ammonia concentration. CPS1 deficiency is the most severe of the urea cycle disorders. Individuals with complete CPS1 deficiency rapidly develop hyperammonemia and are at risk for additional hyperammonemia events.

I. Definitions

To facilitate an understanding of the present application, a number of terms and phrases are defined below.

The terms "a" and "an" as used herein mean "one or more" and include the plural unless the context is inappropriate.

As used herein, the term "Carbamoyl-Phosphate Synthetase 1" or "CPS1" refers to the protein of UniProt Accession No. P31327 as set forth in the applicable database as of the priority date of the instant application and related isoforms and orthologs, the gene encoding the protein (e.g., NCBI Entrez Gene: 1373), or the mRNA encoding the protein (e.g., Accession Nos. NM_001122633.3, NM_001369256.1, NM_001369257.1, and NM_001875.5).

As used herein, the terms "regulatory RNA" and "regRNA" are used interchangeably to refer to a noncoding RNA transcribed from a regulatory element of a gene (e.g., a protein-coding gene), wherein the gene is not the noncoding RNA itself. Exemplary regulatory elements include but are not limited to promoters, enhancers, and super-enhancers. A noncoding RNA transcribed from a promoter, in the antisense direction, is also called "promoter RNA" or "paRNA." A noncoding RNA transcribed from an enhancer or super-enhancer, in either the sense direction or the antisense direction, is also called "enhancer RNA" or "eRNA." It is understood that a natural antisense transcript (NAT) complementary with at least a portion of the transcript of the gene is not a regulatory RNA as used herein.

As used herein, the term "nascent RNA" refers to an RNA that is still being transcribed or has just been transcribed by RNA polymerase and remains tethered to the DNA from which it is transcribed. An RNA that has dissociated from the DNA from which it is transcribed is also called an "untethered RNA."

As used herein, the term "antisense oligonucleotide" or "ASO" refers to a single-stranded oligonucleotide having a nucleotide sequence that hybridizes with a target nucleic acid under suitable conditions or a conjugate comprising such single-stranded oligonucleotide.

As used herein, the stability of a regRNA is reversely correlated with the degradation rate of the regRNA. Where an ASO increases the stability of a regRNA, it reduces the degradation rate of the regRNA. Where an ASO decreases the stability of a regRNA, it increases the degradation rate of the regRNA. The degradation rate of a regRNA can be measured by blocking synthesis of new regRNA and assessing the half-life of the existing regRNA.

As used herein, the terms "subject" and "patient" refer to an organism to be treated by the methods and compositions described herein. Such organisms preferably include, but are not limited to, mammals (e.g., rodents, primates, simians, equines, bovines, porcines, canines, felines, and the like), and more preferably include humans.

As used herein, the term "effective amount" refers to the amount of a compound (e.g., a compound of the present application) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, *Remington's Pharmaceutical Sciences,* 15th Ed., Mack Publ. Co., Easton, PA (1975).

Throughout the description, where compositions are described as having, including, or comprising specific components, or where processes and methods are described as having, including, or comprising specific steps, it is contemplated that, additionally, there are compositions described in the present application that consist essentially of, or consist of, the recited components, and that there are processes and methods according to the present application that consist essentially of, or consist of, the recited processing steps.

As a general matter, compositions specifying a percentage are by weight unless otherwise specified. Further, if a variable is not accompanied by a definition, then the previous definition of the variable controls.

II. Antisense Oligonucleotides

The antisense oligonucleotides (ASOs) disclosed herein hybridize with a regRNA transcribed from a regulatory element of a target gene. It is understood that both eRNAs and paRNAs are regRNAs facilitating or upregulating gene expression (FIG. 1). In certain embodiments, the target regRNA is an eRNA. In certain embodiments, the target regRNA is a paRNA. eRNAs can be identified using methods known in the art, such as Assay for Transposase-Accessible Chromatin using sequencing (ATAC-seq), global run-on sequencing, precision run-on sequencing, cap analysis gene expression, and histone modification analysis (see, e.g., Sartorelli & Lauberth, Nat. Struct. Mol. Biol. (2020) 27:521-28; PCT Application Publication No. WO2013/177248). paRNAs are RNAs transcribed from promoters of target genes in the antisense direction (transcripts in the sense direction are mRNAs of the target genes). They can be identified by similar methods, taking into account their specific location and orientation. In the human CPS1 gene, multiple, distinct eRNAs have been identified to transcribe from the same enhancer region. The nucleotide sequences of exemplary regRNAs are provided in Table 1 below. Any of these regRNAs are contemplated as a target regRNA of an ASO disclosed herein.

TABLE 1

Exemplary reqRNAs

| regRNA | Nucleotide Sequence |
|---|---|
| Human CPS1 RR44_v1 SEQ ID NO: 49 | GCCTGATGTGTGTGCCTGCATTCATGCCTGTCACTCTGCTCAGCTGCGTGCAGACAG CTTATATGAAGGAGGACTGTGTACATGTGGTCAGAGAAGAAAAAAATGCTTATTTT TTAAAATGTTTTGAAAAATAATCTGTCCTAAAAGTGTAACATTTCCACTAAATTTTT TCATGTCTGACTTTAACATTCCCTACCAACCAACTCTTATAGCCTCAACTCCTTTGA TCTATCCTAATGTAAACTCCCTCACTAATGTGTAATATATTTTTTCCAGTTTGGTTA TAGATTTCAGTCTAGCCTGAACACTCAAGTATGAAACTAGCCACTATTTTATTTATT GGCTGTTCCAACCTCCATTGTGGAATTATAATTGATGGATTTTCCAAGTCTCTAATT CAGAATATTTAATCAAATTTTCCAAAATTTCTGCCTTCTCCTCCTTCATTCTGATGA CTAAAGACATGGACCATAAAATATATACATATATACATACATATGTATATGTAT GTATATACACATATATATATGTATGTATATATACATACATATATATATGTATATATA CACACACATATACATATGTATGTATATACACACACACATATATATATGTATGTA TATATATACACACACATATATATATGTATGTATATATATACACACACATATATATAT GTATGTATATATATACACACACACCGTAGTTTGCAAGTCTGCATCTGGGACCCT TTACTGATAAAAATGAAAGCCCATTAAAACTCTCATGCCCACATTTCTCTCTAGACT TTAGAGTAGGAGAATTCTATCCTAGAATTGTTGATTGTTGACATTTCTATGGAAAA ACATGTTTAATTCATCATGCTTTGTAGTCAACTGCTATAAATGGTGATGAAGTCTTT TCCTTGGTCAAGCTCTGGACTCCTCAGTACTTCCACTGTCATATTTGATTAAAACAT AAGTGATGAAGGGAGGAAATATATTATAGTATTCATTGCATGGGTACCTTAGGGTA ATGGGACTATGACTGATTTAAATTTATTTTGCATCCTAAAAAGTTTCCATTAGTGGG TGCAGCACACCAGCATGGCACATGTATACATATGTAACTAACCTGCACAATGTGCA CATGTACCCTAAAACTTAAAGTATAATAATAAAAGAAAAAAAAACTTAAAAAGAA AAGTTTCCATAATGAGGATTGAGTTTATATCGTTTTCTTAATTAAGGAAAGACAAC CCTCACTACACACACACACACACACACACACACATAAAAAGACAAGAGGTG AGATCAAGGCGTAAACTAGTATTGGACTAAGCCAGTAAGTACTGCTTCTCAGTCCT CAGTTCTCTAGGTTGGGAGTTTTCCTTTTGCTATTTTCATTCTCCTCCAATTCATTTT TCAATGATCTTCAACACAAATTTCGCCTTTATTTCTTGTTCAAAATACTTCCATGAC TATTATGAATACTATTTATGGATGAAGGCTGAACATTTTAAGGCATACTAAGTCTC CCATGATATGGTACCTTTTCATTTTCCCATTCTATACCCTGCATCTAGGCTTTTAAA AAATATACCACATGACTTCATGCCTCTAGGCTATTGCTCATGCCACGGCATCCCTTC TGGGTTTTTTCCCCTCTTTATCTACTTGGTGAATTTGCATCCTTCAGTATAACACAGC TCAACATAATTCTATGCTTAAACTTTACTGAAAATGCACAAGGAACTTGATCTTTCT TTCTTATTTTCCCCATTTTATTTATTTTCCCATTGCATTTGGGCAACTTTCATGGCAC CAGTTATTTTATTAATTATTTGTATAAACTAGTATGAGCCTATTTTGTTTAGCTTTCT ATCACCAGGAGCCATGAAGCACTTTGAAATCAAATACTGTTTGTACTTGAATATAT TAAGTAAGCGTGAGGACTTAAATTAAACTTTGTTCCTCTTTAAAAAAATCCTTACCC CAACTCTAGCACTGA |
| Human CPS1 RR44_v2 SEQ ID NO: 50 | ATGAAAATGGAATATTTTGTAATCATTTAAAGTAATGTTTTAAAAGAACTTTGTAA TAACATCAAAATACATTTAACATAATATTGCCTCCAAAAAGCATTATGCAAGTCAA TGGCAATTTTCAAAACTATGTTCTGAGCATTGACATAAATGCTAGAAGATAATACT TTAGTGTTAACAGAGATTATGTTTGTGGTGGGTTATTATCTATTATTCTGTATTTC CACATTTCTTTAAATATCAAATGAAAGTGAATACAACCTAGTACTTGACATTTTAA CATTTTCAATACCAGATATGTCAATAAGGAATTCATAAAATAAAGTGCCCTGAGGG ATTTCACAGGCTAAATGCTTCTATTTTTTAAAATGTATTAATAGAAAAGAAGACTA AATCTAAAAAAAAAAATTCATTTTATCAGAGAGTGACTCATAAGTTTAGAAAACCT TTGATGACCTGGCTCACAAAGAATGTACTTCCAAGTACACAGGGTCCCCAGCCTGA TGTGTGTGCCTGCATTCATGCCTGTCACTCTGCTCAGCTGCGTGCAGACAGCTTA |
| Human CPS1 RR7_v1 SEQ ID NO: 69 | TAGATAGAAAGGAGCAGCCAGAGATGTGCCTCAGGCTGAAGCCAGTGCTGCAAAT GGGACAGCGCTCTCAAGCTACATTATATGCATTTCATTATCCAACAATTTGTTCTGG GAGGACAGTTTGATTGGCCAGGCAAGAAATTCAAATGAGAGACTTTTAAATATC ACAACTCAGCTAAAAGAGCTCTTCTGTTTTCTGACCTGAGAAATTCACTTCTATCAG TCTCAATAAAGATGCTTGTAATATTAGGTGATGCAGACTCTGAACATTTGTCCCTCT GGACTGAGTGCACTCCCGATGATCTGAGTCTTGGGGCTATGCCTCAGGCTTCACAA TTCCTAGTGTGAAAGCTACTTGCATATCCACCCCTCCATCCAGCTGGGTTTGTTCT GCTTTTCTTGTGTAACTAATGACTGTGAGTCAAAAAGATGGGAGGTCAACTACTTG CCTTTGACCATTAAATAGGTGTTTAAACTAAGCTAACTAAGGAATAACATTGTTTTT CCATTTCGTGATATCGTTTTCCATTTTATCCTAGATTCTTAACTAGGATGTGAAGAA AATAATAGTAGTCAATATTATAAAGTTTAAAATAATACAAAGTAGTCGATATTATA AACACAGACATATTTCTAGAATGGAACAATAAGATAGTAGGCTTCTATGTTTTATT TTAAAAGGTTCCGAAATTACCCACTTACCATTTGTGTGACCTTGAACAAGTTGCTTT AACTCCGAACCTCAGTTTCTTCATATACAAAATGGGAATACACCTACTATGGAGGT TTGCTGATAGAATTTAAACAGAATAAGTTACGCAAAATATCTGGTGTTAGTAAAGA ATTCTCTCAGTGACTCATAGCAAGAGTATAAATTGGTCTAGTCACTTTGTAGCATG ATTTGTCATTATACAGTGAAATGTAAAATGTGCATACCTTACAGCAATTACATTTTT TCAGGATGAAACTCAGAAAAATACTAAAACATGTGCACAAAATGATAGATACATA CATAGATATATAGATATTCATTGCAGCATAAATGAACCAGTGGGAATAATATTTAA ATGCATGAATGTTCTTTTCCCTTTTGAAATTATTTTACTGACCTTCTCCACAAACTCA CCTATTTCTTTTGGGTGGTTTGGAATTATTACAACAGGAAGGCAAAGAGAAAGAAA AAGTTAATATTTATCTTCTGGCAAGGCAACGGGATTTGCAGTAAGAACACAGTGCT AACAAGTAGATTTAATCAGGGAGAGGGGAGTTCGTTAAATTCTTAAACTGCTTTAA CTTATCATAACTCAAACTAGAGGATTCAGATTATATGAATTTTTCACATCTGGTGAA GTGGTAGGAAGAAGAATGGAAACACAGACGTCACATCAGCGTCCTTTATTTCCACT TCCACTTTCAACCCCTGATCCAGGACCACTCTTTAAGGCAGTAAAGGAGCAATGTA GTAGAAATGACAGCAGCAGGCCAGCAGATACCTATTCCTGAGACAGAGCCCATGG CATTCAGGGCCTGGAAACTGGGGACCCAAAATAACCCAAGTCTGGTTGTGACAAC |

TABLE 1-continued

Exemplary regRNAs

| regRNA | Nucleotide Sequence |
|---|---|
| | ACAGAGGTTCTGAGAGTACAGGAAGAATTAAGAAGCCTGGGGACAAGGTAGAAA<br>ACCACTGCAGGTAGATCATAACAGACAAGGGACAAATGACCAGACCCCCTAACGC<br>CCCAAAGAGCAGATGTCAACAGCACAGAGAGCAGACCAGCTCAGCTGCTCTGCAG<br>ATATCAAGGAGGACTCAGAGGATACATCAATCTGATTACCCTTTCCTTCTGCACCA<br>CTAAATCATGTAAACTAAACAACCAGATGCCCTCTTGAAGAGGAATAGGGTAAGC<br>AGGTCAAACTTGGAAAAGTGGAACAAATTGACCAAGCAAGGACAGGGTTACCTAA<br>ATGGAGTATTGGACTGCATTACTGGACTCAAGACAAAACTTACCAGATTAGACTCG<br>TAGATCAGATCAGTTATTTAAAAAATAAATAAAATAAGGTA |
| Human CPS1<br>RR8_v1<br>SEQ ID<br>NO: 70 | GTCCATCCTGACTCCTGGCAGGGACCAGGGCCATCCAGTTATACTACGGTGTTCTTT<br>CACCACCTCAGTGATGGCAGCTGGCTGGAGTCCAAAGCGTTTCAGTACTCCCAAGC<br>TCTGACTACTTTTTTCTCTTCTTTTCTTCATCTTGCCCTACACATTTATCCAAAGAAA<br>ATATTTAGGATGTGAAAGAAGGGGTGTAGATAAGAAATGAATCAAAGGAGAAATG<br>TGTGATTATAAAACAATAAAATACGTAACTGAACCTTACTGTGGCTTAACACACAG<br>CCAATAGTGCCAAAGATCATATAACTTCTGTCTGCTGAAGTTTTCTCTTTATTAAAT<br>GGCATTGACAGAGAAAAACTATAAAGAATAATTAATTGAAATAGACTGCAAATCA<br>CTTAGCCAACATAAAATGATGCAATATTTTATCTGATGAAGAAACCTAAAGTTAAA<br>TATTGGTTAGATCAATTTTATCAATTTGTCTATATCCTATCAATCCTTCAAAGCCAT<br>ATGAAATCATACTCTTTTAATGAACTTTATGTATGTATATCTTGTTTGTATCATACA<br>ATTAATATACTGTCCACGTACTCTTATTTCACACATTAATATCTTCCTGGTTGAAAT<br>CATTAAATAGCTCCACACTGCTTAACTACAGTGCGAAGTTAAAAATAAATATATT<br>CATTTTTCTAAAGCTTTAGGCTTTTGTTTGCTTCATTCACGTTGTGTGATCTAAATTA<br>GTATCTTCACTGTCTCTGTTTAATATCGACAAATTAGAAAGAGTAACAACCATGAC<br>CTCTCATAGTCCATAAGTAATAATTAATTCTTCAATTCCTTCTATAAATACTTATTA<br>AAGCCCTTTTACATGCCAAGCATGGTGCTAGATCCGAGAATTAAAAATAAGTCTGGA<br>ACACAGACTTGTCCCTCAAAAGCTCCCTCTTGAGAAGCCTTTCAGTTTTATTCTTAG<br>AAGTGGACAAAAATGTGTATTTTCTACTCTCAAGATTGAA |
| Human CPS1<br>RR9_v1<br>SEQ ID<br>NO: 71 | AAATTAAACATATTTGAGGATCACAGAGAAGCATGTGGTGCAACATGTCTTGAAGT<br>TACCGACTTCGTGAAGTGTAAGGGGCAGTAGTTTACACTGGAATGACGTAGAGAA<br>CAGGTCACCTACGCACATTCCTACTCCACCCCCTTTTGTAGAAAATTTGTTATACTG<br>AACCTGATTTCTTCCATGGCCTCCTATTTTCAGCGGAATGTGATTCAGGAAGATACA<br>TTCCACCCTCCTGGAAATCGGAAATAGGACCCGTGCTTTCACAAACATTAAGTTCC<br>ATCTTCCCTAAAACTTTATTGCAATTCCCCAGGAATGGATCACAGAGCTATTTCTTC<br>CTCCAGGTTTGTAGATTTGTAAGTTGAGTCATAGGGCAGGAGTACCTTTTTTTATTT<br>TATATAGGCTAAAAATTTGTTGGAGAAGATTAGTGATCTGGAGAGGGGAAAAAAA<br>AGAAGAACAAGAAGGAGATGAAGAAGGGGAGGAAGAAGAGAAAGAAAGACAAA<br>AGGAAGCCAACCCTAATCCTTGAATTCTACAAACTACTAACAATTAGTCAAAAGTG<br>CCTACTTGGATTTCAATACCTGACATGCCTTTGAGTGTTGAAGAATTAAATGTTTTA<br>TTCTGGTATTGTTTTTTGATGTCATTTATTTTTAACCTATACTTGCCCCTATCAAGAT<br>CATTCTCAGTTGATAGTAAGAAAAATATGTAATGTTGTTGCTAATTTATCTTGCATT<br>AGGTAATTGATTATTTCAAAAGAGCATTCTTGAACATCTTGTAAACTAAAAAAGCA<br>AAGAACTCGGTATGAGGAAGTTAAAAACTCTGTCAAGATTTCAAAAATTTGTGTAT<br>AAAAATTAATTGCCATGTTAGAAGTCGAGGTCAAGCAGTAATGATAGAAATTTTGT<br>GAAATGATGATTAGACATAAAATGTAAGACAAATGAGAGAAACAAAGGTACACAA<br>TAGAAAAAGTATTATTAGTACTATATTAGTGACTCTGAATGGCATAA |
| Human CPS1<br>RR21_v1<br>SEQ ID<br>NO: 72 | GTGCAGAAGGAAAGGGTAATCAGATTGATGTATCCTCTGAGTCCTCCTTGATATCT<br>GCAGAGCAGCTGAGCTGGTCTGCTCTCTGTGCTGTTGACATCTGCTCTTTGGGGCGT<br>TAGGGGGTCTGGTCATTTGTCCCTTGTCTGTTATGATCTACCTGCAGTGGTTTTCTA<br>CCTTGTCCCCAGGCTTCTTAATTCTTCCTGTACTCTCAGAACCTCTGTGTTGTCACA<br>ACCAGACTTGGGTTATTTTGGGTCCCCAGTTTCCAGGCCCTGAATGCCATGGGCTCT<br>GTCTCAGGAATAGGTATCTGCTGGCCTGCTGCTGTCATTTCTACTACATTGCTCCTT<br>TACTGCCTTAAAGAGTGGTCCTGGATCAGGGGTTGAAAGTGGAAGTGGAAATAAA<br>GGACGCTGATGTGACGTCTGTGTTTCCATTCTTCTTCCTACCACTTCACCAGATGTG<br>AAAAATTCATATAATCTGAATCCTCTAGTTTGAGTTATGATAAGTTAAAGCAGTTT<br>AAGAATTTAACGAACTCCCCTCTCCCTGATTAAATCTACTTGTTAGCACTGTGTTCT<br>TACTGCAAATCCCGTTGCCTTGCCAGAAGATAAATATTAACTTTTTCTTTCTCTTTG<br>CCTTCCTGTTGTAATAATTCCAAACCACCCAAAAGAAATAGGTGAGTTTGTGGAGA<br>AGGTCAGTAAAATAATTTCAAAAGGGAAAAGAACATTCATGCATTTAAATATTATT<br>CCCACTGGTTCATTTATGCTGCAATGAATATCTATATATCTATGTATGTATCTATCA<br>TTTTGTGCACATGTTTAGTATTTTCTGAGTTTCATCCTGAAAAATGTAATTGCT<br>GTAAGGTATGCACATTTTACATTTCACTGTATAATGACAAATCATGCTACAAAGTG<br>ACTAGACCAATTTATACTCTTGCTATGAGTCACTGAGAGAATTCTTTACTAACACCA<br>GATATTTTGCGTAACTTATTCTGTTTAAATTCTATCAGCAAACCTCCATAGTAGGTG<br>TATTCCCATTTTGTATATGAAGAAACTGAGGTTCGGAGTTAAAGCAACTTGTTCAA<br>GGTCACACAAATGGTAAGTGGGTAATTTCGGAACCTTTTAAAATAAAACATAGAA<br>GCCTACTATCTTATTGTTCCATTCTAGAAATATGTCTGTGTTTATAATATCGACTAC<br>TTTGTATTATTTTAAACTTTATAATATTGACTACTATTATTTTCTTCACATCCTAGTT<br>AAGAATCTAGGATAAAATGGAAAACGATATCACGAAATGGAAAAACAATGTTATT<br>CCTTAGTTAGCTTAGTTTAAACACCTATTTAATGGTCAAAGGCAAGTAGTTGACCTC<br>CCATCTTTTTGACTCACAGTCATTAGTTACACAAGAAAAGCAGAACAAAACCCAGC<br>TGGATGGAGGGGTGGATATGCAAGTAGCTTTCACACTAGGAATTGTGAAGCCTGA<br>GGCATAGCCCCAAGACTCAGATCATCGGGAGTGCACTCAGTCCAGAGGGACAAAT<br>GTTCAGAGTCTGCATCACCTAATATTACAAGCATCTTTATTGAGACTGATAGAAGT<br>GAATTCTCAGGTCAGAAAACAGAAGAGCTCTTTTAGCTGAGTTGTGATATTTAAA |

TABLE 1-continued

Exemplary regRNAs

| regRNA | Nucleotide Sequence |
|---|---|
| | AGTCTCTCATTTTGAATTTCTTGCCTGGCCAATCAAACTGTCCTCCCAGAACAAATT<br>GTTGGATAATGAAATGCATATAATGTAGCTTGAGAGCGCTGTCCCATTTGCAGCAC<br>TGGCTTCAGCCTGAGGCACATCTCTGGCTGCTCCTTTCTATCTATAAGTTAAAGCAA<br>TGGCCTCAGCAAGCAGTACACTCTGTACAGCAGCTGCAACTCGTTATCGGCTTTGT<br>CCAGAATAACAAACAGAACAAACACATTTTGCAAGGGCTTTTACCCCTCTTATGTA<br>GAGAAGGAGGAATTAAGCAATCAGTGAAATGCTGATTGATCAGTTGTGCTGACTA<br>AGAGAAGTCCAAGGCCACATTAGTACTATTAAGCCCTAAAAAACAAAGCAAAAG<br>AAAATGTTCTTAGAACTTTATTTAAACCAGTATTTCTGTGATGTGAAGTACATTTCC<br>CCCAAAGGGAAAAATGGGAAAATATTTGCATTTCACTTAGTACACTTTACTCATCC<br>AGACTGCTTTGTAATGTAATGATGGTTAAGTATTTTTACAAAGATAATTCATGTTTT<br>TTGGCAGATTTTGGTTGATCATGGAGTATCAGGGTTGTGTGAACAAAGGTGTGAT<br>GCAGAGCAGCTTTAGTAAACCATCCCATTCCTATGCCACCCGTTTGATTTCAGTACC<br>AACTGCTGTGGCCACATCTAGACCACTCTTTACCAGAAACTGTGCCACCTTCAAAA<br>TTCCAGCATCCTTTTCCCCTCCTCCCTTATTTTTTGATCTCATATACTCAAGTATTCT<br>TAGTGTAACAATTCTTTGAGCATTCTTTCTTATCTAGCTTAAAATCTAGGGTCTACC<br>ATTATAATCATTCCTTTCAAGATAACCTTAACTTCCACACCCCAATTTCTAACTGGC<br>CTGGCAAAACTCAGACCTTTGGTGCAAAATCCTCCATCTCTATGCCTGAGCCCTTGT<br>GTTTGAGAATGGCTGAAGAAAACCATGTGCATGGACATTCTGATGTCACTATAAAT<br>TCATGGTCACGGATCTCAAATGGGAGCCCAAGACTACTGGCTTTCCTGCTGTGGTT<br>GTCTAATGACAGCATGATCTTACTCTTCACAGATATTAGTTTAAACTCTCCAACCTT<br>CAATTGAAAAGTCTACATCTTACTTTATTAGAAAGTAGAAACAATCAAGGGTTATG<br>CTCCCATTTTCACACTACCAAGTAAACAAACCTTCAGTAAGAGAAGATATATTTCC<br>TATATCTCCTCCTACCCTCCTGTTAAAAGGGTGCAAACGTCCCCCCTCCTAACAAAA<br>ACCAATCCTTCTTCATGCTCTTTAGATGCCGTGTTGTCTCTCTTTCTCAAAGTCTTCA<br>TTTTTTGGTTATACTCTTTCTCTCATGCAAATTTTTCTCTCTTTTTCAAGTAGAGCAG<br>GCTCAGCAGCCTACAAACGTGTCTTGGGCACCTTTCATCAAAAAATAAAAAACATA<br>AAAACAACAAACGAAACCCTTCTTGGCTCCACATTCTCATCCAGTTTCTATTCTTTC<br>ACTTAGCTGCTTTTCTTCTCATGTTTTGTCTATTTTTAACATCCTAGTCACTCTCTG<br>ATCTACTTCAGTTTGACTTCTACCTCCATCACTTGAGTAAATTCAATACATGGTTTC<br>AAGTATATTCTAGCCCTAGCCTGATCCACAGGGAAGGTTCTGGACCACAAGCAACA<br>TGGCAGAGTTGTTCACTCTTGAGGTAAAGGAGTTTGGCACCTCATGCCCCTATAAT<br>GGATTAAAGAAACACTCCTTAATCGGGGTTAGTCCCTGGGAAAGGTTTTAGGTGTG<br>AGCAATTAGCAACCATCACCCACAGTGGCTGGGAGAGGGGGGCACTAGCCCAATA<br>AAGAGGATCTAAGTAGTGCACCCAAGCAGGTCTACCACAGTTAGCTTCCTATGTGG<br>GCTCACGTTGCATGCAGTGCATCTCTATACAGCAATTAATCTATTTCATAATATTAA<br>TAAAATAATTTCACTTTCCATGTTAAAATCCTTCAATGACTTCCTATTGCACTATAA<br>ATGGCAAATCAATATGTTAACATGCCCTGCCAACACCTACAGGGTCTGGGGTCTGA<br>TTGCCTTTCAGATCTCTC |
| Human CPS1<br>RR22_v1<br>SEQ ID<br>NO: 73 | GAAAGAACACCGTAGTATAACTGGATGGCCCTGGTCCCTGCCAGGAGTCAGGATG<br>GACTTTCAGTGTTGAAGAGCCATCTTGGCCTGTTACTAGCGCTGCCCCACACCATTG<br>TGTTTGCCTAAGAGCTGAGCCAAAGAATTTACATATGTATGAGCCAAGGTCTGAAA<br>ATAGAAGTTAAAAAAATGGTGCTAAATTGACATATTTGCTATTTTATTTTTTGGTC<br>AGTTAATATGATAAACTTTTATTTAAATGTAAACATTATTTTAAAAAGCACTTTGTT<br>TTAAATAACTGATTTTCATTGAAATTAATTCTGGCCTCTAAGCAGAGTTAGCTACAA<br>AGACAATTTGTAAAAATGCAGAAAATTCAGAGTTTAACTTGGAGTTGTTTAAAGTT<br>TATTTTCATATTTGAGTCTGATATTTCAGTTCACTGTAATATTTCAATTTATTTAAAA<br>TATTATCAAGACAAATATTGGGTTACCTTCACAATATTTTTTCATTTTTCTTACCCC<br>ATATATTAAAAATGAACAAAAATGAAAGAATTATATAGTCTAGTGGATGGCAATTC<br>TCTTGGTACAGTACTCACAGGATGTCAGAAGTGCTTTGATTTGCATGCAAATAGAA<br>ACTGCATTCCTAAAAGACCCTTAATTGAAGATATTAATAATTTTCATTAGGTTTTAA<br>GTCTTTTAACCTTATCATATGGATAGAAAAGTAAAAGATGTGTTTAATAAAATGTC<br>TTTTACTTATTTTTATTTGTCATTTATTTAAAGGTTTATTAGTGAATCTGTTTACCTG<br>GAAAATGTGCAATTCTATTTGCAAATTTGGAGCACTACATATATTTAAGAGAATCC<br>TTAGTTTCTGTTGGGAGTGGCAATATTTTATAACTGGGCCTTCATATTCCTATGTTA<br>CAGCCCTGGTCCCTGAAAGTCCTACAGCTATCTTTGTTTCAAGTGTGTATGTGTTAT<br>AATAAGATAAGTGTTAATTAGTTAATCAAGTACTAATTAACCTTTTTAATTTATAGA<br>AAAACAGACATTTATGGACAAGTAAATTTTTGGGGTCAAAGTCTTTAATAATTTGA<br>AGAATGCAGTTATTTTTAGCACAAATATTCTAATGTGAAAAGAATTTCTTTTTCTGA<br>GTTATATATTTTTATGCCATTCAGAGTCACTAATATAGTACTAATAATACTTTTTCT<br>ATTGTGTACCTTTGTTTCTCTCATTTGTCTTACATTTTATGTCTAATCATCATTTCAC<br>AAAATTTCTATCATTACTGCTTGACCTCGACTTCTAACATGGCAATTAATTTTTATA<br>CACAAATTTTTGAAATCTTGACAGAGTTTTTAACTTCCTCATACCGAGTTCTTTGCT<br>TTTTTAGTTTACAAGATGTTCAAGAATGCTCTTTTGAAATAATCAATTACCTAATGC<br>AAGATAAATTAGCAACAACATTACATATTTTTCTTACTATCAACTGAGAATGATCTT<br>GATAGGGGCAAGTATAGGTTAAAAATAAATGACATCAAAAAACAATACCAGAATA<br>AAACATTTAATTCTTCAACACTCAAAGGCATGTCAGGTATTGAAATCCAAGTAGGC<br>ACTTTTGACTAATTGTTAGTAGTTTGTAGAATTCAAGGATTAGGGTTGGCTTCCTTT<br>TGTCTTTCTTTCTCTTCTTCCTCCCCTTCTTCATCTCCTTCTTGTTCTTCTTTTTTTCC<br>CCTCTCCAGATCACTAATCTTCTCCAACAAATTTTAGCCTATATAAAATAAAAAA<br>AGGTACTCCTGCCCTATGACTCAACTTACAAATCTACAAACCTGGAGGAAGAAATA<br>GCTCTGTGATCCATTCCTGGGGAATTGCAATAAAGTTTTAGGGAAGATGGAACTTA<br>ATGTTTGTGAAAGCACGGGTCCTATTTCCGATTTCCAGGAGGGTGGAATGTATCTT<br>CCTGAATCACATTCCGCTG |

TABLE 1-continued

Exemplary regRNAs

| regRNA | Nucleotide Sequence |
|---|---|
| Human CPS1 RR23_v1 SEQ ID NO: 74 | CATTCCGCTGAAAATAGGAGGCCATGGAAGAAATCAGGTTCAGTATAACAAATTTT<br>CTACAAAAGGGGTGGAGTAGGAATGTGCGTAGGTGACCTGTTCTCTACGTCATTC<br>CAGTGTAAACTACTGCCCCTTACACTTCACGAAGTCGGTAACTTCAAGACATGTTG<br>CACCCACATGCTTCTCTGTGATCCTCAAATATGTTTAATTTAAAGAGGGTCCAGTAGT<br>GTCCTGGCACATGATCTGGATTGCCATAGATAACCATCTACCTCACAGCTAGGGTT<br>GCTCTTTAGAATCTTGCAAATCATTTGTTTACTCTTGACAAAAGTTAAGAAAACA<br>AGCCCATCAGAGTTGTTTGTTCTGTCAGCATGTTAGAAGATGGTTTTGTTGCAATGA<br>TAATCGTTGTGCAAAGAAGACTGATGATGATTTTTTTTTACATTTTCTTAACAGTAT<br>TTGCTATTTAGAATGAATGTTGTCTAATTATTTAGCCATTTTATTTTGTAAAATTTAT<br>GTTGTAGGCATATTTAGACCAAGTTATAAGAAAATGCTTCAGCCAAAATTAAGTGT<br>TGAGTTTGATTTGTGTAATTGTTAGTTTCTTTACTAGTTGTTCCATCATTTACACAAT<br>TATTTCTATTTGAAATGCAGTAATTGTTCAGAACTTATATTTCTATACTGATGTCTA<br>CTAACAGCTTTAGATCAAATATTAAATAACTCAAGAATAATGAGATGATCTTGGCT<br>TACTTAGATATTTGGTTTTTATATCTATAGAACAAAGGAATTAGAAAATAATTTTGA<br>AGATTTCATCCAGCTATGTAAAACTATCTAGGGAATACATTTACTAGGTTTTCAATT<br>TTCTACAAAACATCTTTCAGCAGAAAGCAATCCTGTTTCCTGATATACAATGTCTGA<br>TACATAGAAACTACTCAGTACATAATTCCTGAATTGATTATTCTTTTGGAAATCCTA<br>GATTTGATTTCTGAACAATCATAAACATTTAATGGCATGAAATTACCCAGATTCCA<br>TGGTTCTGGAATACATAACTTCAAGCAATAAGATGCAAGATAGAAACATATAAGA<br>CATTCTTTGCTATTTTAGGTAAGTCCAGCTGAATCAGTTAATCAGCTAGAAACGTG<br>GCTCACAGATGAATTAGTTTTTATTATTAGGTGGATTACTGAAAAATTAATAGCTTTA<br>TTTCCGTATTACCTTATCATTTATTTAATATAAAACATAATAAACCAGAGAAGTTGT<br>GGTTACTTTCTTCTGTCTCATTGTTCAGTTTTTACTGAAGTTATGTTTTACTGATTTT<br>CACGAAATGCAAATATTTCTGAGCATCAGAAATCCAGCTTTTGCTACCTCCCACTC<br>ATGTATTCTTCCCATCAAATTGAATCTTAACCAGGTCACTCTTTCCTGTTCATTCCAT<br>GCTGTTGCCCCTGTTTTCTCCAGATATAATTGACATGCTCCAAGAGGATGAACATTG<br>CCTAAGACTTGATTTCTGGTCTTGGCTTTGCAACTTACTAGCTGTGTGACCTTGAAC<br>AAGCTACTTAATTCTCTGAGACTCATCATTATTGTTTATAAAATAGGGATAGCATTA<br>GCTTATTTCAAGAATTGTTTTTAAAATTAGCAAGGAAGGCATACCAATGCCTAGCT<br>CAGGGGATCAACAAGTGGCAAGTACCTCAACTTTCAGGCAAGATCATACTTATCAT<br>CAGTGGAGCCAATAGAACAGATTTATTTAAATACCCTATTTTCACTTACTGGCATA<br>ACAGCAAGTGGTGTACATATTTATATATCTCTCTATATAGATGCAGATAATATACT<br>AATATATTGTGGTTATATCTTCCAATGTTTTAGTTTCTATTGAGGG |
| Human CPS1 RR43_v1 SEQ ID NO: 75 | TCATATAAGCTGTCTGCACGCAGCTGAGCAGAGTGACAGGCATGAATGCAGGCAC<br>ACACATCAGGCTGGGGACCCTGTGTACTTGGAAGTACATTCTTTGTGAGCCAGGTC<br>ATCAAAGGTTTTCTAAACTTATGAGTCACTCTCTGATAAAATGAATTTTTTTTTTA<br>GATTTAGTCTTCTTTTCTATTAATACATTTTAAAAAATAGAAGCATTTAGCCTGTGA<br>AATCCCTCAGGGCACTTTATTTTATGAATTCCTTATTGACATATCTGGTATTGAAAA<br>TGTTAAAATGTCAAGTACTAGGTTGTATTCACTTTCATTTGATATTTAAAGAAATGT<br>GGAAATACAGAATAATAGATAATAACCCACCACACAAACATAATCTCTGTTAACA<br>CTAAAGTATTATCTTCTAGCATTTATGTCAATGCTCAGAACATAGTTTTGAAAATTG<br>CCATTGACTTGCATAATGCTTTTTGGAGGCAATATTATGTTAAATGTATTTTGATGT<br>TATTACAAAGTTCTTTTAAAACATTACTTTAAATGATTACAAAATATTCCATTTTCA<br>TTGCTGCTACAATGCATGTCAATATTGCCATATTTGATTACTATTTACAAATTTCTC<br>TCCAAAGAGAGTGTACTCACCTACATACCAGTGCAATATATGGGTGTCCCTTTAAA<br>AATGTCCTCACCAACATTATGTATTATCTTTCATTTTATTTGCTCCGCTGTAGAAAA<br>TATTATTTTGCTTTCATTTCTATTTTAAATCACTGGTGAAGTTGAATACTTCACAGTA<br>TGTTTTTAATTGATACTATTCTTTTATCAACTACTGTTTACATTTTTGTTTCCATTAA<br>CTCATTTATATTAATCATTACGAAAATGTCTTTAAAGGAAACATAAAGAAACACTG<br>ACAGCCTGTGTCTATACTGATTTAAACAGTCCACTTCTCAAACAGTCCACTCTTCAT<br>TTAAACAGTCCACTGACATAAGCAAGGGAAGACCTGCTACAGATTGAAAAAAAAA<br>ATGAGAACAGGATGTCTTAGAGAATAAAGGTCTTAGGTTTTGGAATGAAGAGAAA<br>ATAAGGGTGTTAGTAATTCCTTTGAAGGTACAGAGACTTCCAACTGCCCTCTTGAA<br>ATGTTCCTAAGTAATGAATCAGAAACAACTCTAAGAAGTTGGTGCATCTATCAAAA<br>AGTCTCTAACATAGCAAGCATGCAAGAGATGCTTCTGGAAAAATGACTGAATGAA<br>TGGATTGCTGTGTGCTTAATTCCTGCCTGATCAGTGATGATTATTTAAGCAGGAACA<br>AATAAAATTACATCAGTTAAGCATGAGAGGAAATAAGGATGCTTAGGAGTCATGA<br>AAAAAAAACCTGGCAATCAATAATTCTATAAAGTCTATTTTTGAAGAGATACATT<br>AAAGCAAGGAGTAAGGTATGACTGGAGAGCAAACAAATTCAGAGTAAAAGGAGG<br>TGCAATAACTCCCTGAAGAAAGTTCTACTGTTTTGTGTTTGACCAGAAATGTGTGA<br>AAATAGAATATAAAAGGTAGAAGTAATTGGGTTCAGTTCTATGATTTTTATTAGCC<br>TTAGTATCATAACAAGGAACACGGTCACAATTAAAGATATGGATGAAGAAGGCAT<br>CTCTGAGGGAAAGTGGTGTGGATTGTACCCATGTAAAAGGCACACATTTTCTCCTA<br>TCACAGAAACTAGGACAAGCTGGTAGGAGGATTCCTCAAAGTTTGGCCAGGAAGA<br>AGACTTAAAGTTGTTTGAAAAACCTTCCCAATATGTCAAGGATTGAAAATGACAGAC<br>AGATATCATGTTGTTAGATGATGAGGGTTCAAACTAACCAGATATCCTTGGAAATC<br>CAATCAAGTAAAACCTATTCATTAAGATCCAATTGGCATTTTGAGGAATAGAAAGT<br>GAGGATCAAATTATGATGAATATGCTTATCAATCTAACATTTGATAACATAAAGTT<br>TGGAGTGATACAAAAGAAGGTGAAAAATGAAGCTG |
| Human CPS1 RR21_v2 SEQ ID NO: 76 | GCCTGATGTGTGTGCCTGCATTCATGCCTGTCACTCTGCTCAGCTGCGTGCAGACAG<br>CTTATATGAAGGAGGACTGTGTACATGTGGTCAGAGAAGAAAAAAATGCTTATTTT<br>TTAAAATGTTTTGAAAATAATCTGTCCTAAAAGTGTAACATTTCCACTAAATTTTT<br>TCATGTCTGACTTTAACATTCCCTACCAACCAACTCTTATAGCCTCAACTCCTTTGA<br>TCTATCCTAATGTAAACTCCCTCACTAATGTGTAATATATTTTTTCCAGTTTGGTTA |

TABLE 1-continued

Exemplary regRNAs

| regRNA | Nucleotide Sequence |
|---|---|
| | TAGATTTCAGTCTAGCCTGAACACTCAAGTATGAAACTAGCCACTATTTTATTTATT<br>GGCTGTTCCAACCTCCATTGTGGAATTATAATTGATGGATTTTCCAAGTCTCTAATT<br>CAGAATATTTAATCAAATTTTCCAAAATTTCTGCCTTCTCCTCCTTCATTCTGATGA<br>CTAAAGACATGGACCATAAAATATATATACATATATACATACATATGTATATGTAT<br>GTATATACACATATATATATGTATGTATATATACATACATATATATATGTATATATA<br>CACACACATATACATATGTATGTATATATACACACACACATATATATATGTATGTA<br>TATATATACACACACATATATATATGTATGTATATATATACACACACATATATATAT<br>GTATGTATATATATACACACACACACCGTAGTTTGCAAGTCTGCATCTGGGACCCT<br>TTACTGATAAAAATGAAAGCCCATTAAAACTCTCATGCCCACATTTCTCTCTAGACT<br>TTAGAGTAGGAGAATTCTATCCTAGAATTGTTGATTGTTGACATTTCTATGGAAAA<br>ACATGTTTAATTCATCATGCTTTGTAGTCAACTGCTATAAATGGTGATGAAGTCTTT<br>TCCTTGGTCAAGCTCTGGACTCCTCAGTACTTCCACTGTCATATTTGATTAAAACAT<br>AAGTGATGAAGGGAGGAAATATATTATAGTATTCATTGCATGGGTACCTTAGGGTA<br>ATGGGACTATGACTGATTTAAATTTATTTTGCATCCTAAAAAGTTTCCATTAGTGGG<br>TGCAGCACACCAGCATGGCACATGTATACATATGTAACTAACCTGCACAATGTGCA<br>CATGTACCCTAAAACTTAAAGTATAATAATAAAGAAAAAAAAACTTAAAAGAA<br>AAGTTTCCATAATGAGGATTGAGTTTATATCGTTTTCTTAATTAAGGAAAGACAAC<br>CCTCACTACACACACACACACACACACACACACATAAAAAGACAAGAGGTG<br>AGATCAAGGCGTAAACTAGTATTGGACTAAGCCAGTAAGTACTGCTTCTCAGTCCT<br>CAGTTCTCTAGGTTGGGAGTTTTCCTTTTGCTATTTTCATTCTCCTCCAATTCATTTT<br>TCAATGATCTTCAACACAAATTTCGCCTTTATTTCTTGTTCAATATACTTCCATGAC<br>TATTATGAATACTATTTATGGATGAAGGCTGAACATTTTAAGGCATACTAAGTCTC<br>CCATGATATGGTACCTTTTCATTTTCCCATTCTATACCCTGCATCTAGGCTTTTAAA<br>AAATATACCACATGACTTCATGCCTCTAGGCTATTGCTCATGCCACGGCATCCCTTC<br>TGGGTTTTTTCCCCTCTTTATCTACTTGGTGAATTTGCATCCTTCAGTATAACACAGC<br>TCAACATAATTCTATGCTTAAACTTTACTGAAAATGCACAAGGAACTTGATCTTTCT<br>TTCTTATTTTCCCCATTTTATTTATTTTCCCATTGCATTTGGGCAACTTTCATGGCAC<br>CAGTTATTTTATTAATTATTTGTATAAACTAGTATGAGCCTATTTTGTTTAGCTTTCT<br>ATCACCAGGAGCCATGAAGCACTTTGAAATCAAATACTGTTTGTACTTGAATATAT<br>TAAGTAAGCGTGAGGACTTAAATTAAACTTTGTTCCTCTTTAAAAAAATCCTTACCC<br>CAACTCTAGCACTGA |
| Human CPS1 RR7_v2 SEQ ID NO: 77 | TCTTCCTATGGGAAAAAATAATTTCCTCTATCAGAGGAAAAATTTATTACTATTATG<br>ATAATACCCCTTCAGACCTTTTTCTAGTCACTTACAGGTAAAAATTGTAGTACTGGT<br>TGGTACATAGTGTATTTTATTAATGTTTTACTGCGTATATTGTTGTATAAATTGCTTT<br>CCGCACTCATTGGCATGCCTTAGAATTCTTTTTATTTAGGCTTCATGACTAATTTGT<br>AGTGGAACCTCAAGAAGATCACTTATGTGCTTCACTTTCCACATATGTAAAATGGG<br>AATAACAACAGAATCTGCCTCATAGTACTGCTGAAGGGTGACATGGGAACACCT<br>GTGAGGCATTCAGAACAGAGCCTGTCATACAATAAATGCCATGTCAGTGTTTGCTC<br>TTATTCTCAGTATACAGAGATCTGCTTTGATCTTTTCATCTTCTGCAAAATATTCCA<br>CAAATTGGCATATTGTGTTTTGTAATAATCTCTATTGATTATTTTCAAGCAAGATTT<br>GGAATTATCCGCAGTAGTTTCAAATGTACAAAAAAGTACCTTATTTTATTTATTTTT<br>TAAATAACTGATCTGATCTACGAGTCTAATCTGGTAAGTTTTGTCTTGAGTCCAGTA<br>ATGCAGTCCAATACTCCATTTAGGTAACCCTGTCCTTGCTTGGTCAATTTGTTCCAC<br>TTTTCCAAGTTTGACCTGCTTACCCTATTCCTCTTCAAGAGGGCATCTGGTTGTTTA<br>GTTTACATGATTTAGTGGTGCAGAAGGAAAGGGTAATCAGATTGATGTATCCTCTG<br>AGTCCTCCTTGATATCTGCAGAGCAGCTGAGCTGGTCTGCTCTCTGTGCTGTTGACA<br>TCTGCTCTTTGGGGCGTTAGGGGGTCTGGTCATTTGTCCCTTGTCTGTTATGATCTA<br>CCTGCAGTGGTTTTCTACCTTGTCCCCAGGCTTCTTAATTCTTCCTGTACTCTCAGAA<br>CCTCTGTGTTGTCACAACCAGACTTGGGTTATTTTGGGTCCCCAGTTTCCAGGCCCT<br>GAATGCCATGGGCTCTGTCTCAGGAATAGGTATCTGCTGGCCTGCTGCTGTCATTTC<br>TACTACATTGCTCCTTTACTGCCTTAAAGAGTGGTCCTGGATCAGGGGTTGAAAGT<br>GGAAGTGGAAATAAAGGACGCTGATGTGACGTCTGTGTTTCCATTCTTCTTCCTAC<br>CACTTCACCAGATGTGAAAAATTCATATAATCTGAATCCTCTAGTTTGAGTTATGAT<br>AAGTTAAAGCAGTTTAAGAATTTAACGAACTCCCCTCTCCCTGATTAAATCTACTTG<br>TTAGCACTGTGTTCTTACTGCAAATCCCGTTGCCTTGCCAGAAGATAAATATTAACT<br>TTTTCTTTCTCTTTGCCTTCCTGTTGTAATAATTCCAAACCACCCAAAAGAAATAGG<br>TGAGTTTGTGGAGAAGGTCAGTAAAATAATTTCAAAAGGGAAAAGAACATTCATG<br>CATTTAAATATTATTCCCACTGGTTCATTTATGCTGCAATGAATATCTATATATCTA<br>TGTATGTATCTATCATTTTGTGCACATGTTTTAGTATTTTTCTGAGTTTCATCCTGAA<br>AAAATGTAATTGCTGTAAGGTATGCACATTTTACATTTCACTGTATAATGACAAAT<br>CATGCTACAAAGTGACTAGACCAATTTATACTCTTGCTATGAGTCACTGAGAGAAT<br>TCTTTACTAACACCAGATATTTTGCGTAACTTATTCTGTTTAAATTCTATCAGCAAA<br>CCTCCATAGTAGGTGTATTCCCATTTTGTATATGAAGAAACTGAGGTTCGGAGTTA<br>AAGCAACTTGTTCAAGGTCACACAAATGGTAAGTGGGTAATTTCGGAACCTTTTAA<br>AATAAACATAGAAGCCTACTATCTTATTGTTCCATTCTAGAAATATGTCTGTGTTT<br>ATAATATCGACTACTTTGTATTATTTTAAACTTTATAATATTGACTACTATTATTTTC<br>TTCACATCCTAGTTAAGAATCTAGGATAAAATGGAAAACGATATCACGAAATGGA<br>AAAACAATGTTATTCCTTAGTTAGCTTAGTTTAAACACCTATTTAATGGTCAAAGGC<br>AAGTAGTTGACCTCCCATCTTTTTGACTCACAGTCATTAGTTACACAAGAAAAGCA<br>GAACAAAACCCAGCTGGATGGAGGGGTGGATATGCAAGTAGCTTTCACACTAGGA<br>ATTGTGAAGCCTGAGGCATAGCCCCAAGACTCAGATCATCGGGAGTGCACTCAGTC<br>CAGAGGGACAAATGTTCAGAGTCTGCATCACCTAATATTACAAGCATCTTTATTGA<br>GACTGATAGAAGTGAATTTCTCAGGTCAGAAAACAGAAGAGCTCTTTTAGCTGAGT<br>TGTGATATTTAAAAGTCTCTCATTTTGAATTTCTTGCCTGGCCAATCAAACTGTCCT<br>CCCAGAACAAATTGTTGGATAATGAAATGCATATAATGTAGCTTGAGAGCGCTGTC |

TABLE 1-continued

Exemplary regRNAs

| regRNA | Nucleotide Sequence |
|---|---|
| | CCATTTGCAGCACTGGCTTCAGCCTGAGGCACATCTCTGGCTGCTCCTTTCTATCTA<br>TAAGTTAAAGCAATGGCCTCAGCAAGCAGTACACTCTGTACAGCAGCTGCAACTCG<br>TTATCGGCTTTGTCCAGAATAACAAACAGAACAAACACATTTTGCAAGGGCTTTTA<br>CCCCTCTTATGTAGAGAAGGAGGAATTAAGCAATCAGTGAAATGCTGATTGATCAG<br>TTGTGCTGACTAAGAGAAGTCCAAGGCCACATTAGTACTATTAAGCCCTAAAAAAC<br>AAAGCAAAAGAAAATGTTCTTAGAACTTTATTTAAACCAGTATTTCTGTGATGTG<br>AAGTACATTTCCCCCAAAGGGAAAATGGGAAATATTTGCATTTCACTTAGTACA<br>CTTTACTCATCCAGACTGCTTTGTAATGTAATGATGGTTAAGTATTTTTACAAAGAT<br>AATTCATGTTTTTTGGCAGATTTTGGTTGATCATGGAGTATCAGGGTTGTGTGAACC<br>AAAGGTGTGATGCAGAGCAGCTTTAGTAAACCATCCCATTCCTATGCCACCCGTTT<br>GATTTCAGTACCAACTGCTGTGGCCACATCTAGACCACTCTTTACCAGAAACTGTG<br>CCACCTTCAAAATTCCAGCATCCTTTTCCCCTCCTCCCTATTTTTTGATCTCATATA<br>CTCAAGTATTCTTAGTGTAACAATTCTTTGAGCATTCTTTCTTATCTAGCTTAAAAT<br>CTAGGGTCTACCATTATAATCATTCCTTTCAAGATAACCTTAACTTCCACACCCCAA<br>TTTCTAACTGGCCTGGCAAAACTCAGACCTTTGGTGCAAAATCCTCCATCTCTATGC<br>CTGAGCCCTTGTGTTTGAGAATGGCTGAAGAAACCATGTGCATGGACATTCTGAT<br>GTCACTATAAATTCATGGTCACGGATCTCAAATGGGAGCCCAAGACTACTGGCTTT<br>CCTGCTGTGGTTGTCTAATGACAGCATGATCTTACTCTTCACAGATATTAGTTTAAA<br>CTCTCCAACCTTCAATTGAAAAGTCTACATCTTACTTTATTAGAAAGTAGAAACAA<br>TCAAGGGTTATGCTCCCATTTTCACACTACCAAGTAAACAAACCTTCAGTAAGAGA<br>AGATATATTTCCTATATCTCCTCCTACCCTCCTGTTAAAAGGGTGCAAACGTCCCCC<br>CTCCTAACAAAAACCAATCCTTCTTCATGCTCTTTAGATGCCGTGTTGTCTCTCTTTC<br>TCAAAGTCTTCATTTTTTGGTTATACTCTTTCTCTCATGCAAATTTTTCTCTCTTTTTC<br>AAGTAGAGCAGGCTCAGCAGCTACAAACGTGTCTTGGGCACCTTTCATCAAAAAA<br>TAAAAAACATAAAAA |
| Human CPS1<br>RR23_v2<br>SEQ ID<br>NO: 78 | TGTTTGTTCTGTTTGTTATTCTGGACAAAGCCGATAACGAGTTGCAGCTGCTGTACA<br>GAGTGTACTGCTTGCTGAGGCCATTGCTTTAACTTATAGATAGAAAGGAGCAGCCA<br>GAGATGTGCCTCAGGCTGAAGCCAGTGCTGCAAATGGGACAGCGCTCTCAAGCTA<br>CATTATATGCATTTCATTATCCAACAATTTGTTCTGGGAGGACAGTTTGATTGGCCA<br>GGCAAGAAATTCAAATGAGAGACTTTTAAATATCACAACTCAGCTAAAAGAGCT<br>CTTCTGTTTTCTGACCTGAGAAATTCACTTCTATCAGTCTCAATAAGATGCTTGTA<br>ATATTAGGTGATGCAGACTCTGAACATTTGTCCCTCTGGACTGAGTGCACTCCCGA<br>TGATCTGAGTCTTGGGGCTATGCCTCAGGCTTCACAATTCCTAGTGTGAAAGCTACT<br>TGCATATCCACCCCTCCATCCAGCTGGGTTTTGTTCTGCTTTTCTTGTGTAACTAATG<br>ACTGTGAGTCAAAAAGATGGGAGGTCAACTACTTGCCTTTGACCATTAAATAGGTG<br>TTTAAACTAAGCTAACTAAGGAATAACATTGTTTTTCCATTTCGTGATATCGTTTTC<br>CATTTTATCCTAGATTCTTAACTAGGATGTGAAGAAAATAATGTAGTGCAATATTA<br>TAAAGTTTAAAATAATACAAAGTAGTCGATATTATAAACACAGACATATTTCTAGA<br>ATGGAACAATAAGATAGTAGGCTTCTATGTTTTATTTTAAAAGGTTCCGAAATTAC<br>CCACTTACCATTTGTGTGACCTTGAACAAGTTGCTTTAACTCCGAACCTCAGTTTCT<br>TCATATACAAAATGGGAATACACCTACTATGGAGGTTTGCTGATAGAATTTAAACA<br>GAATAAGTTACGCAAAATATCTGGTGTTAGTAAAGAATTCTCTCAGTGACTCATAG<br>CAAGAGTATAAATTGGTCTAGTCACTTTGTAGCATGATTTGTCATTATACAGTGAA<br>ATGTAAAATGTGCATACCTTACAGCAATTACATTTTTTCAGGATGAAACTCAGAAA<br>AATACTAAAACATGTGCACAAAATGATAGATACATACATAGATATATAGATATTCA<br>TTGCAGCATAAATGAACCAGTGGGAATAATATTTAAATGCATGAATGTTCTTTTCC<br>CTTTTGAAATTATTTTACTGACCTTCTCCACAAACTCACCTATTTCTTTTGGGTGGTT<br>TGGAATTATTACAACAGGAAGGCAAAGAGAAAGAAAAAGTTAATATTTATCTTCT<br>GGCAAGGCAACGGGATTTGCAGTAAGAACACAGTGCTAACAAGTAGATTTAATCA<br>GGGAGAGGGGAGTTCGTTAAATTCTTAAACTGCTTTAACTTATCATAACTCAAACT<br>AGAGGATTCAGATTATATGAATTTTTCACATCTGGTGAAGTGGTAGGAAGAAGAAT<br>GGAAACACAGACGTCACATCAGCGTCCTTTATTTCCACTTCCACTTTCAACCCCTGA<br>TCCAGGACCACTCTTTAAGGCAGTAAAGGAGCAATGTAGTAGAAATGACAGCAGC<br>AGGCCAGCAGATACCTATTCCTGAGACAGAGCCCATGGCATTCAGGGCCTGGAAA<br>CTGGGGACCCAAAATAACCCAAGTCTGGTTGTGACAACACAGAGGTTCTGAGAGT<br>ACAGGAAGAATTAAGAAGCCTGGGGACAAGGTAGAAAACCACTGCAGGTAGATCA<br>TAACAGACAAGGGACAAATGACCAGACCCCCTAACGCCCCAAAGAGCAGATGTCA<br>ACAGCACAGAGAGCAGACCAGCTCAGCTGCTCTGCAGATATCAAGGAGGACTCAG<br>AGGATACATCAATCTGATTACCCTTTCCTTCTGCACCACTAAATCATGTAAACTAAA<br>CAACCAGATGCCCTCTTGAAGAGGAATAGGGTAAGCAGGTCAAACTTGGAAAAGT<br>GGAACAAATTGACCAAGCAAGGACAGGGTTACCTAAATGGAGTATTGGACTGCAT<br>TACTGGACTCAAGACAAAACTTACCAGATTAGACTCGTAGATCAGATCAGTTATTT<br>AAAAAATAAATAAAATAAGGTACTTTTTTGTACATTTGAAACTACTGCGGATAATT<br>CCAAATCTTGCTTGAAAATAATAATAGAGATTATTACAAAACACAATATGCCAAT<br>TTGTGGAATATTTTGCAGAAGATGAAAAGATCAAAGCAGATCTCTGTATACTGAGA<br>ATAAGAGCAAACACTGACATGGCATTTATTGTATGACAGGCTCTGTTCTGAATGCC<br>TCACAGGTGTTCCCCATGTCACCCTTCAGCAGTACTATGAGGCAGATTCTGTTGTTA<br>TTCCCATTTTACATATGTGGAAAGTGAAGCACATAAGTGATCTTCTTGAGGTTCCAC<br>TACAAATTAGTCATGAAGCCTAAATAAAAAGAATTCTAAGGCATGCCAATGAGTG<br>CGGAAAGCAATTTATCAACAATATACGCAGTAAAACATTAATAAAATACACTAT<br>GTACCAACCAGTACTACAATTTTTACCTGTAAGTGACTAGAAAAAGGTCTGAAGGG<br>GTATTATCATAATAGTAATAAATTTTTCCTCTGATAGAGGAATTATTTTTTCCCAT<br>AGGAAGATCTTAAACTTATTTGTAATGTTTCAATTTTTTCACATGATGAACAAAGCA<br>ATACACTGCTCATGTTACTGAAACTCGATAAAATATATGAAGCTAAAATTGGTCAT<br>CTAAAAGTATGATAATATATAATATTTATTTTCTACTTTATCTCCAATATGCTTATC |

TABLE 1-continued

Exemplary regRNAs

| regRNA | Nucleotide Sequence |
|---|---|
| | ATACAGAAATTATAACAAAATGCAAGCAAATGTTTTGGATAATTTGAAAGTTAATA
AGTTGTACACTGTAGCCCTACCATCCCCACTGATGTCAAAGGGCTGATTTTTAATTA
TGCAATAGTAATTAAATAGGGATCAATGTCATTACCTGAGAAAACAC |
| Human CPS1 RR9_v2 SEQ ID NO: 79 | AATTCTAAGTCAGGTGGTCCAACAAGGCCTCTCATCCTATTGGTATTACAGTATGA
CCTGTCTCCTGAACTTTGAAGCCATTTCTTTCCTTCAGAGGAGATAAGAAAATGTGT
CTTATCTTAAGTCTGGAAGAAAACACGGAGCCCAGTATCAAGGGAGTGGAGTAGTTC
TTTTCCCAGACGTAGCACAGGGTTTTTCAAGCCTGAAGAAAAAGATTAATCTCCTT
AAAACAAGGCTTTGTTGACTTGGGTCTGGTCATGGCAATCCTGTTTCCAGCCATCCT
GTGTATAAGCTCTAACGGTCAGAAGTTTGTTTGCTTTGATTTTGATGTGGCTCATCT
TTTCTTAGCTGCTCATATTCAAGATTTGGAAAAGAAGGAACGGTGGTGAGCTGAGC
AATTAATTGGATTCTGATAAGGAGTTCTGGAGAAATTTTATTATTCCTGAGTTTTAA
ACCCGTGTAACTTTAATATAACTTTGGTATGAGCCTTTACATTTTTTCTCTGTGTTTT
TGTAATTATATATTGTGGCATTCTTATTGGGTGTGGTAGTAGCAATAAATTATAAATGT
ATGAATTTATACATTATGGATTTATAATTTCATAAGTTTTTGAGATTTTAAGACTTA
CTATTTTTTACACGATGCCTTATGTATTTATAGCATTTAATATTAATCTAAATTCATT
TTGAGATATATTTTATCATGCTTTTATCTTTTATATGTTATTAGAAAGCACTTGGTAT
TTTAAAAATATATATTAATGTGAGATTTCACAATTTATACCTTGTCTTTGTAGTCAC
ATGCGTAGAGGATATTTACAATTTTACTCAAGTTAATTTGCTCAGTGTTGATCATCA
GACCTTTTAGCCAGTATTGGCTGGGAAAAAAGTGTAATTCTTTTTGTTCTCTTGAG
AATTTTTTGGATCTAAAGTGATTCCTAGGGTGTGGGTCAACTTCTATGATATGAAA
GATGACATGGAGGTTTTTTATTTTGTGAAGTGCATTAATAGGTGATCACATTTCATC
CTGGGAGAGCTGCTGGAGAGGAATATTGATTTAGCCTGTTATGGTTGAGTCTTTGG
GGTCTTGAGCTTCTTAGATTTTTAGTTCTTTTTGTTATTCTTTATTGTTCAATCTTGA
GAGTAGAAAATACACATTTTTGTCCACTTCTAAGAATAAAACTGAAAGGCTTCTCA
AGAGGGAGCTTTTGAGGGACAAGTCTGTGTTCCAGACTTATTTTTATTCTCGGATCT
AGCACCATGCTTGGCATGTAAAAGGGCTTTAATAAGTATTTATAGAAGGAATTGAA
GAATTAATTATTACTTATGGACTATGAGAGGTCATGGTTGTTACTCTTTCTAATTTG
TCGATATTAAACAGAGACAGTGAAGATACTAATTTAGATCACACAACGTGAATGA
AGCAAACAAAAGCCTAAAGCTTTAGAAAAATGAATATATTATATTTTTAACTTCGC
ACTGTAGTTAAGCAGTGTGGAGCTATTTAATGATTTCAACCAGGAAGATATTAATG
TGTGAAATAAGAGTACGTGGACAGTATATTAATTGTATGATACAAACAAGATATAC
ATACATAAAGTTCATTAAAAGAGTATGATTTCATATGGCTTTGAAGGATTGATAGG
ATATAGACAAATTGATAAAATTGATCTAACCAATATTTAACTTTAGGTTTCTTCATC
AGATAAAATATTGCATCATTTTATGTTGGCTAAGTGATTTGCAGTCTATTTCAATTA
ATTATTCTTTATAGTTTTTCTCTGTCAATGCCATTTAATAAAGAGAAAACTTCAGCA
GACAGAAGTTATATGATCTTTGGCACTATTGGCTGTGTTAAGCCACAGTAAGGT
TCAGTTACGTATTTTATTGTTTTATAATCACACATTTCTCCTTTGATTCATTTCTTAT
CTACACCCCTTCTTTCACATCCTAAATATTTTCTTTGGATAAATGTGTAGGGCAAGA
TGAAGAAAAGAAGAGAAAAAAGTAGTCAGAGCTTGGGAGTACTGAAACGCTTTGG
ACTCCAGCCAGCTGCCATCACTGAGGTGGTGAAAGAACACCGTAGTATAACTGGAT
GGCCCTGGTCCCTGCCAGGAGTCAGGATGGACTTTCAGTGTTGAAGAGCCATCTTG
GCCTGTTACTAGCGCTGCCCCACACCATTGTGTTTGCCTAAGAGCTGAGCCAAAGA
ATTTACATATGTATGAGCCAAGGTCTGAAAATAGAAGTTAAAAAAATGGTGCTAA
ATTGACATATTTGCTATTTTATTTTTTTGGTCAGTTAATATGATAAACTTTTATTTAA
ATGTAAACATTATTTTAAAAAGCACTTTGTTTTAAATAACTGATTTTCATTGAAATT
AATTCTGGCCTCTAAGCAGAGTTAGCTACAAAGACAATTTGTAAAAATGCAGAAA
ATTCAGAGTTTAACTTGGAGTTGTTTAAAGTTTATTTTCATATTTGAGTCTGATATTT
CAGTTCACTGTAATATTTCAATTTATTTAAAATATTATCAAGACAAATATTGGGTTA
CCTTCACAATATTTTTTCATTTTTCTTACCCCATATATTAAAAATGAACAAAAATG
AAAGAATTATATAGTCTAGTGGATGGCAATTCTCTTGGTACAGTACTCACAGGATG
TCAGAAGTGCTTTGATTTGCATGCAAATAGAAACTGCATTCCTAAAAGACCCTTAA
TTGAAGATATTAATAATTTTCATTAGGTTTTAAGTCTTTTAACCTTATCATATGGAT
AGAAAAGTAAAAGATGTGTTTAATAAAATGTCTTTTACTTATTTTTATTTGTCATTT
ATTTAAAGGTTTATTAGTGAATCTGTTTACCTGGAAAATGTGCAATTCTATTTGCAA
ATTTGGAGCACTACATATATTTAAGAGAATCCTTAGTTTCTGTTGGGAGTGGCAAT
ATTTTATAACTGGGCCTTCATATTCCTATGTTACAGCCCTGGTCCCTGAAAGTCCTA
CAGCTATCTTTGTTTCAAGTGTGTATGTGTTATAATAAGATAAGTGTTAATTAGTTA
ATCAAGTACTAATTAACCTTTTAATTTATAGAAAAACAGACATTTATGGACAAGT
AAATTTTTGGGGTCAAAGTCTTTAATAATTTGAAGAATGCAGTTATTTTTAGCACAA
ATATTCTAATGTGAAAAGAATTTCTTTTTCTGAGTTATATATTTTATGCCATTCAG
AGTCACTAATATAGTACTAATAATACTTTTTCTATTGTGTACCTTTGTTTCTCTCATT
TGTCTTACATTTTATGTCTAATCATCATTTCACAAAATTTCTATCATTACTGCTTGAC
CTCGACTTCTAACATGGCAATTAATTTTTATACACAAATTTTTGAAATCTTGACAGA
GTTTTTAACTTCCTCATACCGAGTTCTTTGCTTTTTTAGTTTACAAGATGTTCAAGAA
TGCTCTTTTGAAATAATCAATTACCTAATGCAAGATAAATTAGCAACAACATTACA
TATTTTTCTTACTATCAACTGAGAATGATCTTGATAGGGCAAGTATAGGTTAAAA
ATAAATGACATCAAAAAACAATACCAGAATAAAACATTTAATTCTTCAACACTCAA
AGGCATGTCAGGTATTGAAATCCAAGTAGGCACTTTTGACTAATTGTTAGTAGTTT
GTAGAATTCAAGGATTAGGGTTGGCTTCCTTTTGTCTTTCTTTCTCTTCTTCCTCCCC
TTCTTCATCTCCTTCTTGTTCTTCTTTTTTTCCCCTCTCCAGATCACTAATCTTCTCC
AACAAATTTTTAGCCTATATAAAATAAAAAAAGGTACTCCTGCCCTATGACTCAAC
TTACAAATCTACAAACCTGGAGGAAGAAATAGCTCTGTGATCCATTCCTGGGGAAT
TGCAATAAAGTTTTAGGGAAGATGGAACTTAATGTTTGTGAAAGCACGGGTCCTAT
TTCCGATTTCCAGGAGGGTGGAATGTATCTTCCTGAATCACATTCCGCTGAAAATA
GGAGGCCATGGAAGAAATCAGGTTCAGTATAACAAATTTTCTACAAAAGGGGGTG |

TABLE 1-continued

Exemplary regRNAs

| regRNA | Nucleotide Sequence |
|---|---|
| | GAGTAGGAATGTGCGTAGGTGACCTGTTCTCTACGTCATTCCAGTGTAAACTACTG<br>CCCCTTACACTTCACGAAGTCGGTAACTTCAAGACATGTTGCACCACATGCTTCTCT<br>GTGATCCTCAAATATGTTTAATTTAAAGAGGGTCCAGTAGTGTCCTGGCACATGAT<br>CTGGATTGCCATAGATAACCATCTACCTCACAGCTAGGGTTGCTCTTTAGAATCTTG<br>CAAAATCATTTGTTTACTCTTGACAAAAGTTAAGAAAACAAGCCCATCAGAGTTGT<br>TTGTTCTGTCAGCATGTTAGAAGATGGTTTTGTTGCAATGATAATCGTTGTGCAAAG<br>AAGACTGATGATGATTTTTTTTTACATTTTCTTAACAGTATTTGCTATTTAGAATGA<br>ATGTTGTCTAATTATTTAGCCATTTTATTTTGTAAAATTTATGTTGTAGGCATATTTA<br>GACCAAGTTATAAGAAAATGCTTCAGCCAAAATTAAGTGTTGAGTTTGATTTGTGT<br>AATTGTTAGTTTCTTTACTAGTTGTTCCATCATTTACACAATTATTTCTATTTGAAAT<br>GCAGTAATTGTTCAGAACTTATATTTCTATACTGATGTCTACTAACAGCTTTAGATC<br>AAATATTAAATAACTCAAGAATAATGAGATGATCTTGGCTTACTTAGATATTTGGT<br>TTTTATATCTATAGAACAAAGGAATTAGAAAATAATTTTGAAGATTTCATCCAGCT<br>ATGTAAAACTATCTAGGGAATACATTTACTAGGTTTTCAATTTTCTACAAAACATCT<br>TTCAGCAGAAAGCAATCCTGTTTCCTGATATACAATGTCTGATACATAGAAACTAC<br>TCAGTACATAATTCCTGAATTGATTATTCTTTTGGAAATCCTAGATTTGATTTCTGA<br>ACAATCATAAACATTTAATGGCATGAAATTACCCAGATTCCATGGTTCTGGAATAC<br>ATAACTTCAAGCAATAAGATGCAAGATAGAAACATATAAGACATTCTTTGCTATTT<br>TAGGTAAGTCCAGCTGAATCAGTTAATCAGCTAGAAACGTGGCTCACAGATGAATT<br>AGTTTTATTATTAGGTGGATTACTGAAAAATTAATAGCTTTATTTCCGTATTACCTT<br>ATCATTTATTTAATATAAAACATAATAAACCAGAGAAGTGTGGTTACTTTC |
| Mouse CPS1<br>RR52_v1<br>SEQ ID<br>NO: 80 | CACTGCTGGTTCCACCTCCTTCTCTCACCATGGGGAGAAAAGGTGACCTCTTCTG<br>GCATTGCAAGCACAACCTGACTCACAGGGCAATGCTTTTGTATCTGAGTGTCTTTC<br>ACAATCCATTTACTATCTGTAACTAGCTGTTCTGTTACTAACCTTTAAAAACTGCTC<br>CCATGCCCTTCAATGACAATTATGTAAATATACTCTAATGACTTTTAACTATCTTTA<br>AAATACTGTGCCCACATCAAAAAGAATTAATTTGGATGTGTATTTCTTAGAAAATT<br>GAGTTTTAAAAGAGAAGGCAAAAAAAAAATCATACATAAAGGACTATTTCAAAAT<br>AAGTGACTAAGAACACAGGTCCCCCTTGGACTCTGTGGGACTTTAATTCACTACCA<br>TGAAGCTTAAGAACTTCCATTTTTCATGCCTGGCATTCCTCCAAAGTTCTGGCCAGT<br>AATGACTGTATGTGAGTAATGGCTTTTGCACCTTGAAATGATGGCTTATTCCTCCTG<br>AAAATTTGTCATTCTTAGCTATGAACTATGGAAGACCCTTGAAACAGATCTACCAC<br>CATGAGCTAGAACTGCTTTCCCAGGGGTCGGTCCACATAATTAGCTCATGTTGTTGT<br>GTGGTAATTGCTGTGTAGAGTGCTTGCTGAGTCTAGGGATCTGATTTATAATTATTG<br>TGGCCTCCACTATTCATTGCTCTGTTTTTGGTATTTAACAGAGACCTGCTCATCCTT<br>AGCTACCCACTTCTGTGAGAATAAAGTGGTCCAGGTGACACAGTTCAGAAATATGA<br>CAAAGCACTTAAACTGTAGATGGTACTGTTGTCCTTACAGTTTCTTCTCTTCAAGAT<br>GGCATGTGATGTCTTCAAGGCATTGAAACACTTAACTAAAGCTAAACCACCATTCT<br>CTGTATATCAAGGTACTATGTCCTTATTGATGCTTTAGAATATCCATTCTCCTTTCTG<br>GCTTCCATCTTATTATCAAAATGAATCCAACATGGCTTTCTTAGGCTTTGTAATAAA<br>TTCTCAGGGTAGCAGGCTCAAGTTGGTATCATGTCATTGATGTAAGCATAAGTGTC<br>TCTCTCCCTTTCCCTCCCACTCCTCCTCCCCTTCCCATCCTCCTCTTCCTCTCCCTAC<br>CCTCCATGCCACCATCCTTTCCTTCCACCCTCTTTTTCTCTCCCACCAGTCTTCTTAT<br>GTCTCTCTCCTGTCCCTGGAATCTATAAGAACCTATAGAAATTGCCTGTTCCCACAC<br>ATGCCAGAATCCAAAGCCCCTGAAATCCTGACCAAGGCATTATAAGCAAAAGAAT<br>CTCTTTTGGTATAGCATTGGAAATGTAAATGAGCTAAATACCTAATAAAAAATGGA<br>AAAAAAAAAAGAGTCAAATGTCAAAAAAAAAAAAAAAAGGAATCTAAGGAGCACC |
| Mouse CPS1<br>RR34_v1<br>SEQ ID<br>NO: 81 | ACTTCTTTTGCTTCATAATCATGTTACAAGAGGCCCTTGACCTGAGGTACCCTCCAC<br>TAAATACACATTTGATTTGCACAGTGGGGTCATTGGCTCTGGCAAACAGCAGTGTC<br>AACATTGCTAATCTGAAACAACAATCTCTCATGCCCCTCTCTGCCCCACCTTCAAAC<br>ACACCCACAGCAAGTTCTGACAAACACTTTATATGTGCCGAACTGAGCATTCTTTA<br>TCACTTGAGTAGACATGACAACCAGCTAACCTTGCAGGAACGTCCCTCTCTCCTGG<br>CTTCTTTCTAGTGAGAATGGAATCCAGCTCACCTTATCCTAAAATACTTGGTGTAGA<br>ACATGAAATTGTTTTGGAGTTTTCTTCATATATATTTAGATCTAGATAGAGCCCATG<br>CTTATCTTAAGTTAACGAAAGAGAAATTCAAATTAAAACAAAAAAAAAAACAAAC<br>AAACAAACAATTGCTCAATCCCTCACACTTGTTAGCTCTGGGCCTGGTCTTTAACCC<br>CGGTTTTCCATTTCTACTTTAGTTCTTTTCTCAGTCAGCAGGGTTTGCTAAGATTCAT<br>GCTTGCTTTACATTTTCTACAAAAGCCCAGAGACTGAAACCATGTGTTTTAAGTGGT<br>TTTAACTCAAAATGTTCTTTTTTGCTTGTTGAGAACTCATAACCCAACTTGATAGAA<br>TGTTCTTTCTAATTATAAAGTATTGTAATGAGGTCCCTGTATCCAAGAAGCACCATT<br>TAATGTCCGCTCTGATCTCTGAGGGTTTTATTTTTACATCAATCCAGTTCTGACCAC<br>CCAGACATGAAAGTGCCTTGGTCACTGAGCCAGCAGCACCCTCCAGTTGGCAAAA<br>GCAAGGTCATGAGAAATGGTGACAAATTTCAGAGCTTCTTACTCCTCATTTGGATT<br>CAAAGTCCCTAAATGGAAATATAATTCTTTTACCACTTCTTGAACTACTCTATCAG<br>GCAGGGTTCAAAAAATAAAATCCACTTTGAGAGTTTCTTTAAATAGTAACACCCTT<br>AATAATATCAAAACATGATTTGCATAATTGCACTCTATTAACTAATATGAGTGTATT<br>TCTTGTGAATAGTTATGTTGAAAAGACGTTCTTGGAAGCATCAAAAATATTAACTA<br>AAATATTTAAAGAATGATTTAAGCTCCATCAAAATTTTAAAATGTTTACTCAAAAG<br>ATACTGTTAAGAAAGTGAAAAATAAGGCATAGACTTAAAAGCAAATATTCACAAA<br>TGATATTATTGGTAAAAAAAAAAAAATTGTATCCAGGCAGATCAAGAGCTTTTA<br>GAAGTAGATAGCAAGATGAATGAGCCAACTTAAAATAAGCAGAATAGGAGCTGGA<br>AAATGCTCAGTGGGAAATGCTTGCTATGCAAACATGAGGATCAGATCTCAGATAC<br>CCAACACCCCTATAGCTCACAGCCAACAATTGGACTGAGCTCCAGGGGACCTGGAT<br>GGAGGAGATGGAGAAGGGATTGAAGGAGCTAGGGGTTTGCAGCCCCATGGAGGG<br>AGCAAGAAGTGTCAACAGGCCAGATACCCTAGAGCTTCCAGGGACTGGATCAACC |

TABLE 1-continued

Exemplary regRNAs

| regRNA | Nucleotide Sequence |
|---|---|
| | ACCAAAGAATACACATGGAGCAGCCCATGGCGCTGGCCACATATGTGGCAGAAGA<br>TGGCCTGGTTGAACATCAGTGAGAGGAGAGGCCCTTGGGCCTGAAGGTGTTCAATG<br>TCCCAGTGTAGGAGAATGCCAGGGAGGGAGAATGGGAGTGAGGGAGTCGGGGAG<br>CACCCTCATAGAGGCATGGGAGGGGGAATGGGATAGGG |
| Mouse CPS1<br>RR35_v1<br>SEQ ID<br>NO: 82 | AGTTTTGGCACACCATTTTAATGAGACAGCAGATGCAAAAGTGCTTACAACAGCTG<br>CCCTAAGTAGACATTTTATCATCCTCCCTCACAGCAGCCATTCTGTGCCTTCTTCTG<br>CATGGCTATTTAGCAATTGTAAGTCTCTAGAACCATTCAATGGTATTCTGTACAGTT<br>AATGTTTTTAATTATATTCTGCTTCAGACTTTGATTCTTTTGTAAGCTTTTTCTTTAC<br>ATAAAATTTACCAACTGCTTCTTTTCCTTCTTGGACTTACACATGTCTATCATAACC<br>ACACTGACTTTATTTGGAGACAAAGTAATAAGGTAACTAAACTTTACTTACTCATT<br>ATAGTGTTAAGGAATCAACCTCATGTCTCACACAGACTAGGTAACTGTTCTGTCAC<br>TGAGCTGATTCCTAGCCTTTCTAATGTTCTATGAGTGATTATTATAATCTACGAAAG<br>ACTAAGGGCACAGTAAGGAACAACACAAAATTTTCTGCCTCCACTGAACTTGTATT<br>GTAAATGTTATAATGAAATGTAGGGACCATGAATGAATAATGGATATGGTATCTCC<br>AAATCTTATGCATCGTCATTTTCTAATTCCTGTATCCTGATATTTTGTGGGAAACTT<br>GCTACCCTGTTTGACTGATGTCTTGGTGGGACAGTCTTTGATCTTACTCCAATCTCG<br>TTCTCTTTGCCAACTTGTAGACACCTGATCATGCTTGTCCAATCAGACTCTCAGGAA<br>AACTGAATATAATTGGACTATGTTCAACTCAAAGATGGCTCTTTGACAAAGGCCAT<br>TGACTCCTGCCACCTAGTCCTCAGGGACTCATTTGTCCTTATTTGTTCCAAAGGCCT<br>CTTTCCTTGGCTACTCCTTGTATGCAAAATCTTCACTGTTTCTTGCAAGTTATTTTAA<br>GTGTAATTTTGTGTTGGCTGGAATCCAGTTATTCTAATACATTAAATTTGGCAAAGG<br>AAAGAGCATAGCATTCTTTATTTCTCCAAGTCAACTGTCTTATCCTTTTATCCACT<br>GGGCTTGTAAGAAATTAAATTGAAACTTTAGTGGGGATTCCCCTCTATGATTCCGT<br>GGCTGAGAACCAGTAGCCAGTTTCTGAGGTGTCCACTGTGGCCGCCTTTGTTCTAT<br>GCCAGGGATAAGAAGATCGTTAGAGAGACTGGTTATCAGGGAGCTAAGGTTCGCT<br>TCTACAGGTGCAACGTGCAAAGCCTACTGTATGTAAGTCTGTATTATGCCTGGGAG<br>ACTTTGTACCATCGGGCTGATTACTCTGATGCAAAGCCTCCCTCAGACAGTTAACTT<br>ATCTTAAAGCCTCTGTTATCGTTCATGAACAGAGGGCAAACTCATGTCCATTCTGTC<br>TTGTTCTCCCACCTGTCTCTTAAGTTGCTCTGGATTGCTACATTAAACTCTGAGGAA<br>CAATGAACCCATTCTTCCATTTAGTATGAATTTAGTAAGTGTCTGATCCATTCCAAA<br>TTCTCTATGAGACTCTGAAAAGACAAAGGGAAACTCCATTTAGTTATTGTTCTACA<br>GGAGTACATTTTGGGTTGGAGAAAGGGAAGATTAAGTAAGCTAGTGGCTAAGCAA<br>CAGGGCAGTGATGAACTCGACAAGAACCATGACAACATAACAATAGAAAAGATCT<br>GAGTCTATTTGGAGAATGTCATGTCAGACATGGACTACAAAAGGAGAGAACGGCT<br>GGGTTGGACCTTTGGGAGGATGTGGGAATTTGCTTACTATACAGGTGACCAGTAAT<br>GGCACATACCAAATCATAGAGGGAGGAGGAAAGAAAGGAAGGAAAAGAGCAGGT<br>TATAAAGAAGGAGGAAGAAACAACATGGGAAAAAAACAGGGTCAGAGAAGAGGC<br>AAGAATAAGAACAAGAGAGAAGGAAGGAGGGAGAGGAAAAGGAAAAGGAAGAA<br>AGAAAAGAAAAAAAAACAGAAGAAGGCTGGGGGGGGGGGTTATGTTGTCCT<br>GTAACAAGTAGCACACTATAGCTGACAGGATTAGGGTGAAGTCCACTAAGAGGCT<br>TGGGTGAGACAGACATAGGAAACAGGTAGACAGAAAAACCCGAAGGAACATTG<br>TCATCTTGCTCTCCTGTGTGAAAACGGAAGCTTTGCCTCTGTGAATCCAAGAAAGA<br>GACGTACCTCTGTTCTTATCTACACAAAAGAGAAGGTGGCAGAAACCTCATCTTAC<br>TGTCACTGAGAGGACTAAATGGACTTTTGAATCAAAAGCACTTAGCACAGTACCTA<br>CCACACAGCAGAAATCAAGGGCTTTTACCTGTCCTCCTTCTTCCAAACCTCACACCC<br>TGAAAATCCATCACAAACCCTGTGAACCATAAAAAGATATCCACCCCT |
| Mouse CPS1<br>RR36_v1<br>SEQ ID<br>NO: 83 | CCTCTATCTCCACTCTCATTAATATGGGTGTCCTATTGCTCTTATTTTCTTATTAAAA<br>GAAAAGGGGACACAGACACACACATAAATATATACAAACACATGCACACACACA<br>TACATATATACACACATGTACATACACTCCAAGATGTTTTGATGAAAAAGGCAGTT<br>ATAAATTAGAATCTGGATGAGAATCAAGCCAGGCAGGTTTTATTTCTTGCTATCTG<br>TTGGTTTGGTTTTACTTGGGTTGGAGACTAGGGCTGTGTTTTGAGATGGGAGACA<br>ATGAACAAATATCTGGATATTTACCTGGAAAGTGGAGTTGTAAATTTTTATGATAG<br>AAAGGGTATAACCAAGGAGTAAAGACTCAAAGAGTGGCCAAAGGGGGGATATGA<br>AGAAGATGGAAAGTAAGTCATTTCTGATCTGCCAGACATACTTCCACTAGTATAAC<br>TGGAAGGCAGAAGGACTAGACAACCTTTCCTTCCTGCAAGTTGATAAATTCAGTAG<br>TGTAAAGAGTAGAGCACAGCCATCTCATGACTTCCATTTTTCAGTGATGTGGGGTG<br>CAGTTTTTCACTGAAGGTTGCAAGGATGCAAACCCTTTAAAGGATTTGACCTGTGA<br>TAGGCTGCCCATGACCCAGTAGATGCCCTGTACCTATGCTCATACTGGCAGCACTA<br>AGTAAACTCAGTGAGTTTAAAAAACAAAACGAAATATAAAGCTTTGGGAGGGAGG<br>GGATGGTGGTGGGCAGGAAGGAGGAGTTGGAGAGGGGAGAATGGAAGGAGACTA<br>GATCAAAACATGTTATGTGCCTGAATGAATTCTCAAACAGTAACAAAAGAAAACTC<br>CTTAGGAGTAAACTAGATCAAAACATGTTATGTGCATTCATGAATTCCCAAACAGT<br>AACAAAAGAAAAGTCTCAGGAAACTAGGGCCATGTTCTCCTTACAGTAAGATCCTC<br>AGTAGTATCAGATTTTCACCCGCGATAGCAATGGTGAATTCATATGACATCAGAAT<br>GTACATGAATATGGCTTTCTCCAGCTATTTTCAAAAACAAGTGTGCAGCCTAGCAG<br>GTGGCATATTACTCACCGAGAGTTCAAGCATTACCTAGCAATATAGGAAGAAATGG<br>GGTGTGAAATATGAGACTCTAGAAAGAAATAACTACAATAGTAGACCCTAAATTCT<br>AAGACAAATGAAAGATTGCTCAAAAGTGAGGAGATGTCTCAGTCAGTGGTGGCA<br>CATACCTTTAATCCCAGCACCCTAGAGGCAGGGGAATCTCTGAGTTCGAGGACAGA<br>CAAGTAAGTCTCCAGAGCAAGTTCTGGGACAGCCAAGGCTACACAGAGAATCCCT<br>GACACATGCATGTGCACATATGTACCTACGTGTACACACCACACACACACACAC<br>ACACACACACACACACAAAAATCACAGCTCTAAAAACTACTGAGGCAGATTCT<br>GAAAGATCCATACAGTAAATATATGAATTCAAAAAATAGGAAAAAAGATGAGAAA<br>ACTAAGACATTTGGATTTTAAAGGTGGCTCTGTTTCTGATAAAGATCATCTGGGAG |

TABLE 1-continued

Exemplary reqRNAs

| regRNA | Nucleotide Sequence |
|---|---|
| | TTGGGGGGGCATAATTAAGCTGTTACGCTGACAATCTTTTTTCATTTCACACAATT<br>CTACCTCTCTGTGGTCAACCAACACAGTCCAAATACTATGAATCCTGTTTATAAGG<br>CATAACCACCATCAATATGAGAAAATCATAATAAACAAAGCAAATTTCTTTCCTTT<br>CTTTAGGCAAAATTGAACATCACAGAAATATTAGTATAAATAAAGTTCTAAGAGTA<br>ATCTTTGTTGAGATTTTCTTTTTTCATTTTACAGGGTTAATAGCACTCATGTGGCCTT<br>GAACCTCTCTATGCCAGTACAATTGATCAATCAGCATTTCACCGATTGCTTCACTCC<br>TCCTTCTCCCCATAAGAGGAGAGAAACCCTTGCAAAACGTGTTTGTTCTGTTTGTTA<br>TTCTGGATAAAGCCGATAACGAGTTGCAGCTGCTGAACAGGGTGTACTGCTTGCCG<br>AGGCCACGGCTGTAACTTATAGATAGAACAGAGCAGCCAAAGATGTGCCTCGGGC<br>TGGAGCCAGCTCTGCAAATAGGCCACACTCTGGGCTATGATACATGCATTTCATTA<br>GCTGACAATTTACTCCTGGAGAAGCTTGATTGGCGACAGACTCAAAAAGAGAGAA<br>TTTGAAATATCACTCCTCAGCTCAAAGTGTTTTTCTCTGTTTCTGACCTGAAGGATT<br>GGCTTATGTCAGTCTCAATCAAGATGCCTTTAGTAGTACTTGAGGCTGACTTGGAA<br>CAATATGGGTCCCTCTGGACAGAGTGTACACCTGATGATTCGTGTCTTGGGGCAAT<br>GCCTGAGGCCGCACAGTCCCTAGTGCTGAAACTGAGCTCACGCCCAACTCAACTGA<br>GTTTTGTGCCTCTTCCCTGTGTACTTAAGGGCTGTGGGCAAAAAGACATGCAGCC<br>AACAATCTGCCCTGAACCATTAAACAGCTCTCTAAACCGAGCTGATGGGGAACAG<br>AGTATCATTGTCCATTATTTATAATGTGATCTTCTACTTTTATCCTCAATTATTAAGA<br>CACAAGGAAAACAAGAACAGTCAACATTATAAGGATTGGGTCAAAATGAATACAT<br>GCTTTGAGCATAAACCAGAATCAAGATAACTCTTGTGCTTGCTTGAAAAAAGTTTT<br>CAAGCCTTCATCCTTTAGCAAGTTGCTCTGACTCCTCAGACCTCTGTTTGTTCACAG<br>GTAGAATGGGAATGATCCTCACAGCTGTGGAGGGTTATCCAGAGACTTCTGATAAA<br>GTAAGTTATATGAAATGTCTACCATTAGCAAGGAATACTCTAAAGTTGTCTAGCAG<br>AAATGACGAGCAGGTTCAGCCAGTCAAGGTTCCTGTCACCAAGCCTGAAGACTAA<br>CTTCATCCCCGGGATCCACATAATGGAAGGAGAGTGAGAACCCCACAGTTGTCCTC<br>TACATACACACACGCACATACACCACAAAATAAGATGTAATAAAATATGTTCTAAT<br>GCAATTTTTCATTATATAGTGGAATATCAATTGTGTATATCCTATAGTAATTGTACT<br>TTTCAATATGTAACTTAAAGAGATACAAAAATGTGTGCAAAAATTATATATGTTTT<br>TACAATAAGAATATATATATATACACACTGTGCCATTAATGAATCAAGCCAAATAA<br>CATTTTAATGTATTAGTGTTCTTTTCTGTTTTGAAAGTCATCTTACTGGCCTTGCCCG<br>CTTATATGTTTGAACTCCTTTTGGATTATTGTAACTGGAAAACAATGTGAGGTCTGG<br>GATCCAGATAAAAAGACTCCCTGAGGCAGATTACTCCACACACCTAAGTATCACAT<br>GGCTGAACCAGTATCCAGTACCACACTCAGTGAACAGACTGAGCAGCAAACAAGG<br>CGCTGAGGGCCAATACAGGGCCCCCAACAATTCATCCCTCTGCAGAAATCATGGAT<br>GGTCCAGAGCACACCACTGGTCCCTACCACCTTTCCCCTCTCTACCACCCAATCAAT<br>CACATGAGCTAAACAACTGTCTTGAATTGGAATGGCGAGCCAGTTCCCTAAATGGA<br>GGGCTTGGACCGCAGAGCTGCACCTAAGAAGAGAATTTAGCTCGTTAAATGAAAG<br>ATGTGTTTCCAGTCAATGAAATAGATCAGGTTAATTATTTAAAAATCTCCAGCTTCA<br>TTGCACATGTGAGTCGACTGCAGGGAATTCGAAACCTTGCTGCAAAGTAATCAATA<br>GAGATATTTCTAGGCAAAAAAAAAAAAGTATGTTGGTGAGCATGGTGGCACACG<br>CCTTTAATCCCAGCAGTCAGGAGGCAAGTGGAGCCATGAGTGCGAGGCCAGCCTG<br>ATCTACAGAGTGAGTTCTGGGACAGCCAGGACTACACAGAGACACCATCTCAAAA<br>AATAATAATAATAACAACAATAATAATAAAAGTATTTGGACCACAGGCTGCACGT<br>CTCTCTCACAAGATCAGAGTGACCTGGCACAGTGTCACTGCATAACAGCTCTGGTC<br>TGAGGGTTTCAAAGACATTAACTGGTATCATGCATAATGCAAGATAGATGCTGTTG<br>TTCTTTCCATTACACATATAAGGGAACTGAAGCAGAGACTCCCTTAAGTTGTCTTCT<br>CAAGGTTTCCCTATTTATTTATGATGGGCTTAAATTGAAAAAGTCCTAAGGCACA<br>CAGATGTGTCTTTTTTTTAAGCAATTATACAGAGCAATGCATCTCTTCAAACGTTAG<br>TAATGCAGACACATGCCGGCATTTCATAGTTTCATTAGCAAATGACTAGGACAAAA<br>TCTAAAGAAATATTGTAAAGTTCATCATGATGCTTCCCTCTGCACTTAAAAATATTA<br>TCACTTCATAGGGAGGTTTGTTTTTAAGTTTATCTCTGATAATTTAATTATCTCACTT<br>TGGAAATATGGCAATGTACTGCTCATTTGACTAAAATTGGATAAAATAAATGAAGC<br>TAAGAAGGATGGTATGGTAATATTAGCAATAGTTTGTACTTTATTTGAAATACGTTT<br>GTATTATAGAAATAAAAGTAAACATGGGAAGTATGTTAGATGCTGTTGAAAAAC<br>AGTGCCACATTGTTTCCCTAACATTCCCAGTGATTGTCAAAGAGCTGCTTTCTAATT<br>ATAGAATAGTATTTAAATAGGGACCAATGACATTCTAAAGAACACTAATAGAAAG<br>TAGTTATTATTCTCCTGTATTTCTTTAATAATAATAGCTACTTTCTATTAGTGTTCTT<br>TAGAATAGAACCTTGGTTGAGTGGTTACTCTGGTCAGTCTACCCTTGATTTTCTGTC<br>TTGGATGAGTTTGCGTTGTGTGTCTACAAAAAAATCTCACAAACAGCAGCATATGA<br>GGAATCACATTAAAACTTCTTTGAAAAAAGAAAGTATTTATTATAAGCAACATAAT<br>TTCCATTGAAAAGTAAAAGAATGGAAAGTCAATTTCTAAAATTAAATACATAAGG<br>ATAACTCACTTCAATAAATTGAGTAAGTTTTGCAATTATAGAATTATATTTTCCTAA<br>ATTCTCATGAAGAAGTAAACATCTGTAATTCCAGAACTTGGGAAGCTAAACCAAGA<br>AAATCATGAGTTTGGAGCTAACCTGAACTTCATAGTCACCCTGACTCAAAACAAAA<br>GTTCTGATTCCTGATAAAGAGCAATTTGATACTCATTCTATATGGGTTCTATTATGC<br>AATCTTTAATATACAAAACAGAATACTTTAAAATGACATTATTATTGTGAATTGAT<br>GGAAAAATAGACAAAGCTTTATTATAAAATTAAATATAAGTTTGTATGAAATTCA<br>TAATGTCCTTTAAAATGTGAATGACATATTAGAAAAAAGTCACCTTATCAACTGT<br>GAATCTAATTTTATATATAGTTACATTATCTTTATAACTGTTTTAAGTCCTGTCAGA<br>AAAAAATGTATAATTAATGAAAGATGATGACTGACAGCACCATCTCTCAGATCAG<br>GAAAACCAGCTCAGATGAAATGAGAAAAAGAATACAATGTTCTACCAAAAAATC<br>TATATCAGGTAGTTTATTTATTTAGATTTTTAACATTGTTCCTGGTCTATATATCAAG<br>GTGATGCAGATAGATAGATAGATAGATAGATA |
| Mouse CPS1<br>RR37_v1 | TTTAAATAATTAACCTGATCTATTTCATTGACTGGAAACACATCTTTCATTTAACGA<br>GCTAAATTCTCTTCTTAGGTGCAGCTCTGCGGTCCAAGCCCTCCATTTAGGGAACTG |

TABLE 1-continued

Exemplary regRNAs

| regRNA | Nucleotide Sequence |
|---|---|
| SEQ ID NO: 84 | GCTCGCCATTCCAATTCAAGACAGTTGTTTAGCTCATGTGATTGATTGGGTGGTAG<br>AGAGGGGAAAGGTGGTAGGGACCAGTGGTGTGCTCTGGACCATCCATGATTCTGC<br>AGAGGGATGAATTGTTGGGGGCCCTGTATTGGCCCTCAGCGCCTTGTTTGCTGCTC<br>AGTCTGTTCACTGAGTGTGGTACTGGATACTGGTTCAGCCATGTGATACTTAGGTGT<br>GTGGAGTAATCTGCCTCAGGGAGTCTTTTTATCTGGATCCCAGACCTCACATTGTTT<br>TCCAGTTACAATAATCCAAAAGGAGTTCAAACATATAAGCGGGCAAGGCCAGTAA<br>GATGACTTTCAAAACAGAAAAGAACACTAATACATTAAAATGTTATTTGGCTTGAT<br>TCATTAATGGCACAGTGTGTATATATATATATTCTTATTGTAAAAACATATATAATT<br>TTTGCACACATTTTTGTATCTCTTTAAGTTACATATTGAAAAGTACAATTACTATAG<br>GATATACACAATTGATATTCCACTATATAATGAAAAATTGCATTAGAACATATTTT<br>ATTACATCTTATTTTGTGGTGTATGTGCGTGTGTATGTAGAGGACAACTGTGGGG<br>TTCTCACTCTCCTTCCATTATGTGGATCCCGGGGATGAAGTTAGTCTTCAGGCTTGG<br>TGACAGGAACCTTGACTGGCTGAACCTGCTCGTCATTTCTGCTAGACAACTTTAGA<br>GTATTCCTTGCTAATGGTAGACATTTCATATAACTTACTTTATCAGAAGTCTCTGGA<br>TAACCCTCCACAGCTGTGAGGATCATTCCCATTCTACCTGTGAACAAACAGAGGTC<br>TGAGGAGTCAGAGCAACTTGCTAAAGGATGAAGGCTTGAAAACTTTTTTCAAGCAA<br>GCACAAGAGTTATCTTGATTCTGGTTTATGCTCAAAGCATGTATTCATTTTGACCCA<br>ATCCTTATAATGTTGACTGTTCTTGTTTTCCTTGTGTCTTAATAATTGAGGATAAAA<br>GTAGAAGATCACATTATAAATAATGGACAATGATACTCTGTTCCCCATCAGCTCGG<br>TTTAGAGAGCTGTTTAATGGTTCAGGGCAGATTGTTGGCTGCATGTCTTTTTGGCCC<br>ACAGCCCTTAAGTACACAGGGAAGAGGCACAAAACTCAGTTGAGTGGGCGTGAG<br>CTCAGTTTCAGCACTAGGGACTGTGCGGCCTCAGGCATTGCCCCAAGACACGAATC<br>ATCAGGTGTACACTCTGTCCAGAGGGACCCATATTGTTCCAAGTCAGCCTCAAGTA<br>CTACTAAAGGCATCTTGATTGAGACTGACATAAGCCAATCCTTCAGGTCAGAAACA<br>GAGAAAAACACTTTGAGCTGAGGAGTGATATTTCAAATTCTCTCTTTTTGAGTCTGT<br>CGCCAATCAAGCTTCTCCAGGAGTAAATTGTCAGCTAATGAAATGCATGTATCATA<br>GCCCAGAGTGTGGCCTATTTGCAGAGCTGGCTCCAGCCCGAGGCACATCTTTGGCT<br>GCTCTGTTCTATCTATAAGTTACAGCCGTGGCCTCGGCAAGCAGTACACCCTGTTCA<br>GCAGCTGCAACTCGTTATCGGCTTTATCCAGAATAACAAACAGAACAAACACGTTT<br>TGCAAGGGTTTCTCTCCTCTTATGGGGAGAAGGAGGAGTGAAGCAATCGGTGAAAT<br>GCTGATTGATCAATTGTACTGGCATAGAGAGGTTCAAGGCCACATGAGTGCTATTA<br>ACCCTGTAAAATGAAAAAAGAAAATCTCAACAAAGATTACTCTTAGAACTTTATTT<br>ATACTAATATTTCTGTGATGTTCAATTTTGCCTAAAGAAAGGAAAGAAATTTGCTTT<br>GTTTATTATGATTTTCTCATATTGATGGTGGTTATGCCTTATAAACAGGATTCATAG<br>TATTTGGACTGT |
| Mouse CPS1 RR38_v1 SEQ ID NO: 85 | AGAAAGTTCAGTGTTATTCAGCGGCAGATTTCCTCACAGGGCAAAGCATTGCATTA<br>ATTTATGTTGGCTGAGTGAGTCACAGTCTGCTCTATTTATTTTTCCCCTGTCAACTTC<br>ATTTTGTACAGAGAAAACTTTAGTAAACACAAGGCGGATGGTTTTTGACACAGGGA<br>GTGTCAAGCCACTGTAAAGAATCAGTTATGTATTTTAGCTGTATTATTTTACAATCA<br>TGTGGTCCCCCTCCCCCCCGGGATTTTTTTTTTTCTTCTTCTTTGCCCCCCACTCTA<br>TCATGTCCTTAGTAATTTTTTCTGGTGAAATTTGTATTGCTAGAGGAGAAAAGTATC<br>ATGTGGGATTGTGAGTACTAGAACAGGCTGGAGTCCAGCCAGCCGTCCTAGTGAA<br>GAATTCACAGAACTGGATCTTCCTCTCCCAGTCTCTGCCAGAAATCTCTGTTCACA<br>GTAATGCTCAAAAGCCATTTTGGCCTATCACCGTCCCTGTCACACCTAGAATATGA<br>TCTCAAAATTCTACTTTCAAACTTTAAGGGCGGAAAAAGGACCATGTAAATGAAGC<br>AATGATGCTAAATTAATATATTTTCTACTTTTGTCTTATAGAAGCATTTACTTCAAT<br>GTAAATCTTATTTAAGAAAGTGCTTCCTCGTTAAAACATAGACTTTCATGGTACTTC<br>TCCTGATGTCGACGTGAAGTGAAGTAGCTACAAAGGCAGTTTGTATGTGCAGACAA<br>CTCAGAACTTAGTTTTGAGATATTAAAACTTCTTATTACCATAGTTGCATTCCTACT<br>CCTCAGGTCACTATAACATTTTAATTTTCTATAATCAAGACAAGTTGGACTATATCT<br>TCACAATAAGTACATTTATTTCTCTTACCTTGTCTACCAAAAAGAAAATTAAAATG<br>GAAGTTTTTCTTTTTTCGCCATCCTAATGGACAACAAATCTTTTGTGCTGTGTTCA<br>AAGAACAACCAAGGTGTTTT |
| Mouse CPS1 RR39_v1 SEQ ID NO: 86 | GAGCAGTTTGTTCTGTTCAGCACATTATAAGAGGGGGAGGGTTTTGGCAATAATAA<br>TCACTGTGCAAAGAAGGGCTGCTGATGAATTTGCTGTTTTCAAAAAACATTTTCGT<br>AGAAATAATTTACTAGTTAGAATGAGCACATATCTAATGATTTAGTCATCACACTC<br>TATGAAATTTACACTGTAAGCATGTTTTGGTCAAGTTTTAAGAAACTTCTTTGACCA<br>GGATTAGCTAAACTGACACAGTTAGCATCTTTCTAATTGTTTTAATATTCATCAAGT<br>TATTTTTTTAAAGGTATCAATTATGTGGAACTCAGGTCTAGATTGACCCTTTTTTCC<br>TTTTTAAAGAAAAGCTAAACTAAAAACTTTTACTAAAGGCTATTTAGTACTGAATA<br>ACTCATAAATAACGAGATGACTCTATATTTATCCAGATGCCAGATTTTTATATATAC<br>AAAACAAAAGAACCAGAAAACTATTTTAAAGGTTTATTTTTTAATCTATCTAAAAC<br>TATCTATATAATTTATACTATTTGCCTTCTAAAAATGTAGGTAAGGCACTTAGATGT<br>TGTGAATTTTCTTGAAATCATTTTTAGTTAAAGCCAATACTGTTTCCTGATATATAT<br>TGATTGATATCCTAGCATTTCTTAGTAAGCATTTCCTGAATTCTTTTAGTTACTCTAC<br>ATCTTATTTCCAAACAAATATAAGAATTCAGTGAGACTAAAGTACTCAGATCCTGT<br>GGCTTTGGAATGAAAAATTATAAACATAAGGTATAAGATAGAAAACAGTGAGAA<br>CATGATTTGCTATTGTAGTTAAGTCTGGTCAAGTCTCAATCCAATTTACCTGATCTG<br>AATTACAAAAACAAGATAGCCAGTATAATTCCCTGCTATTTGAATATTTGTTATT<br>TTTAAATTTAAATGTAATACCAAAAGTAAAGTCAGAATTACTTTCATCCCTCATTTT<br>TTGACATTTACTTAAGTTGTATCATCTTAACTTTACGTGATGGCATAAACCCTTCTG<br>AGCTCTGAAATCTGTTCTTTGCACCTCCACTCTCGGGTGTGCTTTCTGTCTTGCTGG<br>ATCTTGCCCAGCCCACTCTCTCCACCTCATTCTACACCGTCACACCCGCTTTTCCAA<br>GTATGACCAATACACAGGAAGAGGATGGACATTGGCTAAGAGCTGAATTCTGATT |

TABLE 1-continued

Exemplary reqRNAs

| regRNA | Nucleotide Sequence |
|---|---|
| | CTGGCCTCGACTCTTTCAGTGTGGTGCTAGACAAGCTAGTTACAAAGCTAAGACAC<br>ACTATCAGCTATACAACAGGAACAGCAATCGATAACCAGGAGTTGTTTCTAAACTT<br>AATGGAGAAGGCAAGCAGGTGCCTAACGATGAGAATAAATGGCAAATTACTTAAC<br>ATTATTCATGACTAGAACAATTAAAACAAGTTTATTTAAATATGTATTTATGCACAC<br>ATAGACATACCTTTTATTATAAATATGCAATGTGCTAAAATTGTAATCATACACTA<br>GTGTCTTAGCTTCTTATGTAAGATTTTTAAATTTATTATTGAATAATTTCCATTTTTC<br>ATCATTAAAGATTAAGTTTGATTAATTAACTCTACATGACATGTTTTTAAATTTTAA<br>TTGTCACCAAAGTAGTACTTTTTACATCTTTATTCAATATTTAACTTTACAAGTAAT<br>TTTCAGTTTATTTTCTTAATTTCTATTCTAGATTCTGTTATCTAAATATACTTTATGC<br>AAGCATAGTCAGCTATGACTAACTTAGGACCTCTTGCTATTCAATATTAGCACTAC<br>ATATGCCTGTCTTCCAAAAAACAATCTATCCACCACAGTTTTCTTTTTTGGCAGACA<br>TTTTTCCTCCATCTTTTGGACTGACTTACATCTGACCTTCCCACTTGGATTTTGCTCT<br>GCTCTGTTTCTGTTTAACTGTGCCTTCAATTTTTCCAAGGTCACTTGAATTCTGAATC<br>AACTTTCGAAGGAGTTGTCTATTTTCTTTTCATTTCACTTGCCCTCAACATACTTGGC<br>T |
| Mouse CPS1<br>RR40_v1<br>SEQ ID<br>NO: 87 | TCCCTTTAGCAGGATATTTGATATAATAAATCTGACACCTTCTGGGCCTCCTGTTT<br>CCAAGGGAATTTGATCTAGGAAGATGTGTTTCAGATTCTCGGAAACTGGAATAATG<br>CTTTCACAAACTTTAAGTTTCATTATCCTAAAATGTTATCGCAGCTCGCCAGGAAAG<br>GAACGCACAATTATTTCTCCCTCCAATGTCGAAGGTTGAGAATGGCATTATTATAA<br>GGCATGAGTATTGTTGTTGTTGTTGCTGCTGCTGCTGCTGCTGCTGCTGCTGTT<br>CTTGTTCTTGTTGACGTGGTTATGGTAGTGAGATGGAGTTGGTGGTGGTGTTGTTTA<br>TAAAGACTTTTTATTTTAGAAAATCAATGCTATGAAAGGAAAATGAGAATAAGCTA<br>GAAAGGAAGGACAATAAAAGGAGAAAGAAAGAGAAGGCGGCAGACTGATCTCTG<br>AACTCTACTAACTGCTAACAATTAGTCAAAGAACCTCCTTGGATATCAAATTTCTG<br>ATATAGCTTTGAGTATTGGAGAATTGGTTGGTTTCTTTTTTCTGGTATTGTTCACTTG<br>ATGTCATTCATCCTTAACCTGCTCTTGCCTTCACTAAGATCATTCACAGCTCAGAAG<br>AATTAAATATATATTCCCATCAATTGATTCTGGGTTGGAAAATAAAAAGTGTTCTT<br>AAAAACTTCAGGAAATTCAAAAGCAAAGCAAGGATCATTTTTTAAAAAGTTAAAG<br>ACTGTGAAAAGATTTCAAAATGTTGTATTTAAAAGTTACCTGACTAACTGGGCATT<br>TGGCGGGTGGGCCTGTAAAATCTCAACACTTGAGAGATGGGAAGGCCTGAAGTTC<br>AAGGCCAGTCTTTAGCTGCTACATAGTAAGTTTAAGACTAAACTGTGCTATGTTAG<br>ACCTTGTCTCAAAAATGAAAAGCAAATGTTATTGTGGTGAGAAGCTGAGGCTGAA<br>GTAGTGTTCTAGGAGTCTGACAAAAAGAATGATTACACATGTTTAAAGAGCAGGG<br>GAAATGACATAATCAAAGTACTGTGTTAGTATAAATCGTACATTAACGTGTTGCTT<br>GGAAAAGGGCTTTTCAAATGTGAATAATAATTATGTTAACAATGGTAAATGCATTC<br>TTTAATTATTAAATATTCTGACTCAGTCACTTGCCCATGTCTGGTTTCTACAATTG<br>TCTTCTCTCTCTCTCTCTCTCTCTCTCTCTCTCTCTCTCTCTCTCTCTCTCTCTCTCT<br>CTCTCTCTCAGAGCTGAGGACTAAACCCAAGATCTTGCACTTACTAGGCAAGCGCT<br>CTACCACTGAGCTAAATCCCCAACCCCTTCTACTGTTGTCTAATCAATTTATTTGTG<br>TTTGATTGACTCAGCAACACTTATCTTATTACAATCCATCTATCTTTTAAATCAAAG<br>ATAAATGAAGGGCTCTTAGGGAACAGGCTTATAACATAAAAGTGCAAAGGCCCCA<br>GTATAAAATGTTACTACTCTCATAGGAACTGAGGACTCTCTAAGAAGTGGAACCAA<br>CTCATCTCTAAATCTCAAACACATACAACTGAAGATCATATAGATAGATTGGTTCA<br>CAGACAAACCTTTAAATAAAGGACAAAAATACTTTAAATAAAGACTTTTATTGCCT<br>GTGGTTGAATTAGGGAAAGACTGGAAGAAGCTGAGGAGGAGGGCGACCCTGTAGG<br>AGGACCAGCAGTCTCAATTAACCTGGTCCTCCGAGATCTCTCAAACACTGGACCAT<br>CATGCACCAACTGATATGAGGCCCCCAACACATACACAGCAGAGGACTTCAGGAT<br>TTGGTTTCAGCCAGAGAAGATGTACCTAACCCTCAAGAGACTGGAGGCCCCAAAG<br>AGTTTAGAGTTCTGGTTGGGTGTGGGGTGGGTGATAGGGACATACTCGTGGAGACA<br>GGGGGGCGGGGAGGAGGTATGGGATGTGGAAAATTAGGAGGGTGGACCAGGTAG<br>GGAATAAATCTGCAGTGTAAATTAATTAATTAATTTAAAAAAACTTTTGTTGGCAC<br>TTTATTTTTTTCTTTTCCTCTCCAGAGGCTGAGGCTGGACCACCTGACCATAACA<br>AAAGCTCCATGCCTTCGTCAGACACTTTTCAGGACGGTAATTTTTATTCACACGTG<br>AATCAAAACACCTTGGTTGTTCTTTGAACACAGCACAAAAGATTTGTTGTCCATTA<br>GGATGGCGAAAAAGAAAAAACTTCCATTTTAATTTTCTTTTTGGTAGACAAGGTA<br>AGAGAAATAAATGTACTTATTGTGAAGATATAGTCCAACTTGTCTTGATTATAGAA<br>AATTAAAATGTTATAGTGACCTGAGGAGTAGGAATGCAACTATGGTAATAAGAAG<br>TTTTAATATCTCAAAACTAAGTTCTGAGTTGTCTGCACATACAAACTGCCTTTGTAG<br>CTACTTCACTTCACGTCGACATCAGGAGAAGTACCATGAAAGTCTATGTTTTAACG<br>AGGAAGCACTTTCTTAAATAAGATTTACATTGAAGTAAATGCTTCTATAAGACAAA<br>AGTAGAAAATATATTAATTTAGCATCATTGCTTCATTTACATGGTCCTTTTTCCGCC<br>CTTAAAGTTTGAAAGTAGAATTTTGAGATCATATTCTAGGTGTGACAGGGACGGTG<br>ATAGGCAAAATGGCTTTTGAGCATTACTGTGAACAGAGATTTCTGGCAGAGACTA<br>GGGAGAGGAAGATCCAGTTCTGTGAATTCTTCACTAGGACGGCTGGCTGGACTCCA<br>GCCTGTTCTAGTACTCACAATCCCACATGATACTTTTCTCCTCTAGCAATACAAATT<br>TCACCAGAAAAAATTACTAAGGACATGATAGAGTGGGGGCAAGAAGAAGAAA<br>AAAAAAAATCCCGGGGGGGAGGGGGACCACATGATTGTAAAATAATACAGCTAA<br>AATACATAACTGATTCTTTACAGTGGCTTGACACTCCCTGTGTCAAAACCATCCG<br>CCTTGTGTTTACTAAAGTTTTCTCTGTACAAAATGAAGTTGACAGGGGAAAAATAA<br>ATAGAGCAGACTGTGACTCACTCAGCCAACATAAATTAATGCAATGCTTTCCCTG<br>TGAGGAAATCTGCCGCTGAATAACACTGAACTTTCTCTGTTTGCCTGTATTCGATGA<br>AATCTTTGAATTCCTACAGAATGCTGTTCTTTTTTTTTTTTTCTGACATGAGACAA<br>ATTCTTTATAAACATCTTGTTTGGATCAGCCACCACATTGTAACATTGTTTCTTACA<br>CTAAGGCTACTATTCTATAAAACTGTTACATATCTCCACTCTAACTACAGTGCAAA<br>GCTAAAAAAAAATTAAAAAAAATAAAAAAATAAAAAAAAGCAACACCTTCAGTTT |

TABLE 1-continued

Exemplary regRNAs

| regRNA | Nucleotide Sequence |
|---|---|
| | TCTAAGACTTTACTCTCATTGCTTCCACATTTTGGATGTATAATCCTAAATTAATCT<br>CTTCCTTGCCTCTTTTTAGCATCAACAAATAGGATATTTCCTAATGTAGCAAGCATT<br>AGTTCTATGAGCCATGAGGGGTAGTTTTTAACCCCTCCTTCATTCAATGTTAACTAA<br>AAGTCTTTTACATGCCAAGAGGGCTACAGTCAAGCCACTGTAAAGAATCAGTTATG<br>TATTTTAGCTGTATTATTTTATTTATTTTATTACTTTATTTATTATTTATTTTCAAAAG<br>TTCTGAAATAAAAATGAGCTCAGAAACTCTCTCTGCAAACTCACTCTCAAAGAGC<br>CTTTACAGTTTATTCTTAGAAAGAGCCATGTCGTATCTAGTCTCAAGACTAAACAAT<br>AAAGAAAGACAAAGGGAACTGTAAACCTACAAATCTCAAGACCCCAAGACCCAAG<br>AACAACAGACCAAATCAATATTCCTCTCCAGCAGCCACACGACGATGAAGTGTGA<br>GCATGTGTCTGTACACTTCACAAAATACAAAGCCCCCTGCATCAGCTTTCATATCCC<br>AAAGGAGTTGACCCACACTTCTAGGAAGCCCTTCACATCCTACAACTTCTCAGAAA<br>ACAAGAAGAATCAGATTTTTTTGAGCAGACAATTGTGGCTGGAAGTTGAGTTATTA<br>TTACTGAGCAAATTGACTAAACTTTTAACATATGCAGGACTAAAAGATAAAGTATA<br>AAATGAAAACTCATATATATGAGTAACTTTTTAAAACAAATGTTTTCTAAAAATAT<br>ATGAAAGATAAGTCCAAGATCAAATGTGTTTCATGGACTTAGATTAATAGTCAATG<br>GTAGAAACATGAGTCAAAACATTTTTTCATAAAATAACAAATCTTAAATTAAAACC<br>CCAAATACTCATGAAACAACAAATCTTTAGCTCTTATCCCACCTAACAAATATACC<br>ACAATATAATTACTACTTGACAGAGAGAAAAGTAAAGGTTCATACCAGATTATGTT<br>AAAGTTATAGGGATTTGTAATCAATTTTCTCAAGATCTCCTCATCAGAATCCAATG<br>AGTCACTCAGCTCACCACTGTTTCTTCTTTTCCAAATCTTGACTGTGAGCAGCTAAG<br>AAAAGATGAGCCACATCAGAATCAAGGCAAGCAAAGTTTTGCTGTTCAAGCTTA<br>GACTCAGGATGGCTGGAAACAAGACTTCCATGTCCAAGCCCAAGTCAGGACAGTC<br>CTTTTTTAAAGCAGATTAATCTTTTTCTTCAGACTTGAAAACTCTGTGCTATGTCTA<br>GGAAAGTAACTACTCCGCTACCTTGATACTGAACTCTGTGTTTCTCCCAGACCTAA<br>GATAAGACACCTTTCTTTATCTCCTCGGGGAAAGAAAATGGCTTCAAAGTCCAGT<br>CCAGGAGACAAGCCATACGGCAATGCCAATAGTATCAGAGGCCTTGTTGGATCAC<br>CTGACTTAGAATTACTATAGGAGGCAATGTAACAAACACTTCAATTTTTAAAAATC<br>CAAAATTAGCATATTCCTTAGTAAAAATGGTCACGAATGTCTTACAGAATGTCAC<br>TATTAAGTGACAACTATTGGTTTGCACATTAACTAATGCTTCTGGATGATTTAACCA<br>ACAGAAATGTGCTACAACTTACAACTTTAATCTC |
| Mouse CPS1<br>RR41_v1<br>SEQ ID<br>NO: 88 | TTGGTCATACTTGGAAAAGCGGGTGTGACGGTGTAGAATGAGGTGGAGAGAGTGG<br>GCTGGGCAAGATCCAGCAAGACAGAAAGCACACCCGAGAGTGGAGGTGCAAAGA<br>ACAGATTTCAGAGCTCAGAAGGGTTTATGCCATCACGTAAAGTTAAGATGATACAA<br>CTTAAGTAAATGTCAAAAAATGAGGGATGAAAGTAATTCTGACTTTACTTTTGGTA<br>TTACATTTAAATTTAAAAATAACAACAATATTCAAATAGCAGGGAATTATACTGGC<br>TATCTTGTTTTTGTAATTCAGATCAGGTAAATTGGATTGAGACTTGACCAGACTTAA<br>CTACAATAGCAAATCATGTTCTCACTGTTTTCTATCTTATACCTTATTGTTTATAATT<br>TTTCATTCCAAAGCCACAGGATCTGAGTACTTTAGTCTCACTGAATTCTTATATTTG<br>TTTGGAAATAAGATGTAGAGTAACTAAAAGAATTCAGGAAATGCTTACTAAGAAA<br>TGCTAGGATATCAATCAATATATATCAGGAAACAGTATTGGCTTTAACTAAAAATG<br>ATTTCAAGAAAATTCACAACATCTAAGTGCCTTACCTACATTTTTAGAAGGCAAAT<br>AGTATAAATTATATAGATAGTTTTAGATAGATTAAAAAATAAACCTTTAAAATAGT<br>TTTCTGGTTCTTTTGTTTTGTATATATAAAAATCTGGCATCTGGATAAATATAGAGT<br>CATCTCGTTATTTATGAGTTATTCAGTACTAAATAGCCTTTAGTAAAAGTTTTTAGT<br>TTAGCTTTTCTTTAAAAAGGAAAAAAGGGTCAATCTAGACCTGAGTTCCACATAAT<br>T |
| Human CPS1<br>RR89_v1<br>SEQ ID NO:<br>89 | TTCTTATCAAATACCTTGTCATTGCAACAACTTGTAGTCCATAAAAAACATAAGGA<br>CTCTTTGATCTAACCCTCTACTAAGTCCTTCTACTAAAATGTATAGAATGGAATTTT<br>TTTTTAAATATCCAGTTTTTGCTTTAAAATGTTCAGTTTAATGGTTTAAATTTAAAA<br>CTTTAAAGATTTTTGAGAATTGTTCATGTGTGACAATCACATAATTTGTCAAGTAAA<br>TCAGTCATCATTTGCACTATACAGATGACAAAACTTAGGTTCAGAGAATATGTGAC<br>TTGTCCAAGAACAGGGCATTAGGAAATGCATAACAGGGGTTAGATTCCAGATCTTT<br>TTGTGCCCAATCCAGAGTATATCCCACTATTACACTGTTACAGCCTGCTGAATGTAA<br>TAATGAGTGCTGAACATTTTCAGTACTAATGGAAAAAGATTATGGTATCTAAAACT<br>TTTTAGTATTTAGTATTTTATGGTTGTTGATCATTTATACCCTTGATATCAACTTTCT<br>TTAAAATATAGAGCACCTTGAAATTCTTTCCTCTTTCCTGTAAGTAAAATACAACTG<br>TGCCGATTGGCAAAGCACTCTATAAATATTAGCCGCTGACAAATACCCAGGGAAG<br>GGCCACATAAAATTATAAGTGCGTCATTGCTGTCGTCAAACCCACCGTCTCTGTCA<br>TCAAAGAGAGGAAAAGCAAACCTCTAAATATGTCGAAAAAGCAACCCAATTTA<br>CAGGGCAATGATTATAGATGTGACTACAGGGTGTCTTTCCCAATCCATTTACCATCT<br>ATAACTGGACATAATGCTACTAACCTTTAAAGTGACTGTTCTCAGTGCCCTTCACTG<br>ACCATTATGTAACTACATCCTAATGATTTTAACTATCTTTAAAATATGATGTCCATC<br>TAAAAATAGTAAATTTGGATATATTTTTCTAAGACAGTTGAGTTTTTAAAGTGAAG<br>GCAGGAAGAAAAGTAGATAGAGGACTATTTCACAATAACTGAATAATAACACAAG<br>TCCCCTTGGGCTGTTCTATGGAATTTTAATTCACTATTGTGAAGTTCAAGAACTTCT<br>ATTTTTTGTGCTTGGCATTCCTCCAAAACTCTGGCCAGTAATGATTGAGTGTGAGTA<br>ATGGCTTTTACACCATGAAATGATGGCTTAGTGCTCCTACAAATTTGTCATTCTTAG<br>CTGTGCACTGTGACAGACCCTTGAAACAGATCTGTCACCATGAGCTAGAACTGCTT<br>TCACAGTAATCCATCCACATAATTAGACCATTTTGTCGTGGTTGTGATTGTGGTGGT<br>GGTTGTATGGAGCACTTATTGTGATCTTGGAGAATTGGATTCTAATTTCAATCATAT<br>CTGTGCCATTTTAAGTAAGTACTCAATTTCGCGGTTTCTGGGGTCTGATGAAGATGC<br>ACCTATCCTTACCTACATACCTACCTTCTCACAGAGTGAGAAGAAGATATTCCAAG<br>TCACCCAACTTTGAAGTATTAGATGGCACATATAATCATAGGGGATAACTTTCATT<br>ACTATTGATTTTCTCTGAACTGATACATGAGTACCTTGAGGTATTACTAACAATAAA |

TABLE 1-continued

Exemplary regRNAs

| regRNA | Nucleotide Sequence |
|---|---|
| | TTCTCATAGTTTACATCTAGTTACAATGTCTTTGATGTTAGTTTAGAATATTCTCCTT<br>TCCCATTCTTTTGCTATAATTAAGCTAAATTCAAGAAAATATATATAACTAGACATA<br>ATGCCACTAACCTTTAGTGACTGCTCCCAGTGCCCTTTATGGCCATTATGTAACTAC<br>ATCCTAATGATTTTAACTATCTTTAAAACATGATGTCCATTTA |
| Human CPS1<br>RR90_v1<br>SEQ ID NO:<br>90 | TTATGGTATTGCTGTTGAATCATTTATCTACGTAAACTATTTGCACTTCAGAAAAAG<br>TAGAGGCCCCACATGTTTTTTTTCCATTTTCACCAAGGCCTAAGGCTATATAACATA<br>CGTGCTTTCTGGCTTACCTGATGTTTCTAAGCTATTAGTTCGCCTCAGTACTCATCCT<br>CTTAAAAAATAAATCTGAACTAAGCACTGAAAAGTAGAAAGCCTAAAGCCAGAAT<br>TTATTTCAGGTAATTATTGTGTAGATAATATGGTAAAAAGTTAAAATCAAGTAAAT<br>GAAATCTTATTCTTTTATTCTTGGAATTACACTATTAAGATATGGATTTTTGAAATT<br>TAGAATTTCAGCACAATTTGTCTTTGAAATATTTCATGAGACTTCTCTGCAGTTACA<br>AGGCCTAACACTTCAAAATTCTGAAGCACTGTAACAGCAGTAATCAATTAGGCCTT<br>ACCACATTCTCAGTTAATAATCTTACAACATTCCAAGTTAATATTAAGTCATCGGTC<br>TTTGGTTAAACATAAGCCAATGTTAAGGGGACAAAATCAAAAGGTTAATTTACTTA<br>AGTACTTTTATGTTTGAACATTTATAAACAAAAGATTAAGATTTATGAATCATTTTT<br>ATTCTAATAAGGTTTCTCATTGTAAATAAAATACAGCATTTATAAAAATTTCATTAC<br>AAAGTATGTTCATAAAGTGTAGGTTTATTAATATGCCTTACTGAGCATCTGCTATGT<br>GGCAAGTTGTTCAGAATCCTGGAGGAACCTACATATCATAAGCTAATTTTTACTGT<br>ATGGTGGTGATAAATTAAAATGGTCTTATATTTCAGTCTGCATTATAGAAGAAACT<br>TAGTAAAATTCTTTCATAATGTAGCAACCCTATTGATTCATTTATGAGAACTTCAAA<br>TTAGTCAGTTACCTCCCTATGAAATTTAAAAGATCAATGTATAGCATTTAACAAGTT<br>GAAAAAAATAAAAAGCAAACAGAGTAGCCTTGAAAATATTTTTATAAGTTCAACT<br>CATTTAGATCACATGAAGAAAATCAAATGGAAGCTAAAGATCCCTAGGGCTAAGG<br>AGCCTAACACAAACTTTGACCTTGGCCCGCGCAGCTTTTTCGGGCCTCCGTCATTG<br>CAAATGCCCCAGGAAATACAAATCCCATCAAGGGCAGTCAGCGTAGCATACCAAA<br>CTCCTCCTGAAGGCTTGAAGTGAATTCTAGCATGCCCATTGCCTAAGAGATACTGA<br>AAACTTTCTACAGCACCCCTCAATTTTTGGAACAGGTTGGAAATATGAAGAAAGTC<br>TAATACAGATGTAAAGGCAGAGGAATAGTCTCCATTTCCATAGCAATAAGACCTAA<br>TGTCACCTCTAGATCGTCAGAAAGTCTGGCTAGACATGAGCAAATTGGAATGAGGG<br>AGAGGAAAGCACAGGTCAAGATTAGTACTAGTCCCTTGGGCAGTTCTACAGCCAG<br>AATGCTTAGCTTCTGACCCAAAGCTGGGACTAGGGTACTGAGTGATGTGCTTAGGG<br>CCTAACTCTCAAAGAGATACACCATGACACTAACAGTGACAGCCTCCTTAAATTTT<br>GCATCTCAGGTACCTCACTCACTTAACCTAGTCTAGGACATTTAAACTATAGTTTTT<br>TCAAGAGTTTTATGTCAAGAAGCTCATAATGTCAAGGCGTTGTTGGTGACTAATAA<br>ATGAATCTATATTTTAGAAAATTGGGGATATAAAAAATGGAAAAAATTAAAATGTT<br>CAAAAGAAAGGCCATCTCCCAATTAGAGAAGTATTGCATGCCAAAAGTATGTAAA<br>GTTGTCCATCAGGCAAACTAATTCTGCAACAGCTCATTTGGGACTGAACACAATTA<br>ATATTTCAAAAATGTAGTTTGCCATAGATGAAATCCGTCCTAAAATGTGTCTATAT<br>GTAGTAAAAGTCCAATAAAATAGTTATTCTTAAAAGTGTGTGATAACCCCATCCCC<br>ACTCTTACATCTAACGTGTACAGAGGCTCCAATATGATAATGAGTTATATTTCCTGT<br>GACTATCTTTAAAGCTACTACAATGTAAGTAAATTATTCTAATTGTAGGAGTTTTTA<br>TAGTTGCCAATTTCTAATCAAATGACAATAGCTCCTCAAGACGGAACTAAATAGAT<br>ACTTCTATGTGAAAATCAGAATATAAAATCTTAAAAATGAATGCCTTTCAAAAGAA<br>ATAATGACTACCAGTGCTCATTCGTAGCTGAAGTATCAGAGAGGACACTTGGATTG<br>TTAGGTTCCTAGCTTAATTATAACACAGGTCACCATTGTTAAAAAATGAGTGGATT<br>AATGTTAGAAGGAGTACTTATTGAACACTTTTCTATTCATAGGGAACTTAAGCTTTA<br>CAATTTAATACTTTTGATTTCCAAATTCAT |

The present disclosure describes ASOs that increase the amount or stability of the target regRNA, thereby to increase expression of the target gene. This is different from the ASOs previously described that were designed to inhibit eRNAs (see, e.g., PCT Application Publication No. WO2013/177248 and PCT Application Publication No. WO2017/075406). Without wishing to be bound by theory, it is hypothesized that the ASOs' ability to upregulate regRNAs is attributable to the selection of a target sequence in the regRNA and/or the chemical modifications of the ASOs.

Sequences of ASOs

As disclosed herein, ASOs that bind a sequence closer to the 5' or 3' end of the target CPS1 regRNA are more likely to upregulate the regRNA. Without wishing to be bound by theory, it is hypothesized that such ASO hybridizes to a terminal portion of the target CPS1 regRNA and prevents or slows 5'→3' and/or 3'→5' RNA degradation without blocking the functional region of the regRNA. In certain embodiments, the ASO disclosed herein is complementary to a sequence in the target regRNA that is no more than 300, 250, 200, 150, 100, 50, 40, 30, 20, or 10 nucleotides from the 5' or 3' end of the target regRNA. In certain embodiments, the ASO disclosed herein is complementary to a sequence in the target regRNA that is no more than 300, 250, 200, 150, 100, 50, 40, 30, 20, or 10 nucleotides from the 5' end of the target regRNA (i.e., the 5' most nucleotide of the regRNA sequence forming a duplex with the ASO is no more than 300, 250, 200, 150, 100, 50, 40, 30, 20, or 10 nucleotides from the 5' end of the target regRNA). In certain embodiments, the ASO disclosed herein is complementary to a sequence in the target regRNA that is no more than 300, 250, 200, 150, 100, 50, 40, 30, 20, or 10 nucleotides from the 3' end of the target regRNA (i.e., the 3' most nucleotide of the regRNA sequence forming a duplex with the ASO is no more than 300, 250, 200, 150, 100, 50, 40, 30, 20, or 10 nucleotides from the 3' end of the target regRNA).

In certain embodiments, the ASO is no more than 25, 30, 40, 50, 60, 70, 80, 90, or 100 nucleotides in length. In certain embodiments, the ASO is no more than 8, 10, 15, 20, 25, 30, 35, 40, 45, 50, 55, 60, 65, 70, 75, 80, 85, 90, 95, or 100 nucleotides in length. In certain embodiments, the ASO is at least 8, 10, 15, 20, 25, 30, 35, 40, 45, 50, 55, 60, 65, 70, 75, 80, 85, 90, 95, or 100 nucleotides in length. In certain embodiments, the ASO is at least 8, 9, 10, 11, 12, 13, 14, 15, 16, 17, 18, 19, 20, 21, 22, 23, 24, 25, 26, 27, 28, 29, or 30 nucleotides in length.

In certain embodiments, the ASO is designed to lack a stable secondary structure formed within itself or between other identical ASO molecules, thereby increasing the amount of the ASO in a single-stranded form available to hybridize with the target regRNA. Methods to predict secondary structures are known in the art (see, e.g., Seetin and Mathews, Methods Mol. Biol. (2012) 905:99-122; Zhao et al., PLoS Comput. Biol. (2021) 17(8):e1009291) and web-based programs (e.g., RNAfold) are available to public users.

For example, ASOs have been designed to target a human CPS1 eRNA. The nucleotide sequences of these ASOs are provided in Table 2 below.

TABLE 2

Exemplary ASO sequences targeting regRNAs

| Name | Sequence | SEQ ID NO |
|---|---|---|
| hCPS1-ASO-1 | TGCAGGCACACACATCAGGC | 1 |
| hCPS1-ASO-2 | ATGCAGGCACACACATCAGGCT | 2 |
| hCPS1-ASO-3 | AATGCAGGCACACACATCAGGCTG | 3 |
| hCPS1-ASO-4 | GCACACACATCAGGCTGGGG | 4 |
| hCPS1-ASO-5 | AATGCAGGCACACACATCAG | 5 |
| hCPS1-ASO-6 | TGAATGCAGGCACACACATC | 6 |
| hCPS1-ASO-7 | GGGACCCTGTGTACTTGGAA | 7 |
| hCPS1-ASO-8 | GCAGAGTGACAGGCATGAAT | 8 |
| hCPS1-ASO-9 | TGCCATTGACTTGCATAATG | 9 |
| hCPS1-ASO-10 | GTCAATGCTCAGAACATAGT | 10 |
| hCPS1-ASO-11 | TAGATAATAACCCACCACAC | 11 |
| hCPS1-ASO-12 | GTCAAGTACTAGGTTGTATT | 12 |
| hCPS1-ASO-13 | TTAGCCTGTGAAATCCCTCA | 13 |
| hCPS1-ASO-14 | CTTATGAGTCACTCTCTGAT | 14 |
| hCPS1-ASO-15 | TCTTTGTGAGCCAGGTCATC | 15 |
| hCPS1-ASO-16 | CGCAGCTGAGCAGAGTGACA | 91 |
| hCPS1-ASO-17 | CAGTCCTCCTTCATATAAGC | 92 |
| hCPS1-ASO-18 | TGACCACATGTACACAGTCC | 93 |
| hCPS1-ASO-19 | GTTACACTTTTAGGACAGAT | 94 |
| hCPS1-ASO-20 | GGTAGGGAATGTTAAAGTCA | 95 |
| hCPS1-ASO-21 | TATAAGAGTTGGTTGGTAGG | 96 |
| hCPS1-ASO-22 | CAAAGGAGTTGAGGCTATAA | 97 |
| hCPS1-ASO-23 | GGGAGTTTACATTAGGATAG | 98 |
| hCPS1-ASO-24 | GGCTAGACTGAAATCTATAA | 99 |
| hCPS1-ASO-25 | GCTAGTTTCATACTTGAGTG | 100 |
| hCPS1-ASO-26 | CACAATGGAGGTTGGAACAG | 101 |

TABLE 2-continued

Exemplary ASO sequences targeting regRNAs

| Name | Sequence | SEQ ID NO |
|---|---|---|
| hCPS1-ASO-27 | TCCATCAATTATAATTCCAC | 102 |
| hCPS1-ASO-28 | ATTAGAGACTTGGAAAATCC | 103 |
| hCPS1-ASO-29 | GGTCCATGTCTTTAGTCATC | 104 |
| hCPS1-ASO-30 | AGACTTGCAAACTACGGTGT | 105 |
| hCPS1-ASO-31 | TTTTATCAGTAAAGGGTCCC | 106 |
| hCPS1-ASO-32 | AGTCTAGAGAGAAATGTGGG | 107 |
| hCPS1-ASO-33 | GGATAGAATTCTCCTACTCT | 108 |
| hCPS1-ASO-34 | CAACAATCAACAATTCTAGG | 109 |
| hCPS1-ASO-35 | TTCCATAGAAATGTCAACAA | 110 |
| hCPS1-ASO-36 | GACTACAAAGCATGATGAAT | 111 |
| hCPS1-ASO-37 | CATTTATAGCAGTTGACTAC | 112 |
| hCPS1-ASO-38 | GCTTGACCAAGGAAAAGACT | 113 |
| hCPS1-ASO-39 | GTGGAAGTACTGAGGAGTCC | 114 |
| hCPS1-ASO-40 | TAATCAAATATGACAGTGGA | 115 |
| hCPS1-ASO-41 | CCTCCCTTCATCACTTATGT | 116 |
| hCPS1-ASO-42 | ACTATAATATATTTCCTCCC | 117 |
| hCPS1-ASO-43 | CCCTAAGGTACCCATGCAAT | 118 |
| hCPS1-ASO-44 | GTCATAGTCCCATTACCCTA | 119 |
| hCPS1-ASO-45 | GGAAACTTTTTAGGATGCAA | 120 |
| hCPS1-ASO-46 | CCTCATTATGGAAACTTTTC | 121 |
| hCPS1-ASO-47 | CGATATAAACTCAATCCTCA | 122 |
| hCPS1-ASO-48 | GTAGTGAGGGTTGTCTTTCC | 123 |
| hCPS1-ASO-49 | CTCTTGTCTTTTTATGTGTG | 124 |
| hCPS1-ASO-50 | CGCCTTGATCTCACCTCTTG | 125 |
| hCPS1-ASO-51 | GTCCAATACTAGTTTACGCC | 126 |
| hCPS1-ASO-52 | AGTACTTACTGGCTTAGTCC | 127 |
| hCPS1-ASO-53 | CTAGAGAACTGAGGACTGAG | 128 |
| hCPS1-ASO-54 | GGAAAACTCCCAACCTAGAG | 129 |
| hCPS1-ASO-55 | AAATGAATTGGAGGAGAATG | 130 |
| hCPS1-ASO-56 | GGCGAAATTTGTGTTGAAGA | 131 |
| hCPS1-ASO-57 | TTGAACAAGAAATAAAGGCG | 132 |
| hCPS1-ASO-58 | GTATTCATAATAGTCATGGA | 133 |
| hCPS1-ASO-59 | TCAGCCTTCATCCATAAATA | 134 |
| hCPS1-ASO-60 | TATGCCTTAAAATGTTCAGC | 135 |
| hCPS1-ASO-61 | CATGGGAGACTTAGTATGCC | 136 |
| hCPS1-ASO-62 | TGAAAAGGTACCATATCATG | 137 |
| hCPS1-ASO-63 | GTATAGAATGGGAAAATGAA | 138 |

TABLE 2-continued

Exemplary ASO sequences targeting reqRNAs

| Name | Sequence | SEQ ID NO |
|---|---|---|
| hCPS1-ASO-64 | AGCCTAGATGCAGGGTATAG | 139 |
| hCPS1-ASO-65 | ATGAAGTCATGTGGTATATT | 140 |
| hCPS1-ASO-66 | GCCGTGGCATGAGCAATAGC | 141 |
| hCPS1-ASO-67 | TGCAAATTCACCAAGTAGAT | 142 |
| hCPS1-ASO-68 | TGTGTTATACTGAAGGATGC | 143 |
| hCPS1-ASO-69 | GCATAGAATTATGTTGAGCT | 144 |
| hCPS1-ASO-70 | AGATCAAGTTCCTTGTGCAT | 145 |
| hCPS1-ASO-71 | CTGGTGCCATGAAAGTTGCC | 146 |
| hCPS1-ASO-72 | GGCTCATACTAGTTTATACA | 147 |
| hCPS1-ASO-73 | AAGCTAAACAAAATAGGCTC | 148 |
| hCPS1-ASO-74 | CATGGCTCCTGGTGATAGAA | 149 |
| hCPS1-ASO-75 | GATTTCAAAGTGCTTCATGG | 150 |
| hCPS1-ASO-76 | AGTCCTCACGCTTACTTAAT | 151 |
| hCPS1-ASO-77 | CAGGCACACACATCAGGCTG | 152 |
| hCPS1-ASO-78 | GCAGGCACACACATCAGGCT | 153 |
| hCPS1-ASO-79 | ATGCAGGCACACACATCAGG | 154 |
| hCPS1-ASO-80 | GAATGCAGGCACACACATCA | 155 |
| hCPS1-ASO-81 | TGCAGGCACACACATCAGGC | 156 |
| hCPS1-ASO-82 | TGCAGGCACACACATCAGGCTG | 157 |
| hCPS1-ASO-83 | CAGGCACACACATCAGGCTG | 158 |
| hCPS1-ASO-84 | GCAGGCACACACATCAGGCT | 159 |
| hCPS1-ASO-85 | ATGCAGGCACACACATCAGG | 160 |
| hCPS1-ASO-86 | TGCAGGCACACACATCAGGC | 161 |
| hCPS1-ASO-87 | TGCAGGCACACACATCAGG | 162 |
| hCPS1-ASO-88 | TGCAGGCACACACATCAG | 163 |
| hCPS1-ASO-89 | TGCAGGCACACAT | 164 |
| hCPS1-ASO-91 | TGCAGGCACACACATCAGGC | 166 |
| hCPS1-ASO-92 | CAGGCATGAATGCAGGCACA | 167 |
| hCPS1-ASO-93 | ACAGGCATGAATGCAGGCAC | 168 |
| hCPS1-ASO-94 | GTGACAGGCATGAATGCAGG | 169 |
| hCPS1-ASO-95 | AGTGACAGGCATGAATGCAG | 170 |
| hCPS1-ASO-96 | GAGTGACAGGCATGAATGCA | 171 |
| hCPS1-ASO-97 | AATGCAGGCACACACA | 172 |
| hCPS1-ASO-98 | TGAATGCAGGCACACA | 173 |
| hCPS1-ASO-99 | CATGAATGCAGGCACA | 174 |
| hCPS1-ASO-100 | TGCAGGCACACACATC | 175 |
| hCPS1-ASO-101 | CAGGCACACACATCAG | 176 |
| hCPS1-ASO-102 | GGCACACACATCAGGC | 177 |
| hCPS1-ASO-103 | CACACACATCAGGCTG | 178 |
| hCPS1-ASO-104 | CACACATCAGGCTGGG | 179 |
| hCPS1-ASO-105 | TGCAGGCACACACATCAGGCTTTTTTTTT | 180 |
| hCPS1-ASO-106 | TTTTTTTTTTGCAGGCACACACATCAGGC | 181 |
| hCPS1-ASO-107 | ACATTACTTTAAATGATTAC | 182 |
| hCPS1-ASO-108 | GATGTTATTACAAAGTTCTT | 183 |
| hCPS1-ASO-109 | GGAGGCAATATTATGTTAAA | 184 |
| hCPS1-ASO-110 | GCATAATGCTTTTTGGAGGC | 185 |
| hCPS1-ASO-111 | CTTGCATAATGCTTTTTGGA | 186 |
| hCPS1-ASO-112 | ACTTGCATAATGCTTTTTGG | 187 |
| hCPS1-ASO-113 | GACTTGCATAATGCTTTTTG | 188 |
| hCPS1-ASO-114 | CCATTGACTTGCATAATGCT | 189 |
| hCPS1-ASO-115 | GCCATTGACTTGCATAATGC | 190 |
| hCPS1-ASO-116 | TCTAGCATTTATGTCAATGC | 191 |
| hCPS1-ASO-117 | CTCTGTTAACACTAAAGTAT | 192 |
| hCPS1-ASO-118 | TCTCTGTTAACACTAAAGTA | 193 |
| hCPS1-ASO-119 | ATCTCTGTTAACACTAAAGT | 194 |
| hCPS1-ASO-120 | GATAATAACCCACCACACAA | 195 |
| hCPS1-ASO-121 | GAAATGTGGAAATACAGAAT | 196 |
| hCPS1-ASO-122 | ATGTCAAGTACTAGGTTGTA | 197 |
| hCPS1-ASO-123 | CCTTATTGACATATCTGGTA | 198 |
| hCPS1-ASO-124 | TCAGGGCACTTTATTTTATG | 199 |
| hCPS1-ASO-125 | GAAATCCCTCAGGGCACTTT | 200 |
| hCPS1-ASO-126 | TGAAATCCCTCAGGGCACTT | 201 |
| hCPS1-ASO-127 | GTGAAATCCCTCAGGGCACT | 202 |
| hCPS1-ASO-128 | TGTGAAATCCCTCAGGGCAC | 203 |
| hCPS1-ASO-129 | CTGTGAAATCCCTCAGGGCA | 204 |
| hCPS1-ASO-130 | GCATTTAGCCTGTGAAATCC | 205 |
| hCPS1-ASO-131 | TAGAAGCATTTAGCCTGTGA | 206 |
| hCPS1-ASO-132 | GTCTTCTTTTCTATTAATAC | 207 |
| hCPS1-ASO-133 | AGTCACTCTCTGATAAAATG | 208 |
| hCPS1-ASO-134 | GTGAGCCAGGTCATCAAAGG | 209 |
| hCPS1-ASO-135 | TTTGTGAGCCAGGTCATCAA | 210 |
| hCPS1-ASO-136 | CATTCTTTGTGAGCCAGGTC | 211 |
| hCPS1-ASO-137 | GGAAGTACATTCTTTGTGAG | 212 |
| hCPS1-ASO-138 | ACTTGGAAGTACATTCTTTG | 213 |

TABLE 2-continued

Exemplary ASO sequences targeting reqRNAs

| Name | Sequence | SEQ ID NO |
|---|---|---|
| hCPS1-ASO-139 | GTGTACTTGGAAGTACATTC | 214 |
| hCPS1-ASO-140 | GACCCTGTGTACTTGGAAGT | 215 |
| hCPS1-ASO-141 | TGGGGACCCTGTGTACTTGG | 216 |
| hCPS1-ASO-142 | ATCAGGCTGGGGACCCTGTG | 217 |
| hCPS1-ASO-143 | ACACATCAGGCTGGGGACCC | 218 |
| hCPS1-ASO-144 | GGCACACACATCAGGCTGGG | 219 |
| hCPS1-ASO-145 | ATGAATGCAGGCACACACAT | 220 |
| hCPS1-ASO-146 | AGGCATGAATGCAGGCACAC | 221 |
| hCPS1-ASO-147 | TGACAGGCATGAATGCAGGC | 222 |
| hCPS1-ASO-148 | AGAGTGACAGGCATGAATGC | 223 |
| hCPS1-ASO-149 | GAGCAGAGTGACAGGCATGA | 224 |
| hCPS1-ASO-150 | CAGCTGAGCAGAGTGACAGG | 225 |
| hCPS1-ASO-151 | TGCACGCAGCTGAGCAGAGT | 226 |
| hCPS1-ASO-152 | TGTCTGCACGCAGCTGAGCA | 227 |
| hCPS1-ASO-153 | AAGCTGTCTGCACGCAGCTG | 228 |
| hCPS1-ASO-154 | ATATAAGCTGTCTGCACGCA | 229 |
| hCPS1-ASO-155 | CCTTCATATAAGCTGTCTGC | 230 |
| hCPS1-ASO-156 | GTCCTCCTTCATATAAGCTG | 231 |
| hCPS1-ASO-157 | TTCTTCTCTGACCACATGTA | 232 |
| hCPS1-ASO-158 | ACATTTAAAAAATAAGCAT | 233 |
| hCPS1-ASO-159 | ACACTTTTAGGACAGATTAT | 234 |
| hCPS1-ASO-160 | TGTTACACTTTTAGGACAGA | 235 |
| hCPS1-ASO-161 | GGAAATGTTACACTTTTAGG | 236 |
| hCPS1-ASO-162 | GACATGAAAAAATTTAGTGG | 237 |
| hCPS1-ASO-163 | GGTTGGTAGGGAATGTTAAA | 238 |
| hCPS1-ASO-164 | TGGTTGGTAGGGAATGTTAA | 239 |
| hCPS1-ASO-165 | TTGGTTGGTAGGGAATGTTA | 240 |
| hCPS1-ASO-166 | GTTGGTTGGTAGGGAATGTT | 241 |
| hCPS1-ASO-167 | AGTTGGTTGGTAGGGAATGT | 242 |
| hCPS1-ASO-168 | GAGTTGGTTGGTAGGGAATG | 243 |
| hCPS1-ASO-169 | AGAGTTGGTTGGTAGGGAAT | 244 |
| hCPS1-ASO-170 | AAGAGTTGGTTGGTAGGGAA | 245 |
| hCPS1-ASO-171 | TAAGAGTTGGTTGGTAGGGA | 246 |
| hCPS1-ASO-172 | ATAAGAGTTGGTTGGTAGGG | 247 |
| hCPS1-ASO-173 | CTATAAGAGTTGGTTGGTAG | 248 |
| hCPS1-ASO-174 | GAGGGAGTTTACATTAGGAT | 249 |
| hCPS1-ASO-175 | TGGAAAAAAATATATTACAC | 250 |
| hCPS1-ASO-176 | GCTAGACTGAAATCTATAAC | 251 |
| hCPS1-ASO-177 | GTGTTCAGGCTAGACTGAAA | 252 |
| hCPS1-ASO-178 | AGTGTTCAGGCTAGACTGAA | 253 |
| hCPS1-ASO-179 | GAGTGTTCAGGCTAGACTGA | 254 |
| hCPS1-ASO-180 | TGAGTGTTCAGGCTAGACTG | 255 |
| hCPS1-ASO-181 | TTGAGTGTTCAGGCTAGACT | 256 |
| hCPS1-ASO-182 | CTTGAGTGTTCAGGCTAGAC | 257 |
| hCPS1-ASO-183 | ACTTGAGTGTTCAGGCTAGA | 258 |
| hCPS1-ASO-184 | TACTTGAGTGTTCAGGCTAG | 259 |
| hCPS1-ASO-185 | ATACTTGAGTGTTCAGGCTA | 260 |
| hCPS1-ASO-186 | CATACTTGAGTGTTCAGGCT | 261 |
| hCPS1-ASO-187 | TCATACTTGAGTGTTCAGGC | 262 |
| hCPS1-ASO-188 | TTCATACTTGAGTGTTCAGG | 263 |
| hCPS1-ASO-189 | GTTTCATACTTGAGTGTTCA | 264 |
| hCPS1-ASO-190 | GGCTAGTTTCATACTTGAGT | 265 |
| hCPS1-ASO-191 | GTGGCTAGTTTCATACTTGA | 266 |
| hCPS1-ASO-192 | AGTGGCTAGTTTCATACTTG | 267 |
| hCPS1-ASO-193 | GGAGGTTGGAACAGCCAATA | 268 |
| hCPS1-ASO-194 | CAATGGAGGTTGGAACAGCC | 269 |
| hCPS1-ASO-195 | ACAATGGAGGTTGGAACAGC | 270 |
| hCPS1-ASO-196 | CCACAATGGAGGTTGGAACA | 271 |
| hCPS1-ASO-197 | TCCACAATGGAGGTTGGAAC | 272 |
| hCPS1-ASO-198 | TTCCACAATGGAGGTTGGAA | 273 |
| hCPS1-ASO-199 | ATTCCACAATGGAGGTTGGA | 274 |
| hCPS1-ASO-200 | AATTCCACAATGGAGGTTGG | 275 |
| hCPS1-ASO-201 | TAATTCCACAATGGAGGTTG | 276 |
| hCPS1-ASO-202 | ATCCATCAATTATAATTCCA | 277 |
| hCPS1-ASO-203 | AATCCATCAATTATAATTCC | 278 |
| hCPS1-ASO-204 | AAATCCATCAATTATAATTC | 279 |
| hCPS1-ASO-205 | AAAATCCATCAATTATAATT | 280 |
| hCPS1-ASO-206 | GAAAATCCATCAATTATAAT | 281 |
| hCPS1-ASO-207 | GGAAAATCCATCAATTATAA | 282 |
| hCPS1-ASO-208 | TGGAAAATCCATCAATTATA | 283 |
| hCPS1-ASO-209 | TTGGAAAATCCATCAATTAT | 284 |
| hCPS1-ASO-210 | CTTGGAAAATCCATCAATTA | 285 |
| hCPS1-ASO-211 | ACTTGGAAAATCCATCAATT | 286 |
| hCPS1-ASO-212 | GACTTGGAAAATCCATCAAT | 287 |
| hCPS1-ASO-213 | AGACTTGGAAAATCCATCAA | 288 |

TABLE 2-continued

Exemplary ASO sequences targeting reqRNAs

| Name | Sequence | SEQ ID NO |
|---|---|---|
| hCPS1-ASO-214 | GAGACTTGGAAAATCCATCA | 289 |
| hCPS1-ASO-215 | AGAGACTTGGAAAATCCATC | 290 |
| hCPS1-ASO-216 | GAATTAGAGACTTGGAAAAT | 291 |
| hCPS1-ASO-217 | TGAATTAGAGACTTGGAAAA | 292 |
| hCPS1-ASO-218 | CTGAATTAGAGACTTGGAAA | 293 |
| hCPS1-ASO-219 | TCTGAATTAGAGACTTGGAA | 294 |
| hCPS1-ASO-220 | TTCTGAATTAGAGACTTGGA | 295 |
| hCPS1-ASO-221 | ATTCTGAATTAGAGACTTGG | 296 |
| hCPS1-ASO-222 | TATTCTGAATTAGAGACTTG | 297 |
| hCPS1-ASO-223 | GGAGAAGGCAGAAATTTTGG | 298 |
| hCPS1-ASO-224 | GTCCATGTCTTTAGTCATCA | 299 |
| hCPS1-ASO-225 | ACGGTGTGTGTGTGTATATA | 300 |
| hCPS1-ASO-226 | AACTACGGTGTGTGTGTGTA | 301 |
| hCPS1-ASO-227 | TGCAAACTACGGTGTGTGTG | 302 |
| hCPS1-ASO-228 | GACTTGCAAACTACGGTGTG | 303 |
| hCPS1-ASO-229 | ATGCAGACTTGCAAACTACG | 304 |
| hCPS1-ASO-230 | CCAGATGCAGACTTGCAAAC | 305 |
| hCPS1-ASO-231 | GGTCCCAGATGCAGACTTGC | 306 |
| hCPS1-ASO-232 | AAAGGGTCCCAGATGCAGAC | 307 |
| hCPS1-ASO-233 | CAGTAAAGGGTCCCAGATGC | 308 |
| hCPS1-ASO-234 | TATCAGTAAAGGGTCCCAGA | 309 |
| hCPS1-ASO-235 | GGCATGAGAGTTTTAATGGG | 310 |
| hCPS1-ASO-236 | GATAGAATTCTCCTACTCTA | 311 |
| hCPS1-ASO-237 | CCATAGAAATGTCAACAATC | 312 |
| hCPS1-ASO-238 | GCATGATGAATTAAACATGT | 313 |
| hCPS1-ASO-239 | CCATTTATAGCAGTTGACTA | 314 |
| hCPS1-ASO-240 | TTGACCAAGGAAAAGACTTC | 315 |
| hCPS1-ASO-241 | AGCTTGACCAAGGAAAAGAC | 316 |
| hCPS1-ASO-242 | AGTCCAGAGCTTGACCAAGG | 317 |
| hCPS1-ASO-243 | GAGGAGTCCAGAGCTTGACC | 318 |
| hCPS1-ASO-244 | AGTACTGAGGAGTCCAGAGC | 319 |
| hCPS1-ASO-245 | AGTGGAAGTACTGAGGAGTC | 320 |
| hCPS1-ASO-246 | TGACAGTGGAAGTACTGAGG | 321 |
| hCPS1-ASO-247 | TATGACAGTGGAAGTACTGA | 322 |
| hCPS1-ASO-248 | TCCTCCCTTCATCACTTATG | 323 |
| hCPS1-ASO-249 | ACCCATGCAATGAATACTAT | 324 |
| hCPS1-ASO-250 | TACCCATGCAATGAATACTA | 325 |
| hCPS1-ASO-251 | GTACCCATGCAATGAATACT | 326 |
| hCPS1-ASO-252 | GGTACCCATGCAATGAATAC | 327 |
| hCPS1-ASO-253 | AGGTACCCATGCAATGAATA | 328 |
| hCPS1-ASO-254 | AAGGTACCCATGCAATGAAT | 329 |
| hCPS1-ASO-255 | TAAGGTACCCATGCAATGAA | 330 |
| hCPS1-ASO-256 | CCTAAGGTACCCATGCAATG | 331 |
| hCPS1-ASO-257 | TTTAAATCAGTCATAGTCCC | 332 |
| hCPS1-ASO-258 | GCTGCACCCACTAATGGAAA | 333 |
| hCPS1-ASO-259 | GTGCTGCACCCACTAATGGA | 334 |
| hCPS1-ASO-260 | GGAAACTTTTCTTTTTAAGT | 335 |
| hCPS1-ASO-261 | ACGATATAAACTCAATCCTC | 336 |
| hCPS1-ASO-262 | TAGTGAGGGTTGTCTTTCCT | 337 |
| hCPS1-ASO-263 | TGTAGTGAGGGTTGTCTTTC | 338 |
| hCPS1-ASO-264 | GTGTAGTGAGGGTTGTCTTT | 339 |
| hCPS1-ASO-265 | GTGTGTAGTGAGGGTTGTCT | 340 |
| hCPS1-ASO-266 | TCTTGTCTTTTTATGTGTGT | 341 |
| hCPS1-ASO-267 | TACTAGTTTACGCCTTGATC | 342 |
| hCPS1-ASO-268 | GCAGTACTTACTGGCTTAGT | 343 |
| hCPS1-ASO-269 | GAAAACTCCCAACCTAGAGA | 344 |
| hCPS1-ASO-270 | TTGGAGGAGAATGAAAATAG | 345 |
| hCPS1-ASO-271 | CGAAATTTGTGTTGAAGATC | 346 |
| hCPS1-ASO-272 | CATAATAGTCATGGAAGTAT | 347 |
| hCPS1-ASO-273 | AATGTTCAGCCTTCATCCAT | 348 |
| hCPS1-ASO-274 | TCATGGGAGACTTAGTATGC | 349 |
| hCPS1-ASO-275 | CTAGATGCAGGGTATAGAAT | 350 |
| hCPS1-ASO-276 | CATGAAGTCATGTGGTATAT | 351 |
| hCPS1-ASO-277 | CCGTGGCATGAGCAATAGCC | 352 |
| hCPS1-ASO-278 | AAGTAGATAAAGAGGGGAAA | 353 |
| hCPS1-ASO-279 | GGCATGAATGCAGGCA | 354 |
| hCPS1-ASO-280 | CAGGCATGAATGCAGG | 355 |
| hCPS1-ASO-281 | GACAGGCATGAATGCA | 356 |
| hCPS1-ASO-282 | GTGACAGGCATGAATG | 357 |
| hCPS1-ASO-283 | CACATCAGGCTGGGA | 358 |
| hCPS1-ASO-284 | CATCAGGCTGGGGACC | 359 |
| hCPS1-ASO-285 | TCAGGCTGGGGACCCT | 360 |
| hCPS1-ASO-286 | AGGCTGGGGACCCTGT | 361 |
| hCPS1-ASO-287 | CATGAATGCAGGCACA | 362 |
| hCPS1-ASO-288 | TGAATGCAGGCACACA | 363 |

TABLE 2-continued

Exemplary ASO sequences targeting reqRNAs

| Name | Sequence | SEQ ID NO |
|---|---|---|
| hCPS1-ASO-289 | AATGCAGGCACACACA | 364 |
| hCPS1-ASO-290 | TGCAGGCACACACATC | 365 |
| hCPS1-ASO-291 | CAGGCACACACATCAG | 366 |
| hCPS1-ASO-292 | GGCACACACATCAGGC | 367 |
| hCPS1-ASO-293 | CACACACATCAGGCTG | 368 |
| hCPS1-ASO-294 | CACACATCAGGCTGGG | 369 |
| hCPS1-ASO-295 | GGCATGAATGCAGGCA | 370 |
| hCPS1-ASO-296 | CAGGCATGAATGCAGG | 371 |
| hCPS1-ASO-297 | GACAGGCATGAATGCA | 372 |
| hCPS1-ASO-298 | GTGACAGGCATGAATG | 373 |
| hCPS1-ASO-299 | CACATCAGGCTGGGGA | 374 |
| hCPS1-ASO-300 | CATCAGGCTGGGGACC | 375 |
| hCPS1-ASO-301 | TCAGGCTGGGGACCCT | 376 |
| hCPS1-ASO-302 | AGGCTGGGGACCCTGT | 377 |
| hCPS1-ASO-303 | GCATGAATGCAGGCACAC | 378 |
| hCPS1-ASO-304 | GCACACACATCAGGCTGG | 379 |
| hCPS1-ASO-305 | ACACACATCAGGCTGGGG | 380 |
| hCPS1-ASO-306 | CACACACATCAGGCTGGG | 381 |
| hCPS1-ASO-307 | GGCATGAATGCAGGCACACA | 382 |
| hCPS1-ASO-308 | GGCATGAATGCAGGCACACA | 383 |
| hCPS1-ASO-309 | GGCACACACATCAGGCTGGG | 384 |
| hCPS1-ASO-310 | CACACACATCAGGCTGGGGA | 385 |
| hCPS1-ASO-311 | GCACACACATCAGGCTGGGG | 386 |
| hCPS1-ASO-312 | TGCAGGCACACACATCAGGC | 387 |
| hCPS1-ASO-313 | ATCAGGCTGGGGACCCTGTG | 388 |
| hCPS1-ASO-314 | GGCACACACATCAGGCTGGG | 389 |
| hCPS1-ASO-315 | ATGAATGCAGGCACACACAT | 390 |
| hCPS1-ASO-316 | TGCAGGCACACACATCAGGC | 391 |
| hCPS1-ASO-317 | GCAATGACAAGGTATTTGAT | 487 |
| hCPS1-ASO-318 | GGACTACAAGTTGTTGCAAT | 488 |
| hCPS1-ASO-319 | GTTAGATCAAAGAGTCCTTA | 489 |
| hCPS1-ASO-320 | TTAGTAGAGGGTTAGATCAA | 490 |
| hCPS1-ASO-321 | GTAGAAGGACTTAGTAGAGG | 491 |
| hCPS1-ASO-322 | GTCACACATGAACAATTCTC | 492 |
| hCPS1-ASO-323 | GATGACTGATTTACTTGACA | 493 |
| hCPS1-ASO-324 | TGTATAGTGCAAATGATGAC | 494 |
| hCPS1-ASO-325 | TTTTGTCATCTGTATAGTGC | 495 |
| hCPS1-ASO-326 | TCACATATTCTCTGAACCTA | 496 |
| hCPS1-ASO-327 | TTCTTGGACAAGTCACATAT | 497 |
| hCPS1-ASO-328 | TAATGCCCTGTTCTTGGACA | 498 |
| hCPS1-ASO-329 | CTGTTATGCATTTCCTAATG | 499 |
| hCPS1-ASO-330 | GAATCTAACCCCTGTTATGC | 500 |
| hCPS1-ASO-331 | GGCACAAAAGATCTGGAAT | 501 |
| hCPS1-ASO-332 | GTAATAGTGGGATATACTCT | 502 |
| hCPS1-ASO-333 | AGGCTGTAACAGTGTAATAG | 503 |
| hCPS1-ASO-334 | TTATTACATTCAGCAGGCTG | 504 |
| hCPS1-ASO-335 | GAAAATGTTCAGCACTCATT | 505 |
| hCPS1-ASO-336 | GGTATAAATGATCAACAACC | 506 |
| hCPS1-ASO-337 | GAAAGTTGATATCAAGGGTA | 507 |
| hCPS1-ASO-338 | AGAATTTCAAGGTGCTCTAT | 508 |
| hCPS1-ASO-339 | TTTTACTTACAGGAAAGAGG | 509 |
| hCPS1-ASO-340 | CCAATCGGCACAGTTGTATT | 510 |
| hCPS1-ASO-341 | TAGAGTGCTTTGCCAATCGG | 511 |
| hCPS1-ASO-342 | GCGGCTAATATTTATAGAGT | 512 |
| hCPS1-ASO-343 | GGTATTTGTCAGCGGCTAAT | 513 |
| hCPS1-ASO-344 | TAATTTTATGTGGCCCTTCC | 514 |
| hCPS1-ASO-345 | GCAATGACGCACTTATAATT | 515 |
| hCPS1-ASO-346 | GTTTGACGACAGCAATGACG | 516 |
| hCPS1-ASO-347 | GAGACGGTGGGTTTGACGAC | 517 |
| hCPS1-ASO-348 | TTTGATGACAGAGACGGTGG | 518 |
| hCPS1-ASO-349 | TTCCTCTCTCTTTGATGACA | 519 |
| hCPS1-ASO-350 | AGGTTTGCTTTTCCTCTCTC | 520 |
| hCPS1-ASO-351 | CGACATATTTAGAGGTTTGC | 521 |
| hCPS1-ASO-352 | GGGTTGCTTTTTCGACATAT | 522 |
| hCPS1-ASO-353 | CCTGTAAATTGGGTTGCTTT | 523 |
| hCPS1-ASO-354 | CATCTATAATCATTGCCCTG | 524 |
| hCPS1-ASO-355 | AGACACCCTGTAGTCACATC | 525 |
| hCPS1-ASO-356 | TAGATGGTAAATGGATTGGG | 526 |
| hCPS1-ASO-357 | TATGTCCAGTTATAGATGGT | 527 |
| hCPS1-ASO-358 | AAGGTTAGTAGCATTATGTC | 528 |
| hCPS1-ASO-359 | CAGTCACTTTAAAGGTTAGT | 529 |
| hCPS1-ASO-360 | GTAGTTACATAATGGTCAGT | 530 |
| hCPS1-ASO-361 | ATCATTAGGATGTAGTTACA | 531 |
| hCPS1-ASO-362 | GCCTTCACTTTAAAAACTCA | 532 |
| hCPS1-ASO-363 | ACTTTTCTTCCTGCCTTCAC | 533 |

TABLE 2-continued

Exemplary ASO sequences targeting reqRNAs

| Name | Sequence | SEQ ID NO |
|---|---|---|
| hCPS1-ASO-364 | TAGTCCTCTATCTACTTTTC | 534 |
| hCPS1-ASO-365 | GTTATTGTGAAATAGTCCTC | 535 |
| hCPS1-ASO-366 | GGACTTGTGTTATTATTCAG | 536 |
| hCPS1-ASO-367 | ATTCCATAGAACAGCCCAAG | 537 |
| hCPS1-ASO-368 | GGAGGAATGCCAAGCACAAA | 538 |
| hCPS1-ASO-369 | CCAGAGTTTTGGAGGAATGC | 539 |
| hCPS1-ASO-370 | CAATCATTACTGGCCAGAGT | 540 |
| hCPS1-ASO-371 | GCCATTACTCACACTCAATC | 541 |
| hCPS1-ASO-372 | TCATTTCATGGTGTAAAAGC | 542 |
| hCPS1-ASO-373 | CACTAAGCCATCATTTCATG | 543 |
| hCPS1-ASO-374 | GACAAATTTGTAGGAGCACT | 544 |
| hCPS1-ASO-375 | ACAGTGCACAGCTAAGAATG | 545 |
| hCPS1-ASO-376 | AAGGGTCTGTCACAGTGCAC | 546 |
| hCPS1-ASO-377 | ACAGATCTGTTTCAAGGGTC | 547 |
| hCPS1-ASO-378 | CAGTTCTAGCTCATGGTGAC | 548 |
| hCPS1-ASO-379 | GGATGGATTACTGTGAAAGC | 549 |
| hCPS1-ASO-380 | TGGTCTAATTATGTGGATGG | 550 |
| hCPS1-ASO-381 | CCACGACAAAATGGTCTAAT | 551 |
| hCPS1-ASO-382 | TCCATACAACCACCACCACA | 552 |
| hCPS1-ASO-383 | CAATAAGTGCTCCATACAAC | 553 |
| hCPS1-ASO-384 | GAATCCAATTCTCCAAGATC | 554 |
| hCPS1-ASO-385 | GGCACAGATATGATTGAAAT | 555 |
| hCPS1-ASO-386 | GAGTACTTACTTAAAATGGC | 556 |
| hCPS1-ASO-387 | ACCGCGAAATTGAGTACTTA | 557 |
| hCPS1-ASO-388 | AGACCCCAGAAACCGCGAAA | 558 |
| hCPS1-ASO-389 | GGTGCATCTTCATCAGACCC | 559 |
| hCPS1-ASO-390 | GTAGGTAAGGATAGGTGCAT | 560 |
| hCPS1-ASO-391 | CACTCTGTGAGAAGGTAGGT | 561 |
| hCPS1-ASO-392 | GAATATCTTCTTCTCACTCT | 562 |
| hCPS1-ASO-393 | GGGTGACTTGGAATATCTTC | 563 |
| hCPS1-ASO-394 | TAATACTTCAAAGTTGGGTG | 564 |
| hCPS1-ASO-395 | TATGTGCCATCTAATACTTC | 565 |
| hCPS1-ASO-396 | CCCTATGATTATATGTGCCA | 566 |
| hCPS1-ASO-397 | GTAATGAAAGTTATCCCCTA | 567 |
| hCPS1-ASO-398 | GTACTCATGTATCAGTTCAG | 568 |
| hCPS1-ASO-399 | TTGTTAGTAATACCTCAAGG | 569 |
| hCPS1-ASO-400 | ACTAGATGTAAACTATGAGA | 570 |
| hCPS1-ASO-401 | AGACATTGTAACTAGATGTA | 571 |
| hCPS1-ASO-402 | TAGCAAAAGAATGGGAAAGG | 572 |
| hCPS1-ASO-403 | AAGGTTAGTGGCATTATGTC | 573 |
| hCPS1-ASO-404 | GGAGCAGTCACTAAAGGTTA | 574 |
| hCPS1-ASO-405 | GCACGTATGTTATATAGCCT | 575 |
| hCPS1-ASO-406 | GTAAGCCAGAAAGCACGTAT | 576 |
| hCPS1-ASO-407 | CTTAGAAACATCAGGTAAGC | 577 |
| hCPS1-ASO-408 | AGGCGAACTAATAGCTTAGA | 578 |
| hCPS1-ASO-409 | GGATGAGTACTGAGGCGAAC | 579 |
| hCPS1-ASO-410 | TTCAGTGCTTAGTTCAGATT | 580 |
| hCPS1-ASO-411 | GGCTTTCTACTTTTCAGTGC | 581 |
| hCPS1-ASO-412 | TCTGGCTTAGGCTTTCTAC | 582 |
| hCPS1-ASO-413 | GACAAATTGTGCTGAAATTC | 583 |
| hCPS1-ASO-414 | CCTTGTAACTGCAGAGAAGT | 584 |
| hCPS1-ASO-415 | GAAGTGTTAGGCCTTGTAAC | 585 |
| hCPS1-ASO-416 | GCTGTTACAGTGCTTCAGAA | 586 |
| hCPS1-ASO-417 | ATTGATTACTGCTGTTACAG | 587 |
| hCPS1-ASO-418 | GTGGTAAGGCCTAATTGATT | 588 |
| hCPS1-ASO-419 | AACTGAGAATGTGGTAAGGC | 589 |
| hCPS1-ASO-420 | TAACCAAAGACCGATGACTT | 590 |
| hCPS1-ASO-421 | GGCTTATGTTTAACCAAAGA | 591 |
| hCPS1-ASO-422 | CCCCTTAACATTGGCTTATG | 592 |
| hCPS1-ASO-423 | TAACCTTTTGATTTTGTCCC | 593 |
| hCPS1-ASO-424 | CCTACACTTTATGAACATAC | 594 |
| hCPS1-ASO-425 | GCTCAGTAAGGCATATTAAT | 595 |
| hCPS1-ASO-426 | CTGAACAACTTGCCACATAG | 596 |
| hCPS1-ASO-427 | CTCCAGGATTCTGAACAACT | 597 |
| hCPS1-ASO-428 | TTATGATATGTAGGTTCCTC | 598 |
| hCPS1-ASO-429 | ATTTATCACCACCATACAGT | 599 |
| hCPS1-ASO-430 | GCAGACTGAAATATAAGACC | 600 |
| hCPS1-ASO-431 | CTTCTATAATGCAGACTGAA | 601 |
| hCPS1-ASO-432 | GGTTGCTACATTATGAAAGA | 602 |
| hCPS1-ASO-433 | TGAATCAATAGGGTTGCTAC | 603 |
| hCPS1-ASO-434 | GGTAACTGACTAATTTGAAG | 604 |
| hCPS1-ASO-435 | AAATTTCATAGGGAGGTAAC | 605 |
| hCPS1-ASO-436 | TTCAAGGCTACTCTGTTTGC | 606 |
| hCPS1-ASO-437 | GTGATCTAAATGAGTTGAAC | 607 |
| hCPS1-ASO-438 | GCTTCCATTTGATTTTCTTC | 608 |

TABLE 2-continued

Exemplary ASO sequences targeting reqRNAs

| Name | Sequence | SEQ ID NO |
|---|---|---|
| hCPS1-ASO-439 | CCCTAGGGATCTTTAGCTTC | 609 |
| hCPS1-ASO-440 | GGTCAAAGTTTGTGTTAGGC | 610 |
| hCPS1-ASO-441 | GAGGCCCGAAAAAAGCTGCG | 611 |
| hCPS1-ASO-442 | ATTTGCAATGACGGAGGCCC | 612 |
| hCPS1-ASO-443 | CTTGATGGGATTTGTATTTC | 613 |
| hCPS1-ASO-444 | TACGCTGACTGCCCTTGATG | 614 |
| hCPS1-ASO-445 | GAGGAGTTTGGTATGCTACG | 615 |
| hCPS1-ASO-446 | TCACTTCAAGCCTTCAGGAG | 616 |
| hCPS1-ASO-447 | GGCATGCTAGAATTCACTTC | 617 |
| hCPS1-ASO-448 | TCAGTATCTCTTAGGCAATG | 618 |
| hCPS1-ASO-449 | GGGTGCTGTAGAAAGTTTTC | 619 |
| hCPS1-ASO-450 | CATATTTCCAACCTGTTCCA | 620 |
| hCPS1-ASO-451 | GCCTTTACATCTGTATTAGA | 621 |
| hCPS1-ASO-452 | GACTATTCCTCTGCCTTTAC | 622 |
| hCPS1-ASO-453 | TGCTATGGAAATGGAGACTA | 623 |
| hCPS1-ASO-454 | TAGGTCTTATTGCTATGGAA | 624 |
| hCPS1-ASO-455 | CGATCTAGAGGTGACATTAG | 625 |
| hCPS1-ASO-456 | GACTTTCTGACGATCTAGAG | 626 |
| hCPS1-ASO-457 | ATTTGCTCATGTCTAGCCAG | 627 |
| hCPS1-ASO-458 | CCCTCATTCCAATTTGCTCA | 628 |
| hCPS1-ASO-459 | GTGCTTTCCTCTCCCTCATT | 629 |
| hCPS1-ASO-460 | TAATCTTGACCTGTGCTTTC | 630 |
| hCPS1-ASO-461 | GGACTAGTACTAATCTTGAC | 631 |
| hCPS1-ASO-462 | ACTGCCCAAGGGACTAGTAC | 632 |
| hCPS1-ASO-463 | AGCATTCTGGCTGTAGAACT | 633 |
| hCPS1-ASO-464 | TTGGGTCAGAAGCTAAGCAT | 634 |
| hCPS1-ASO-465 | CAGTACCCTAGTCCCAGCTT | 635 |
| hCPS1-ASO-466 | GCACATCACTCAGTACCCTA | 636 |
| hCPS1-ASO-467 | CTTTGAGAGTTAGGCCCTAA | 637 |
| hCPS1-ASO-468 | TAGTGTCATGGTGTATCTCT | 638 |
| hCPS1-ASO-469 | AGGAGGCTGTCACTGTTAGT | 639 |
| hCPS1-ASO-470 | GAGTGAGGTACCTGAGATGC | 640 |
| hCPS1-ASO-471 | CTAGGTTAAGTGAGTGAGGT | 641 |
| hCPS1-ASO-472 | GTTTAAATGTCCTAGACTAG | 642 |
| hCPS1-ASO-473 | GAGCTTCTTGACATAAAACT | 643 |
| hCPS1-ASO-474 | CAACGCCTTGACATTATGAG | 644 |
| hCPS1-ASO-475 | TAGTCACCAACAACGCCTTG | 645 |
| hCPS1-ASO-476 | AGATGGCCTTTCTTTTGAAC | 646 |
| hCPS1-ASO-477 | TCTAATTGGGAGATGGCCTT | 647 |
| hCPS1-ASO-478 | GCAATACTTCTCTAATTGGG | 648 |
| hCPS1-ASO-479 | TACTTTTGGCATGCAATACT | 649 |
| hCPS1-ASO-480 | GATGGACAACTTTACATACT | 650 |
| hCPS1-ASO-481 | AATTAGTTTGCCTGATGGAC | 651 |
| hCPS1-ASO-482 | GAGCTGTTGCAGAATTAGTT | 652 |
| hCPS1-ASO-483 | AGTCCCAAATGAGCTGTTGC | 653 |
| hCPS1-ASO-484 | TTAATTGTGTTCAGTCCCAA | 654 |
| hCPS1-ASO-485 | CATCTATGGCAAACTACATT | 655 |
| hCPS1-ASO-486 | GGACGGATTTCATCTATGGC | 656 |
| hCPS1-ASO-487 | TATAGACACATTTTAGGACG | 657 |
| hCPS1-ASO-488 | GGTTATCACACACTTTTAAG | 658 |
| hCPS1-ASO-489 | GTACACGTTAGATGTAAGAG | 659 |
| hCPS1-ASO-490 | TATTGGAGCCTCTGTACACG | 660 |
| hCPS1-ASO-491 | CTCATTATCATATTGGAGCC | 661 |
| hCPS1-ASO-492 | GTCACAGGAAATATAACTCA | 662 |

TABLE 3

Additional Chemical Modifications of selected hCPS1-ASOs
Key: MOE (M); DNA (d); LNA (L); PS (=); PO(-); 5-MethylCytosine (5C); GalNAc (ag); Teg-GalNAc (TEG); cET (c); AlaGal-GalNAc (AlGal); cholesterol (CholTEG)

| SEQ ID NO | Name | Sequence |
|---|---|---|
| 16 | hCPS1-ASO-1a | MT=.MG=.M5C=.MA=.MG=.dG=.dC=.dA=.dC=.dA=.dC=.dA=.dC=.dA=.dT=.M5C=.MA=.MG=.MG=.M5C |
| 17 | hCPS1-ASO-1b | MT=.MG=.M5C=.MA=.MG=.MG=.M5C=.MA=.M5C=.MA=.M5C=.MA=.M5C=.MA=.MT=.M5C=.MA=.MG=.MG=.M5C |

TABLE 3-continued

Additional Chemical Modifications of selected hCPS1-ASOs
Key: MOE (M); DNA (d); LNA (L); PS (=); PO(-); 5-MethylCytosine (5C); GalNAc (ag); Teg-GalNAc (TEG); cET (c); AlaGal-GalNAc (AlGal); cholesterol (CholTEG)

| SEQ ID NO | Name | Sequence |
|---|---|---|
| 18 | hCPS1-ASO-1c | MT=.MG=.M5C=.MA=.MG=.dG=.dC=.dA=.M5C=.dA=.dC=.MA=.dC=.dA=.dT=.M5C=.MA=.MG=.MG=.M5C |
| 19 | ASO-1d | MT=.MG=.M5C=.MA=.MG=.LG=.dC=.dA=.L5C=.dA=.dC=.LA=.dC=.dA=.LT=.M5C=.MA=MG=.MG=.M5C |
| 20 | hCPS1-ASO-1e | MT=.MG=.M5C=.LA=.MG=.dG=.dC=.LA=.dC=.dA=.dC=.LA=.dC=.dA=.dT=.L5C=.MA=.MG=.MG=.M5C |
| 21 | hCPS1-ASO-1f | MT=.MG=.M5C=.MA=.LG=.dG=.dC=.dA=.L5C=.dA=.dC=.dA=.L5C=.dA=.dT=.M5C=.LA=.MG=.MG=.M5C |
| 22 | hCPS1-ASO-1g | MT=.MG=.M5C-.MA-.MG=.dG=.dC=.dA=.dC=.dA=.dC=.dA=.dC=.dA=.dT=.M5C-.MA-MG=.MG=.M5C |
| 23 | hCPS1-ASO-2 | MA=.MT=.MG=.M5C=.MA=.MG=.dG=.dC=.dA=.dC=.dA=.dC=.dA=.dC=.dA=.dT=.M5C=.MA=.MG=.MG=.M5C=.MT |
| 24 | hCPS1-ASO-3 | MA=.MA=.MT=.MG=.M5C=.MA=.MG=.dG=.dC=.dA=.dC=.dA=.dC=.dA=.dC=.dA=.dT=.M5C=.MA=.MG=.MG=.M5C=.MT=.MG |
| 392 | hCPS1-ASO-81a | MT=.MG=.M5C=.MA=.MG=.LG=.M5C=.MA=.L5C=.MA=.M5C=.LA=.M5C=.MA=.LT=.M5C=.MA=.MG=.MG=.M5C |
| 393 | hCPS1-ASO-81b | MT=.MG=.M5C=.LA=.MG=.LG=.M5C=.LA=.M5C=.LA=.M5C=.LA=.M5C=.LA=.MT=.L5C=.MA=.LG=.MG=.M5C |
| 394 | hCPS1-ASO-81c | MT=.MG=.L5C=.MA=.LG=.MG=.L5C=.MA=.L5C=.MA=.L5C=.MA=.L5C=.MA=.LT=.M5C=.LA=.MG=.MG=.M5C |
| 395 | hCPS1-ASO-81d | MT=.MG=.L5C=.MA=.MG=.LG=.M5C=.MA=.L5C=.MA=.M5C=.LA=.M5C=.MA=.LT=.M5C=.MA=.LG=.MG=.M5C |
| 396 | hCPS1-ASO-81e | MT=.MG=.M5C=.MA=.LG=.MG=.M5C=.MA=.M5C=.MA=.L5C=.MA=.M5C=.MA=.MT=.M5C=.LA=.MG=.MG=.M5C |
| 397 | hCPS1-ASO-81f | MT=.MG=.M5C=.LA=.MG=.MG=.M5C=.LA=.M5C=.MA=.M5C=.LA=.M5C=.MA=.MT=.L5C=.MA=.MG=.MG=.M5C |
| 398 | hCPS1-ASO-81g | MT=.MG=.M5C=.MA=.AlGal.LG=.M5C=.MA=.M5C=.MA=.L5C=.MA=.M5C=.MA=.MT=.L5C=.MA=.MG=.MG=.M5C |
| 399 | hCPS1-ASO-81h | MT=.MG=.M5C=.MA=.LG=.MG=.M5C=.MA=.M5C=.LA=.M5C=.MA=.M5C=.MA=.LT=.M5C=.MA=.MG=.MG=.M5C |
| 400 | hCPS1-ASO-81i | LT=.MG=.L5C=.MA=.LG=.dG=.dC=.dA=.dC=.dA=.dC=.dA=.dC=.dA=.dT=.L5C=.MA=.LG=.MG=.L5C |
| 401 | hCPS1-ASO-81j | LT=.MG=.L5C=.MA=.LG=.MG=.M5C=.MA=.M5C=.MA=.M5C=.MA=.M5C=.MA=.MT=.L5C=.MA=.LG=.MG=.L5C |
| 402 | hCPS1-ASO-81k | MT=.MG=.M5C=.MA=.MG=.MG=.dC=.dA=.M5C=.dA=.dC=.MA=.dC=.dA=.MT=.M5C=.MA=.MG=.MG=.M5C |
| 403 | hCPS1-ASO-81l | MT=.MG=.M5C=.MA-.MG=.dG=.d5C=.dA=.d5C=.dA=.d5C=.dA=.d5C=.dA=.dT=.M5C-MA=.MG=.MG=.M5C |

TABLE 3-continued

Additional Chemical Modifications of selected hCPS1-ASOs
Key: MOE (M); DNA (d); LNA (L); PS (=); PO (-); 5-MethylCytosine (5C); GalNAc (ag); Teg-GalNAc (TEG); cET (c); AlaGal-GalNAc (AlGal); cholesterol (CholTEG)

| SEQ ID NO | Name | Sequence |
|---|---|---|
| 404 | hCPS1-ASO-81m | MT=.MG=.M5C-.MA-.MG=.dG=.d5C=.dA=.d5C=.dA=.d5C=.dA=.dT=.M5C-.MA-.MG=.MG=.M5C |
| 405 | hCPS1-ASO-81n | MT=.MG-.M5C-.MA-.MG=.dG=.d5C=.dA=.d5C=.dA=.d5C=.dA=.dT=.M5C-.MA-.MG-.MG=.M5C |
| 406 | hCPS1-ASO-81o | MT-.MG-.M5C-.MA-.MG=.dG=.d5C=.dA=.d5C=.dA=.d5C=.dA=.dT=.M5C-.MA-.MG-.MG-.M5C |
| 407 | hCPS1-ASO-82a | MT=.MG=.M5C-.MA=.MG=.MG=.dC=.dA=.dC=.dA=.dC=.dA=.dC=.dA=.dT=.dC=.MA=.MG=.MG=.M5C=.MT=.MG |
| 408 | hCPS1-ASO-86a | MT=.MG=.L5C=.MA=.LG=.dG=.dC=.dA=.dC=.dA=.dC=.dA=.dC=.dA=.dT=.L5C=.MA=.LG=.MG=.M5C |
| 409 | hCPS1-ASO-86b | MT=.MG=.M5C-.MA-.MG=.dG=.d5C=.dA=.d5C=.dA=.d5C=.dA=.d5C=.dA=.dT=.M5C-.MA-.MG=.MG=.M5C-.[TEG] |
| 410 | hCPS1-ASO-87a | MT=.MG=.M5C-.MA-.MG=.dG=.dC=.dA=.dC=.dA=.dC=.dA=.dC=.dA=.dT=.M5C-.MA-.MG=.MG |
| 411 | hCPS1-ASO-88a | MT=.MG=.M5C-.MA-.MG=.dG=.dC=.dA=.dC=.dA=.dC=.dA=.dC=.dA=.dT=.M5C-.MA-.MG |
| 412 | hCPS1-ASO-89a | MT=.MG=.M5C-.MA-.MG=.dG=.dC=.dA=.dC=.dA=.dC=.dA=.dC=.dA=.dT |
| 414 | hCPS1-ASO-91a | MT=.MG=.M5C-.MA-.MG=.dG=.d5C=.dA=.d5C=.dA=.d5C=.dA=.d5C=.dA=.dT=.M5C-.MA-.MG=.MG=.M5C-.[AlGal] |
| 415 | hCPS1-ASO-91b | MT=.MG=.M5C-.MA-.MG-.dG-.d5C-.dA-.d5C-.dA-.d5C-.dA-.d5C-.dA-.dT-.M5C-.MA-.MG=.MG=.M5C-.[TEG] |
| 416 | hCPS1-ASO-91c | dT=.dG=.d5C=.dA=.dG=.dG=.d5C=.dA=.d5C=.dA=.d5C=.dA=.d5C=.dA=.dT=.d5C=.dA=.dG=.dG=.d5C-.[TEG] |
| 417 | hCPS1-ASO-91d | CholTEG-.MT=.MG=.M5C=.MA=.MG=.dG=.d5C=.dA=.d5C=.dA=.d5C=.dA=.d5C=.dA=.dT=.M5C=.MA=.MG=.MG=.M5C |
| 418 | hCPS1-ASO-91e | CholTEG-.MT=.MG=.M5C=.MA-.MG=.dG=.d5C=.dA=.d5C=.dA=.d5C=.dA=.d5C=.dA=.dT=.M5C-.MA=.MG=.MG=.M5C |
| 419 | hCPS1-ASO-91f | CholTEG-.MT=.MG=.M5C-.MA-.MG=.dG=.d5C=.dA=.d5C=.dA=.d5C=.dA=.d5C=.dA=.dT=.M5C-.MA-.MG=.MG=.M5C |
| 420 | hCPS1-ASO-91g | CholTEG-.MT-.MG=.M5C-.MA-.MG=.dG=.d5C=.dA=.d5C=.dA=.d5C=.dA=.d5C=.dA=.dT=.M5C-.MA-.MG-.MG-.M5C |
| 421 | hCPS1-ASO-91h | CholTEG-.MT=.MG=.M5C=.MA=.MG=.dG=.d5C=.dA=.d5C=.dA=.d5C=.dA=.d5C=.dA=.dT=.M5C=.MA=.MG=.MG=.M5C |
| 422 | hCPS1-ASO-91i | CholTEG-.MT=.MG=.M5C=.MA-.MG=.dG=.d5C=.dA=.d5C=.dA=.d5C=.dA=.d5C=.dA=.dT=.M5C-.MA=.MG=.MG=.M5C |

TABLE 3-continued

Additional Chemical Modifications of selected hCPS1-ASOs
Key: MOE (M); DNA (d); LNA (L); PS (=); PO(-); 5-MethylCytosine (5C); GalNAc (ag); Teg-GalNAc (TEG); cET (c); AlaGal-GalNAc (AlGal); cholesterol (CholTEG)

| SEQ ID NO | Name | Sequence |
|---|---|---|
| 423 | hCPS1-ASO-91j | CholTEG=.MT=.MG=.M5C=.MA-.MG=.dG=.d5C=.dA=.d5C=.dA=.d5C=.dA=.d5C=.dA=.dT=.M5C=.MA-.MG=.MG=.M5C |
| 424 | hCPS1-ASO-91k | CholTEG=.MT-.MG-.M5C-.MA-MG=.dG=.d5C=.dA=.d5C=.dA=.d5C=.dA=.d5C=.dA=.dT=.M5C-.MA-.MG-.MG-.M5C |
| 425 | hCPS1-ASO-97a | cA=.cA=.cT=.dG=.d5C=.dA=.dG=.dG=.d5C=.dA=.d5C=.dA=.d5C=.cA=.c5C=.cA |
| 426 | hCPS1-ASO-98a | cT=.cG=.cA=.dA=.dT=.dG=.d5C=.dA=.dG=.dG=.d5C=.dA=.d5C=.cA=.c5C=.cA |
| 427 | hCPS1-ASO-99a | c5C=.cA=.cT=.dG=.dA=.dA=.dT=.dG=.d5C=.dA=.dG=.dG=.d5C=.cA=.c5C=.cA |
| 428 | hCPS1-ASO-100a | cT=.cG=.c5C=.dA=.dG=.dG=.d5C=.dA=.d5C=.dA=.d5C=.dA=.d5C=.cA=.cT=.c5C |
| 429 | hCPS1-ASO-101a | c5C=.cA=.cG=.dG=.d5C=.dA=.d5C=.dA=.d5C=.dA=.d5C=.dA=.dT=.c5C=.cA=.cG |
| 430 | hCPS1-ASO-102a | cG=.cG=.c5C=.dA=.d5C=.dA=.d5C=.dA=.d5C=.dA=.dT=.d5C=.dA=.cG=.cG=.c5C |
| 431 | hCPS1-ASO-103a | c5C=.cA=.c5C=.dA=.d5C=.dA=.d5C=.dA=.dT=.d5C=.dA=.dG=.dG=.c5C=.cT=.cG |
| 432 | hCPS1-ASO-104a | c5C=.cA=.c5C=.dA=.d5C=.dA=.dT=.d5C=.dA=.dG=.dG=.d5C=.dT=.cG=.cG=.cG |
| 433 | hCPS1-ASO-105a | MT-.MG-.M5C-.MA-.MG-.dG-.d5C-.dA-.d5C-.dA-.d5C-.dA-.d5C-.dA-.dT-.M5C-.MA-.MG-MG-.M5C-.dT-.dT-.dT-.dT-.dT-dT-dT-dT-dT-dT-[BioTEG] |
| 434 | hCPS1-ASO-106a | [BioTEG]P.dT-.dT-.dT-.dT-.dT-.dT-.dT-dT-dT-dT-MT-MG-.M5C-.MA-MG-.dG-.d5C-.dA-.d5C-.dA-.d5C-.dA-.d5C-.dA-.dT-.M5C-.MA-.MG-.MG-.M5C |
| 435 | hCPS1-ASO-279a | cG=.cG=.c5C=.dA=.dT=.dG=.dA=.dA=.dT=.dG=.d5C=.dA=.dG=.cG=.c5C=.cA |
| 436 | hCPS1-ASO-280a | c5C=.cA=.cG=.dG=.d5C=.dA=.dT=.dG=.dA=.dA=.dT=.dG=.d5C=.cA=.cG=.cG |
| 437 | hCPS1-ASO-281a | cG=.cA=.c5C=.dA=.dG=.dA=.dT=.dG=.dA=.dA=.dT=.cG=.c5C=.cA |
| 438 | hCPS1-ASO-282a | cG=.cT=.cG=.dA=.d5C=.dA=.dG=.dG=.d5C=.dA=.dT=.dG=.dA=.cA=.cT=.cG |
| 439 | hCPS1-ASO-283a | c5C=.cA=.c5C=.dA=.dT=.d5C=.dA=.dG=.dG=.d5C=.dT=.dG=.dG=.cG=.cG=.cA |
| 440 | hCPS1-ASO-284a | c5C=.cA=.cT=.d5C=.dA=.dG=.dG=.d5C=.dT=.dG=.dG=.dG=.dG=.cA=.c5C=.c5C |

TABLE 3-continued

Additional Chemical Modifications of selected hCPS1-ASOs
Key: MOE (M); DNA (d); LNA (L); PS (=); PO(-); 5-MethylCytosine (5C); GalNAc (ag); Teg-GalNAc
(TEG); cET (c); AlaGal-GalNAc (AlGal); cholesterol (CholTEG)

| SEQ ID NO | Name | Sequence |
|---|---|---|
| 441 | hCPS1-ASO-285a | cT=.c5C=.cA=.dG=.dG=.d5C=.dT=.dG=.dG=.dG=.dG=.dA=.d5C=.c5C=.c5C=.cT |
| 442 | hCPS1-ASO-286a | cA=.cG=.cG=.d5C=.dT=.dG=.dG=.dG=.dG=.dA=.d5C=.d5C=.d5C=.cT=.cG=.cT |
| 443 | hCPS1-ASO-287a | L5C=.LA=.LT=.dG=.dA=.dA=.dT=.dG=.d5C=.dA=.dG=.d5C=.LA=.L5C=.LA |
| 444 | hCPS1-ASO-288a | LT=.LG=.LA=.dA=.dT=.dG=.d5C=.dA=.dG=.d5C=.dA=.d5C=.LA=.L5C=.LA |
| 445 | hCPS1-ASO-289a | LA=.LA=.LT=.dG=.d5C=.dA=.dG=.dG=.dA=.d5C=.dA=.d5C=.LA=.L5C=.LA |
| 446 | hCPS1-ASO-290a | LT=.LG=.L5C=.dA=.dG=.dG=.d5C=.dA=.d5C=.dA=.d5C=.dA=.d5C=.LA=.LT=.L5C |
| 447 | hCPS1-ASO-291a | L5C=.LA=.LG=.dG=.d5C=.dA=.d5C=.dA=.d5C=.dA=.dA=.dT=.L5C=.LA=.LG |
| 448 | hCPS1-ASO-292a | LG=.LG=.L5C=.dA=.d5C=.dA=.d5C=.dA=.d5C=.dA=.dT=.dA=.LG=.LG=.L5C |
| 449 | hCPS1-ASO-293a | L5C=.LA=.L5C=.dA=.d5C=.dA=.dT=.d5C=.dA=.dG=.d5C=.LT=.LG |
| 450 | hCPS1-ASO-294a | L5C=.LA=.L5C=.dA=.d5C=.dA=.dT=.d5C=.dA=.dG=.dG=.d5C=.dT=.LG=.LG |
| 451 | hCPS1-ASO-295a | LG=.LG=.L5C=.dA=.dT=.dG=.dA=.dA=.dT=.dG=.d5C=.dA=.dG=.LG=.L5C=.LA |
| 452 | hCPS1-ASO-296a | L5C=.LA=.LG=.dG=.d5C=.dA=.dT=.dG=.dA=.dA=.dT=.dG=.d5C=.LA=.LG=.LG |
| 453 | hCPS1-ASO-297a | LG=.LA=.L5C=.dA=.dG=.dG=.d5C=.dA=.dT=.dG=.dA=.dA=.dT=.LG=.L5C=.LA |
| 454 | hCPS1-ASO-298a | LG=.LT=.LG=.dA=.d5C=.dA=.dG=.dG=.d5C=.dA=.dT=.dG=.dA=.LA=.LT=.LG |
| 455 | hCPS1-ASO-299a | L5C=.LA=.L5C=.dA=.dT=.d5C=.dA=.dG=.d5C=.dT=.dG=.dG=.LG=.LG=.LA |
| 456 | hCPS1-ASO-300a | L5C=.LA=.LT=.d5C=.dA=.dG=.dG=.d5C=.dT=.dG=.dG=.dG=.dG=.LA=.L5C=.L5C |
| 457 | hCPS1-ASO-301a | LT=.L5C=.LA=.dG=.dG=.d5C=.dT=.dG=.dG=.dG=.dG=.dA=.d5C=.L5C=.L5C=.LT |
| 458 | hCPS1-ASO-302a | LA=.LG=.LG=.d5C=.dT=.dG=.dG=.dG=.dG=.dA=.d5C=.d5C=.d5C=.LT=.LG=.LT |

TABLE 3-continued

Additional Chemical Modifications of selected hCPS1-ASOs
Key: MOE (M); DNA (d); LNA (L); PS (=); PO (-); 5-MethylCytosine (5C); GalNAc (ag); Teg-GalNAc
(TEG); cET (c); AlaGal-GalNAc (AlGal); cholesterol (CholTEG)

| SEQ ID NO | Name | Sequence |
|---|---|---|
| 459 | hCPS1-ASO-303a | MG=.M5C=.MA=.MT=.dG=.dA=.dA=.dT=.dG=.d5C=.dA=.dG=.dG=.d5C=.MA=.M5C=.MA=.M5C |
| 460 | hCPS1-ASO-303b | LG=.M5C=.LA=.MT=.dG=.dA=.dA=.dT=.dG=.d5C=.dA=.dG=.dG=.d5C=.MA=.L5C=.MA=.L5C |
| 461 | hCPS1-ASO-304a | MG=.M5C=.MA=.M5C=.dA=.d5C=.dA=.d5C=.dA=.dT=.d5C=.dA=.dG=.dG=.M5C=.MT=.MG=.MG |
| 462 | hCPS1-ASO-304b | LG=.M5C=.LA=.M5C=.dA=.d5C=.dA=.d5C=.dA=.dT=.d5C=.dA=.dG=.dG=.M5C=.LT=.MG=.LG |
| 463 | hCPS1-ASO-305a | MA=.M5C=.MA=.M5C=.dA=.d5C=.dA=.dT=.d5C=.dA=.dG=.dG=.dT=.MG=.MG=.MG |
| 464 | hCPS1-ASO-305b | LA=.M5C=.LA=.M5C=.dA=.d5C=.dA=.dT=.d5C=.dA=.dG=.dG=.dT=.MG=.LG=.MG=.LG |
| 465 | hCPS1-ASO-306a | L5C=.MA=.M5C=.MA=.d5C=.dA=.d5C=.dA=.dT=.d5C=.dA=.dG=.dG=.d5C=.MT=.MG=.MG=.LG |
| 466 | hCPS1-ASO-306b | L5C=.MA=.L5C=.MA=.d5C=.dA=.d5C=.dA=.dT=.d5C=.dA=.dG=.dG=.d5C=.MT=.LG=.MG=.LG |
| 467 | hCPS1-ASO-307a | MG=.MG=.M5C=.MA=.MT=.dG=.dA=.dA=.dT=.dG=.d5C=.dA=.dG=.dG=.d5C=.MA=.M5C=.MA=.M5C=.MA |
| 468 | hCPS1-ASO-307b | LG=.MG=.L5C=.MA=.MT=.dG=.dA=.dA=.dT=.dG=.d5C=.dA=.dG=.dG=.d5C=.MA=.M5C=.LA=.M5C=.LA |
| 469 | hCPS1-ASO-308a | LG=.MG=.L5C=.MA=.MT=.dG=.dA=.dA=.LT=.dG=.d5C=.LA=.dG=.dG=.d5C=.MA=.M5C=.LA=.M5C=.LA |
| 470 | hCPS1-ASO-308b | MG=.MG=.M5C=.MA-.MT-.dG=.dA=.dA=.dT=.dG=.d5C=.dA=.dG=.dG=.d5C=.MA-.M5C-.MA=.M5C=.MA |
| 471 | hCPS1-ASO-309a | LG=.MG=.L5C=.MA=.M5C=.dA=.d5C=.dA=.d5C=.dA=.dT=.d5C=.dA=.dG=.dG=.M5C=.MT=.LG=.MG=.LG |
| 472 | hCPS1-ASO-309b | LG=.MG=.L5C=.MA=.M5C=.dA=.d5C=.dA=.L5C=.dA=.dT=.L5C=.dA=.dG=.dG=.M5C=.MT=.LG=.MG=.LG |
| 473 | hCPS1-ASO-309c | MG=.MG=.M5C=.MA-.M5C-.dA=.d5C=.dA=.d5C=.dA=.dT=.d5C=.dA=.dG=.dG=.M5C-.MT-.MG=.MG=.MG |
| 474 | hCPS1-ASO-310a | M5C=.MA=.M5C=.MA=.M5C=.dA=.d5C=.dA=.dT=.d5C=.dA=.dG=.dG=.d5C=.dT=.MG=.MG=.MG=.MG=.MA |
| 475 | hCPS1-ASO-310b | L5C=.MA=.L5C=.MA=.M5C=.dA=.d5C=.dA=.dT=.d5C=.dA=.dG=.dG=.d5C=.dT=.MG=.MG=.LG=.MG=.LA |
| 476 | hCPS1-ASO-310c | L5C=.MA=.L5C=.MA=.M5C=.dA=.d5C=.dA=.LT=.d5C=.dA=.LG=.dG=.d5C=.dT=.MG=.MG=.LG=.MG=.LA |

TABLE 3-continued

Additional Chemical Modifications of selected hCPS1-ASOs
Key: MOE (M); DNA (d); LNA (L); PS (=); PO(-); 5-MethylCytosine (5C); GalNAc (ag); Teg-GalNAc
(TEG); cET (c); AlaGal-GalNAc (AlGal); cholesterol (CholTEG)

| SEQ ID NO | Name | Sequence |
|---|---|---|
| 477 | hCPS1-ASO-310d | M5C=.MA=.M5C=.MA-.M5C-.dA=.d5C=.dA=.dT=.d5C=.dA=.dG=.dG=.d5C=.dT=.MG-MG-.MG=.MG=.MA |
| 478 | hCPS1-ASO-311a | MG=.M5C=.MA=.M5C=.MA=.d5C=.dA=.d5C=.dA=.dT=.d5C=.dA=.dG=.dG=.d5C=.MT=.MG=.MG=.MG=.MG |
| 479 | hCPS1-ASO-311b | LG=.M5C=.LA=.M5C=.MA=.d5C=.dA=.d5C=.dA=.dT=.d5C=.dA=.dG=.dG=.d5C=.MT=.MG=.LG=.MG=.LG |
| 480 | hCPS1-ASO-311c | MG=.M5C=.MA=.M5C=.MA-.d5C=.dA=.d5C=.dA=.dT=.d5C=.dA=.dG=.dG=.d5C=.MT-MG-.MG=.MG=.MG |
| 481 | hCPS1-ASO-312a | dT=.dG=.d5C=.dA=.dG=.dG=.d5C=.dA=.d5C=.dA=.d5C=.dA=.d5C=.dA=.dT=.d5C=.dA=.dG=.dG=.d5C |
| 482 | hCPS1-ASO-313a | MA=.MT=.M5C=.MA=.MG=.dG=.d5C=.dT=.dG=.dG=.dG=.dG=.dA=.d5C=.d5C=.M5C=.MT=.MG=.MT=.MG-.[TEG] |
| 483 | hCPS1-ASO-314a | MG=.MG=.M5C=.MA=.M5C=.dA=.d5C=.dA=.d5C=.dA=.dT=.d5C=.dA=.dG=.dG=.M5C=.MT=.MG=.MG=.MG-.[TEG] |
| 484 | hCPS1-ASO-315a | MA=.MT=.MG=.MA=.MA=.dT=.dG=.d5C=.dA=.dG=.dG=.d5C=.dA=.d5C=.dA=.M5C=.MA=.M5C=.MA=.MT-.[TEG] |
| 485 | hCPS1-ASO-316a | MT=.MG=.M5C=.MA=.MG=.dG=.d5C=.dA=.d5C=.dA=.d5C=.dA=.d5C=.dA=.dT=.M5C=.MA=.MG=.MG=.M5C-.[TEG] |
| 486 | hCPS1-ASO-316b | MT=.MG=.M5C=.MA-.MG=.dG=.mC=.dA=.d5C=.dA=.d5C=.dA=.d5C=.dA=.dT=.M5C=.MA-MG=.MG=.M5C-.[TEG] |

In some embodiments, hCPS1-ASO-317-492 (SEQ ID NOs: 487-662) comprise pS bonds, 5-MethylCytosines and fully MOE nucleotides.

Hybridization and ΔG

The term "hybridizing" or "hybridizes" as used herein is to be understood as two nucleic acid strands (e.g., an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy ΔG° is a more accurate representation of binding affinity and is related to the dissociation constant ($K_d$) of the reaction by ΔG°=−RTln($K_d$), where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the free energy associated with a reaction where aqueous concentrations are 1M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, Chem, Comm. 36-38 and Holdgate et al., 2005, Drug Discov Today. The skilled person will know that commercial equipment is available for ΔG° measurements. ΔG° can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides of the present disclosure hybridize to a target nucleic acid with estimated ΔG° values below −10 kcal/mol for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal/mol, such as below −15 kcal/mol, such as below −20 kcal/mol and such as below −25 kcal/mol for oligonucleotides that are 8-30 nucleotides in length. In some embodiments the oligonucleotides hybridize to a target nucleic acid with an estimated ΔG° value of −10 to −60 kcal/mol, such as −12 to −40 kcal/mol, −15 to −30 kcal/mol, −16 to −27 kcal/mol, or −18 to −25 kcal/mol.

Duplex Region

The phrase "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex region" has 19 base pairs. The remaining bases may, for example, exist as 5' and 3' overhangs. Further, within the duplex region, 100% complementarity is not required; substantial complementarity is allowable within a duplex region. Substantial complementarity refers to 70% or greater complementarity. For example, a mismatch in a duplex region consisting of 19 base pairs results in 94.7% complementarity, rendering the duplex region substantially complementary. Duplex regions can be formed by two separate oligonucleotide strands, as well as by single oligonucleotide strands that can form hairpin structures comprising a duplex region.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of a CPS1 regRNA, such as an eRNA or paRNA. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides. Generally, the duplex structure is between 15 and 50 base pairs in length, e.g., between, 15-50, 15-49, 15-48, 15-47, 15-46, 15-45, 15-44, 15-43, 15-42, 15-41, 15-40, 15-39, 15-38, 15-37, 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 18-50, 18-49, 18-48, 18-47, 18-46, 18-45, 18-44, 18-43, 18-42, 18-41, 18-40, 18-39, 18-38, 18-37, 18-36, 18-35, 18-34, 18-33, 18-32, 18-31, 18-30, 18-30, 18-29, 18-28, 18-27, 18-26, 18-25, 18-24, 18-23, 18-22, 18-21, 18-20, 19-50, 19-49, 19-48, 19-47, 19-46, 19-45, 19-44, 19-43, 19-42, 19-41, 19-40, 19-39, 19-38, 19-37, 19-36, 19-35, 19-34, 19-33, 19-32, 19-31, 19-30, 19-30, 19-29, 19-28, 19-27, 19-26, 19-25, 19-24, 19-23, 19-22, 19-21, 19-20, 20-50, 20-49, 20-48, 20-47, 20-46, 20-45, 20-44, 20-43, 20-42, 20-41, 20-40, 20-39, 20-38, 20-37, 20-36, 20-35, 20-34, 20-33, 20-32, 20-31, 20-30, 20-30, 20-29, 20-28, 20-27, 20-26, 20-25, 20-24, 20-23, 20-22, 20-21, 21-50, 21-49, 21-48, 21-47, 21-46, 21-45, 21-44, 21-43, 21-42, 21-41, 21-40, 21-39, 21-38, 21-37, 21-36, 21-35, 21-34, 21-33, 21-32, 21-31, 21-30, 21-29, 21-28, 21-27, 21-26, 21-25, 21-24, 21-23, 21-22, 22-50, 22-49, 22-48, 22-47, 22-46, 22-45, 22-44, 22-43, 22-42, 22-41, 22-40, 22-39, 22-38, 22-37, 22-36, 22-35, 22-34, 22-33, 22-32, 22-31, 22-30, 22-29, 22-28, 22-27, 22-26, 22-25, 22-24, 22-23, 23-50, 23-49, 23-48, 23-47, 23-46, 23-45, 23-44, 23-43, 23-42, 23-41, 23-40, 23-39, 23-38, 23-37, 23-36, 23-35, 23-34, 23-33, 23-32, 23-31, 23-30, 23-29, 23-28, 23-27, 23-26, 23-25, or 23-24 base pairs in length. Ranges and lengths intermediate to the above recited ranges and lengths are also contemplated to be part of the disclosure.

Similarly, the region of complementarity to the target sequence can be between 15 and 50 nucleotides in length, e.g., between 15-50, 15-49, 15-48, 15-47, 15-46, 15-45, 15-44, 15-43, 15-42, 15-41, 15-40, 15-39, 15-38, 15-37, 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 18-50, 18-49, 18-48, 18-47, 18-46, 18-45, 18-44, 18-43, 18-42, 18-41, 18-40, 18-39, 18-38, 18-37, 18-36, 18-35, 18-34, 18-33, 18-32, 18-31, 18-30, 18-30, 18-29, 18-28, 18-27, 18-26, 18-25, 18-24, 18-23, 18-22, 18-21, 18-20, 19-50, 19-49, 19-48, 19-47, 19-46, 19-45, 19-44, 19-43, 19-42, 19-41, 19-40, 19-39, 19-38, 19-37, 19-36, 19-35, 19-34, 19-33, 19-32, 19-31, 19-30, 19-30, 19-29, 19-28, 19-27, 19-26, 19-25, 19-24, 19-23, 19-22, 19-21, 19-20, 20-50, 20-49, 20-48, 20-47, 20-46, 20-45, 20-44, 20-43, 20-42, 20-41, 20-40, 20-39, 20-38, 20-37, 20-36, 20-35, 20-34, 20-33, 20-32, 20-31, 20-30, 20-30, 20-29, 20-28, 20-27, 20-26, 20-25, 20-24, 20-23, 20-22, 20-21, 21-50, 21-49, 21-48, 21-47, 21-46, 21-45, 21-44, 21-43, 21-42, 21-41, 21-40, 21-39, 21-38, 21-37, 21-36, 21-35, 21-34, 21-33, 21-32, 21-31, 21-30, 21-29, 21-28, 21-27, 21-26, 21-25, 21-24, 21-23, 21-22, 22-50, 22-49, 22-48, 22-47, 22-46, 22-45, 22-44, 22-43, 22-42, 22-41, 22-40, 22-39, 22-38, 22-37, 22-36, 22-35, 22-34, 22-33, 22-32, 22-31, 22-30, 22-29, 22-28, 22-27, 22-26, 22-25, 22-24, 22-23, 23-50, 23-49, 23-48, 23-47, 23-46, 23-45, 23-44, 23-43, 23-42, 23-41, 23-40, 23-39, 23-38, 23-37, 23-36, 23-35, 23-34, 23-33, 23-32, 23-31, 23-30, 23-29, 23-28, 23-27, 23-26, 23-25, or 23-24 nucleotides in length. Ranges and lengths intermediate to the above recited ranges and lengths are also contemplated to be part of the disclosure.

Chemical Modifications of ASOs

Figure 14:
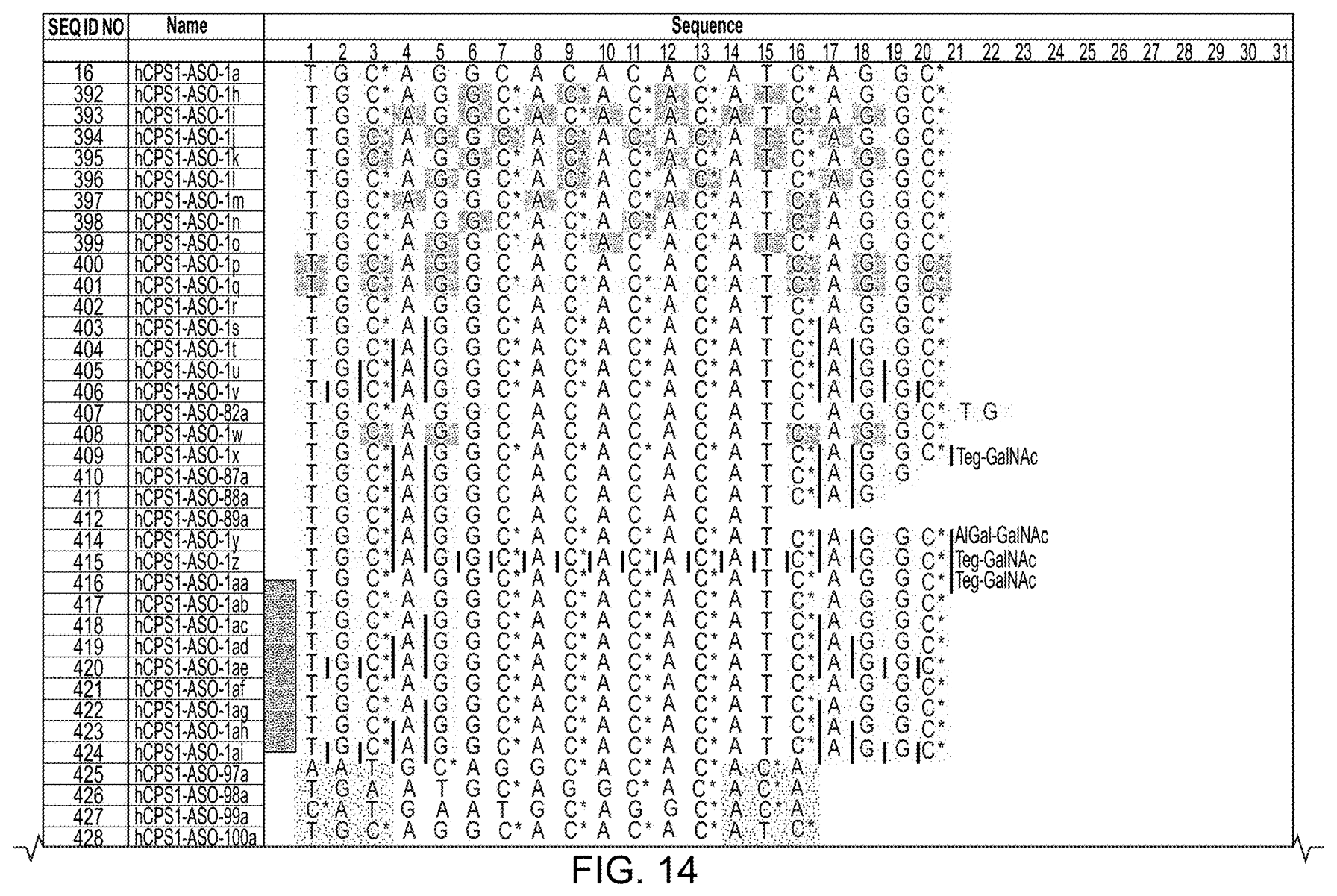
Figure 14:
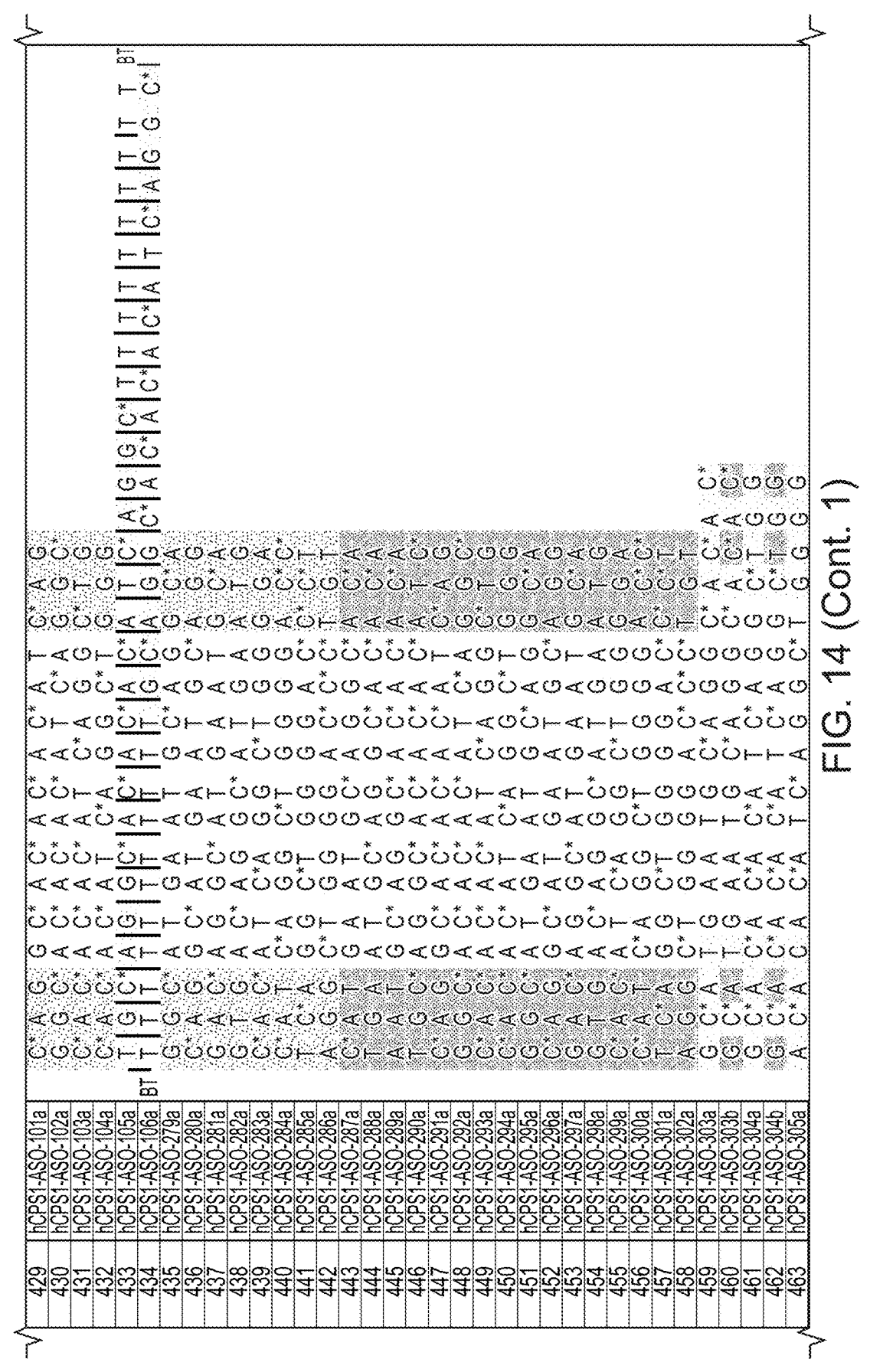

In certain embodiments, the ASO does not consist of only DNA. In certain embodiments, the ASO comprises at least one chemical modification relative to a natural nucleotide (e.g., ribonucleotide). Various chemical modifications can be included in the ASOs of the present disclosure. The modifications can include one or more modifications in a ribose group, one or more modifications in a phosphate group, one or more modifications in a nucleobase, one or more terminal modifications, or a combination thereof. In some embodiments, an exemplary ASO sequence targeting a regRNA as shown in Table 2 is chemically modified. For example, hCPS1-ASO-1 may be chemically modified to comprise the modifications of any one of hCPS1-ASO1-1a to hCPS1-ASO1-1g as shown in FIG. 5A. Such modifications can be, but are not limited to, 2'-O-(2-methoxyethyl) (2'-MOE, MOE), locked nucleic acid (LNA), 5-methyl on the cytidine, cET, phosphorothioate (PS) linkage, and/or a phosphodiester (PO) linkage, or any combination thereof. Chemical modifications of RNA are known in the art and described in, for example, PCT Application Publication No. WO2013/177248. In certain embodiments, each cytidine in the ASO is modified by 5-methyl. Exemplary ASOs comprising chemical modifications are shown in FIGS. 5A and 14.

Various chemical modifications for use with ASOs of the present disclosure include, but are not limited to: 3'-terminal deoxy-thymine (dT) nucleotides, 2'-O-methyl modified nucleotides, 2'-fluoro modified nucleotides, 2'-deoxy-modified nucleotides, locked nucleotides, unlocked nucleotides, conformationally restricted nucleotides, constrained ethyl nucleotides, abasic nucleotides, 2'-amino-modified nucleotides, 2'-O-allyl-modified nucleotides, 2'-C-alkyl-modified nucleotides, 2'-hydroxyl-modified nucleotides, 2'-methoxyethyl modified nucleotides, 2'-O-alkyl-modified nucleotides, morpholino nucleotides, phosphoramidates, non-natural base comprising nucleotides, tetrahydropyran modified nucleotides, 1,5-anhydrohexitol modified nucleotides, cyclohexenyl modified nucleotides, nucleotides comprising a phosphorothioate group, nucleotides comprising a methylphosphonate group, nucleotides comprising a 5'-phosphate, and nucleotides comprising a 5'-phosphate mimic.

In certain embodiments, the ASO comprises an RNA polynucleotide chemically modified to be resistant to one or more nuclear RNases (e.g., the exosome complex). In some embodiments, all nucleotide bases are modified in the ASO. In certain embodiments, the chemical modifications comprises β-D-ribonucleosides, 2'-modified nucleosides (e.g., 2'-O-(2-methoxyethyl) (2'-MOE), 2'-O—CH$_3$, or 2'-fluoro-arabino (FANA)), bicyclic sugar modified nucleosides (e.g., having a constrained ethyl or locked nucleic acid (LNA)), and/or one or more modified internucleotide bonds (e.g., phosphorothioate internucleotide linkage). In certain embodiments, the chemical modification comprises 2'-MOE and a phosphorothioate internucleotide bond. In certain embodiments, at least 8, 9, 10, 11, 12, 13, 14, 15, 16, 17, 18, 19, 20, or more consecutive nucleotides of the ASO are modified by 2'-MOE. In certain embodiments, each nucleotide of the ASO is modified by 2'-MOE. In certain embodiments, at least 7, 8, 9, 10, 11, 12, 13, 14, 15, 16, 17, 18, 19, 20, or more consecutive internucleotide bonds of the ASO are phosphorothioate internucleotide bonds. In certain embodiments, each internucleotide bond of the ASO is a phosphorothioate internucleotide bond.

Internucleotide linkage modifications that can be used with the ASOs of the present disclosure include, but are not limited to, phosphorothioate "PS" (P(S)), phosphoramidate (P(NR1R2) such as dimethylaminophosphoramidate(P(N(CH3)2)), phosphonocarboxylate (P(CH2)nCOOR) such as phosphonoacetate "PACE" (P(CH2COO—)), thiophosphonocarboxylate ((S)P(CH2)nCOOR) such as thiophosphonoacetate "thioPACE" ((S)P(CH2COO—)), alkylphosphonate (P(C1-3alkyl) such as methylphosphonate —P(CH3), boranophosphonate (P(BH3)), and phosphorodithioate (P(S)2).

The chemical structures can also be described in writing. In such cases, 'M' indicates MOE; 'd' indicates DNA, 'L' indicates LNA, '=' indicates a phosphorothioate (PS) linkage, '—' indicates a phosphodiester (PO) linkage; '5C' indicates 5-MethylCytosine, 'ag' indicates GalNAc, 'tg' or "TEG" indicates Teg-GalNAc, 'ag' or 'AlGal' indicates GalNAc, 'BioTEG' indicated biotin, 'CholTEG' indicates cholesterol, 'c' indicates cET, and '^' indicates FANA.

To avoid ambiguity, this LNA has the formula:

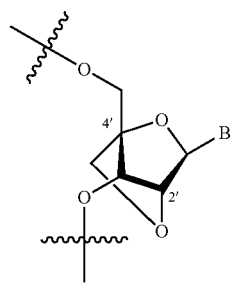

wherein B is the particular designated base.

Exemplary written descriptions of selected ASOs are provided in Table 3, with corresponding FIGS. 5A and 14 providing visual representation of the modifications.

In some embodiments, the ASO comprises a sequence selected from the group consisting of SEQ ID NOs: 1-15, 91-391, or 487-662. In some embodiments, the ASO comprises a sequence and chemical modification selected from the group consisting of SEQ ID NOs: 16-48, 392-480, or 482-486. In some embodiments, the ASO comprises a sequence and/or chemical modification selected from the group consisting of SEQ ID NOs: 1-48 or 91-662.

In some embodiments, the regulatory RNA comprises a sequence selected from the group consisting of SEQ ID NOs: 80-88. In some embodiments, the ASO comprises a sequence selected from the group consisting of SEQ ID NOs: 51-68.

In some embodiments, the ASO comprises a sequence set forth in Table 2. In some embodiments, the ASO comprises a sequence and/or the chemical modification set forth in Table 3, and FIGS. 4A, 5A, 5B, and 14.

In certain embodiments, the ASO comprises one or more chemical modifications at the 5' end, the 3' end, or both. Without wishing to be bound by theory, chemical modifications at one or both termini of a polynucleotide (e.g., polyribonucleotide) may stabilize the polynucleotide. In certain embodiments, the ASO comprises one or more chemical modifications in at least 1, 2, 3, 4, or 5 nucleotides at the 5' end of the ASO. In certain embodiments, the ASO comprises one or more chemical modifications in at least 1, 2, 3, 4, or 5 nucleotides at the 3' end of the ASO. In certain embodiments, the ASO comprises one or more chemical modifications in at least 1, 2, 3, 4, or 5 nucleotides at the 5' end of the ASO and one or more chemical modifications in at least 1, 2, 3, 4, or 5 nucleotides at the 3' end of the ASO.

High Affinity Modified Nucleosides

A high affinity modified nucleoside is a modified nucleoside which, when incorporated into the oligonucleotide enhances the affinity of the oligonucleotide for its complementary target, for example as measured by the melting temperature (Tm). A high affinity modified nucleoside of the present disclosure preferably result in an increase in melting temperature between +0.5 to +12° C., such as between +1.5 to +10° C. or +3 to +8° C. per modified nucleoside. Numerous high affinity modified nucleosides are known in the art and include for example, many 2' substituted nucleosides as well as locked nucleic acids (LNA) (see e.g. Freier & Altmann, Nucl. Acid Res., 1997, 25, 4429-4443 and Uhlmann, Curr. Opinion in Drug Development, 2000, 3(2), 293-213), each of which is hereby incorporated by reference.

Sugar Modifications

The ASOs described herein may comprise one or more nucleosides which have a modified sugar moiety, i.e. a modification of the sugar moiety when compared to the ribose sugar moiety found in DNA and RNA. Numerous nucleosides with modification of the ribose sugar moiety have been made, primarily with the aim of improving certain properties of oligonucleotides, such as affinity and/or nuclease resistance. Such modifications include those where the ribose ring structure is modified, e.g. by replacement with a hexose ring (HNA), or a bicyclic ring, which typically have a biradical bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (see e.g., PCT Application Publication No. WO2011/017521) or tricyclic nucleic acids (see e.g., PCT Application Publication No. WO2013/154798), both of which are hereby incorporated by reference. Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

In some embodiments, oligonucleotides comprise modified sugar moieties, such as any one of a 2'-O-methyl (2'OMe) moiety, a 2'-O-methoxyethyl moiety, a bicyclic sugar moiety, PNA (e.g., an oligonucleotide comprising one or more N-(2-aminoethyl)-glycine units linked by amide bonds or carbonyl methylene linkage as repeating units in place of a sugar-phosphate backbone), locked nucleoside (LNA) (e.g., an oligonucleotide comprising one or more locked ribose, and can be a mixture of 2'-deoxy nucleotides or 2'OMe nucleotides), c-ET (e.g., an oligonucleotide comprising one or more cET sugar), cMOE (e.g., an oligonucleotide comprising one or more cMOE sugar), morpholino oligomer (e.g., an oligonucleotide comprising a backbone comprising one or more phosphorodiamidate morpholino oligomers), 2'-deoxy-2'-fluoro nucleoside (e.g., an oligonucleotide comprising one or more 2'-fluoro-β-D-arabino-nucleoside), tcDNA (e.g., an oligonucleotide comprising one or more tcDNA modified sugar), constrained ethyl 2'-4'-bridged nucleic acid (cEt), S-cEt, ethylene bridged nucleic acid (ENA) (e.g., an oligonucleotide comprising one or more ENA modified sugar), hexitol nucleic acids (HNA) (e.g., an oligonucleotide comprising one or more HNA modified sugar), or tricyclic analog (tcDNA) (e.g., an oligonucleotide comprising one or more tcDNA modified sugar).

In some embodiments, oligonucleotides comprise nucleobase modifications selected from the group consisting of 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU") 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil ("5-allyl U"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), and isocytosine ("isoC"), glycerol nucleic acid (GNA), thiomorpholino (C4H9NS) or thiophosphoramidate morpholinos (TMOs). Synthesis of glycerol nucleic acid (GNA) (also known as glycol nucleic acids) is described in Zhang et al, Current Protocols in Nucleic Acid Chemistry 4.40.1-4.40.18, September 2010, hereby incorporated by reference. Synthesis of thiophosphoramidate morpholino oligonucleotides is described in Langer et al, J. Am. Chem. Soc. 2020, 142, 38, 16240-16253

2' Sugar Modified Nucleosides

A 2' sugar modified nucleoside is a nucleoside which has a substituent other than H or —OH at the 2' position (2' substituted nucleoside) or comprises a 2' linked biradical capable of forming a bridge between the 2' carbon and a second carbon in the ribose ring, such as LNA (2'-4' biradical bridged) nucleosides.

Without wishing to be bound by theory, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937, each of which are hereby incorporated by reference.

Locked Nucleic Acid Nucleosides (LNA Nucleoside)

A "LNA nucleoside" is a 2'-sugar modified nucleoside which comprises a biradical linking the C2' and C4' of the ribose sugar ring of said nucleoside (also referred to as a "2'-4' bridge"), which restricts or locks the conformation of the ribose ring. In other words, a locked nucleoside is a nucleoside comprising a bicyclic sugar moiety comprising a 4'-CH$_2$—O-2' bridge. This structure effectively "locks" the ribose in the 3'-endo structural conformation. The addition of locked nucleosides to oligonucleotides has been shown to increase oligonucleotide stability in serum, and to reduce off-target effects (Grunweller, A. et al., (2003) Nucleic Acids Research 31(12):3185-3193). These nucleosides are also sometimes termed bridged nucleic acid or bicyclic nucleic acid (BNA). The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex. Exemplary LNA nucleosides include beta-D-oxy-LNA, 6'-methyl-beta-D-oxy LNA such as (S)-6'-methyl-beta-D-oxy-LNA (ScET) and ENA.

Examples of bicyclic nucleosides for use in the polynucleotides of the invention include without limitation nucleosides comprising a bridge between the 4' and the 2' ribosyl ring atoms. In certain embodiments, the polynucleotide agents of the invention include one or more bicyclic nucleosides comprising a 4' to 2' bridge. Examples of such 4' to 2' bridged bicyclic nucleosides, include but are not limited to 4'-(CH$_2$)—O-2' (LNA); 4'-(CH$_2$)$_2$—S-2'; 4'-(CH$_2$)2-O-2' (ENA); 4'-CH(CH$_3$)—O-2' (also referred to as "constrained ethyl" or "cEt") and 4'-CH(CH$_2$OCH$_3$)—O-2' (and analogs thereof; see, e.g., U.S. Pat. No. 7,399,845); 4'-C(CH$_3$)(CH$_3$)—O-2' (and analogs thereof; see e.g., U.S. Pat. No. 8,278,283); 4'-CH$_2$—N(OCH$_3$)-2' (and analogs thereof; see e.g., U.S. Pat. No. 8,278,425); 4'-CH$_2$—O—N(CH$_3$)$_2$-2' (see, e.g., U.S. Patent Publication No. 2004/0171570); 4'-CH$_2$—N(R)—O-2', wherein R is H, C$_1$-C$_{12}$ alkyl, or a protecting group (see, e.g., U.S. Pat. No. 7,427,672); 4'-CH$_2$—C(H)(CH$_3$)-2' (see, e.g., Chattopadhyaya et al., J. Org. Chem., 2009, 74, 118-134); and 4'-CH$_2$—C(=CH$_2$)-2' (and analogs thereof; see, e.g., U.S. Pat. No. 8,278,426). The entire contents of each of the foregoing are hereby incorporated herein by reference.

Additional representative U.S. patents and US patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see PCT Publication No. WO 99/14226, contents of which are incorporated by reference herein).

An oligonucleotide of the invention can also be modified to include one or more constrained ethyl nucleosides. As used herein, a "constrained ethyl nucleoside" or "cEt" is a locked nucleoside comprising a bicyclic sugar moiety comprising a 4'-CH($CH_3$)—O-2' bridge. In some embodiments, a constrained ethyl nucleoside is in the S conformation referred to herein as "S-cEt."

An oligonucleotide of the invention may also include one or more "conformationally restricted nucleosides" ("CRN"). CRN are nucleoside analogs with a linker connecting the C2' and C4' carbons of ribose or the -C3 and -C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT Publication No. WO 2013/036868, the entire contents of each of which are hereby incorporated herein by reference.

In some embodiments, an oligonucleotide of the invention comprises one or more monomers that are UNA (unlocked nucleoside) nucleosides. UNA is unlocked acyclic nucleoside, wherein any of the bonds of the sugar has been removed, forming an unlocked "sugar" residue. In one example, UNA also encompasses monomer with bonds between C1'-C4' have been removed (i.e., the covalent carbon-oxygen-carbon bond between the C1' and C4' carbons). In another example, the C2'-C3' bond (i.e., the covalent carbon-carbon bond between the C2' and C3' carbons) of the sugar has been removed (see Nuc. Acids Symp. Series, 52, 133-134 (2008) and Fluiter et al., Mol. Biosyst., 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

The ribose molecule may also be modified with a cyclopropane ring to produce a tricyclodeoxynucleic acid (tricyclo DNA). The ribose moiety may be substituted for another sugar such as 1,5,-anhydrohexitol, threose to produce a threose nucleoside (TNA), or arabinose to produce an arabino nucleoside. The ribose molecule can also be replaced with non-sugars such as cyclohexene to produce cyclohexene nucleoside or glycol to produce glycol nucleosides.

Potentially stabilizing modifications to the ends of nucleoside molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other alternatives chemistries of an oligonucleotide of the invention include a 5' phosphate or 5' phosphate mimic, e.g., a 5'-terminal phosphate or phosphate mimic of an oligonucleotide. Suitable phosphate mimics are disclosed in, for example US Patent Publication No. 2012/0157511, the entire contents of which are incorporated herein by reference.

Additional non-limiting, exemplary LNA nucleosides are disclosed in PCT Publication Nos. WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, Mitsuoka et al., Nucleic Acids Research 2009, 37(4), 1225-1238, and Wan and Seth, J. Medical Chemistry 2016, 59, 9645-9667, each of which are hereby incorporated by reference.

In some embodiments, the length of the ASO is 5×n+5 nucleotides (n is an integer of 3 or greater), wherein the nucleotides at positions 5×m are ribonucleotides modified by LNA (m is an integer from 1 to n) and the nucleotides at the remaining positions are ribonucleotides modified by 2'-O-methoxyethyl.

In some embodiments, the nucleotide sugar modification is 2'-O—C1-4alkyl such as 2'-O-methyl (2'-OMe), 2'-deoxy (2'-H), 2-O—C1-3alkyl-O—C1-3alkyl such as 2'-methoxyethyl ("2'-MOE"), 2'-fluoro ("2'-F"), 2'-amino ("2-NH2"), 2'-arabinosyl ("2'-arabino") nucleotide, 2'-F-arabinosyl ("2'-F-arabino") nucleotide, 2'-locked nucleic acid ("LNA") nucleotide, 2'-amido bridge nucleic acid (AmNA), 2'-unlocked nucleic acid ("ULNA") nucleotide, a sugar in L form ("L-sugar"), or 4'-thioribosyl nucleotide.

Mixmers and Gapmers

The ASO can have a mixmer and/or gapmer structure, for example, in a pattern disclosed by the ASOs in FIG. 5A, FIG. 5B, or FIG. 14.

In certain embodiments, the ASO is a mixmer. As used herein, the term "mixmer" refers to an oligonucleotide comprising an alternating composition of DNA monomers and nucleoside analogue monomers across at least a portion of the oligonucleotide sequence. In certain embodiments, the ASO is a mixmer based on the gapmer structure, comprising a mixture of DNA nucleotides and 2'-MOE nucleotides in the gap, flanked by RNA sequences in the wings. Mixmers may be designed to comprise a mixture of affinity enhancing nucleotide analogues, such as in non-limiting example 2'-O-alkyl-RNA monomers, 2'-amino-DNA monomers, 2'-fluoro-DNA monomers, LNA monomers, arabino nucleic acid (ANA) monomers, 2'-fluoro-ANA monomers, HNA monomers, INA monomers, 2'-MOE-RNA (2'-O-methoxyethyl-RNA), 2'Fluoro-DNA, and LNA. In some embodiments, the mixmer is incapable of recruiting RNase H. In some embodiments, the mixmer comprises one type of affinity enhancing nucleotide analogue together with DNA and/or RNA.

Multiple different modifications can be interspaced in a mixmer. For example, the ASO can comprise LNA modification in a plurality of nucleotides and a different modification in some or all of the rest of the nucleotides. In some embodiments, any two adjacent LNA-modified nucleotides are separated by at least 1, 2, 3, 4, or 5 nucleotides. Throughout the ASO, the distance between adjacent LNA-modified nucleotides can either be constant (e.g., any two adjacent LNA-modified nucleotides are separated by 1, 2, 3, 4, or 5 nucleotides) or variable. In some embodiments, the length of the ASO is 3×n, 3×n−1, or 3×n−2 nucleotides (n is an integer of 6 or greater), wherein (a) (i) the nucleotides at positions 3×m−2 (m is an integer from 1 to n) are ribonucleotides comprising a first modification (e.g., LNA), (ii) the nucleotides at positions 3×m−1 (m is an integer from 1 to n) are ribonucleotides comprising a first modification (e.g., LNA), or (iii) the nucleotides at positions 3×m (m is an integer from 1 to n) are ribonucleotides comprising a first modification (e.g., LNA); and (b) the nucleotides at the remaining positions comprise a second, different modification (e.g., 2'-O-methoxyethyl). The ASO called hCPS1-ASO-1d herein has such a structure. In some embodiments, the length of the ASO is 2×n or 2×n−1 nucleotides (n is an integer of 9 or greater), wherein (a) (i) the nucleotides at positions 2×m−1 (m is an integer from 1 to n) are ribonucleotides comprising a first modification (e.g., LNA), or (ii) the nucleotides at positions 2×m (m is an integer from 1 to n) are ribonucleotides comprising a first modification (e.g., LNA); and (b) the nucleotides at the remaining positions comprise a second, different modification (e.g., 2'-O-methoxyethyl). The ASO called hCPS1-ASO-1e herein has such a structure. Similar modification patterns, for example, where the first modification is repeated every 4, 5, or more nucleotides, are also contemplated herein.

In some embodiments, the ASO further comprises a GalNAc or Teg-GalNAc moiety at the 5' or 3' end of the ASO. In some embodiments, the ASO further comprises a cholesterol or biotin moiety at the 5' or 3' end of the ASO.

In certain embodiments, the ASO comprises a DNA sequence (e.g., having at least 5, 6, 7, 8, 9, 10, 11, 12, 13, 14, or 15 contiguous nucleotides of unmodified DNA) flanked by RNA sequences. Such structure is known as "gapmer," in which the internal DNA region is referred to as the "gap" and the external RNA regions is referred to as the "wings" (see, e.g., PCT Application Publication No. WO2013/177248). Gapmers were known to facilitate degradation of the target RNA by recruiting nuclear RNAses (e.g., RNase H). Surprisingly, in the present disclosure, it has been discovered that a gapmer binding a regRNA (e.g., hCPS1-ASO-1a), like regRNAs having the same sequence but having different chemical modifications (e.g., hCPS1-ASO-1g), can also increase target gene expression.

In certain embodiments, the gapmer is about 15, 16, 17, 18, 19, 20, 21, 22, 23, 24, 25, 26, 27, 28, 29, 30, or more nucleotides in length. In certain embodiments, the gap is about 5, 6, 7, 8, 9, 10, 11, 12, 13, 14, 15, or more nucleotides in length. In certain embodiments, one or both wings are about 2, 3, 4, 5, 6, 7, 8, 9, 10, or more nucleotides in length. In certain embodiments, one or both wings comprises RNA modifications, for example, β-D-ribonucleosides, 2'-modified nucleosides (e.g., 2'-O-(2-methoxyethyl) (2'-MOE), 2'-O—CH$_3$, or 2'-fluoro-arabino (FANA)), and bicyclic sugar modified nucleosides (e.g., having a constrained ethyl or locked nucleic acid (LNA)). In certain embodiments, each ribonucleotide in the gapmer is modified by 2'-MOE. In certain embodiments, the gapmer comprises one or more modified internucleotide bonds, e.g., phosphorothioate (PS) internucleotide linkage. In certain embodiments, each two adjacent nucleotides in the gapmer are linked by a phosphorothioate internucleotide bond.

In certain embodiments, the ASO does not comprise 7 or more, 8 or more, 9 or more, 10 or more, 10 or more, 11 or more, 12 or more, 13 or more, 14 or more, or 15 or more contiguous nucleotides of unmodified DNA. In some embodiments, such a DNA sequence is disrupted by modified (e.g., 2'-MOE modified) ribonucleotides every 2, 3, 4, 5, or more nucleotides. In some embodiments, the ASO comprises only ribonucleotides and no deoxyribonucleotides.

The structural features of mixmer and gapmer can be combined. In certain embodiments, the ASO has a structure similar to that of a mixmer disclosed herein (e.g., one having interspaced modifications), except that the second modification in the gap is changed to a third modification (e.g., deoxyribonucleotide). In certain embodiments, the ASO has a structure similar to that of a gapmer disclosed herein, except that in the gap the nucleotides are modified in a mixmer pattern.

In certain embodiments, the ASO further comprises a ligand moiety, e.g., a ligand moiety that specifically targets a tissue or organ in a subject. For example, N-acetylgalactosamine (GalNAc) specifically targets liver. In certain embodiments, the ligand moiety comprises GalNAc. In certain embodiments, the ligand moiety comprises a three-cluster GalNAc moiety, commonly denoted GAlNAc3. Other types of GalNAc moieties are one-cluster, two cluster or four cluster GAlNAc, denoted as GAlNAc1, GAlNAc2, or GAlNAc4. In certain embodiments, the ligand moiety comprises GalNAc1, GALNAc2, GAlNAc3, or GalNAc4.

III. Pharmaceutical Compositions

In certain embodiments, the ASOs disclosed herein can be present in pharmaceutical compositions. The pharmaceutical composition can be formulated for use in a variety of drug delivery systems. One or more pharmaceutically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer, Science 249:1527-1533, 1990, hereby incorporated by reference in its entirety.

Exemplary carriers and pharmaceutical formulations suitable for delivering nucleic acids are described in Durymanov and Reineke (2018) Front. Pharmacol. 9:971; Barba et al. (2019) Pharmaceutics 11(8): 360; Ni et al. (2019) Life (Basel) 9(3): 59. It is understood that the presence of a ligand moiety conjugated to the ASO may circumvent the need for a carrier for delivery to a tissue or organ targeted by the ligand moiety.

The delivery of an oligonucleotide of the disclosure to a cell e.g., a cell within a subject, such as a human subject e.g., a subject in need thereof, such as a subject having a CPS1 related disorder or other urea cycle disorders can be achieved in a number of different ways. For example, delivery may be performed by contacting a cell with an oligonucleotide of the disclosure either in vitro or in vivo. In vivo delivery may also be performed directly by administering a composition comprising an oligonucleotide to a subject. These alternatives are discussed further below.

In general, any method of delivering a nucleic acid molecule (in vitro or in vivo) can be adapted for use with an oligonucleotide of the disclosure (see e.g., Akhtar S. and Julian R L., (1992) Trends Cell. Biol. 2(5):139-144 and PCT Publication No. WO 94/02595, which are incorporated herein by reference in their entireties). For in vivo delivery, factors to consider in order to deliver an oligonucleotide molecule include, for example, biological stability of the delivered molecule, prevention of non-specific effects, and accumulation of the delivered molecule in the target tissue. The non-specific effects of an oligonucleotide can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the oligonucleotide molecule to be administered.

For administering an oligonucleotide systemically for the treatment of a disease, the oligonucleotide can include alternative nucleobases, alternative sugar moieties, and/or alternative internucleoside linkages, or alternatively delivered using a drug delivery system; both methods act to prevent the rapid degradation of the oligonucleotide by endo- and exo-nucleases in vivo. Modification of the oligonucleotide or the pharmaceutical carrier can also permit targeting of the oligonucleotide composition to the target tissue and avoid undesirable off-target effects. Oligonucleotide molecules can be modified by chemical conjugation to lipophilic groups such as cholesterol to enhance cellular uptake and prevent degradation. In an alternative embodiment, the oligonucleotide can be delivered using drug delivery systems such as a nanoparticle, a lipid nanoparticle, a polyplex nanoparticle, a lipoplex nanoparticle, a dendrimer, a polymer, liposomes, or a cationic delivery system. Positively charged cationic delivery systems facilitate binding of an oligonucleotide molecule (negatively charged) and also enhance interactions at the negatively charged cell membrane to permit efficient uptake of an oligonucleotide by the cell. Cationic lipids, dendrimers, or polymers can either be bound to an oligonucleotide, or induced to form a vesicle or micelle that encases an oligonucleotide. The formation of vesicles or micelles further prevents degradation of the oligonucleotide when administered systemically. In general, any methods of delivery of nucleic acids known in the art may be adaptable to the delivery of the oligonucleotides of the disclosure. Methods for making and administering cationic oligonucleotide complexes are well within the abilities of one skilled in the art (see e.g., Sorensen, D R., et al. (2003) J. Mol. Biol 327:761-766; Verma, U N. et al., (2003) Clin. Cancer Res. 9:1291-1300; Arnold, A S et al., (2007) J. Hypertens. 25:197-205, which are incorporated herein by reference in their entirety). Some non-limiting examples of drug delivery systems useful for systemic delivery of oligonucleotides include DOTAP (Sorensen, D R., et al (2003), supra; Verma, U N. et al., (2003), supra), Oligofectamine™, "solid nucleic acid lipid particles" (Zimmermann, T S. et al., (2006) Nature 441:111-114), cardiolipin (Chien, P Y. et al., (2005) Cancer Gene Ther. 12:321-328; Pal, A. et al., (2005) Int J. Oncol. 26:1087-1091), polyethyleneimine (Bonnet M E. et al., (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A. et al., (2007) Biochem. Soc. Trans. 35:61-67; Yoo, H. et al., (1999) Pharm. Res. 16:1799-1804). In some embodiments, an oligonucleotide forms a complex with cyclodextrin for systemic administration. Methods for administration and pharmaceutical compositions of oligonucleotides and cyclodextrins can be found in U.S. Pat. No. 7,427,605, which is herein incorporated by reference in its entirety. In some embodiments the oligonucleotides of the disclosure are delivered by polyplex or lipoplex nanoparticles. Methods for administration and pharmaceutical compositions of oligonucleotides and polyplex nanoparticles and lipoplex nanoparticles can be found in U.S. Patent Publication Nos. 2017/0121454; 2016/0369269; 2016/0279256; 2016/0251478; 2016/0230189; 2015/0335764; 2015/0307554; 2015/0174549; 2014/0342003; 2014/0135376; and 2013/0317086, which are herein incorporated by reference in their entirety.

In some embodiments, the compounds described herein may be administered in combination with additional therapeutics. Examples of additional therapeutics include standard of care urea cycle disorder treatments such as low protein diet or nitrogen scavengers including, but not limited to, glycerol phenylbutyrate, sodium benzoate, phenylbutyrate, or phenylacetate.

Membranous Molecular Assembly Delivery Methods

Oligonucleotides of the disclosure can also be delivered using a variety of membranous molecular assembly delivery methods including liquid nanoparticles (LNPs), polymeric, biodegradable microparticles, or microcapsule delivery devices known in the art. For example, a colloidal dispersion system may be used for targeted delivery of an oligonucleotide agent described herein. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUVs), which range in diameter from 0.2-4.0 µm can encapsulate a substantial percentage of an aqueous buffer containing large macromolecules. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the oligonucleotide are delivered into the cell where the oligonucleotide can specifically bind to a target RNA. In some cases, the liposomes are also specifically targeted, e.g., to direct the oligonucleotide to particular cell types. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

A liposome containing an oligonucleotide can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The oligonucleotide preparation is then added to the micelles that include the lipid component. The cationic groups on the lipid interact with the oligonucleotide and condense around the oligonucleotide to form a liposome. After condensation, the detergent is removed, e.g., by dialysis, to yield a liposomal preparation of oligonucleotide.

If necessary, a carrier compound that assists in condensation can be added during the condensation reaction, e.g., by controlled addition. For example, the carrier compound can be a polymer other than a nucleic acid (e.g., spermine or spermidine). The pH can also be adjusted to favor condensation.

Methods for producing stable polynucleotide delivery vehicles, which incorporate a polynucleotide/cationic lipid complex as a structural component of the delivery vehicle, are further described in, e.g., WO 96/37194, the entire contents of which are incorporated herein by reference. Liposome formation can also include one or more aspects of exemplary methods described in Feigner, P. L. et al., (1987) Proc. Natl. Acad. Sci. USA 8:7413-7417; U.S. Pat. Nos.

4,897,355; 5,171,678; Bangham et al., (1965) M. Mol. Biol. 23:238; Olson et al., (1979) Biochim. Biophys. Acta 557:9; Szoka et al., (1978) Proc. Natl. Acad. Sci. 75: 4194; Mayhew et al., (1984) Biochim. Biophys. Acta 775:169; Kim et al., (1983) Biochim. Biophys. Acta 728:339; and Fukunaga et al., (1984) Endocrinol. 115:757. Commonly used techniques for preparing lipid aggregates of appropriate size for use as delivery vehicles include sonication and freeze-thaw plus extrusion (see, e.g., Mayer et al., (1986) Biochim. Biophys. Acta 858:161. Microfluidization can be used when consistently small (50 to 200 nm) and relatively uniform aggregates are desired (Mayhew et al., (1984) Biochim. Biophys. Acta 775:169). These methods are readily adapted to packaging oligonucleotide preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) Biochem. Biophys. Res. Commun., 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) Journal of Controlled Release, 19:269-274).

One major type of liposomal composition includes phospholipids other than naturally derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Feigner, (1994) J. Biol. Chem. 269:2550; Nabel, (1993) Proc. Natl. Acad. Sci. 90:11307; Nabel, (1992) Human Gene Ther. 3:649; Gershon, (1993) Biochem. 32:7143; and Strauss, (1992) EMBO J. 11:417.

Non-ionic liposomal systems have also been examined to determine their utility in the delivery of drugs to the skin, in particular systems comprising non-ionic surfactant and cholesterol. Non-ionic liposomal formulations comprising NOVASOME™ I (glyceryl dilaurate/cholesterol/polyoxyethylene-10-stearyl ether) and NOVASOME™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) S.T.P.Pharma. Sci., 4(6):466).

Liposomes may also be sterically stabilized liposomes, comprising one or more specialized lipids that result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) FEBS Letters, 223:42; Wu et al., (1993) Cancer Research, 53:3765).

Various liposomes comprising one or more glycolipids are known in the art. Papahadjopoulos et al. (Ann. N.Y. Acad. Sci., (1987), 507:64) reported the ability of monosialoganglio side $G^{M1}$, galactocerebroside sulfate, and phosphatidylinositol to improve blood half-lives of liposomes. These findings were expounded upon by Gabizon et al. (Proc. Natl. Acad. Sci. U.S.A., (1988), 85:6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver oligonucleotides to macrophages.

Further advantages of liposomes include: liposomes obtained from natural phospholipids are biocompatible and biodegradable; liposomes can incorporate a wide range of water and lipid soluble drugs; liposomes can protect encapsulated oligonucleotides in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of oligonucleotide (see, e.g., Feigner, P. L. et al., (1987) Proc. Natl. Acad. Sci. USA 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. LIPOFECTIN™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis (oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (TRANSFECTAM™, Promega, Madison, Wis.) and dipalmitoylphosphatidylethanolamine 5-carboxyspermylamide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) Biochim. Biophys. Res. Commun. 179:280). Lipopolylysine, made by conjugating polylysine to DOPE, has been reported to be effective for transfection in the presence of serum (Zhou, X. et al., (1991) Biochim. Biophys. Acta 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer oligonucleotide into the skin. In some implementations, liposomes are used for delivering oligonucleotide to epidermal cells and also to enhance the penetration of oligonucleotide into dermal tissues, e.g., into skin. For example, the liposomes can be applied topically. Topical delivery of drugs formulated as liposomes to the skin has been documented (see, e.g., Weiner et al., (1992) Journal of Drug Targeting, vol. 2, 405-410 and du Plessis et al., (1992) Antiviral Research, 18:259-265; Mannino, R. J. and Fould-Fogerite, S., (1998) Biotechniques 6:682-690; Itani, T. et al., (1987) Gene 56:267-276; Nicolau, C. et al. (1987) Meth. Enzymol. 149:157-176; Straubinger, R. M. and Papahadjopoulos, D. (1983) Meth. Enzymol. 101:512-527; Wang, C. Y. and Huang, L., (1987) Proc. Natl. Acad. Sci. USA 84:7851-7855).

Non-ionic liposomal systems have also been examined to determine their utility in the delivery of drugs to the skin, in particular systems comprising non-ionic surfactant and cholesterol. Non-ionic liposomal formulations comprising NOVASOME I (glyceryl dilaurate/cholesterol/polyoxyethylene-10-stearyl ether) and NOVASOME II (glyceryl distearate/cholesterol/polyoxyethylene-10-stearyl ether) were used to deliver a drug into the dermis of mouse skin. Such formulations with oligonucleotides are useful for treating a dermatological disorder.

The targeting of liposomes is also possible based on, for example, organ-specificity, cell-specificity, and organelle-specificity and is known in the art. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Additional methods are known in the art and are described, for example in U.S. Patent Application Publication No. 20060058255, the linking groups of which are herein incorporated by reference.

Liposomes that include oligonucleotides can be made highly deformable. Such deformability can enable the liposomes to penetrate through pore that are smaller than the average radius of the liposome. For example, transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes can be made by adding surface edge activators, usually surfactants, to a standard liposomal composition. Transfersomes that include oligonucleotides can be delivered, for example, subcutaneously by infection in order to deliver oligonucleotides to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading. Transfersomes have been used to deliver serum albumin to the skin. The transfersome-mediated delivery of serum albumin has been shown to be as effective as subcutaneous injection of a solution containing serum albumin.

Other formulations amenable to the present disclosure are described in PCT Publication Nos. WO 2009/088891, WO 2009/132131, and WO 2008/042973, which are hereby incorporated by reference in their entirety.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines, and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The oligonucleotides for use in the methods of the disclosure can also be provided as micellar formulations. Micelles are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

Lipid Nanoparticle-Based Delivery Methods

Oligonucleotides of in the disclosure may be fully encapsulated in a lipid formulation, e.g., a lipid nanoparticle (LNP), or other nucleic acid-lipid particle. LNPs are useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present disclosure typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present disclosure are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

Non-limiting examples of cationic lipids include N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)bu-tanoate (MC3), 1,1'-(2-(4-(2-((2-(bis(2-hydroxydodecyl)amino)ethyl)(2-hydroxydodecyl)ami-no) ethyl)piperazin-1-yeethylazanediyedidodecan-2-ol (Tech G1), or a mixture thereof. The cationic lipid can comprise, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 60 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be, for example, from 0 mol % to about 20 mol % or about 2 mol % of the total lipid present in the particle.

In some embodiments, the nucleic acid-lipid particle further includes cholesterol at, e.g., about 10 mol % to about 60 mol % or about 50 mol % of the total lipid present in the particle.

The ASO may also be delivered in a lipidoid. The synthesis of lipidoids has been extensively described and formulations containing these compounds are particularly suited for delivery of modified nucleic acid molecules or ASOs (see Mahon et al, Bioconjug Chem. 2010 21: 1448-1454; Schroeder et al, J Intern Med. 2010 267:9-21; Akinc et al, Nat Biotechnol. 2008 26:561-569; Love et al, Proc Natl Acad Sci USA. 2010 107: 1864-1869; Siegwart et al, Proc Natl Acad Sci USA. 2011 108: 12996-3001; all of which are incorporated herein in their entireties).

Lipid compositions for RNA delivery are disclosed in PCT Publication Nos. WO2012/170930A1, WO2013/149141A1, and WO2014/152211A1, each of which is hereby incorporated by reference.

IV. Therapeutic Applications

The present disclosure provides methods for treating diseases and disorders associated with decreased gene expression (e.g., decreased CPS1 gene expression). The method employs an ASO that hybridizes with a regulatory RNA transcribed from a regulatory element of the target gene (e.g., CPS1) or a pharmaceutical composition comprising the ASO. The oligonucleotide compositions described herein are useful in the methods of the disclosure and, while not bound by theory, are believed to exert their desirable effects through their ability to modulate the level, status, and/or activity of CPS1, e.g., by increasing the level of the CPS1 protein in a cell in a subject (e.g., a mammal, a primate, or a human).

Also provided herein are methods of treating or preventing hyperammonemia in a subject, including administering an ASO described herein to the subject. The disclosure further provides methods of treating or preventing hyperammonemia in a subject that has or is at risk of developing hyperammonemia, including administering an ASO described herein to the subject. In some embodiments, the subject having or at risk of developing hyperammonemia has one or more of the following: a urea cycle disorder, hepatic encephalopathy, acute liver failure, liver cirrhosis, non-alcoholic fatty liver disease, renal dysfunction and/or failure, propionic acidemia, methylmalonic acidemia, isovaleric acidemia, a urinary tract infection, intestinal bacterial overgrowth, a fatty acid oxidation disorder, and a systemic infection. In some embodiments, the subject has or is at risk of developing hyperammonemia associated with the intake of a drug (e.g., valproic acid, carbamazepine, fluorouracil, sulfadiazine, ribavirin, salicylates, and glycine). In some embodiments, the methods include administering an ASO described herein to the subject. In certain embodiments, treatment with an ASO described herein results in decreased ammonia levels (e.g., blood ammonia levels, plasma ammonia levels, systemic ammonia levels, or cerebrospinal fluid ammonia levels) in a subject as compared to a subject (e.g., the same subject prior to the treatment) that has not been treated with the ASO. In some embodiments, the reduction in ammonia levels (e.g., blood ammonia levels, systemic ammonia levels, or cerebrospinal fluid ammonia levels) is a reduction of at least about 5%, 10%, 15%, 20%, 25%, 30%, 40%, 50%, 60%, 70%, 80%, 90%, or 100%, relative to the ammonia levels (e.g., blood ammonia levels, systemic ammonia levels, or cerebrospinal fluid ammonia levels) in the subject (e.g., as compared to the same subject prior to administration of the ASO).

Methods of measuring ammonia levels (e.g., in a plasma sample) are known in the art and include enzymatic kinetic assays in which ammonia reacts with α-ketoglutarate and reduced nicotinamide adenine dinucleotide phosphate (NADPH) in the presence of L-glutamate dehydrogenase resulting in glutamate and $NADP^+$. The amount of oxidized NADPH is then measured (e.g., photometrically) and is equivalent to the amount of ammonia.

An aspect of the present disclosure relates to methods of treating disorders (e.g., a urea cycle disorder) in a subject (e.g., a human subject) in need thereof. In some embodiments, provided herein are methods of treating a urea cycle disorder in a subject (e.g., a human subject) in need thereof, including administering an ASO provided herein to the subject. In some embodiments, the urea cycle disorder is carbamoyl-phosphate synthetase 1 (CPS1) deficiency, ornithine transcarbamylase (OTC) deficiency, citrullinemia type I (argininosuccinate synthetase (ASS) deficiency), argininosuccinate lyase (ASL) deficiency, N-acetyl glutamate synthetase (NAGS) deficiency, arginase deficiency (hyperargininemia, ARG1 deficiency), ornithine translocase deficiency (ORNT1 deficiency, hyperornithinemia-hyperammonemia-homocitrullinuria syndrome (HHH)), or citrin deficiency. In some embodiments, the urea cycle disorder is not N-acetyl glutamate synthetase (NAGS) deficiency. In some embodiments, administration of an ASO provided herein to a subject having a urea cycle disorder reduces the risk, frequency and/or severity of a hyperammonemic crisis in the subject (e.g., as compared to a subject that is not administered the ASO (e.g., the same subject prior to administration of the ASO)).

In some embodiments, the urea cycle disorder is Carbamoylphosphate synthetase I deficiency (CPS1 deficiency). In some embodiments, the urea cycle disorder is hyperammonemia. In some embodiments, the urea cycle disorder is Ornithine transcarbamylase deficiency (OTC deficiency). In some embodiments, the urea cycle disorder is Citrullinemia type I (ASS1 deficiency). In some embodiments, the urea cycle disorder is Argininosuccinic aciduria (ASL deficiencydeficiency). In some embodiments, the urea cycle disorder is Arginase deficiency (hyperargininemia, ARG1 deficiency). In some embodiments, the urea cycle disorder is Ornithine translocase deficiency (ORNT1 deficiency, hyperornithinemia-hyperammonemia-homocitrullinuria syndrome). In some embodiments, the urea cycle disorder is Citrin deficiency.

Another aspect of the disclosure includes methods of increasing the level of CPS1 in a cell of a subject identified as having a CPS1 related disorder (e.g., CPS1 deficiency) or other urea cycle disorder. Still another aspect includes a method of increasing expression of CPS1 in a cell in a subject. The methods may include contacting a cell with an ASO described herein, in an amount effective to increase expression of CPS1 in the cell, thereby increasing expression of CPS1 in the cell. In certain embodiments, the methods include contacting a cell with an ASO described herein, in an amount effective to increase expression of CPS1 in the cell, thereby increasing expression of OTC in the cell. In certain embodiments, the methods include contacting a cell with an ASO described herein, in an amount effective to increase expression of CPS1 in the cell, thereby increasing expression of other urea cycle genes in the cell, such as OTC, ASS1, ASL, ARG1, or ORNT1.

Based on the above methods, further aspects of the present disclosure include an ASO or oligonucleotide of the disclosure, or a composition comprising such an ASO or oligonucleotide, for use in therapy, or for use as a medicament, or for use in treating a CPS1 related disorder (e.g., CPS1 deficiency) or other urea cycle disorder in a subject in need thereof, or for use in increasing the level of CPS1 in a cell of a subject identified as having a CPS1 related disorder or other urea cycle disorder, or for use in increasing expression of CPS1 in a cell in a subject. The uses include the contacting of a cell with the ASO or oligonucleotide, in an amount effective to increase expression of CPS1 in the cell, thereby increasing expression of CPS1 in the cell. Embodiments described below in relation to the methods of the present disclosure are also applicable to these further aspects.

Contacting of a cell with an ASO or oligonucleotide may be done in vitro, ex vivo, or in vivo. Contacting a cell in vivo with the oligonucleotide includes contacting a cell or group of cells within a subject, e.g., a human subject, with the ASO or oligonucleotide. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc3 ligand, or any other ligand that directs the oligonucleotide to a site of interest. The cell can be a liver cell (e.g., a hepatocyte).

Administration of the ASO or oligonucleotide or pharmaceutical composition disclosed herein could be intravenous, intraarterial, intraperitoneal, intramuscular, subcutaneous, intrapleural, intrathecal, intracavitary, by perfusion through a catheter or by direct intralesional injection. In certain embodiments, the ASO or oligonucleotide or pharmaceutical composition is administered systemically. In certain embodiments, the ASO or oligonucleotide or pharmaceutical composition is administered by a parenteral route. For example, in certain embodiments, the ASO or oligonucleotide or pharmaceutical composition is administered by intravenously (e.g., by intravenous infusion), for example, with a prefilled bag, a prefilled pen, or a prefilled syringe. In other embodiments, the ASO or oligonucleotide or pharmaceutical composition is administered locally to an organ or tissue in which an increase in the target gene expression is desirable (e.g., liver).

In some embodiments, the ASO or oligonucleotide is administered to a subject such that the ASO or oligonucleotide is delivered to a specific site within the subject. Such targeted delivery can be achieved by either systemic administration or local administration. The increase of expression of CPS1 may be assessed using measurements of the level or change in the level of CPS1 mRNA or CPS1 protein in a sample derived from a specific site within the subject. In some embodiments, the methods include measuring the levels of ammonia in a sample (e.g., blood, urine, plasma or cerebrospinal fluid) derived from the subject. Methods of measuring ammonia levels are well known in the art and described above. In certain embodiments, the methods include a clinically relevant increase of expression of CPS1, e.g., as demonstrated by a clinically relevant outcome after treatment of a subject with an agent to increase the expression of CPS1.

In other embodiments, the oligonucleotide is administered in an amount and for a time effective to result in reduction (e.g., by 10%, 20%, 30%, 40%, 50%, 60%, 70%, 80%, 90%, or 100%) of one or more symptoms of a CPS1 related disorder or a urea cycle disorder, such as high ammonia level in the blood.

Increase of CPS1 Expression Level

The therapeutic methods disclosed herein, using an ASO that targets CPS1, are designed to increase CPS1 expression level in a subject as compared to an untreated subject (e.g., the same subject prior to administration of the ASO or the pharmaceutical composition). Increasing expression of a CPS1 gene includes any level of increasing of a CPS1 gene, e.g., at least partial increase of the expression of a CPS1 gene. Increase may be assessed by an increase in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control). In certain embodiments, the method causes a clinically relevant increase of expression of CPS1, e.g. as demonstrated by a clinically relevant outcome after treatment of a subject with an agent to increase the expression of CPS1.

In certain embodiments, the methods disclosed herein increases CPS1 gene expression by at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, relative to the pre-dose baseline level. In certain embodiments, the methods disclosed herein increases CPS1 gene expression by at least 2 fold, at least 3 fold, at least 4 fold, at least 5 fold, at least 6 fold, at least 7 fold, at least 8 fold, at least 9 fold, or at least 10 fold relative to the pre-dose baseline level. In certain embodiments, the subject has a deficiency in CPS1 expression, and the method disclosed herein restores the CPS1 expression level or activity to at least 20%, at least 30%, at least 40%, at least 50%, at least 60%, at least 70%, at least 80%, at least 90%, or at least 100% of the average CPS1 expression level or activity in subjects of the species of like age and gender.

The expression of a CPS1 gene may be assessed based on the level of any variable associated with CPS1 gene expression, e.g., CPS1 mRNA level or CPS1 protein level. It is understood that CPS1 is a chromosome-2 gene in certain mammals (e.g., human and mouse). In certain embodiments, the expression level or activity of CPS1 herein refers to the average expression level or activity in the liver.

In certain embodiments, surrogate markers can be used to detect an increase of CPS1 expression level. For example, effective treatment of a CPS1 related disorder, as demonstrated by acceptable diagnostic and monitoring criteria with an agent to increase CPS1 expression can be understood to demonstrate a clinically relevant increase in CPS1.

Increase of the expression of a CPS1 gene may be manifested by an increase of the amount of mRNA expressed by a first cell or group of cells (such cells may be present, for example, in a sample derived from a subject) in which a CPS1 gene is transcribed and which has or have been treated (e.g., by contacting the cell or cells with an oligonucleotide of the disclosure, or by administering an oligonucleotide of the disclosure to a subject in which the cells are or were present) such that the expression of a CPS1 gene is increased, as compared to a second cell or group of cells substantially identical to the first cell or group of cells but which has not or have not been so treated (control cell(s) not treated with an oligonucleotide or not treated with an oligonucleotide targeted to the gene of interest).

In other embodiments, increase of the expression of a CPS1 gene may be assessed in terms of an increase of a parameter that is functionally linked to CPS1 gene expression, e.g., CPS1 protein expression or CPS1 activity. CPS1 increase may be determined in any cell expressing CPS1, either endogenous or heterologous from an expression construct, and by any assay known in the art.

An increase of CPS1 expression may be manifested by an increase in the level of the CPS1 protein that is expressed by a cell or group of cells (e.g., the level of protein expressed in a sample derived from a subject), relative to a control cell or a control group of cells. An increase of CPS1 expression may also be manifested by an increase in the level of the CPS1 mRNA level in a treated cell or group of cells, relative to a control cell or a control group of cells.

A control cell or group of cells that may be used to assess the increase of the expression of a CPS1 gene includes a cell or group of cells that has not yet been contacted with an oligonucleotide of the disclosure. For example, the control cell or group of cells may be derived from an individual subject (e.g., a human or animal subject) prior to treatment of the subject with an oligonucleotide.

The level of CPS1 mRNA that is expressed by a cell or group of cells may be determined using any method known in the art for assessing mRNA expression. In one embodiment, the level of expression of CPS1 in a sample is determined by detecting a transcribed polynucleotide, or portion thereof, e.g., mRNA of the CPS1 gene. RNA may be extracted from cells using RNA extraction techniques including, for example, using acid phenol/guanidine isothiocyanate extraction (RNAzol B; Biogenesis), RNEASY™ RNA preparation kits (Qiagen) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating CPS1 mRNA may be detected using methods described in PCT Publication No. WO 2012/177906, the entire contents of which are hereby incorporated herein by reference. In some embodiments, the level of expression of CPS1 is determined using a nucleic acid probe. The term "probe," as used herein, refers to any molecule that is capable of selectively binding to a specific CPS1 sequence, e.g. to an mRNA or polypeptide. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses, and probe arrays. One method for the determination of mRNA levels involves contacting the isolated mRNA with a nucleic acid molecule (probe) that can hybridize to CPS1 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an AFFYMETRIX gene chip array. A skilled artisan can readily adapt known mRNA detection methods for use in determining the level of CPS1 mRNA.

An alternative method for determining the level of expression of CPS1 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of CPS1 is determined by quantitative fluorogenic RT-PCR (i.e., the TAQMAN™ System) or the DUAL-GLO® Luciferase assay.

The expression levels of CPS1 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722; 5,874,219; 5,744,305; 5,677,195; and 5,445,934, which are incorporated herein by reference. The determination of CPS1 expression level may also comprise using nucleic acid probes in solution.

In some embodiments, the level of mRNA expression is assessed using branched DNA (bDNA) assays or real time RT PCR or qPCR. Such methods can also be used for the detection of CPS1 nucleic acids.

The level of CPS1 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of CPS1 proteins.

V. Additional Embodiments

Embodiment 1 An ASO complementary to at least 8 contiguous nucleotides of a regulatory RNA (regRNA) of Carbamoyl-Phosphate Synthetase 1 (CPS1), wherein the ASO is complementary to a sequence in the regRNA that is no more than 200 nucleotides from a terminus of the regRNA.

Embodiment 2 The ASO of embodiment 1, wherein the ASO is complementary to a sequence in the regRNA that is no more than 200 nucleotides from the 3' end of the regRNA.

Embodiment 3 The ASO of embodiment 1, wherein the ASO is complementary to a sequence in the regRNA that is no more than 200 nucleotides from the 5' end of the regRNA.

Embodiment 4 The ASO of embodiments 1 or 2, wherein the ASO comprises a RNA polynucleotide comprising one or more chemical modifications.

Embodiment 5 The ASO of embodiment 1, wherein at least 3, 4, or 5 nucleotides at the 5' end and at least 3, 4, or 5 nucleotides at the 3' end of the ASO comprise ribonucleotides with one or more chemical modifications.

Embodiment 6 The ASO of embodiments 1 or 2, wherein the one or more chemical modifications comprise 2'-O-methoxyethyl, 5-methyl cytidine, locked nucleic acid (LNA), and phosphorothioate internucleotide bond.

Embodiment 7 The ASO of embodiments 1-3, wherein the ASO does not comprise 8 or more contiguous nucleotides of unmodified DNA.

Embodiment 8 An ASO complementary to at least 8 contiguous nucleotides of a regulatory RNA of a CPS1 gene, wherein the ASO does not comprise 8 or more contiguous nucleotides of unmodified DNA.

Embodiment 9 The ASO of embodiments 1-8, wherein the ASO does not comprise a deoxyribonucleotide.

Embodiment 10 The ASO of embodiments 1-9, wherein the ASO does not comprise an unmodified ribonucleotide.

Embodiment 11 The ASO of embodiments 1-10, wherein the length of the ASO is 3×n+2 nucleotides (n is an integer of 6 or greater), wherein the nucleotides at positions 3×m are ribonucleotides modified by LNA (m is an integer from 1 to n) and the nucleotides at the remaining positions are ribonucleotides modified by 2'-O-methoxyethyl.

Embodiment 12 The ASO of embodiments 1-11, wherein each nucleotide of the ASO is a ribonucleotide modified by 2'-O-methoxyethyl.

Embodiment 13 The ASO of embodiments 1-12, wherein each cytidine in the ASO is modified by 5-methyl.

Embodiment 14 The ASO of embodiments 1-13, wherein the ASO is no more than 50, 40, 30, or 25 nucleotides in length.

Embodiment 15 The ASO of embodiments 1-14, wherein the regRNA is an eRNA.

Embodiment 16 A pharmaceutical composition comprising the ASO of any one of embodiments 1-15 and a pharmaceutically acceptable carrier or excipient carrier.

Embodiment 17 A method of increasing the amount and/or stability of a regulatory RNA in a cell, the method comprising contacting the cell with the ASO of any one of embodiments 1-15 that hybridizes with the regulatory RNA.

Embodiment 18 A method of increasing transcription of a target gene in a cell, the method comprising contacting the cell with the ASO of any one of embodiments 1-15 that hybridizes with a regulatory RNA of the target gene.

Embodiment 19 The method of embodiments 17 or 18, wherein the cell is a mammalian cell.

Embodiment 20 The method of embodiment 19, wherein the cell is a human cell.

Embodiment 21 The method of embodiments 17-20, wherein the target gene is CPS1.

EXAMPLES

Example 1: Modulation of CPS1 Expression Using regRNA-Targeting ASOs

This example was designed to assess modulation of CPS1 expression in human hepatocytes using ASOs targeting eRNAs transcribed from an enhancer of human CPS1.

Figure 2:
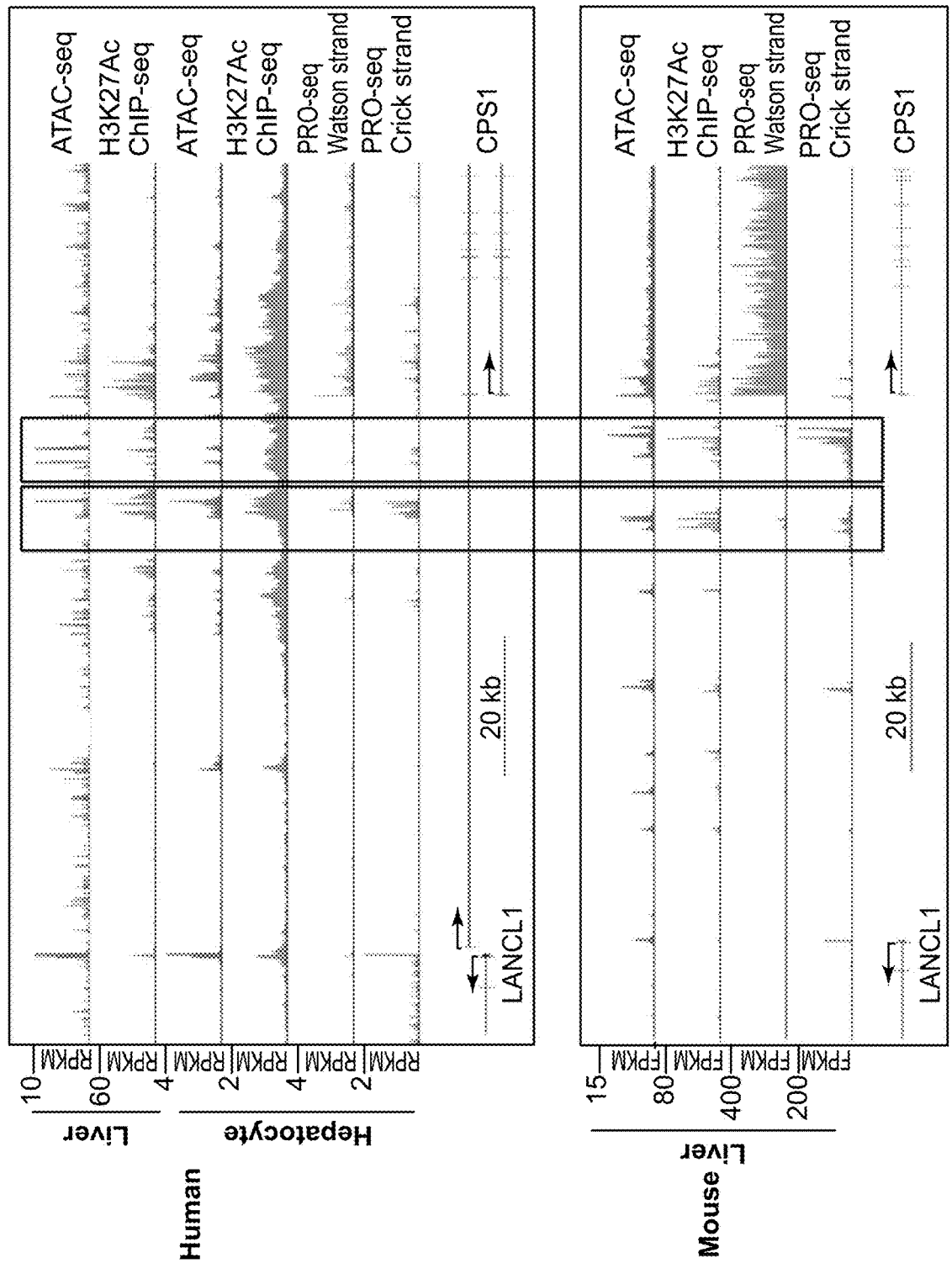
FIG. 2 shows analysis of mouse and human CPS1 ATAC-seq and H3K27Ac ChIP-SEQ for identification of regRNAs.

Regulatory RNAs (regRNAS) within enhancers of CPS1 were identified bioinformatically using ATAC-seq and H3K27Ac ChIP-SEQ data from human and mouse data. Two regRNAs were identified (RR44_v1 and RR44_v2) as conserved between human and mouse, as shown in FIG. 2.

330 unique antisense oligonucleotides (ASOs) targeting CPS1 were designed, 94 of which target the CPS1 regRNA described above (RR44).

Figure 3:
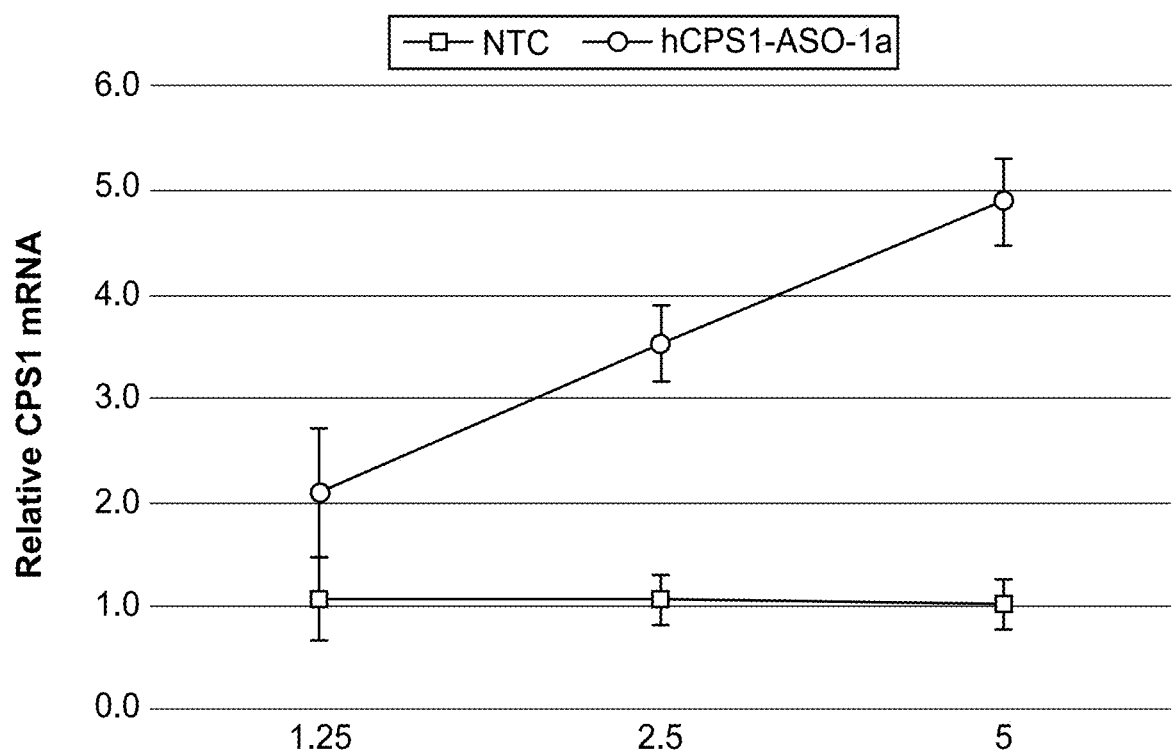
FIG. 3 shows relative CPS1 mRNA expression in hepatocytes treated with an ASO and non-targeting control (NTC).

Donor-derived hepatocytes were cultured in vitro. Cells were plated in growth media and treated 4-6 hours after plating with final concentrations of 1.25 μM, 2.5 μM, or 5 μM, or hCPS1-ASO-1a or control (see FIG. 5A for human CPS1 sequences and chemical modifications of selected ASOs). Cells were collected 48 hr post treatment and processed for RNA isolation, cDNA synthesis and QPCR analysis. A Taqman probe at 60x was used for CPS1 expression. CPS1 levels were normalized to B2M expression. FIG. 3 shows CPS1 mRNA after treatment with hCPS1-ASO-1a, demonstrating the ASO targeting regRNA RR44 increased human CPS1 mRNA in a dose-dependent matter.

Figures 4A, 4B:
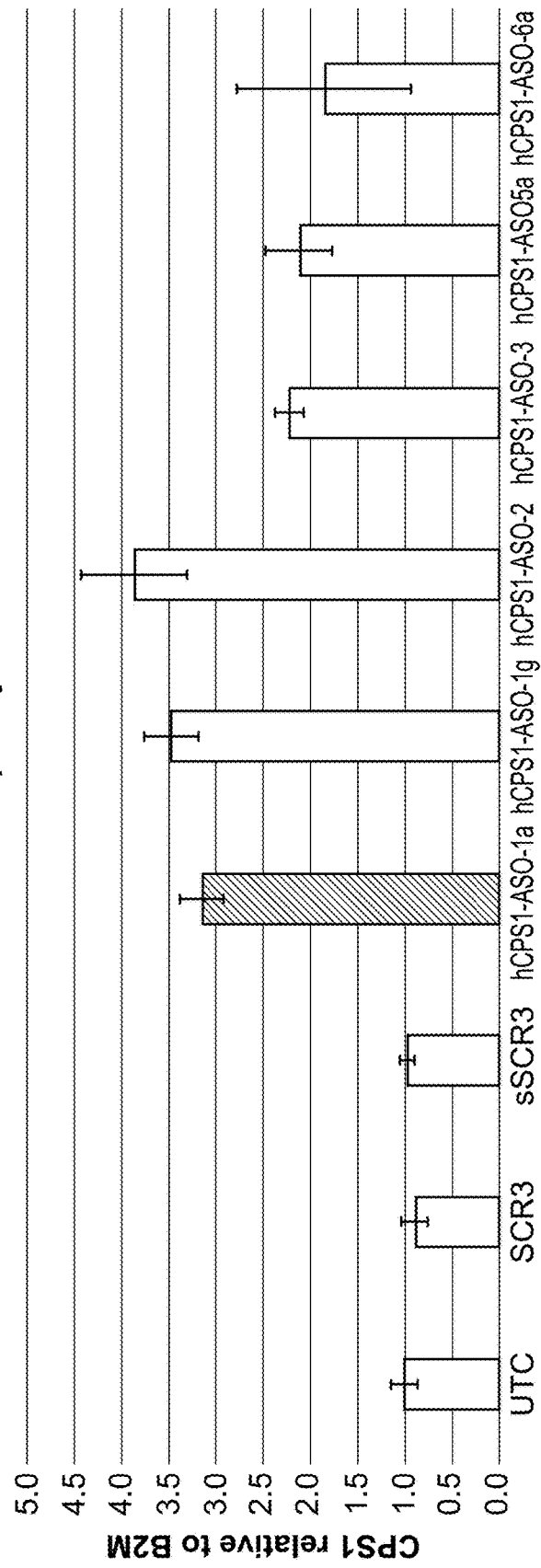
FIG. 4A shows a schematic of various human CPS1 ASOs with chemical modifications. Light gray indicates a 2'-O-(2-methoxyethyl) (2'-MOE) modification. Dark gray indicates a locked nucleic acid (LNA) modification. *C indicates a 5-methyl on the cytidine.
FIG. 4B shows relative CPS1 mRNA expression in hepatocytes treated with the ASOs.

Using hCPS1-ASO-1a as a starting point, additional ASOs were designed by base-walking. These ASOs are shown in FIG. 4A. Using the methods described above, these additional ASOs were assessed for effect on CPS1 mRNA, and results are shown in FIG. 4B. Additional ASOs are shown in FIG. 5A.

The majority of regRNAs do not have large sequence areas that are conserved between human and mouse genomes. For in vivo proof of concept, regRNAs around the mouse CPS1 region were identified and ASOs targeting those mouse regRNA (promoter and enhancer) were designed and screened in both wildtype (B6EiC3SnF1/J, [WT]) primary mouse hepatocytes and CPS1 deficient donor (B6EiC3Sn aIA-CPS1$^{spf-ash}$/J, [CPS1D]) primary mouse hepatocytes.

Primary hepatocytes were isolated from mice of mouse strains B6EiC3SnF1/J (control WT) and OTC deficient donor (B6EiC3Sn aIA-OTC1$^{spf-ash}$/J, catalog: 001811) from JAX lab. The spf$^{ash}$ mouse has a variant c.386G>A, p.Arg129His in the OTC gene that impacts splicing, resulting in decreased OTC mRNA levels (5~12% of wt control) in spf/ash livers. Thus, male spf$^{ash}$ mice have a mild biochemical phenotype with low OTC activity (5%-10% of wild-type).

Primary hepatocytes were seeded at 20,000 cells per well on day 0. Cells were treated with ASO on day 2 at concentrations of 1.25 μM, 2.5 μM, and 5 μM. Cells were incubated for 2 days and lysate was collected on Day 2 post treatment for mRNA analysis. A Taqman probe was used for determining mouse CPS1 and OTC expression. Ppia and Hprt were used as housekeeper genes for gene expression normalization. Statistics were performed using one-way ANOVA in Prism (GraphPad)

Figure 6A:
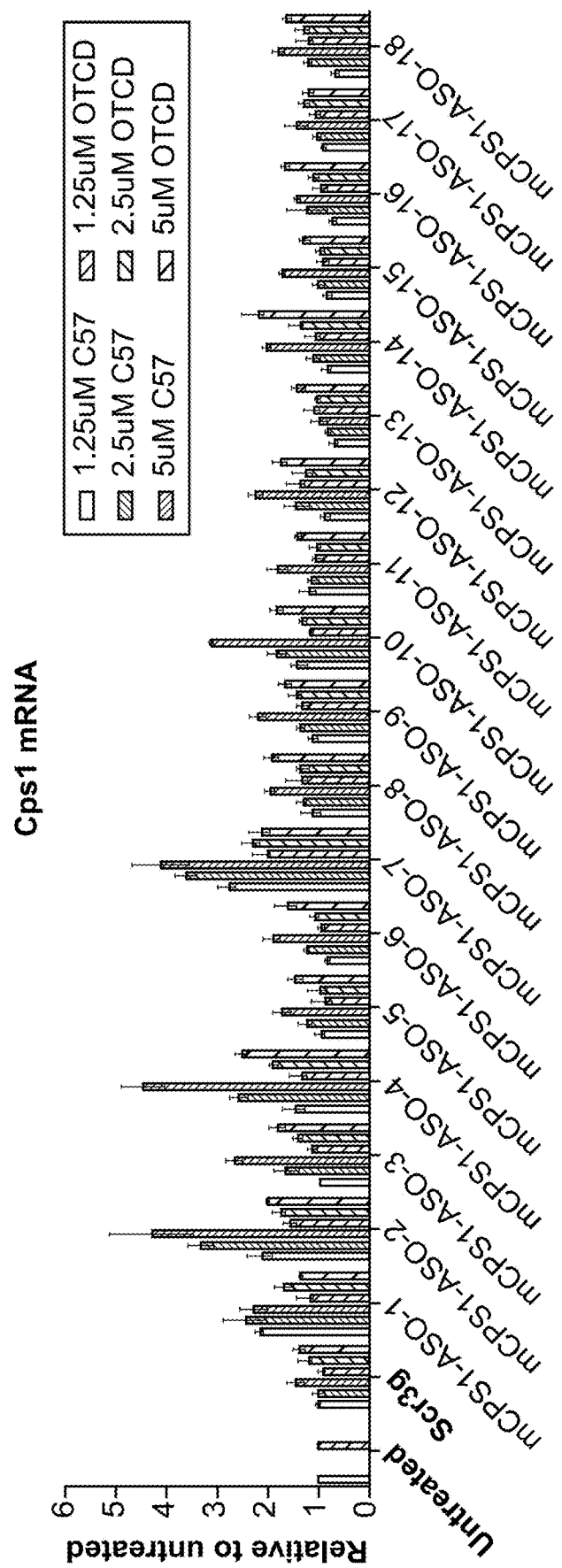
FIG. 6A shows CPS1 mRNA levels in wildtype and OTC-deficient hepatocytes treated with CPS1 ASOs. Heatmaps of CPS1 and OTC mRNA levels are shown in FIG. 6B and FIG. 6C.
Figure 7A:
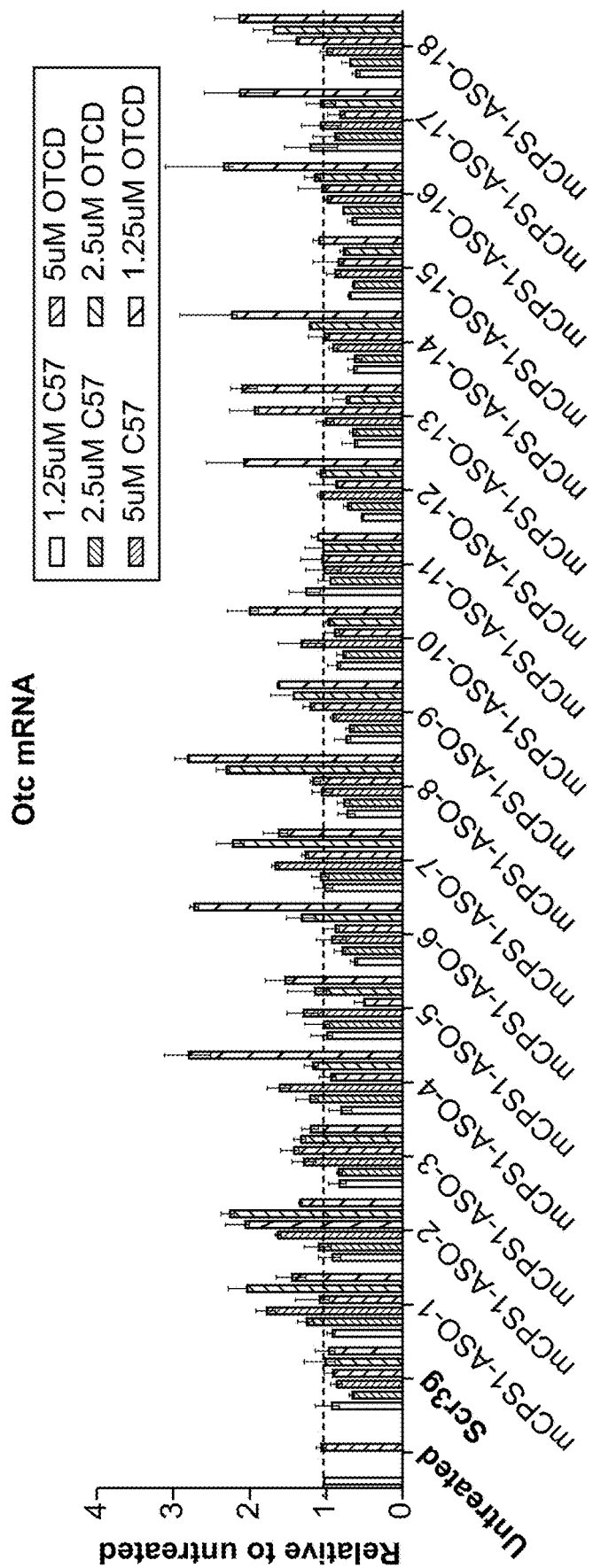
FIG. 7A shows OTC mRNA levels in wildtype and OTC-deficient hepatocytes treated with CPS1 ASOs. Heatmaps of CPS1 and OTC mRNA levels are shown in FIG. 7B and FIG. 7C.

CPS1 mRNA levels in treated wildtype and OTC-deficient hepatocytes in vitro, are shown in FIG. 6A, heatmaps are shown in FIG. 6B and FIG. 6C. As shown, a subset of the identified ASOs upregulate CPS1 mRNA by 2-fold in treated hepatocytes. Additionally, it was observed that ASOs that upregulate CPS1 may also increases expression of OTC (OTC mRNA levels shown in FIG. 7A and heatmaps are shown in FIG. 7B and FIG. 7C). Thus, ASO targeting regRNA can be used to increase CPS1 expression in diseased mice liver cells. ASO mediated CPS1 upregulation in OTC deficient mouse cells allow these to be tested in a disease model, and have an in vivo phenotypic readout.

In Vivo Modulation of CPS1

Figure 8:
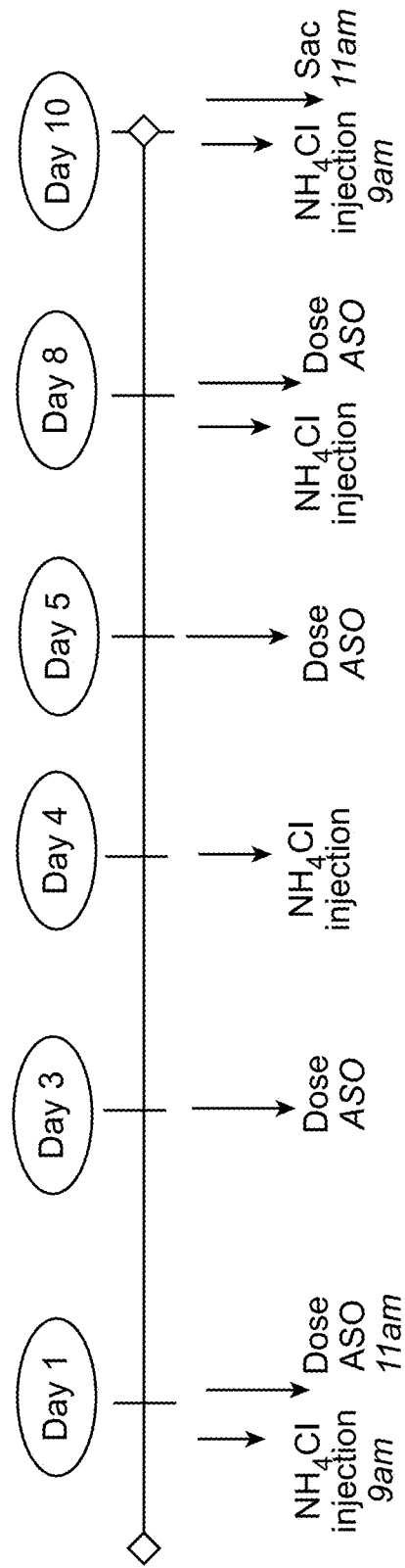
FIG. 8 is a schematic depiction of the in vivo ammonia challenge for mice treated with CPS1 ASOs.

Male B6EiC3Sn a/A-Otc$^{spf-ash}$/J Mice (homozygous), 4-5 mice/group, were fasted, then challenged with 0.75M NH$_4$Cl injected intraperitoneally. Two hours later, a dose of 200 mg/kg/wk subcutaneous injection of GalNAc-conjugated ASO was administered. Mice were again dosed with GalNAc-conjugated ASO about 48 hours later. About 24 hours later, mice were challenged with 0.75M NH$_4$Cl injected intraperitoneally, and about 24 hours subsequently were again dosed with GalNAc-conjugated ASO. After 72 hours, mice were injected with 0.75M NH$_4$Cl intraperitoneally and dosed with GalNAc-conjugated ASO. 48 hours later, mice were injected with 0.75M NH$_4$Cl intraperitoneally, and 2 hours later, were sacrificed. The timeline is depicted in FIG. 8. Serum was collected 30-60 minutes post-NH$_4$Cl injection, and terminal plasma samples were analyzed by IDEXX for ammonia levels. Liver, serum, and urine were collected following sacrifice.

Figure 9A:
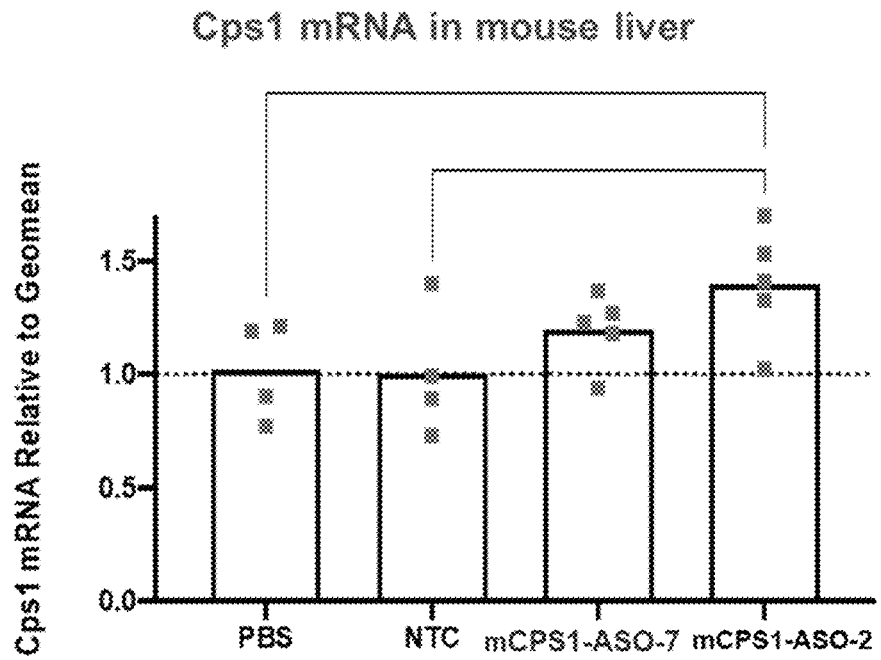
FIG. 9A shows relative CPS1 mRNA expression in the mouse liver.
Figure 9B:
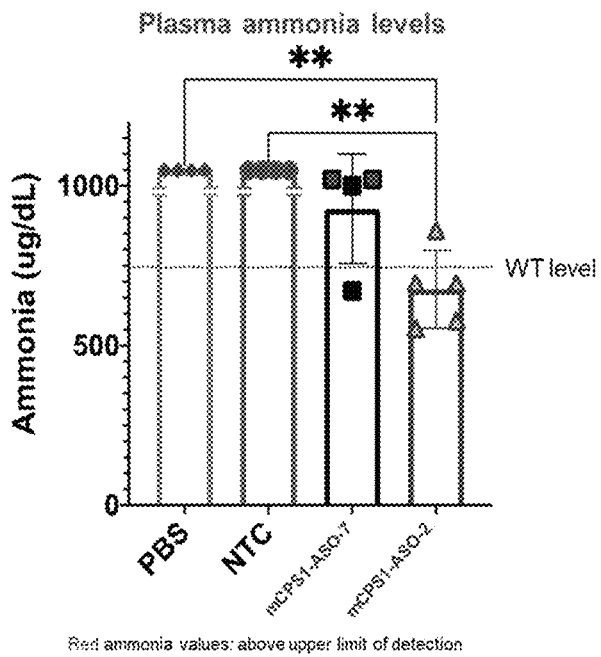
FIG. 9B shows plasma ammonia levels of treated mice.
Figure 9C:
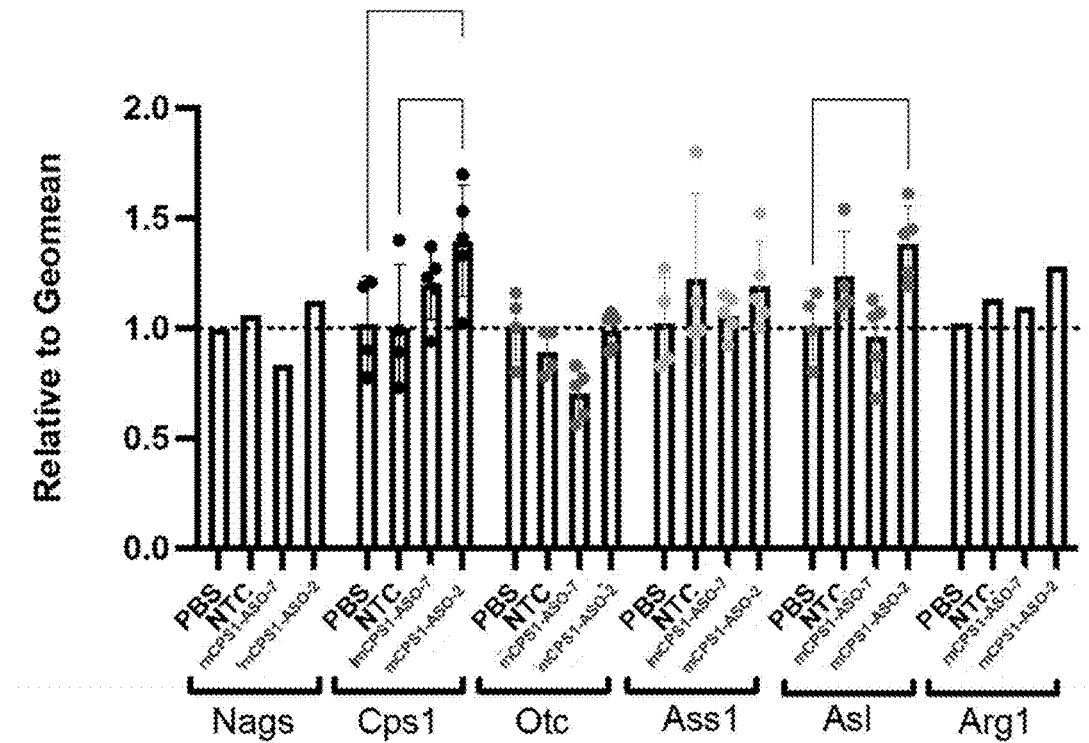
FIG. 9C shows relative mRNA expression of other urea cycle genes in the treated mice.
Figure 9D:
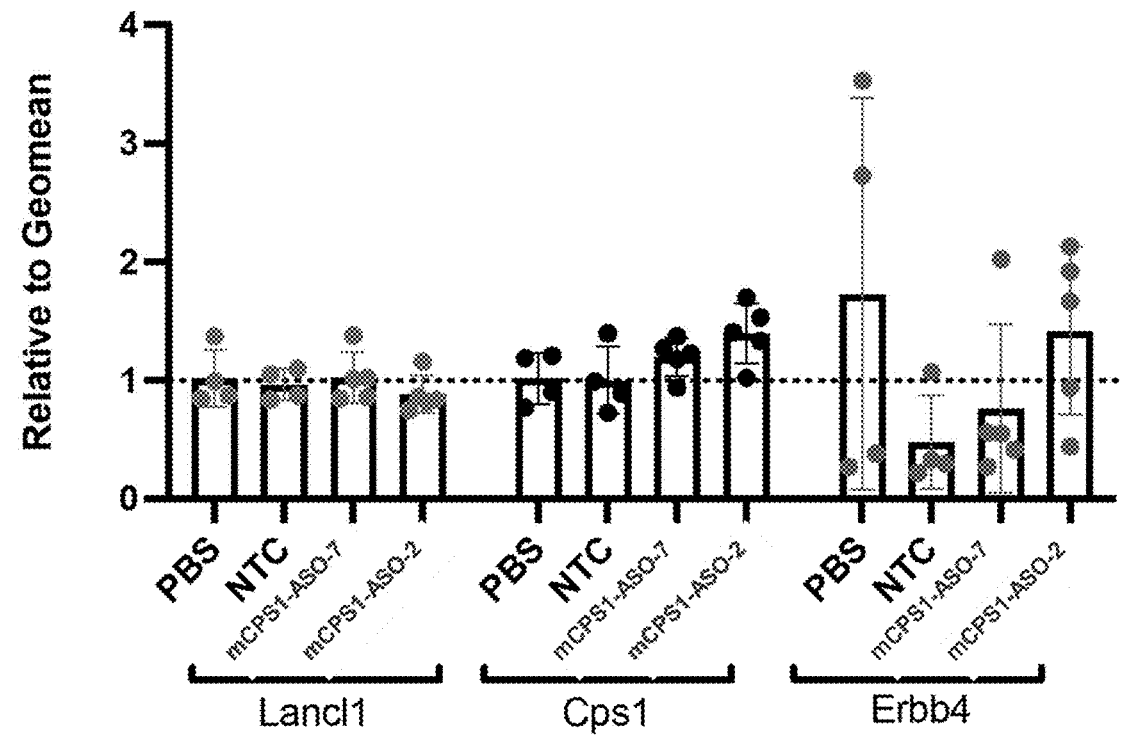
FIG. 9D shows mRNA expression of genes neighboring the CPS1 locus following ASO treatment.

As shown in FIG. 9A, ASO treatment increased CPS1 mRNA in the mouse liver by about 1.4-fold. Additionally, plasma ammonia levels were decreased following treatment, indicated increased ureagenesis (FIG. 9B). ASOs targeting CPS1 regRNA additionally increased a number of other urea cycle genes, including ASS1, ASL, and ARG1 in OTC-deficient mice (FIG. 9C). Importantly, ASOs targeting CPS1 regRNA did not influence expression levels neighboring genes (FIG. 9D).

Figure 10:
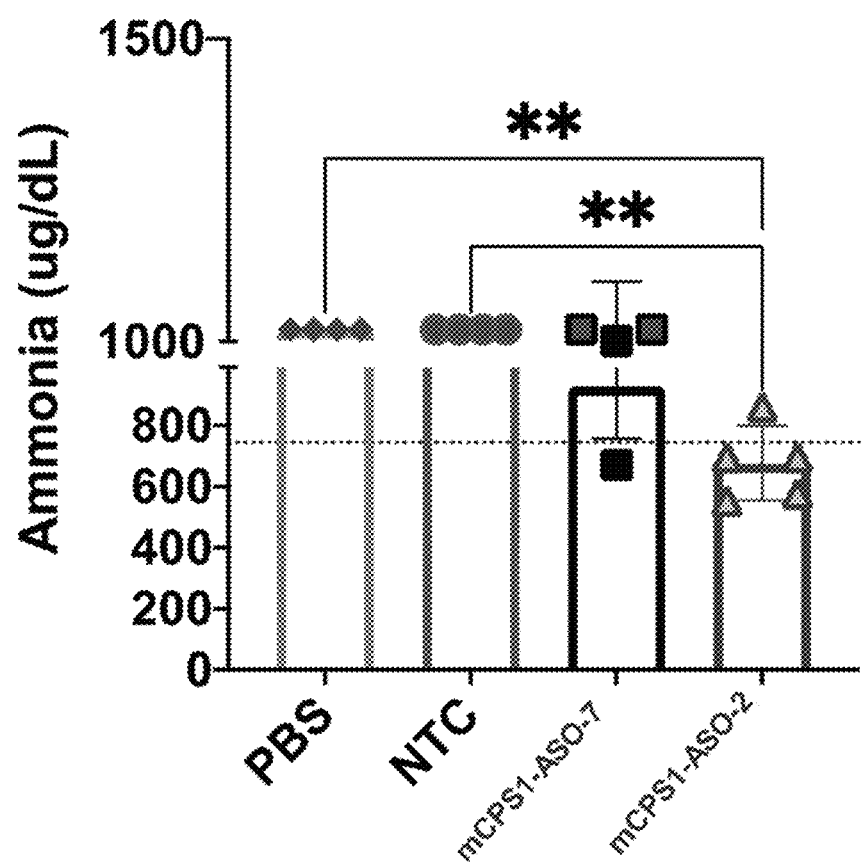
FIG. 10 shows ammonia levels in OTC deficient mice treated with a CPS1 ASO.

In an additional experiment, Male B6EiC3Sn a/A-Otc$^{spf-ash/J}$ Mice (homozygous), 4-5 mice/group, were fasted, then challenged with 0.75M NH$_4$Cl injected intraperitoneally and subcutaneously injected with GalNAc-conjugated ASO. Terminal plasma samples collected 60 min after NH$_4$Cl injection was analyzed by IDEXX for ammonia levels, with an upper detection limit of 1020 μg/dL. As shown in FIG. 10, CPS1 regRNA targeting mCPS1-ASO-2 decreased ammonia back to wildtype levels in the OTC deficient mice.

Figure 11C:
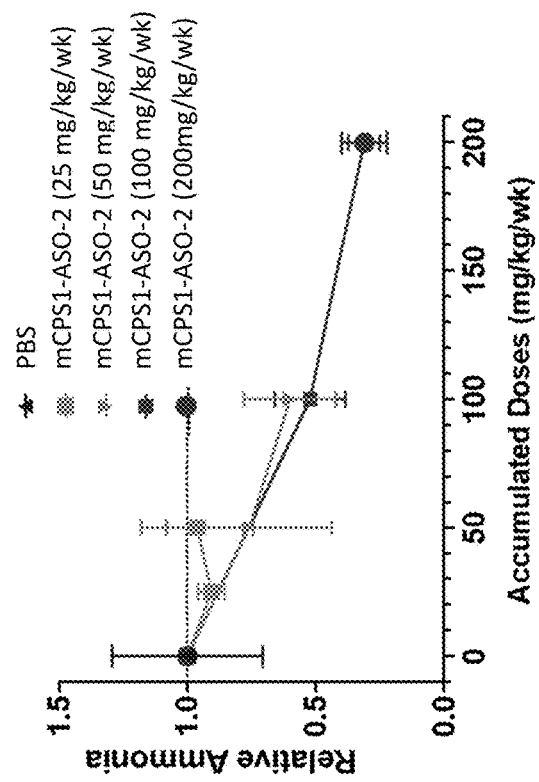
FIG. 11C shows that the reduction in ammonia correlated with the total ASO administered.
Figure 11A:
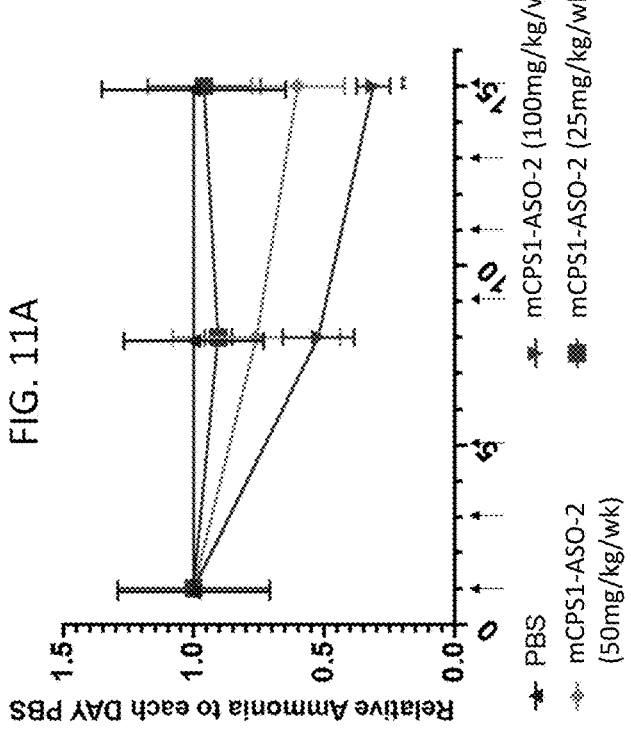
FIG. 11A shows a dose dependent effect on plasma ammonia in vivo in male OTC-D mice ($Otc^{spf/ash}$) after the ASO treatment.
Figure 11B:
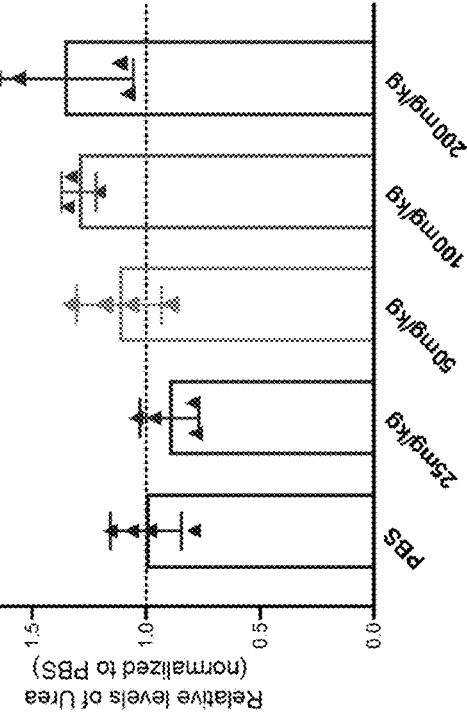
FIG. 11B, there was a dose dependent effect on urea in vivo in male OTC-D mice ($Otc^{spf/ash}$) after the ASO treatment.

As shown in FIGS. 11A and 11B, there was a dose dependent impact on plasma ammonia (FIG. 11A) and urea (FIG. 11B) in vivo in male OTCD mice (Otc$^{spf-ash}$) after the ASO treatment. The ammonia challenge was given after overnight fasting of the mice Briefly, mice received a 0.75 M solution of ammonium chloride via IP injection. Interim plasma was collected at 30 minutes post each ammonium challenge (±5%). Ammonia levels were measured in fresh plasma samples by Beckman Coulter AU® chemistry analyzers. In addition, the reduction in ammonia correlated with the total ASO administered (FIG. 11C). Without wishing to be bound by theory this data suggests dose accumulation of the ASO and thus supports a long duration of action of the ASO. In addition, the data suggests that ASO efficacy can be achieved by splitting the dose over time, allowing for a greater safety margin during dosing. For example, at least a 1 month dosing interval may be used.

A second in vivo experiment was performed to assess the ASO duration of action. Male B6EiC3Sn a/A-Otc$^{spf-ash/J}$ Mice (homozygous) or wild type (C57BL/6) mice, 5 mice/group, were fasted, then challenged with 0.75M NH$_4$Cl injected intraperitoneally. Two hours later, a dose of 100 mg/kg/wk subcutaneous injection of GalNAc-conjugated ASO was administered (day 1). WT and one group of OTC-deficient mice were administered PBS as control groups. Mice were again dosed with GalNAc-conjugated ASO on days 3 and 5. Ammonia was administered intraperitoneally to mice on days 8, 11, 15, 19, 22, and 26. Circulating ammonia was measured post-IP ammonia challenge. Mice were sacrificed on day 26 and livers were collected and processed for mRNA and protein expression. mRNA geomean was quantified by Gusb, Gapdh, Actb, Ppia, and Hprt genes. Statistics were done by two way ANOVA. Two way ANOVA, *: P<0.05, : P<0.01, *: P<0.001, ****: P<0.0001

Figure 12A:
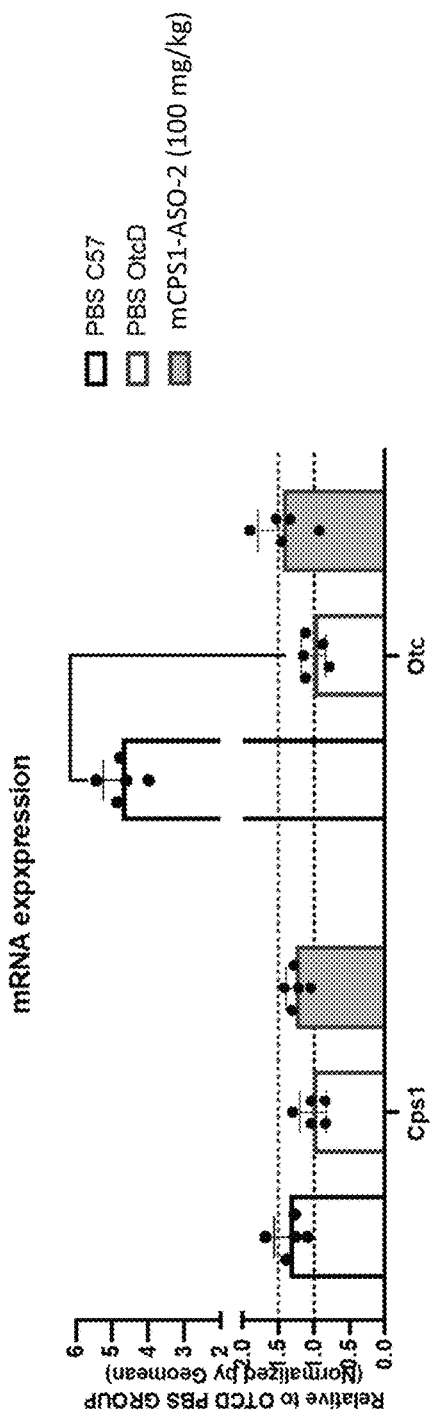
FIG. 12A shows that CPS1 ASO treatment increased mouse OTC and CPS1 mRNA expression in the OTC deficient mice (1.26 FC of CPS1 and 1.43 FC of OTC).
Figure 12B:
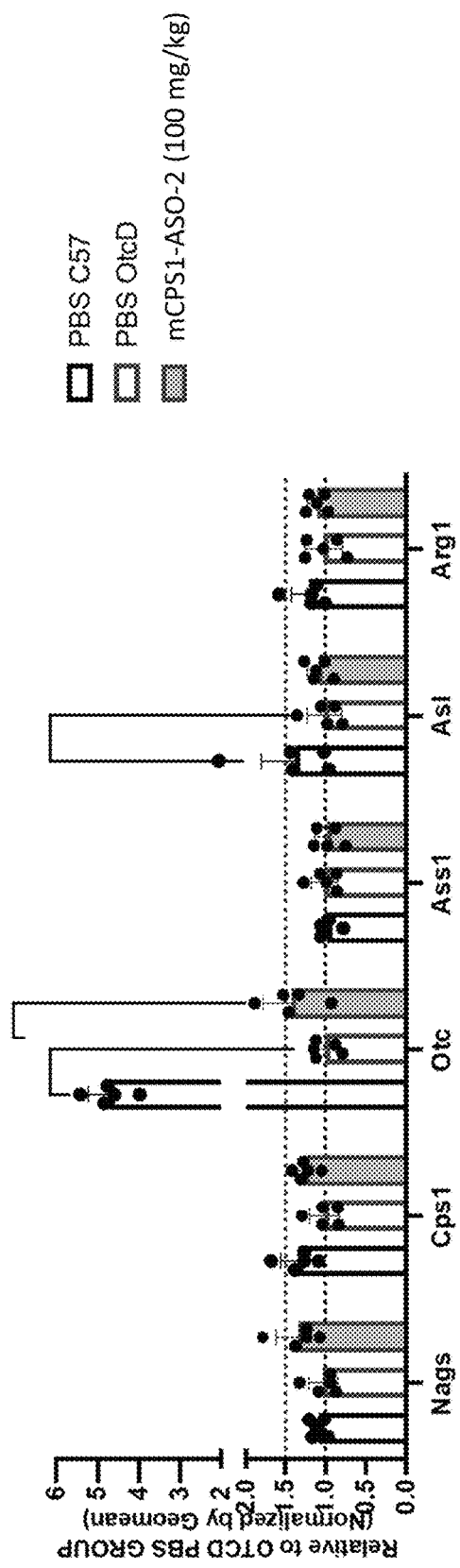
FIG. 12B shows that ASO treatment increased additional urea cycle genes, such as Nags, Ass1, Asl, and Arg1. In both figures WT C57 mice mRNA is shown on the left bar, $Otc^{spf-ash/J}$ treated with PBS is shown in middle bar, and $Otc^{spf-ash/J}$ treated with ASO is shown on the right.

As shown in FIG. 12A, Cps1 ASO treatment increased mouse Otc and Cps1 mRNA expression in the OTC deficient mice (1.26 FC of Cps1 and 1.43 FC of Otc). WT C57 mice mRNA is shown on the left bar, Otc$^{spf-ash/J}$ treated with PBS is shown in middle bar, and Otc$^{spf-ash/J}$ treated with ASO is shown on the right. In addition, ASO treatment increased additional urea cycle genes, such as Nags, Ass1, Asl, and Arg1 (FIG. 12B). WT C57 mice mRNA is shown on the left bar, Otc$^{spf-ash/J}$ treated with PBS is shown in middle bar, and Otc$^{spf-ash/J}$ treated with ASO is shown on the right.

Figure 13:
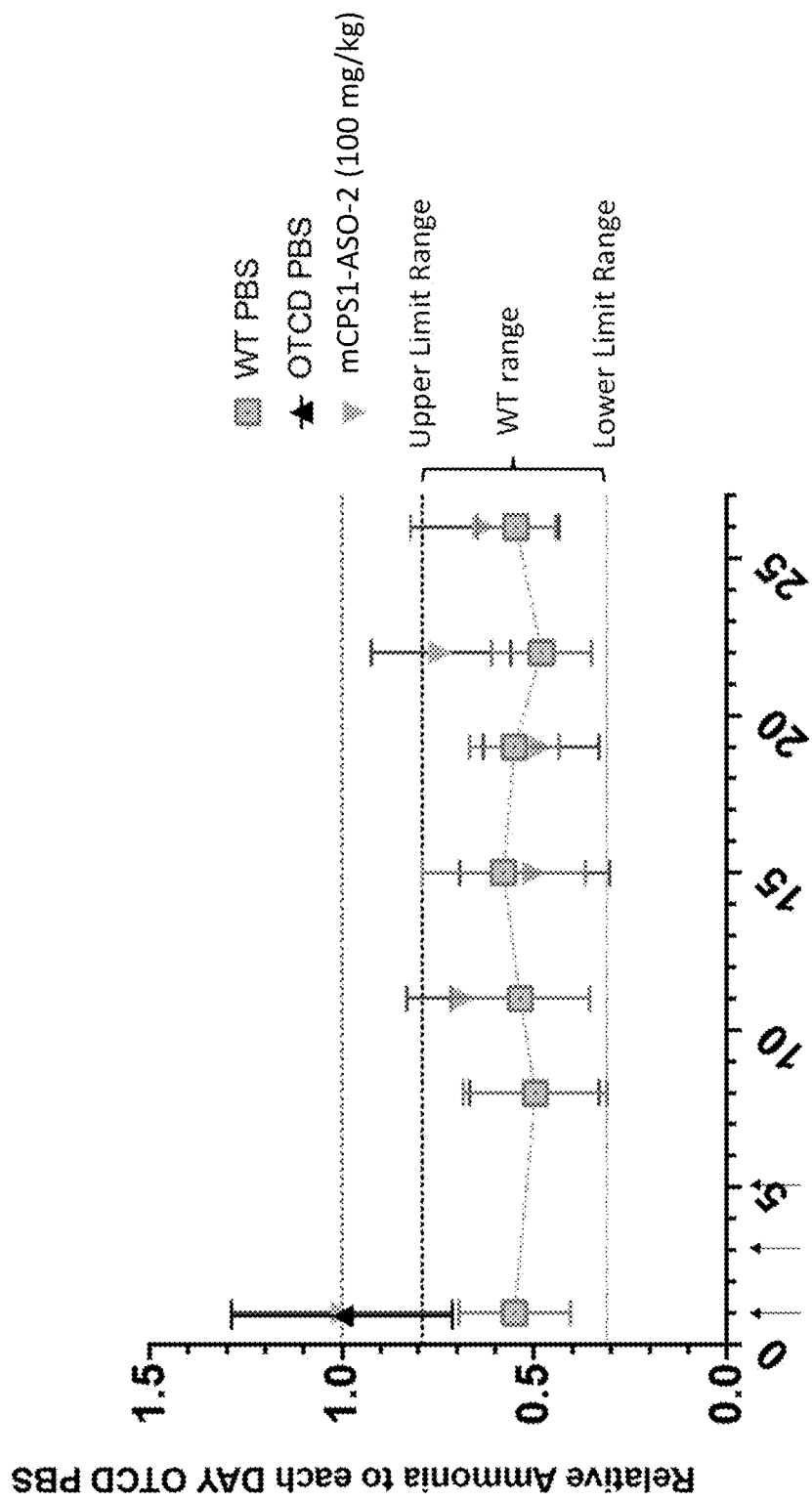
FIG. 13 shows that mouse Otc deficient livers showed hyperammonia 30 min after ammonia treatment. Treatment with mouse CPS1 ASO decreased ammonia to WT levels.

In the PBS control group, mouse Otc deficient livers showed hyperammonia 30 min after ammonia treatment (FIG. 13, see black triangle at 1.0). Ammonia levels were consistent through the study. Treatment with mouse Cps1 ASO (upside down triangles) decreased ammonia to WT levels (squares) and maintained the wild type (WT) levels throughout the study (FIG. 13). ASO was administered on days 1, 3, and 5 but the duration of action was approximately 4 weeks.

The in vivo assay was repeated with hCPS1-ASO-1x in Yecuris mice (Fah$^{-/-}$;Rag2$^{-/-}$;Il2rg$^{-/-}$ (FRG) mice with OTC deficient humanized liver). Male humanized Yecuris mice were repopulated with human ornithine transcarbamylase deficient hepatocytes (OTCD) or with healthy wild-type hepatocytes (WT), 5 mice/group. After fasting overnight, 0.75M $^{15}$NH$_4$Cl was injected intraperitoneally. Two hours later, multiple doses of GalNAc-conjugated hCPS1-ASO-1x were subcutaneously injected on days 1, 8, and 15. In some groups, a single injection of 5, 20, and 50 mg/kg/week doses were performed. WT and one group of OTCD Yecuris FRG mice were administered with PBS as control groups. Ammonia challenge and ureagenesis assay in humanized Yecuris mice were performed in a fasted state, i.e. food withdrawal overnight, prior to the ammonia challenge. After fasting overnight on days 1, 8, 15, and 22 (terminal harvest) the animals were challenged with $^{15}$NH$_4$Cl by intraperitoneal injection. After 30 minutes, urines and plasmas were collected.

As shown in FIGS. 15A and 15B, hCPS1-ASO-1× decreased in vivo plasma ammonia and increased in vivo urea in the OTC$^{def}$ mice with humanized liver. hCPS1-ASO-1g also increased OTC protein levels after treatment at 5 mg/kg and 20 mg/kg (FIG. 15C).

In Vitro Modulation of Ureagenesis in Primary Human Hepatocytes

ASOs were also tested for their ability to agonize ureagenesis in human cells in vitro. Healthy donor primary human hepatocytes and OTC$^{def}$ primary human hepatocytes were plated and 1.25 uM of hCPS1-ASO-1a or hCPS1-ASO-1g were incubated with the cells for two days. On the second day 2 M NH$_4$Cl was added to the cell mixture. Cells and cell media were collected on Day 3 for mRNA and urea quantification. As shown in FIG. 16, both ASOs increased CPS1 mRNA and ureagenesis in both healthy and OTC$^{def}$ primary human hepatocytes.

Synthesis and Characterization of Additional ASOs

Additional ASOs were synthesized and characterized. Hepatocytes were treated with 5 uM ASO as described above and CPS1 mRNA fold change was determined.

Table 4 proves the mRNA FC and standard deviation in CPS1 mRNA.

TABLE 4

| Name | FC | SD | Name | FC | SD | Name | FC | SD |
|---|---|---|---|---|---|---|---|---|
| hCPS1-ASO-1a | 5.5803 | 0.9290 | hCPS1-ASO-85b | 2.4815 | 0.2779 | hCPS1-ASO-204 | 1.0451 | 0.2891 |
| hCPS1-ASO-16 | 1.6607 | 0.2690 | hCPS1-ASO-86 | 2.5546 | 0.1486 | hCPS1-ASO-205 | 1.0432 | 0.1968 |
| hCPS1-ASO-17 | 1.1878 | 0.2382 | hCPS1-ASO-1ab | 1.2337 | 0.1193 | hCPS1-ASO-206 | 0.9000 | 0.1529 |
| hCPS1-ASO-18 | 1.3738 | 0.1466 | hCPS1-ASO-1ac | 1.3452 | 0.4155 | hCPS1-ASO-207 | 1.0064 | 0.2810 |
| hCPS1-ASO-19 | 1.3322 | 0.2929 | hCPS1-ASO-1ad | 1.7071 | 0.3347 | hCPS1-ASO-208 | 0.8499 | 0.1017 |

TABLE 4-continued

| Name | FC | SD | Name | FC | SD | Name | FC | SD |
|---|---|---|---|---|---|---|---|---|
| hCPS1-ASO-20 | 1.4049 | 0.2328 | hCPS1-ASO-1ae | 1.4598 | 0.2254 | hCPS1-ASO-209 | 0.8872 | 0.2187 |
| hCPS1-ASO-21 | 3.6049 | 0.0613 | hCPS1-ASO-1af | 1.1069 | 0.2738 | hCPS1-ASO-210 | 1.0426 | 0.2646 |
| hCPS1-ASO-22 | 1.2367 | 0.1154 | hCPS1-ASO-1ag | 1.2439 | 0.3771 | hCPS1-ASO-211 | 0.8667 | 0.1797 |
| hCPS1-ASO-23 | 1.0846 | 0.1572 | hCPS1-ASO-1ah | 1.9014 | 0.3037 | hCPS1-ASO-212 | 1.1604 | 0.2568 |
| hCPS1-ASO-24 | 1.0683 | 0.1120 | hCPS1-ASO-1ai | 3.0003 | 0.6407 | hCPS1-ASO-213 | 1.0240 | 0.2239 |
| hCPS1-ASO-25 | 0.9967 | 0.1307 | hCPS1-ASO-92 | 1.4093 | 0.0630 | hCPS1-ASO-214 | 0.9408 | 0.2219 |
| hCPS1-ASO-26 | 1.1141 | 0.2129 | hCPS1-ASO-93 | 1.3278 | 0.1805 | hCPS1-ASO-215 | 1.2719 | 0.3355 |
| hCPS1-ASO-27 | 1.2348 | 0.2667 | hCPS1-ASO-94 | 1.1871 | 0.0806 | hCPS1-ASO-216 | 0.9536 | 0.2038 |
| hCPS1-ASO-28 | 3.7994 | 0.7319 | hCPS1-ASO-95 | 1.0937 | 0.1027 | hCPS1-ASO-217 | 0.9589 | 0.2111 |
| hCPS1-ASO-29 | 1.2569 | 0.2946 | hCPS1-ASO-96 | 1.0708 | 0.1544 | hCPS1-ASO-218 | 0.9624 | 0.1812 |
| hCPS1-ASO-30 | 0.9996 | 0.1342 | hCPS1-ASO-97 | 1.8697 | 0.2390 | hCPS1-ASO-219 | 1.0837 | 0.3110 |
| hCPS1-ASO-31 | 1.0879 | 0.2887 | hCPS1-ASO-98 | 2.2671 | 0.0950 | hCPS1-ASO-220 | 1.0236 | 0.1605 |
| hCPS1-ASO-32 | 1.0803 | 0.0754 | hCPS1-ASO-99 | 3.2286 | 0.3834 | hCPS1-ASO-221 | 1.0461 | 0.2903 |
| hCPS1-ASO-33 | 1.0982 | 0.2301 | hCPS1-ASO-100 | 1.6813 | 0.1274 | hCPS1-ASO-222 | 1.0435 | 0.2238 |
| hCPS1-ASO-34 | 0.9376 | 0.0691 | hCPS1-ASO-101 | 2.8205 | 0.0827 | hCPS1-ASO-223 | 1.1306 | 0.4103 |
| hCPS1-ASO-35 | 4.5563 | 0.0988 | hCPS1-ASO-102 | 3.1424 | 0.1637 | hCPS1-ASO-224 | 1.0954 | 0.1792 |
| hCPS1-ASO-36 | 1.1589 | 0.1449 | hCPS1-ASO-103 | 3.7109 | 0.4564 | hCPS1-ASO-225 | 0.8416 | 0.2138 |
| hCPS1-ASO-37 | 1.0707 | 0.1475 | hCPS1-ASO-104 | 5.0641 | 0.2305 | hCPS1-ASO-226 | 1.0220 | 0.2833 |
| hCPS1-ASO-38 | 1.0941 | 0.1276 | hCPS1-ASO-107 | 1.4662 | 0.1834 | hCPS1-ASO-227 | 0.8141 | 0.1635 |
| hCPS1-ASO-39 | 1.1150 | 0.1947 | hCPS1-ASO-108 | 1.3163 | 0.1848 | hCPS1-ASO-228 | 0.7884 | 0.1280 |
| hCPS1-ASO-40 | 1.1812 | 0.0713 | hCPS1-ASO-109 | 1.1404 | 0.1269 | hCPS1-ASO-229 | 0.8821 | 0.1602 |
| hCPS1-ASO-41 | 1.1376 | 0.1669 | hCPS1-ASO-110 | 1.4157 | 0.2399 | hCPS1-ASO-230 | 1.0366 | 0.2360 |
| hCPS1-ASO-42 | 3.9849 | 0.9906 | hCPS1-ASO-111 | 1.3974 | 0.0526 | hCPS1-ASO-231 | 1.0731 | 0.3336 |
| hCPS1-ASO-43 | 1.1340 | 0.1748 | hCPS1-ASO-112 | 1.3309 | 0.2948 | hCPS1-ASO-232 | 1.0336 | 0.2169 |
| hCPS1-ASO-44 | 0.9795 | 0.1452 | hCPS1-ASO-113 | 1.1250 | 0.0133 | hCPS1-ASO-233 | 1.0184 | 0.2427 |
| hCPS1-ASO-45 | 1.0825 | 0.3286 | hCPS1-ASO-114 | 1.4471 | 0.3902 | hCPS1-ASO-234 | 1.0379 | 0.2667 |
| hCPS1-ASO-46 | 1.3008 | 0.2339 | hCPS1-ASO-115 | 1.3250 | 0.2205 | hCPS1-ASO-235 | 0.7109 | 0.1642 |
| hCPS1-ASO-47 | 1.2834 | 0.2346 | hCPS1-ASO-116 | 1.4592 | 0.2191 | hCPS1-ASO-236 | 0.9437 | 0.2016 |
| hCPS1-ASO-48 | 1.0953 | 0.2896 | hCPS1-ASO-117 | 1.5146 | 0.1541 | hCPS1-ASO-237 | 1.1237 | 0.2948 |
| hCPS1-ASO-49 | 1.4947 | 0.3320 | hCPS1-ASO-118 | 1.4798 | 0.3053 | hCPS1-ASO-238 | 0.8325 | 0.1677 |
| hCPS1-ASO-50 | 1.2992 | 0.2852 | hCPS1-ASO-119 | 1.4687 | 0.3357 | hCPS1-ASO-239 | 1.2847 | 0.3268 |
| hCPS1-ASO-51 | 1.0101 | 0.2333 | hCPS1-ASO-120 | 1.4309 | 0.2206 | hCPS1-ASO-240 | 1.0368 | 0.1643 |
| hCPS1-ASO-52 | 1.2026 | 0.2065 | hCPS1-ASO-121 | 1.5330 | 0.4945 | hCPS1-ASO-241 | 1.0348 | 0.2319 |
| hCPS1-ASO-53 | 1.3176 | 0.2462 | hCPS1-ASO-122 | 2.1728 | 1.0205 | hCPS1-ASO-242 | 1.2009 | 0.3035 |
| hCPS1-ASO-54 | 1.2888 | 0.1512 | hCPS1-ASO-123 | 1.3792 | 0.2117 | hCPS1-ASO-243 | 0.8364 | 0.1646 |
| hCPS1-ASO-55 | 0.9070 | 0.0979 | hCPS1-ASO-124 | 1.6351 | 0.2666 | hCPS1-ASO-244 | 0.9177 | 0.1890 |
| hCPS1-ASO-56 | 2.2957 | 0.4780 | hCPS1-ASO-125 | 1.9894 | 0.2327 | hCPS1-ASO-245 | 0.9563 | 0.2149 |
| hCPS1-ASO-57 | 1.3780 | 0.1587 | hCPS1-ASO-126 | 1.8741 | 0.1928 | hCPS1-ASO-246 | 1.0945 | 0.1746 |
| hCPS1-ASO-58 | 1.1027 | 0.1230 | hCPS1-ASO-127 | 1.9805 | 0.5252 | hCPS1-ASO-247 | 1.1518 | 0.1876 |

TABLE 4-continued

| Name | FC | SD | Name | FC | SD | Name | FC | SD |
|---|---|---|---|---|---|---|---|---|
| hCPS1-ASO-59 | 1.2449 | 0.2215 | hCPS1-ASO-128 | 1.7071 | 0.2968 | hCPS1-ASO-248 | 1.1365 | 0.2040 |
| hCPS1-ASO-60 | 1.4067 | 0.1655 | hCPS1-ASO-129 | 1.8255 | 0.4447 | hCPS1-ASO-249 | 0.9208 | 0.2208 |
| hCPS1-ASO-61 | 1.2124 | 0.0876 | hCPS1-ASO-130 | 1.9578 | 0.6166 | hCPS1-ASO-250 | 1.1458 | 0.2996 |
| hCPS1-ASO-62 | 0.9895 | 0.1303 | hCPS1-ASO-131 | 1.3484 | 0.2757 | hCPS1-ASO-251 | 0.8471 | 0.1852 |
| hCPS1-ASO-63 | 2.3654 | 0.4539 | hCPS1-ASO-132 | 1.4400 | 0.3570 | hCPS1-ASO-252 | 0.7147 | 0.0925 |
| hCPS1-ASO-64 | 1.1365 | 0.1718 | hCPS1-ASO-133 | 1.4004 | 0.1358 | hCPS1-ASO-253 | 0.6961 | 0.1808 |
| hCPS1-ASO-65 | 0.8489 | 0.1813 | hCPS1-ASO-134 | 1.5631 | 0.1290 | hCPS1-ASO-254 | 0.8060 | 0.1913 |
| hCPS1-ASO-66 | 1.2409 | 0.1946 | hCPS1-ASO-135 | 1.6723 | 0.4246 | hCPS1-ASO-255 | 0.8039 | 0.1878 |
| hCPS1-ASO-67 | 0.9222 | 0.1245 | hCPS1-ASO-136 | 1.6023 | 0.3159 | hCPS1-ASO-256 | 0.7368 | 0.0548 |
| hCPS1-ASO-68 | 1.3275 | 0.1510 | hCPS1-ASO-137 | 1.5022 | 0.2462 | hCPS1-ASO-257 | 0.9517 | 0.2562 |
| hCPS1-ASO-69 | 1.0944 | 0.2374 | hCPS1-ASO-138 | 1.9038 | 0.5748 | hCPS1-ASO-258 | 1.0658 | 0.3429 |
| hCPS1-ASO-70 | 1.5761 | 0.1388 | hCPS1-ASO-139 | 1.6131 | 0.1660 | hCPS1-ASO-259 | 0.8157 | 0.2459 |
| hCPS1-ASO-71 | 1.3363 | 0.1613 | hCPS1-ASO-140 | 1.6504 | 0.2242 | hCPS1-ASO-260 | 1.1626 | 0.2553 |
| hCPS1-ASO-72 | 1.0412 | 0.1404 | hCPS1-ASO-141 | 1.8803 | 0.2397 | hCPS1-ASO-261 | 0.9754 | 0.1961 |
| hCPS1-ASO-73 | 1.3314 | 0.2056 | hCPS1-ASO-142 | 3.0769 | 0.3542 | hCPS1-ASO-262 | 1.3364 | 0.3546 |
| hCPS1-ASO-74 | 1.2915 | 0.1170 | hCPS1-ASO-143 | 1.9543 | 0.5131 | hCPS1-ASO-263 | 1.0346 | 0.1123 |
| hCPS1-ASO-75 | 1.2395 | 0.0952 | hCPS1-ASO-144 | 3.5634 | 0.5168 | hCPS1-ASO-264 | 0.6237 | 0.0401 |
| hCPS1-ASO-76 | 1.0942 | 0.2650 | hCPS1-ASO-145 | 2.8153 | 0.5824 | hCPS1-ASO-265 | 0.7730 | 0.1091 |
| hCPS1-ASO-1b | 1.1870 | 0.1452 | hCPS1-ASO-146 | 1.5756 | 0.0004 | hCPS1-ASO-266 | 0.8882 | 0.1967 |
| hCPS1-ASO-1c | 1.4590 | 0.2142 | hCPS1-ASO-147 | 1.8075 | 0.1998 | hCPS1-ASO-267 | 0.7796 | 0.2146 |
| hCPS1-ASO-1d | 1.0277 | 0.1069 | hCPS1-ASO-148 | 1.6902 | 0.0950 | hCPS1-ASO-268 | 0.9467 | 0.1832 |
| hCPS1-ASO-1e | 1.0992 | 0.1400 | hCPS1-ASO-149 | 1.5828 | 0.0817 | hCPS1-ASO-269 | 0.9570 | 0.1712 |
| hCPS1-ASO-1f | 1.6978 | 0.4026 | hCPS1-ASO-150 | 1.6598 | 0.1305 | hCPS1-ASO-270 | 0.8511 | 0.1498 |
| hCPS1-ASO-1g | 4.4990 | 0.6087 | hCPS1-ASO-151 | 1.7341 | 0.2274 | hCPS1-ASO-271 | 0.9859 | 0.1688 |
| hCPS1-ASO-2 | 4.3014 | 0.9287 | hCPS1-ASO-152 | 1.7582 | 0.2844 | hCPS1-ASO-272 | 0.7428 | 0.0842 |
| hCPS1-ASO-3 | 2.2218 | 0.1531 | hCPS1-ASO-153 | 1.8459 | 0.3518 | hCPS1-ASO-273 | 0.8121 | 0.1444 |
| hCPS1-ASO-9a | 1.0275 | 0.1642 | hCPS1-ASO-154 | 1.5900 | 0.4826 | hCPS1-ASO-274 | 0.7497 | 0.1493 |
| hCPS1-ASO-10a | 1.1384 | 0.2750 | hCPS1-ASO-155 | 1.3183 | 0.0726 | hCPS1-ASO-275 | 0.7799 | 0.1717 |
| hCPS1-ASO-11a | 1.1334 | 0.1617 | hCPS1-ASO-156 | 0.9952 | 0.1123 | hCPS1-ASO-276 | 0.8826 | 0.1542 |
| hCPS1-ASO-12a | 0.8162 | 0.0866 | hCPS1-ASO-157 | 1.2972 | 0.1294 | hCPS1-ASO-277 | 0.8896 | 0.2650 |
| hCPS1-ASO-13a | 1.5297 | 0.1882 | hCPS1-ASO-158 | 1.7248 | 0.2074 | hCPS1-ASO-278 | 0.4696 | 0.0748 |
| hCPS1-ASO-14a | 0.9744 | 0.0844 | hCPS1-ASO-159 | 1.7892 | 0.3807 | hCPS1-ASO-279 | 1.3629 | 0.1492 |
| hCPS1-ASO-15a | 0.9225 | 0.1756 | hCPS1-ASO-160 | 1.6078 | 0.2263 | hCPS1-ASO-280 | 1.9970 | 0.4340 |
| hCPS1-ASO-7a | 0.6872 | 0.0821 | hCPS1-ASO-161 | 1.0960 | 0.6012 | hCPS1-ASO-281 | 1.9249 | 0.2595 |
| hCPS1-ASO-4a | 1.5925 | 0.1816 | hCPS1-ASO-162 | 1.5522 | 0.6413 | hCPS1-ASO-282 | 1.4252 | 0.4261 |
| hCPS1-ASO-5a | 2.1196 | 0.3491 | hCPS1-ASO-163 | 1.1633 | 0.0408 | hCPS1-ASO-283 | 4.4672 | 1.1138 |
| hCPS1-ASO-6a | 1.8529 | 0.9210 | hCPS1-ASO-164 | 1.3349 | 0.1053 | hCPS1-ASO-284 | 5.0837 | 1.5527 |
| hCPS1-ASO-8a | 1.5270 | 0.8361 | hCPS1-ASO-165 | 1.6669 | 0.2143 | hCPS1-ASO-285 | 4.7339 | 0.3981 |
| hCPS1-ASO-9b | 0.8992 | 0.0590 | hCPS1-ASO-166 | 1.3915 | 0.2569 | hCPS1-ASO-286 | 1.5091 | 0.3739 |

TABLE 4-continued

| Name | FC | SD | Name | FC | SD | Name | FC | SD |
|---|---|---|---|---|---|---|---|---|
| hCPS1-ASO-10b | 0.9770 | 0.0428 | hCPS1-ASO-167 | 1.7175 | 0.2493 | hCPS1-ASO-287 | 1.3469 | 0.3479 |
| hCPS1-ASO-11b | 1.6000 | 0.2631 | hCPS1-ASO-168 | 1.1979 | 0.1337 | hCPS1-ASO-288 | 1.6093 | 0.2169 |
| hCPS1-ASO-12b | 0.9917 | 0.1514 | hCPS1-ASO-169 | 1.3335 | 0.2080 | hCPS1-ASO-289 | 0.9802 | 0.3187 |
| hCPS1-ASO-13b | 1.1117 | 0.1612 | hCPS1-ASO-170 | 1.0882 | 0.3444 | hCPS1-ASO-290 | 1.6650 | 0.1183 |
| hCPS1-ASO-14b | 0.8017 | 0.0536 | hCPS1-ASO-171 | 1.2852 | 0.1472 | hCPS1-ASO-291 | 1.7705 | 0.4831 |
| hCPS1-ASO-15b | 0.8779 | 0.0632 | hCPS1-ASO-172 | 1.3309 | 0.1877 | hCPS1-ASO-292 | 1.8768 | 0.3481 |
| hCPS1-ASO-7b | 0.9488 | 0.0891 | hCPS1-ASO-173 | 1.3430 | 0.2467 | hCPS1-ASO-293 | 1.8295 | 0.3331 |
| hCPS1-ASO-4b | 0.9687 | 0.1444 | hCPS1-ASO-174 | 1.2633 | 0.2020 | hCPS1-ASO-294 | 4.2131 | 0.7748 |
| hCPS1-ASO-5b | 0.9448 | 0.1081 | hCPS1-ASO-175 | 1.6397 | 0.3383 | hCPS1-ASO-295 | 0.8242 | 0.1736 |
| hCPS1-ASO-6b | 0.8277 | 0.0428 | hCPS1-ASO-176 | 1.3926 | 0.5390 | hCPS1-ASO-296 | 1.7239 | 0.4255 |
| hCPS1-ASO-8b | 0.9161 | 0.1199 | hCPS1-ASO-177 | 1.4242 | 0.2749 | hCPS1-ASO-297 | 2.0747 | 0.4485 |
| hCPS1-ASO-77 | 4.1549 | 0.9198 | hCPS1-ASO-178 | 1.4453 | 0.2574 | hCPS1-ASO-298 | 1.1081 | 0.1802 |
| hCPS1-ASO-78 | 2.2972 | 0.1418 | hCPS1-ASO-179 | 1.2086 | 0.0863 | hCPS1-ASO-299 | 5.1515 | 0.9679 |
| hCPS1-ASO-79 | 2.4319 | 0.2248 | hCPS1-ASO-180 | 1.2183 | 0.1814 | hCPS1-ASO-300 | 4.8213 | 0.9887 |
| hCPS1-ASO-80 | 2.7917 | 0.6061 | hCPS1-ASO-181 | 1.3878 | 0.1419 | hCPS1-ASO-301 | 3.3943 | 0.6421 |
| hCPS1-ASO-1h | 1.1727 | 0.1382 | hCPS1-ASO-182 | 1.3813 | 0.1038 | hCPS1-ASO-302 | 1.8365 | 0.4610 |
| hCPS1-ASO-1i | 1.4355 | 0.1558 | hCPS1-ASO-183 | 1.2326 | 0.1733 | hCPS1-ASO-303a | 1.3137 | 0.2222 |
| hCPS1-ASO-1j | 1.2027 | 0.0988 | hCPS1-ASO-184 | 1.3169 | 0.3607 | hCPS1-ASO-303b | 1.7427 | 0.3256 |
| hCPS1-ASO-1k | 1.1188 | 0.0499 | hCPS1-ASO-185 | 1.4697 | 0.2622 | hCPS1-ASO-304a | 2.2107 | 0.3595 |
| hCPS1-ASO-1l | 1.3171 | 0.1662 | hCPS1-ASO-186 | 1.2855 | 0.3984 | hCPS1-ASO-304b | 2.0165 | 0.7982 |
| hCPS1-ASO-1m | 1.1873 | 0.1099 | hCPS1-ASO-187 | 1.3655 | 0.2214 | hCPS1-ASO-305a | 1.8751 | 0.3138 |
| hCPS1-ASO-1n | 1.1683 | 0.1096 | hCPS1-ASO-188 | 1.3777 | 0.1068 | hCPS1-ASO-305b | 2.9614 | 0.4636 |
| hCPS1-ASO-1o | 1.3191 | 0.1220 | hCPS1-ASO-189 | 1.2786 | 0.1922 | hCPS1-ASO-306a | 2.9192 | 0.8811 |
| hCPS1-ASO-1p | 1.9562 | 0.0841 | hCPS1-ASO-190 | 1.0252 | 0.0880 | hCPS1-ASO-306b | 3.4468 | 1.3494 |
| hCPS1-ASO-1q | 1.2673 | 0.1820 | hCPS1-ASO-191 | 1.2291 | 0.1588 | hCPS1-ASO-307a | 1.3314 | 0.3165 |
| hCPS1-ASO-1r | 1.5857 | 0.1339 | hCPS1-ASO-192 | 1.4614 | 0.2198 | hCPS1-ASO-307 | 1.2205 | 0.1267 |
| hCPS1-ASO-1s | 2.5762 | 0.3147 | hCPS1-ASO-193 | 1.4984 | 0.4280 | hCPS1-ASO-308a | 1.2918 | 0.2042 |
| hCPS1-ASO-1t | 2.4333 | 0.2508 | hCPS1-ASO-194 | 0.9625 | 0.3146 | hCPS1-ASO-308 | 1.1019 | 0.1488 |
| hCPS1-ASO-1u | 2.9405 | 0.2842 | hCPS1-ASO-195 | 1.4616 | 0.2171 | hCPS1-ASO-309a | 1.9776 | 0.5046 |
| hCPS1-ASO-1v | 1.9457 | 0.2076 | hCPS1-ASO-196 | 1.3635 | 0.0990 | hCPS1-ASO-309b | 1.4482 | 0.2178 |
| hCPS1-ASO-82a | 2.5019 | 0.3142 | hCPS1-ASO-197 | 1.5088 | 0.2155 | hCPS1-ASO-309c | 1.8643 | 0.3592 |
| hCPS1-ASO-83a | 1.6054 | 0.1333 | hCPS1-ASO-198 | 1.5691 | 0.1943 | hCPS1-ASO-310a | 2.1756 | 0.8122 |
| hCPS1-ASO-83b | 1.3049 | 0.1062 | hCPS1-ASO-199 | 0.8877 | 0.2414 | hCPS1-ASO-310b | 2.1692 | 0.3493 |
| hCPS1-ASO-84a | 1.6594 | 0.1400 | hCPS1-ASO-200 | 0.9393 | 0.1766 | hCPS1-ASO-310c | 1.5170 | 0.2149 |
| hCPS1-ASO-84b | 1.6155 | 0.2525 | hCPS1-ASO-201 | 0.8805 | 0.1631 | hCPS1-ASO-310d | 1.7083 | 0.2543 |
| hCPS1-ASO-85a | 3.1551 | 0.2265 | hCPS1-ASO-202 | 0.9079 | 0.1671 | hCPS1-ASO-311a | 3.7975 | 0.7950 |
| hCPS1-ASO-1 | 1.2847 | 0.4866 | hCPS1-ASO-203 | 0.8525 | 0.1637 | hCPS1-ASO-311b | 2.2173 | 0.2349 |
| | | | | | | hCPS1-ASO-311c | 3.8806 | 0.8311 | hCPS1-ASO-1a and hCPS1-ASO1g were tested in hepatocytes at increasing concentrations. 0.156 to 5 uM ASO was incubated with hepatocytes as described above. As shown in Table 5, both hCPS1-ASO-1a and hCPS1-ASO1g induced a dose dependent increase in CPS1 mRNA.

TABLE 5

| Name | FC | SD | Dose (uM) |
|---|---|---|---|
| hCPS1-ASO-1a | 1.6220 | 0.0932 | 0.156 |
| hCPS1-ASO-1a | 1.9973 | 0.2021 | 0.313 |
| hCPS1-ASO-1a | 2.4574 | 0.1968 | 0.625 |
| hCPS1-ASO-1a | 3.7565 | 0.4598 | 1.25 |
| hCPS1-ASO-1a | 4.9565 | 0.7826 | 2.5 |
| hCPS1-ASO-1a | 4.9868 | 0.4258 | 5 |
| hCPS1-ASO-1g | 1.5646 | 0.0907 | 0.156 |
| hCPS1-ASO-1g | 1.7147 | 0.1318 | 0.313 |
| hCPS1-ASO-1g | 1.9748 | 0.3676 | 0.625 |
| hCPS1-ASO-1g | 3.3634 | 0.7101 | 2.5 |
| hCPS1-ASO-1g | 3.7516 | 0.7574 | 5 |

Additional chemical modifications were made to selected ASOs. The chemical modifications are provided in FIG. 14. Hepatocytes were incubated with 1.25 to 5 uM of the selected ASO as described above. The highest CSP1 mRNA fold change (FC) and standard deviation (SD) is provided in Table 6.

TABLE 6

| Name | FC | DS | Dose (uM) |
|---|---|---|---|
| hCPS1-ASO-1a | 5.5803 | 0.9290 | 5 uM |
| hCPS1-ASO-1b | 1.1870 | 0.1452 | 5 uM |
| hCPS1-ASO-1c | 1.4590 | 0.2142 | 5 uM |
| hCPS1-ASO-1d | 1.0277 | 0.1069 | 5 uM |
| hCPS1-ASO-1e | 1.0992 | 0.1400 | 5 uM |
| hCPS1-ASO-1f | 1.6978 | 0.4026 | 5 uM |
| hCPS1-ASO-1g | 4.4990 | 0.6087 | 5 uM |
| hCPS1-ASO-2 | 4.3014 | 0.9287 | 5 uM |
| hCPS1-ASO-3 | 2.2218 | 0.1531 | 5 uM |
| hCPS1-ASO-1h | 1.1727 | 0.1382 | 1 |
| hCPS1-ASO-1i | 1.4355 | 0.1558 | 5 uM |
| hCPS1-ASO-1j | 1.2027 | 0.0988 | 5 uM |
| hCPS1-ASO-1k | 1.1188 | 0.0499 | 0.2 |
| hCPS1-ASO-1l | 1.3171 | 0.1662 | 5 uM |
| hCPS1-ASO-1m | 1.1873 | 0.1099 | 5 uM |
| hCPS1-ASO-1n | 1.1683 | 0.1096 | 1 |
| hCPS1-ASO-1o | 1.3191 | 0.1220 | 5 uM |
| hCPS1-ASO-1p | 1.9562 | 0.0841 | 5 uM |
| hCPS1-ASO-1q | 1.2673 | 0.1820 | 0.2 |
| hCPS1-ASO-1r | 1.5857 | 0.1339 | 5 |
| hCPS1-ASO-1s | 2.5762 | 0.3147 | 5 |
| hCPS1-ASO-1t | 2.4333 | 0.2508 | 5 |
| hCPS1-ASO-1u | 2.9405 | 0.2842 | 5 |
| hCPS1-ASO-1v | 1.9457 | 0.2076 | 5 |
| hCPS1-ASO-82a | 2.5019 | 0.3142 | 5 |
| hCPS1-ASO-82a | 2.5546 | 0.1486 | 5 |
| hCPS1-ASO-86a | 1.2337 | 0.1193 | 1.25 |
| hCPS1-ASO-86b | 1.3452 | 0.4155 | 2.5 |
| hCPS1-ASO-87a | 1.7071 | 0.3347 | 5 |
| hCPS1-ASO-88a | 1.4598 | 0.2254 | 5 |
| hCPS1-ASO-89a | 1.1069 | 0.2738 | 5 |
| hCPS1-ASO-91a | 1.9014 | 0.3037 | 5 |
| hCPS1-ASO-91b | 3.0003 | 0.6407 | 2.5 |
| hCPS1-ASO-91c | 1.8697 | 0.2390 | 2.5 |
| hCPS1-ASO-91d | 2.2671 | 0.0950 | 2.5 |
| hCPS1-ASO-91e | 3.2286 | 0.3834 | 2.5 |
| hCPS1-ASO-91f | 1.6813 | 0.1274 | 1.25 |
| hCPS1-ASO-91g | 2.8205 | 0.0827 | 2.5 |
| hCPS1-ASO-91h | 3.1424 | 0.1637 | 2.5 |
| hCPS1-ASO-91i | 3.7109 | 0.4564 | 1.25 |
| hCPS1-ASO-91j | 5.0641 | 0.2305 | 5 uM |
| hCPS1-ASO-279a | 1.3629 | 0.1492 | 5 uM |
| hCPS1-ASO-280a | 1.9970 | 0.4340 | 5 uM |
| hCPS1-ASO-281a | 1.9249 | 0.2595 | 5 uM |
| hCPS1-ASO-282a | 1.4252 | 0.4261 | 5 uM |

TABLE 6-continued

| Name | FC | DS | Dose (uM) |
|---|---|---|---|
| hCPS1-ASO-283a | 4.4672 | 1.1138 | 5 uM |
| hCPS1-ASO-284a | 5.0837 | 1.5527 | 5 uM |
| hCPS1-ASO-285a | 4.7339 | 0.3981 | 5 uM |
| hCPS1-ASO-286a | 1.5091 | 0.3739 | 5 uM |
| hCPS1-ASO-287a | 1.3469 | 0.3479 | 5 uM |
| hCPS1-ASO-288a | 1.6093 | 0.2169 | 5 uM |
| hCPS1-ASO-289a | 0.9802 | 0.3187 | 5 uM |
| hCPS1-ASO-290a | 1.6650 | 0.1183 | 5 uM |
| hCPS1-ASO-291a | 1.7705 | 0.4831 | 5 uM |
| hCPS1-ASO-292a | 1.8768 | 0.3481 | 5 uM |
| hCPS1-ASO-293a | 1.8295 | 0.3331 | 5 uM |
| hCPS1-ASO-294a | 4.2131 | 0.7748 | 5 uM |
| hCPS1-ASO-295a | 0.8242 | 0.1736 | 5 uM |
| hCPS1-ASO-296a | 1.7239 | 0.4255 | 5 uM |
| hCPS1-ASO-297a | 2.0747 | 0.4485 | 5 uM |
| hCPS1-ASO-298a | 1.1081 | 0.1802 | 5 uM |
| hCPS1-ASO-299a | 5.1515 | 0.9679 | 5 uM |
| hCPS1-ASO-300a | 4.8213 | 0.9887 | 5 uM |
| hCPS1-ASO-301a | 3.3943 | 0.6421 | 5 uM |
| hCPS1-ASO-302a | 1.8365 | 0.4610 | 5 uM |
| hCPS1-ASO-303a | 1.3137 | 0.2222 | 5 uM |
| hCPS1-ASO-303b | 1.7427 | 0.3256 | 5 uM |
| hCPS1-ASO-304a | 2.2107 | 0.3595 | 5 uM |
| hCPS1-ASO-304b | 2.0165 | 0.7982 | 5 uM |
| hCPS1-ASO-305a | 1.8751 | 0.3138 | 5 uM |
| hCPS1-ASO-305b | 2.9614 | 0.4636 | 5 uM |
| hCPS1-ASO-306a | 2.9192 | 0.8811 | 5 uM |
| hCPS1-ASO-306b | 3.4468 | 1.3494 | 5 uM |
| hCPS1-ASO-307a | 1.3314 | 0.3165 | 5 uM |
| hCPS1-ASO-307b | 1.2205 | 0.1267 | 5 uM |
| hCPS1-ASO-308a | 1.2918 | 0.2042 | 5 uM |
| hCPS1-ASO-308b | 1.1019 | 0.1488 | 5 uM |
| hCPS1-ASO-309a | 1.9776 | 0.5046 | 5 uM |
| hCPS1-ASO-309b | 1.4482 | 0.2178 | 5 uM |
| hCPS1-ASO-309c | 1.8643 | 0.3592 | 5 uM |
| hCPS1-ASO-310a | 2.1756 | 0.8122 | 5 uM |
| hCPS1-ASO-310b | 2.1692 | 0.3493 | 5 uM |
| hCPS1-ASO-310c | 1.5170 | 0.2149 | 5 uM |
| hCPS1-ASO-310d | 1.7083 | 0.2543 | 5 uM |
| hCPS1-ASO-311a | 3.7975 | 0.7950 | 5 uM |
| hCPS1-ASO-311b | 2.2173 | 0.2349 | 5 uM |
| hCPS1-ASO-311c | 3.880599933 | 0.8311 | 5 uM |
| hCPS1-ASO-312a | 1.284688861 | 0.4866 | 5 uM |

In sum, 109 initial ASOs targeting CPS1 RR44 were made, of which 76 ASOs comprising 69 gapmers and 7 steric ASOs passed the first pass screen. These 76 ASOs were selected for tiling, and 9 ASOs, comprising 4 gapmers and 5 sterics were selected from this screen. A further 24 ASOs comprising 12 gapmers and 12 mixmers with additional chemistries were made via fine tuning. hCPS1-ASO-1g (SEQ ID NO: 22) was selected for further characterization. PO bonds, a GalNAc moiety and additional 5meC moieties were added for in vivo studies, resulting in hCPS1-ASO-1x (SEQ ID NO: 409).

Example 2: Synthesis and Characterization of Additional CPS1 regRNA-Targeting ASOs Two additional regRNAs, RR89 and RR90, were identified. ASOs targeting the new regRNA were synthesized and tested at 5 uM in hepatocytes as described above. The CPS1 mRNA fold increase after treatment with these ASOs is provided in Table 7 below.

TABLE 7

| RR | Name | FC | SD | RR | Name | FC | SD |
|---|---|---|---|---|---|---|---|
| RR89 | hCPS1-ASO-317 | 1.5775 | 0.8135 | RR90 | hCPS1-ASO-405 | 1.2012 | 0.2487 |
| RR89 | hCPS1-ASO-318 | 1.5826 | 0.7218 | RR90 | hCPS1-ASO-406 | 1.2865 | 0.2028 |
| RR89 | hCPS1-ASO-319 | 1.5962 | 0.4788 | RR90 | hCPS1-ASO-407 | 1.1295 | 0.2439 |
| RR89 | hCPS1-ASO-320 | 1.4931 | 0.7690 | RR90 | hCPS1-ASO-408 | 1.0533 | 0.2725 |
| RR89 | hCPS1-ASO-321 | 1.6746 | 0.6312 | RR90 | hCPS1-ASO-409 | 0.8087 | 0.1096 |
| RR89 | hCPS1-ASO-322 | 2.0095 | 0.7188 | RR90 | hCPS1-ASO-410 | 1.3942 | 0.5000 |
| RR89 | hCPS1-ASO-323 | 2.0440 | 1.0473 | RR90 | hCPS1-ASO-411 | 1.3583 | 0.3396 |
| RR89 | hCPS1-ASO-324 | 2.3892 | 0.8168 | RR90 | hCPS1-ASO-412 | 1.6266 | 0.7518 |
| RR89 | hCPS1-ASO-325 | 1.5915 | 0.7186 | RR90 | hCPS1-ASO-413 | 1.2538 | 0.4311 |
| RR89 | hCPS1-ASO-326 | 2.1136 | 1.1464 | RR90 | hCPS1-ASO-414 | 1.1461 | 0.3094 |
| RR89 | hCPS1-ASO-327 | 1.9483 | 0.9495 | RR90 | hCPS1-ASO-415 | 0.9143 | 0.0766 |
| RR89 | hCPS1-ASO-328 | 1.6812 | 0.5726 | RR90 | hCPS1-ASO-416 | 1.1560 | 0.1866 |
| RR89 | hCPS1-ASO-329 | 1.8316 | 0.9072 | RR90 | hCPS1-ASO-417 | 1.0591 | 0.2657 |
| RR89 | hCPS1-ASO-330 | 2.0059 | 0.8976 | RR90 | hCPS1-ASO-418 | 1.3887 | 0.3178 |
| RR89 | hCPS1-ASO-331 | 1.8741 | 0.7026 | RR90 | hCPS1-ASO-419 | 1.3402 | 0.4910 |
| RR89 | hCPS1-ASO-332 | 2.1500 | 0.7416 | RR90 | hCPS1-ASO-420 | 1.5140 | 0.3829 |
| RR89 | hCPS1-ASO-333 | 1.5499 | 0.5157 | RR90 | hCPS1-ASO-421 | 1.0943 | 0.2253 |
| RR89 | hCPS1-ASO-334 | 1.5552 | 0.4804 | RR90 | hCPS1-ASO-422 | 1.1711 | 0.1122 |
| RR89 | hCPS1-ASO-335 | 1.9576 | 0.5176 | RR90 | hCPS1-ASO-423 | 0.9694 | 0.1022 |
| RR89 | hCPS1-ASO-336 | 1.8716 | 0.6998 | RR90 | hCPS1-ASO-424 | 1.2236 | 0.1582 |
| RR89 | hCPS1-ASO-337 | 1.8125 | 0.8488 | RR90 | hCPS1-ASO-425 | 1.2610 | 0.1906 |
| RR89 | hCPS1-ASO-338 | 2.0401 | 0.7645 | RR90 | hCPS1-ASO-426 | 1.3614 | 0.2645 |
| RR89 | hCPS1-ASO-339 | 2.2799 | 1.3896 | RR90 | hCPS1-ASO-427 | 1.0732 | 0.1397 |
| RR89 | hCPS1-ASO-340 | 2.4647 | 1.1151 | RR90 | hCPS1-ASO-428 | 1.0589 | 0.2379 |
| RR89 | hCPS1-ASO-341 | 1.6513 | 0.6047 | RR90 | hCPS1-ASO-429 | 0.8780 | 0.1622 |
| RR89 | hCPS1-ASO-342 | 3.0261 | 1.3769 | RR90 | hCPS1-ASO-430 | 1.1569 | 0.1560 |
| RR89 | hCPS1-ASO-343 | 1.6381 | 0.7347 | RR90 | hCPS1-ASO-431 | 1.1585 | 0.1097 |
| RR89 | hCPS1-ASO-344 | 1.5409 | 0.4495 | RR90 | hCPS1-ASO-432 | 1.2950 | 0.2285 |
| RR89 | hCPS1-ASO-345 | 2.0952 | 1.0805 | RR90 | hCPS1-ASO-433 | 1.0298 | 0.2219 |
| RR89 | hCPS1-ASO-346 | 2.3178 | 1.3366 | RR90 | hCPS1-ASO-434 | 1.3012 | 0.0903 |
| RR89 | hCPS1-ASO-347 | 1.4951 | 0.6377 | RR90 | hCPS1-ASO-435 | 1.0841 | 0.1667 |
| RR89 | hCPS1-ASO-348 | 1.6709 | 0.5697 | RR90 | hCPS1-ASO-436 | 1.1873 | 0.2434 |
| RR89 | hCPS1-ASO-349 | 1.1956 | 0.5132 | RR90 | hCPS1-ASO-437 | 0.8902 | 0.4503 |
| RR89 | hCPS1-ASO-350 | 1.3203 | 0.7134 | RR90 | hCPS1-ASO-438 | 1.1951 | 0.1350 |
| RR89 | hCPS1-ASO-351 | 1.7942 | 1.1274 | RR90 | hCPS1-ASO-439 | 0.8887 | 0.0839 |
| RR89 | hCPS1-ASO-352 | 1.5520 | 0.9718 | RR90 | hCPS1-ASO-440 | 1.0615 | 0.1012 |
| RR89 | hCPS1-ASO-353 | 1.7568 | 1.2231 | RR90 | hCPS1-ASO-441 | 0.8649 | 0.0311 |
| RR89 | hCPS1-ASO-354 | 1.8507 | 1.1719 | RR90 | hCPS1-ASO-442 | 0.9772 | 0.1905 |
| RR89 | hCPS1-ASO-355 | 1.5305 | 0.8114 | RR90 | hCPS1-ASO-443 | 0.8815 | 0.2444 |
| RR89 | hCPS1-ASO-356 | 1.7731 | 0.9631 | RR90 | hCPS1-ASO-444 | 1.3442 | 0.1924 |
| RR89 | hCPS1-ASO-357 | 1.2436 | 0.7147 | RR90 | hCPS1-ASO-445 | 0.8889 | 0.0616 |
| RR89 | hCPS1-ASO-358 | 1.6246 | 1.3366 | RR90 | hCPS1-ASO-446 | 1.3171 | 0.2598 |
| RR89 | hCPS1-ASO-359 | 1.5335 | 1.0744 | RR90 | hCPS1-ASO-447 | 1.0407 | 0.0687 |
| RR89 | hCPS1-ASO-360 | 1.9214 | 1.5074 | RR90 | hCPS1-ASO-448 | 1.1217 | 0.1056 |
| RR89 | hCPS1-ASO-361 | 1.4754 | 0.9292 | RR90 | hCPS1-ASO-449 | 1.1537 | 0.3244 |
| RR89 | hCPS1-ASO-362 | 1.6906 | 1.0116 | RR90 | hCPS1-ASO-450 | 1.3109 | 0.2590 |
| RR89 | hCPS1-ASO-363 | 1.3134 | 0.7014 | RR90 | hCPS1-ASO-451 | 1.5129 | 0.6513 |
| RR89 | hCPS1-ASO-364 | 1.7029 | 0.7542 | RR90 | hCPS1-ASO-452 | 1.2111 | 0.1128 |
| RR89 | hCPS1-ASO-365 | 1.6591 | 0.7996 | RR90 | hCPS1-ASO-453 | 1.0163 | 0.1088 |
| RR89 | hCPS1-ASO-366 | 1.6470 | 1.0509 | RR90 | hCPS1-ASO-454 | 1.3094 | 0.3247 |
| RR89 | hCPS1-ASO-367 | 1.8307 | 1.2695 | RR90 | hCPS1-ASO-455 | 1.1397 | 0.2210 |
| RR89 | hCPS1-ASO-368 | 1.6084 | 0.9115 | RR90 | hCPS1-ASO-456 | 1.0946 | 0.1733 |
| RR89 | hCPS1-ASO-369 | 1.3892 | 0.8035 | RR90 | hCPS1-ASO-457 | 1.0506 | 0.1601 |
| RR89 | hCPS1-ASO-370 | 1.5032 | 0.7262 | RR90 | hCPS1-ASO-458 | 1.2491 | 0.2422 |
| RR89 | hCPS1-ASO-371 | 1.4850 | 0.5957 | RR90 | hCPS1-ASO-459 | 1.3670 | 0.2012 |
| RR89 | hCPS1-ASO-372 | 1.5812 | 0.5242 | RR90 | hCPS1-ASO-460 | 1.3623 | 0.1823 |
| RR89 | hCPS1-ASO-373 | 1.6841 | 0.7860 | RR90 | hCPS1-ASO-461 | 1.0625 | 0.2351 |
| RR89 | hCPS1-ASO-374 | 1.4621 | 0.9788 | RR90 | hCPS1-ASO-462 | 1.2013 | 0.4743 |
| RR89 | hCPS1-ASO-375 | 1.6176 | 1.1216 | RR90 | hCPS1-ASO-463 | 1.0886 | 0.1494 |
| RR89 | hCPS1-ASO-376 | 1.3686 | 0.7403 | RR90 | hCPS1-ASO-464 | 1.1047 | 0.2209 |
| RR89 | hCPS1-ASO-377 | 1.2268 | 0.8146 | RR90 | hCPS1-ASO-465 | 1.1645 | 0.1735 |
| RR89 | hCPS1-ASO-378 | 1.6610 | 1.1474 | RR90 | hCPS1-ASO-466 | 1.4413 | 0.3431 |
| RR89 | hCPS1-ASO-379 | 1.4860 | 0.8718 | RR90 | hCPS1-ASO-467 | 1.2275 | 0.0838 |
| RR89 | hCPS1-ASO-380 | 1.5339 | 0.5719 | RR90 | hCPS1-ASO-468 | 1.3235 | 0.1612 |
| RR89 | hCPS1-ASO-381 | 1.3295 | 0.5757 | RR90 | hCPS1-ASO-469 | 0.8282 | 0.2019 |
| RR89 | hCPS1-ASO-382 | 1.9644 | 0.7430 | RR90 | hCPS1-ASO-470 | 0.9232 | 0.2007 |
| RR89 | hCPS1-ASO-383 | 1.8440 | 1.1617 | RR90 | hCPS1-ASO-471 | 1.3966 | 0.5929 |
| RR89 | hCPS1-ASO-384 | 1.5065 | 0.9131 | RR90 | hCPS1-ASO-472 | 1.0118 | 0.3935 |
| RR89 | hCPS1-ASO-385 | 1.5340 | 0.7326 | RR90 | hCPS1-ASO-473 | 0.9936 | 0.0465 |
| RR89 | hCPS1-ASO-386 | 1.6840 | 0.7312 | RR90 | hCPS1-ASO-474 | 1.3558 | 0.1254 |
| RR89 | hCPS1-ASO-387 | 1.3766 | 0.5754 | RR90 | hCPS1-ASO-475 | 1.2423 | 0.2156 |
| RR89 | hCPS1-ASO-388 | 1.4547 | 0.5771 | RR90 | hCPS1-ASO-476 | 1.9336 | 1.7330 |
| RR89 | hCPS1-ASO-389 | 1.3246 | 0.8197 | RR90 | hCPS1-ASO-477 | 0.9444 | 0.2228 |
| RR89 | hCPS1-ASO-390 | 2.5864 | 1.2608 | RR90 | hCPS1-ASO-478 | 1.3043 | 0.4730 |
| RR89 | hCPS1-ASO-391 | 1.5723 | 0.9236 | RR90 | hCPS1-ASO-479 | 1.0763 | 0.2153 |
| RR89 | hCPS1-ASO-392 | 1.4165 | 1.0256 | RR90 | hCPS1-ASO-480 | 1.0685 | 0.0883 |
| RR89 | hCPS1-ASO-393 | 1.6100 | 0.9882 | RR90 | hCPS1-ASO-481 | 1.0366 | 0.2728 |
| RR89 | hCPS1-ASO-394 | 1.2672 | 0.8009 | RR90 | hCPS1-ASO-482 | 1.3154 | 0.2555 |

TABLE 7-continued

| RR | Name | FC | SD | RR | Name | FC | SD |
|---|---|---|---|---|---|---|---|
| RR89 | hCPS1-ASO-395 | 1.6338 | 0.5694 | RR90 | hCPS1-ASO-483 | 1.2040 | 0.0888 |
| RR89 | hCPS1-ASO-396 | 1.5087 | 0.7520 | RR90 | hCPS1-ASO-484 | 1.4609 | 0.3332 |
| RR89 | hCPS1-ASO-397 | 1.7948 | 0.8470 | RR90 | hCPS1-ASO-485 | 1.4426 | 0.3264 |
| RR89 | hCPS1-ASO-398 | 1.6142 | 0.8862 | RR90 | hCPS1-ASO-486 | 1.1654 | 0.3570 |
| RR89 | hCPS1-ASO-399 | 1.6498 | 0.8071 | RR90 | hCPS1-ASO-487 | 1.2836 | 0.1139 |
| RR89 | hCPS1-ASO-400 | 1.3005 | 0.7143 | RR90 | hCPS1-ASO-488 | 1.1598 | 0.5098 |
| RR89 | hCPS1-ASO-401 | 1.2663 | 0.6460 | RR90 | hCPS1-ASO-489 | 1.1434 | 0.1147 |
| RR89 | hCPS1-ASO-402 | 1.3756 | 0.5260 | RR90 | hCPS1-ASO-490 | 1.1133 | 0.1801 |
| RR89 | hCPS1-ASO-403 | 0.9677 | 0.3162 | RR90 | hCPS1-ASO-491 | 1.1545 | 0.0996 |
| RR89 | hCPS1-ASO-404 | 1.3644 | 0.4530 | RR90 | hCPS1-ASO-492 | 1.8287 | 0.8381 |

Example 3: In Vivo Characterization of Selected ASOs in Non-Human Primates

Figure 17:
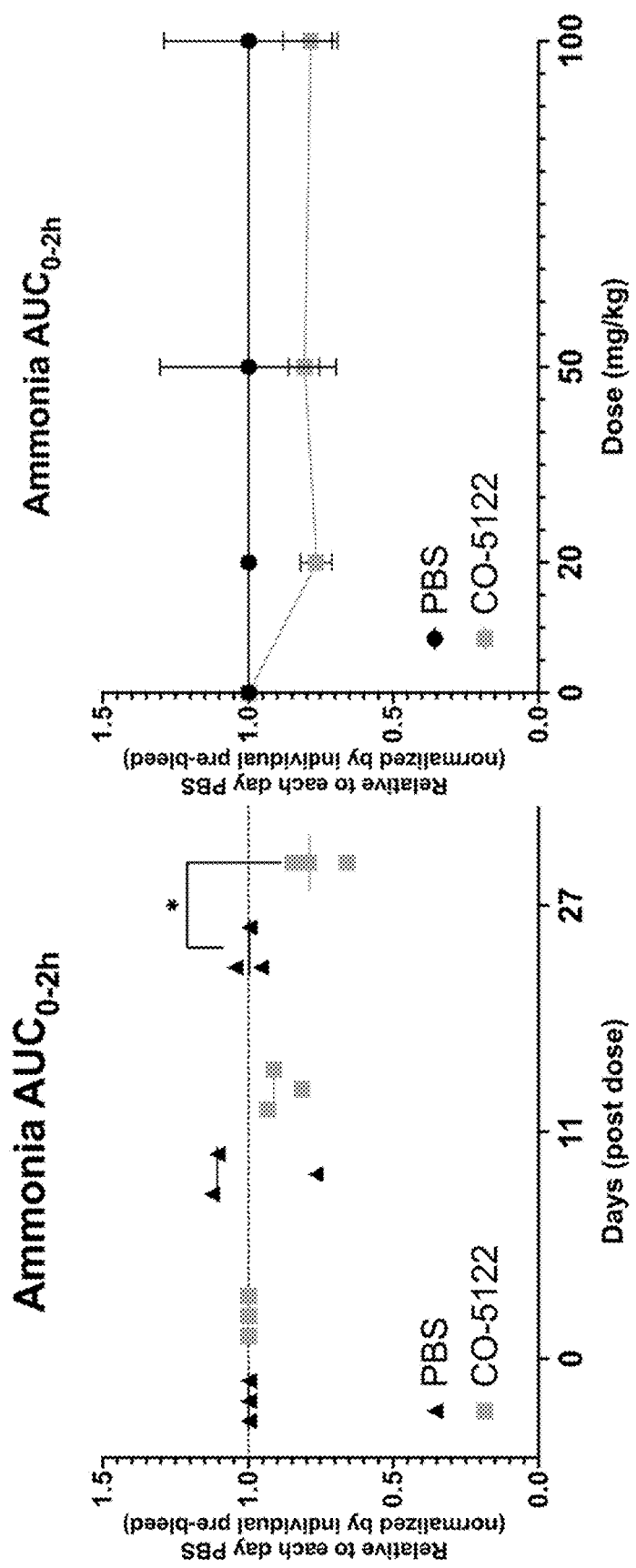
FIG. 17 shows that hCPS1-ASO-1x decreased ammonia production in NHPs by a statistically significant amount as compared to PBS only treatment by Day 27.

Male cynomolgus monkeys (NHP), 2-4 years old, were subcutaneously injected with either 20 mg/kg or 50 mg/kg of hCPS1-ASO-1x on Day 0, and repeated doses were given to some groups on Day 21. Three NHPs were randomly assigned as one group. PBS was administered to one group as a negative control. Ammonia challenge and ureagenesis assay in NHPs were performed in an overnight fasted state prior to the ammonia challenge. 200 mg/kg of $^{15}NH_4Cl$ solution was subcutaneously injected into NHPs and multiple blood draws were performed over 0-120 min and immediately plasmas were obtained by centrifugation.

hCPS1-ASO-1x decreased ammonia production in NHPs by a statistically significant amount as compared to PBS only treatment by Day 27. FIG. 17 provides the ammonia AUC both over time and per dose.

Figure 18:
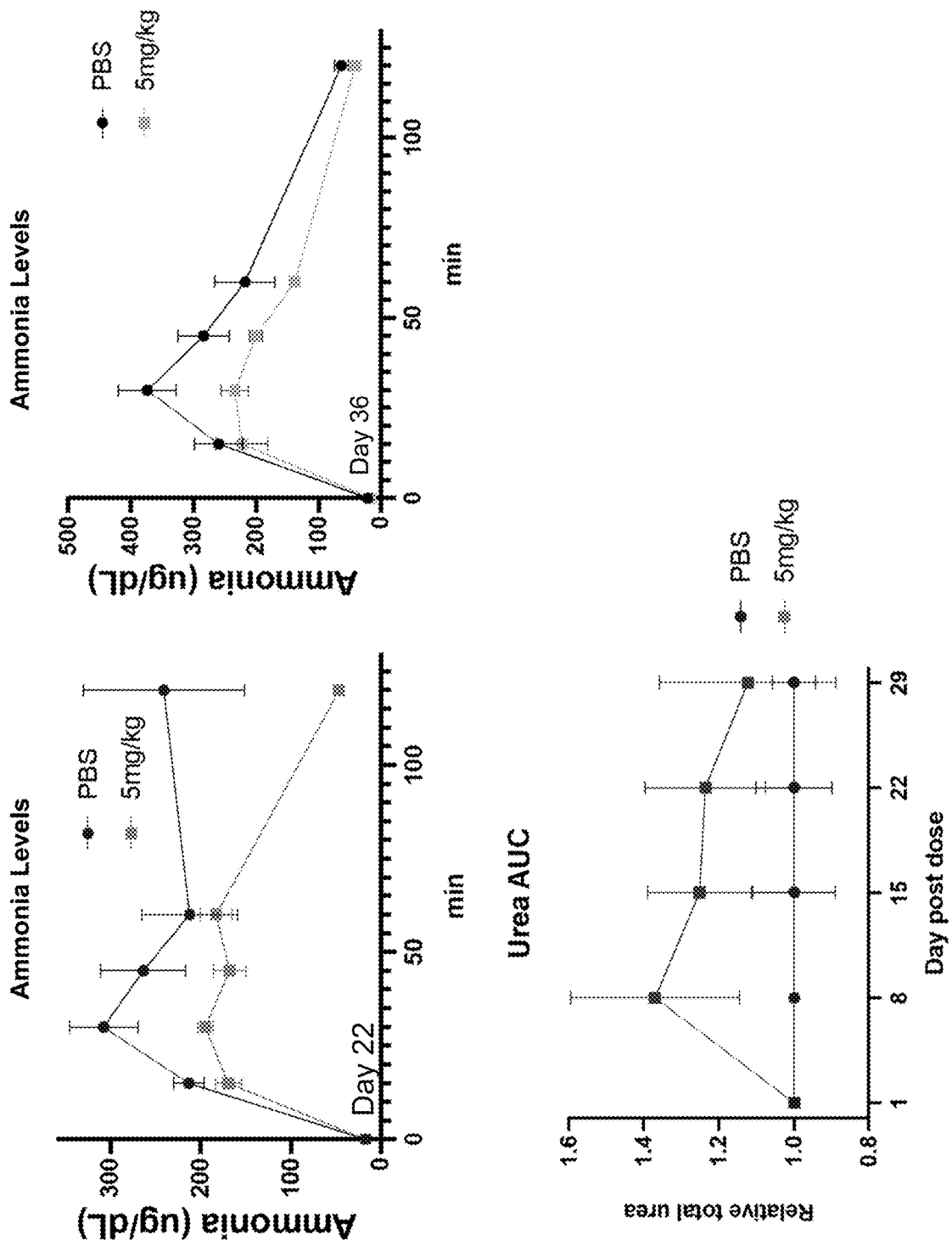
FIG. 18 shows that hCPS1-ASO-1x decreased ammonia in NHPs after a single dose of 5 mg/kg for up to 5 weeks FIG. 19 provides the NHP study ammonia AUC quantification on Days 22, 29 and 36.
Figure 19:
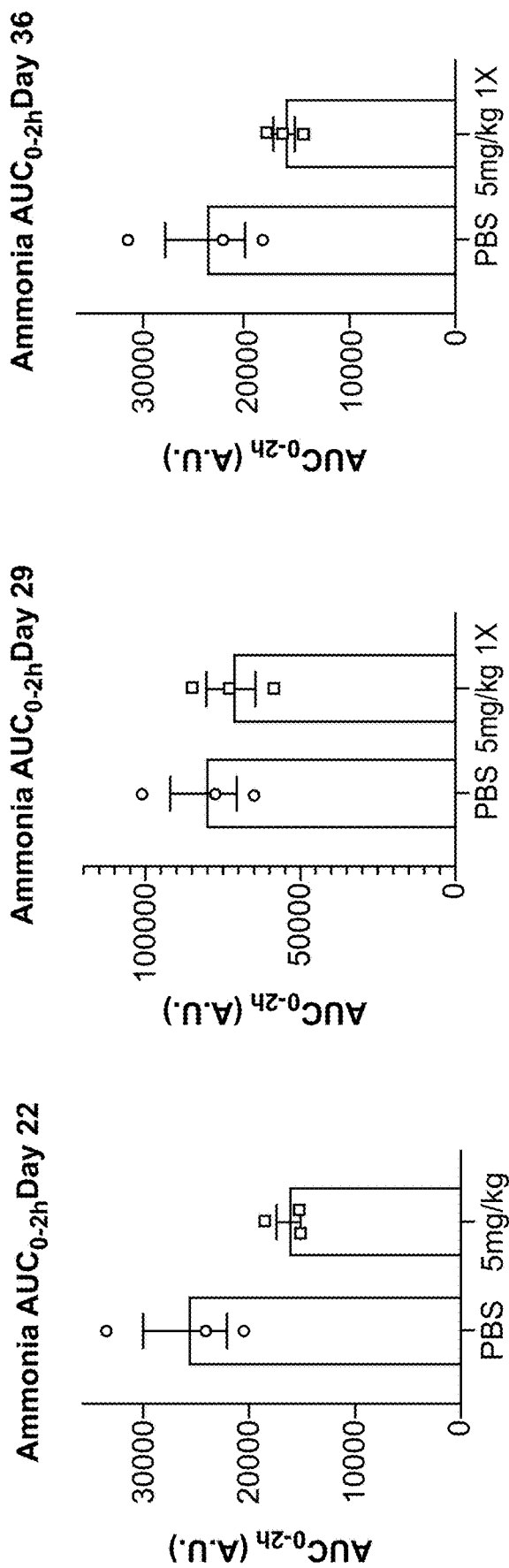

A second in vivo NHP study was performed to assess the efficacy with a lower dose of hCPS1-ASO-1x. Female cynomolgus monkeys (NHP), 2-4 years old, were subcutaneously injected with either 5 mg/kg or 15 mg/kg of hCPS1-ASO-1x on Day 1, and repeated doses were given on Day 36. Each group was consisted with three NHPs. One group was administered with PBS as a negative control. Ammonia challenge and ureagenesis assay in NHPs were performed in an overnight fasted state prior to the ammonia challenge. 200 mg/kg of $^{15}NH_4Cl$ solution was subcutaneously injected into NHPs and several blood draws were performed over 0-120 min and immediately plasmas were obtained by centrifugation. $^{13}C$-ureagenesis assay was performed in an overnight fated state prior to sodium acetate delivery. 55 mg/kg of $^{13}C$-sodium acetate was provided by oral gavage and multiple blood draws were performed over 0-240 min and plasmas were immediately obtained by centrifugation. FIG. 18 shows that hCPS1-ASO-1x decreased ammonia in NHPs after a single dose of 5 mg/kg for up to 5 weeks (shown are ammonia levels on day 22 and Day 36). In addition, urea levels increased in the ASOs treated NHPs up to 29 days post dose. FIG. 19 provides the ammonia AUC quantification on Days 22, 29 and 36.

Figure 20:
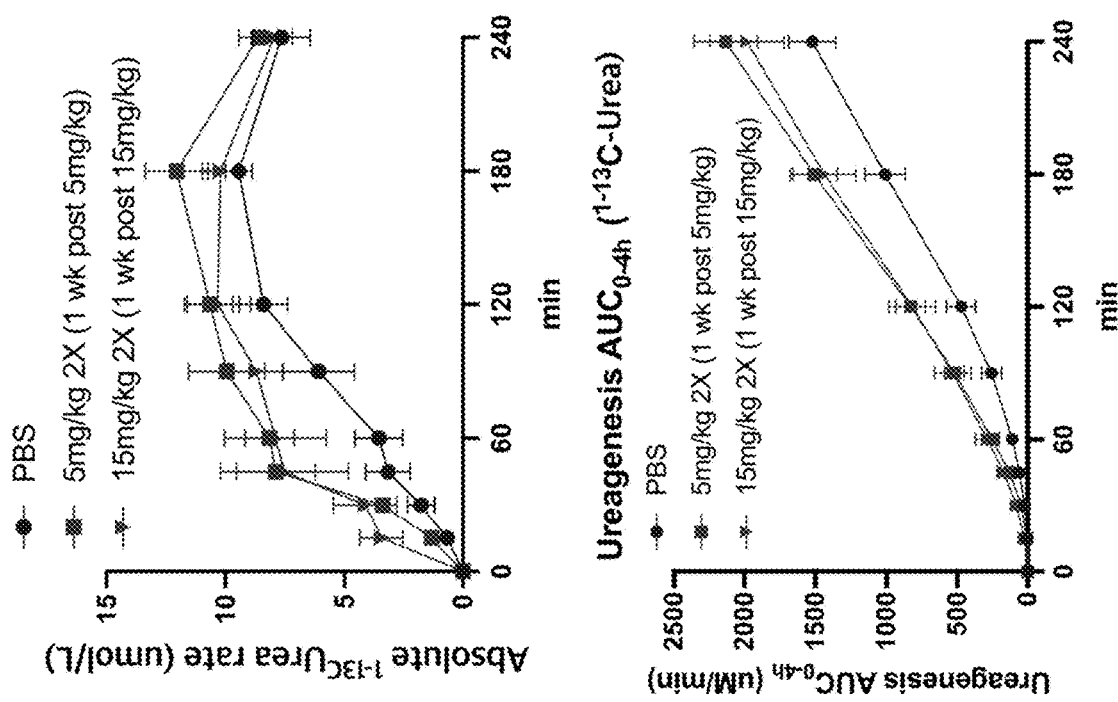
FIG. 20 shows that combination of hCPS1-ASO-1x with $^{13}$C-sodium acetate treatment enhanced ureagenesis in NHPs at day 43 as compared to hCPS1-ASO-1x alone.

Combination of hCPS1-ASO-1x with $^{13}C$-sodium acetate treatment enhanced ureagenesis in NHPs at day 43 as compared to hCPS1-ASO-1x alone (FIG. 20).

In sum, upregulation of CPS1 increased the output of the urea cycle in mouse, NHP, and human hepatocytes, both in vitro and in vivo. Increasing CPS1 mRNA in the mouse $OTC^{def}$ model via ASO treatment also increased the metabolism of ammonia to urea and the NHP data and humanized mouse liver data support this finding.

INCORPORATION BY REFERENCE

Unless stated to the contrary, the entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

---

What is claimed is:

1. An antisense oligonucleotide (ASO) comprising a nucleotide sequence of TGCAGGCACACACATCAGGC (SEQ ID NO: 1), wherein one or more of the nucleotides of the ASO are chemically modified.

2. The ASO of claim 1, wherein the 3' end of the ASO is conjugated to a ligand moiety.

3. The ASO of claim 2, wherein the ligand moiety comprises N-acetylgalactosamine (GalNAc).

4. The ASO of claim 3, wherein the ligand moiety comprises a three-cluster GalNAc moiety (GalNAc3).

5. An antisense oligonucleotide (ASO) comprising MT=MG=M5C-MA-MG=dG=d5C=dA=d5C=dA=d5C-dA=d5C-dA=dT=M5C-MA-MG=MG=M5C-[TEG] (SEQ ID NO: 409), wherein MT, MG, MA, and M5C are 2'-O-methoxyethyl thymidine, 2'-O-methoxyethyl guanosine, 2'-O-methoxyethyl adenosine, and 2'-O-methoxyethyl 5-methyl cytidine ribonucleosides; dA, dG, dT, and d5C are 2'-deoxy adenosine, 2'-deoxy guanosine, 2'-deoxy thymidine and 2'-deoxy 5-methyl cytidine ribonucleosides, "=" is a phosphorothioate linkage, "-" is a phosphodiester linkage, and [TEG] is a ligand moiety comprising a triethyleneglycol linked to N-acetylgalactosamine (GalNAc).

6. The ASO of claim 5, wherein the ligand moiety comprises a three-cluster GalNAc moiety (GalNAc3).

7. An antisense oligonucleotide (ASO) comprising MT=MG=M5C-MA-MG-dG-d5C=dA=d5C=dA=d5C=dA=d5C=dA=dT=M5C-MA-MG-MG=M5C (SEQ ID NO: 404), wherein MT, MG, MA, and M5C are 2'-O-methoxyethyl thymidine, 2'-O-methoxyethyl guanosine, 2'-O-methoxyethyl adenosine, and 2'-O-methoxyethyl 5-methyl cytidine ribonucleosides; dA, dG, dT, and d5C are 2'-deoxy adenosine, 2'-deoxy guanosine, 2'-deoxy thymidine and 2'-deoxy 5-methyl cytidine ribonucleosides, "=" is a phosphorothioate linkage, and "-" is a phosphodiester linkage.

8. A pharmaceutical composition comprising the ASO of claim 1.

9. A pharmaceutical composition comprising the ASO of claim 5.

10. A pharmaceutical composition comprising the ASO of claim 7.

11. The ASO of claim 7, wherein the 3' end of the ASO is conjugated to a ligand moiety.

12. The ASO of claim 11, wherein the ligand moiety comprises N-acetylgalactosamine (GalNAc).

13. The ASO of claim 12, wherein the ligand moiety comprises a three-cluster GalNAc moiety (GalNAc3).

14. A pharmaceutical composition comprising the ASO of claim 6.

15. A pharmaceutical composition comprising the ASO of claim 13.

* * * * *

UNITED STATES PATENT AND TRADEMARK OFFICE
CERTIFICATE OF CORRECTION

PATENT NO. : 12,319,916 B2
APPLICATION NO. : 18/752290
DATED : June 3, 2025
INVENTOR(S) : Alfica Sehgal et al.

Page 1 of 1

It is certified that error appears in the above-identified patent and that said Letters Patent is hereby corrected as shown below:

On the Title Page

Item [71], please change "Camp4" to -- CAMP4 --.

In the Claims

In Claim 5, Column 299, Lines 43-44, delete "d5C-dA=d5C-dA" and insert -- d5C=dA=d5C=dA --, therefor.

In Claim 7, Column 299, Line 57, delete "MG-dG-" and insert -- MG=dG= --, therefor.

In Claim 7, Column 300, Line 32, delete "MG-MG" and insert -- MG=MG --, therefor.

Signed and Sealed this
Twelfth Day of August, 2025

Coke Morgan Stewart
*Acting Director of the United States Patent and Trademark Office*